US007655840B2

(12) United States Patent
Cahoon et al.

(10) Patent No.: US 7,655,840 B2
(45) Date of Patent: Feb. 2, 2010

(54) ALTERATION OF EMBRYO/ENDOSPERM SIZE DURING SEED DEVELOPMENT

(75) Inventors: Rebecca E. Cahoon, Webster Groves, MO (US); Elmer P. Heppard, Wilmington, DE (US); Hajime Sakai, Newark, DE (US); Nobuhiro Nagasawa, Newark, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 239 days.

(21) Appl. No.: 11/394,442

(22) Filed: Mar. 31, 2006

(65) Prior Publication Data

US 2006/0218675 A1 Sep. 28, 2006

Related U.S. Application Data

(63) Continuation-in-part of application No. 10/163,198, filed on Jun. 5, 2002, now abandoned.

(60) Provisional application No. 60/295,921, filed on Jun. 5, 2001, provisional application No. 60/334,317, filed on Nov. 28, 2001.

(51) Int. Cl.

| | |
|---|---|
| ***C12N 15/29*** | (2006.01) |
| ***C12N 15/82*** | (2006.01) |
| ***C12N 5/04*** | (2006.01) |
| ***A01H 5/00*** | (2006.01) |
| ***A01H 5/10*** | (2006.01) |

(52) U.S. Cl. .................... 800/320.1; 800/298; 800/278; 800/287; 536/23.6; 435/419

(58) Field of Classification Search ....................... None
See application file for complete search history.

(56) References Cited

U.S. PATENT DOCUMENTS

| | | | |
|---|---|---|---|
| 5,907,082 | A | 5/1999 | O'Neill et al. |
| 6,121,512 | A | 9/2000 | Siminszky et al. |

FOREIGN PATENT DOCUMENTS

| | | | |
|---|---|---|---|
| EP | 1033405 | A | 9/2000 |

OTHER PUBLICATIONS

Bowie et al, Science 247:1306-1310, 1990.*
McConnell et al, Nature 411 (6838):709-713, 2001.*
Ito et al (2000, The Plant Cell 12:1541-1550).*
Zondlo et al (1999, The Plant Journal 19(3):259-268).*
U.S. Appl. No. 10/183,687, filed Jun. 27, 2002, Stephen M. Allen et al.
Satoh et. al., New Endosperm Mutations Induced by Chemical Mutagens in Rice, *Oryza sativa* L., Jap. J. Breed, 1981, pp. 316-326, vol. 31.
Iwata et. al., Studies on the Trisomics in Rice Plants (*Oryza sativa* L.) VI. An Accomplishment of a Trisomic Series in *Japonica* Rice Plants, Japan J. Genet., 1984, pp. 199-204, vol. 59.
Satoh et. al., Trisomic Analysis of Three Mutants for Endosperm Traits in Rice, Japan J. Breed, 1990, pp. 268-269, vol. 40.
Koh et. al., Molecular Mapping of the GE Gene Controlling the Super-Giant Embryo Character in Rice (*Oryza sativa* L.) Theor. Appl. Genet., 1996, pp. 25-261, vol. 93.
Hong et. al., How Is Embryo Size Genetically Regulated in Rice, Development, 1994, pp. 2051-2058, vol. 122.
Matsuo et. al., Oil Content and Fatty Acid Composition of a Giant Embryo Mutnat in Rice. Japan J. Breed, 1987, pp. 185-191, vol. 37.
Okuno, Lipids, Vitamins and Components of Aroma, Science of the Rice Plant, pp. 430-437, vol. 3, 1997.
National Center for Biotechnology Information General Identifier No. 1173624, Dec. 2, 1996, J.A. Nadeau et. al., Ovule Development:Identification of Stage-Specific and Tissue-Specific CDNAs.
National Center for Biotechnology Information General Identifier No. 12325138, Jan. 19, 2001.
National Center for Biotechnology Information General Identifier No. 8920576, Jul. 6, 2000, S.X. Liu et. al., The Sequence of BAC F21F23 From *Arabidopsis thaliana* Chromosome 1.
National Center for Biotechnology Information General Identifier No. 11249511, Jun. 2, 2000, N. Choisne et. al.
National Center for Biotechnology Information General Identifier No. 5921926, Dec. 15, 1998, B. Siminszky et. al.
National Center for Biotechnology Information General Identifier No. 3831440, Mar. 11, 2002, S.D. Rounsley et. al.
National Center for Biotechnology Information General Identifier No. 15221132, Aug. 20, 2000, C.D. Town et. al., *Arabidopsis thaliana* Chromosome 1 CHR1V07142002 Genomic Sequence.
National Center for Biotechnology Information General Identifier No. 7109461, Oct. 12, 2000, X. Lin et. al., *Arabidopsis thaliana* Chromosome 1 BAC F2P9 Genomic Sequence.
Harushima et. al., A High-Density Rice Genetic Linkage Map With 2275 Markers Using a Single F2 Population, Genetics, 1998, pp. 479-494, vol. 148.
Nadeau et. al., 1996, Ovule Development: Identification of Stage-Specific and Tissue-Specific Cdnas, Plant Cell, 1996, pp. 213-239, vol. 8.
Zondlo et. al., CYP78A5 Encodes a Cytochrome P450 That Marks the Shoot Apical Meristem Boundary in *Arabidopsis*, The Plant J., 1999, pp. 259-268, vol. 19.
Ito et. al., Overexpression of a Gene Encoding a Cytochrome P450, CYP78A9, Induces Large and Seedless Fruit in *Arabidopsis*, The Plant Cell, 2000, pp. 1541-1550, vol. 12.
Ahn et. al., Comparative Linkage Maps of the Rice and Maize Genomes, Proc. Natl. Acad. Sci., 1993, pp. 7980-7984, vol. 90.
Database UniProt, Nov. 1, 1996, Cytochrome P-450, Accession No. Q43071, XP002372705.
Database UniProt, May 1, 2000, Cytochrome P450 (CYP78A9) (AT3G61880), Accession No. Q9SLP1, XP002372706.
Database UniProt, Jun. 1, 1998, Cytochrome P450 78A3 (EC 1.14.-.-), Accession No. O48927, XP002372707.
John C. Larkin, Isolation of a Cytochrome 1-3, 5-39 P450 Homologue Preferentially Expressed in Developing Inflorescences of *Zea mays*, Plant Molecular Biology, vol. 25 (3):343-353, Jun. 1994, XP002114541.

* cited by examiner

*Primary Examiner*—Stuart F. Baum

(57) ABSTRACT

Isolated nucleic acid fragments and recombinant constructs comprising such fragments for altering embryo/endosperm size during seed development are disclosed along with a method of controlling embryo/endosperm size during seed development in plants.

9 Claims, 18 Drawing Sheets

```
     M A L  S S M A  A A Q  E S S  L L L F
1    ATGGCGCTCT CCTCCATGGC CGCGGCGCAA GAGAGCTCCC TCCTCCTCTT
     TACCGCGAGA GGAGGTACCG GCGCCGCGTT CTCTCGAGGG AGGAGGAGAA
                                 *
                           ge-5 A (Q->stop)

      L L P  T S A  A S V F  P P L  I S V
51   CCTCCTCCCG ACGTCGGCCG CCTCCGTGTT CCCGCCGCTC ATCTCCGTGG
     GGAGGAGGGC TGCAGCCGGC GGAGGCACAA GGGCGGCGAG TAGAGGCACC

     V V L A  A L L  L W L  S P G G  P A W
101  TCGTCCTCGC CGCGCTCCTC CTGTGGCTCT CGCCGGGTGG CCCCGCGTGG
     AGCAGGAGCG GCGCGAGGAG GACACCGAGA GCGGCCCACC GGGGCGCACC

      A L S  R C R G  T P P  P P G  V A G G
151  GCGCTGTCCC GTTGCCGTGG CACGCCGCCG CCGCCGGGCG TGGCGGGGGG
     CGCGACAGGG CAACGGCACC GTGCGGCGGC GGCGGCCCGC ACCGCCCCCC

      A A S  A L S  G P A A  H R V  L A G
201  CGCGGCCAGC GCGCTGTCCG GCCCTGCCGC GCACCGCGTG CTCGCCGGGA
     GCGCCGGTCG CGCGACAGGC CGGGACGGCG CGTGGCGCAC GAGCGGCCCT

     I S R A  V E G  G A A  V M S L  S V G
251  TTTCGCGCGC CGTCGAGGGC GGCGCGGCGG TGATGTCGCT CTCCGTCGGC
     AAAGCGCGCG GCAGCTCCCG CCGCGCCGCC ACTACAGCGA GAGGCAGCCG

      L T R  L V V A  S R P  E T A  R E I L
301  CTCACCCGCC TCGTCGTGGC GAGCCGGCCG GAGACGGCGA GGGAGATCCT
     GAGTGGGCGG AGCAGCACCG CTCGGCCGGC CTCTGCCGCT CCCTCTAGGA

      V S P  A F G  D R P V  K D A  A R Q
351  CGTCAGCCCG GCGTTCGGCG ACCGCCCCGT GAAGGACGCG GCGAGGCAGC
     GCAGTCGGGC CGCAAGCCGC TGGCGGGGCA CTTCCTGCGC CGCTCCGTCG

     L L F H  R A M  G F A  P S G D  A H W
401  TGCTGTTCCA CCGCGCCATG GGGTTCGCCC CGTCGGGCGA CGCGCACTGG
     ACGACAAGGT GGCGCGGTAC CCCAAGCGGG GCAGCCCGCT GCGCGTGACC
```

FIGURE 1A

```
     R  G  L   R  R  A  S   A  A  H   L  F  G   P  R  R  V
451  CGCGGGCTCC GCCGCGCCTC CGCGGCGCAC CTCTTCGGCC CGCGCCGCGT
     GCGCCCGAGG CGGCGCGGAG GCGCCGCGTG GAGAAGCCGG GCGCGGCGCA

      A  G  S   A  P  E   R  E  A  I   G  A  R   I  V  G
501  GGCCGGGTCC GCGCCCGAGC GCGAGGCCAT CGGCGCCCGC ATAGTCGGCG
     CCGGCCCAGG CGCGGGCTCG CGCTCCGGTA GCCGCGGGCG TATCAGCCGC

     D  V  A  S   L  M  S   R  R  G   E  V  P  L   R  R  V
551  ACGTCGCCTC CCTCATGTCC CGCCGCGGCG AGGTCCCCCT CCGCCGCGTC
     TGCAGCGGAG GGAGTACAGG GCGGCGCCGC TCCAGGGGGA GGCGGCGCAG
              *
       ge-8 G (S->P)

     L  H  A   A  S  L  G   H  V  M   A  T  V   F  G  K  R
601  CTTCACGCCG CGTCGCTCGG CCACGTCATG GCGACCGTCT TCGGCAAGCG
     GAAGTGCGGC GCAGCGAGCC GGTGCAGTAC CGCTGGCAGA AGCCGTTCGC

      H  G  D   I  S  I   Q  D  G  E   L  L  E   E  M  V
651  GCACGGCGAC ATCTCGATCC AGGACGGCGA GCTCCTGGAG GAGATGGTCA
     CGTGCCGCTG TAGAGCTAGG TCCTGCCGCT CGAGGACCTC CTCTACCAGT

     T  E  G  Y   D  L  L   G  K  F   N  W  A  D   H  L  P
701  CCGAAGGGTA CGACCTCCTC GGCAAGTTCA ACTGGGCCGA CCACCTGCCA
     GGCTTCCCAT GCTGGAGGAG CCGTTCAAGT TGACCCGGCT GGTGGACGGT

      L  L  R   W  L  D  L   Q  G  I   R  R  R   C  N  R  L
751  TTGCTCAGGT GGCTCGACCT CCAGGGCATC CGCCGCCGGT GCAACAGGCT
     AACGAGTCCA CCGAGCTGGA GGTCCCGTAG GCGGCGGCCA CGTTGTCCGA

      V  Q  K   V  E  V   F  V  G  K   I  I  Q   E  H  K
801  AGTCCAGAAG GTGGAGGTGT TCGTCGGAAA GATCATACAG GAGCACAAGG
     TCAGGTCTTC CACCTCCACA AGCAGCCTTT CTAGTATGTC CTCGTGTTCC

     A  K  R  A   A  G  G   V  A  V   A  D  G  V   L  G  D
851  CGAAGCGAGC TGCCGGAGGC GTCGCCGTCG CCGACGGCGT CTTGGGCGAC
     GCTTCGCTCG ACGGCCTCCG CAGCGGCAGC GGCTGCCGCA GAACCCGCTG
```

FIGURE 1B

```
      F  V  D   V  L  L  D   L  Q  G   E  E  K   M  S  D  S
901   TTCGTCGACG TCCTCCTCGA CCTCCAGGGA GAGGAGAAGA TGTCAGACTC
      AAGCAGCTGC AGGAGGAGCT GGAGGTCCCT CTCCTCTTCT ACAGTCTGAG

       D  M  I   A  V  L   W  E  M  I   F  R  G   T  D  T
951   CGACATGATC GCTGTTCTTT GGGAGATGAT CTTTAGAGGG ACGGACACGG
      GCTGTACTAG CGACAAGAAA CCCTCTACTA GAAATCTCCC TGCCTGTGCC
                              /\ site of intron

      V  A  I  L   M  E  W   V  M  A   R  M  V  M   H  P  E
1001  TGGCGATCTT GATGGAGTGG GTGATGGCGA GGATGGTGAT GCACCCGGAG
      ACCGCTAGAA CTACCTCACC CACTACCGCT CCTACCACTA CGTGGGCCTC

      I  Q  A   K  A  Q  A   E  V  D   A  A  V   G  G  R  R
1051  ATCCAGGCGA AGGCGCAGGC GGAGGTGGAC GCCGCCGTGG GGGGACGCCG
      TAGGTCCGCT TCCGCGTCCG CCTCCACCTG CGGCGGCACC CCCCTGCGGC
                      *
                 ge-6 G (Q->P)

       G  G  V   A  D  G   D  V  A  S   L  P  Y   I  Q  S
1101  CGGCGGCGTC GCCGACGGCG ACGTGGCGAG CCTCCCCTAC ATCCAGTCCA
      GCCGCCGCAG CGGCTGCCGC TGCACCGCTC GGAGGGGATG TAGGTCAGGT

      I  V  K  E   T  L  R   M  H  P   P  G  P  L   L  S  W
1151  TCGTGAAGGA GACGCTGCGC ATGCACCCGC CGGGCCCGCT CCTGTCGTGG
      AGCACTTCCT CTGCGACGCG TACGTGGGCG GCCCGGGCGA GGACAGCACC
                                  *
                    ge-3, ge-9 A (P->S)

      A  R  L   A  V  H  D   A  R  V   G  G  H   A  V  P  A
1201  GCGCGCCTCG CCGTGCACGA CGCGCGCGTC GGTGGCCACG CCGTCCCCGC
      CGCGCGGAGC GGCACGTGCT GCGCGCGCAG CCACCGGTGC GGCAGGGGCG

       G  T  T   A  M  V   N  M  W  A   I  A  H   D  A  A
1251  CGGGACGACG GCGATGGTGA ACATGTGGGC GATCGCCCAC GACGCCGCCG
      GCCCTGCTGC CGCTACCACT TGTACACCCG CTAGCGGGTG CTGCGGCGGC
```

FIGURE 1C

```
      V  W  P  E   P  E  A   F  R  P   E  R  F  S   E  G  E
1301 TCTGGCCGGA GCCGGAGGCG TTCCGCCCGG AGCGCTTCTC GGAGGGGGAG
     AGACCGGCCT CGGCCTCCGC AAGGCGGGCC TCGCGAAGAG CCTCCCCCTC
                                  *
                            ge-8 A (P->L)

       D  V  G   V  L  G  G   D  L  R   L  A  P   F  G  A  G
1351 GACGTCGGCG TGCTCGGCGG CGACCTCCGC CTCGCGCCGT TCGGCGCCGG
     CTGCAGCCGC ACGAGCCGCC GCTGGAGGCG GAGCGCGGCA AGCCGCGGCC
                                              *
                                        ge-4 C (P->A)

       R  R  V   C  P  G   R  M  L  A   L  A  T   A  H  L
1401 CCGCCGCGTC TGCCCTGGCA GGATGCTGGC GCTCGCCACC GCCCACCTCT
     GGCGGCGCAG ACGGGACCGT CCTACGACCG CGAGCGGTGG CGGGTGGAGA

      W  L  A  Q   L  L  H   A  F  D   W  S  P  T   A  A  G
1451 GGCTCGCCCA GCTGCTGCAC GCCTTCGACT GGTCCCCCAC CGCCGCCGGC
     CCGAGCGGGT CGACGACGTG CGGAAGCTGA CCAGGGGGTG GCGGCGGCCG
     *                                *
ge-2 T (W->stop)                 ge-1 T (W->stop)

       V  D  L   S  E  R  L   G  M  S   L  E  M   A  A  P  L
1501 GTCGACCTGT CCGAGCGCCT CGGCATGTCG CTGGAGATGG CGGCGCCGCT
     CAGCTGGACA GGCTCGCGGA GCCGTACAGC GACCTCTACC GCCGCGGCGA

       V  C  K   A  V  A   R  A  *
1551 CGTGTGCAAG GCCGTGGCTA GGGCCTGA
     GCACACGTTC CGGCACCGAT CCCGGACT
```

FIGURE 9 A-F
A B
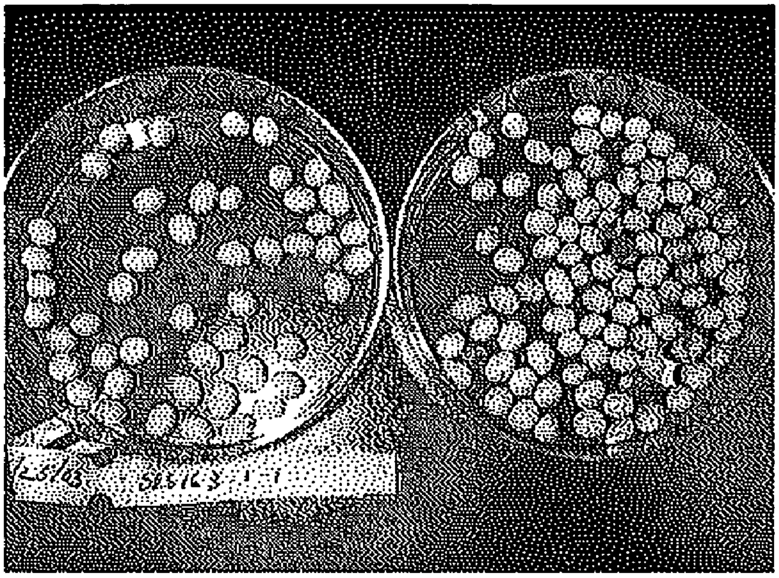
C D
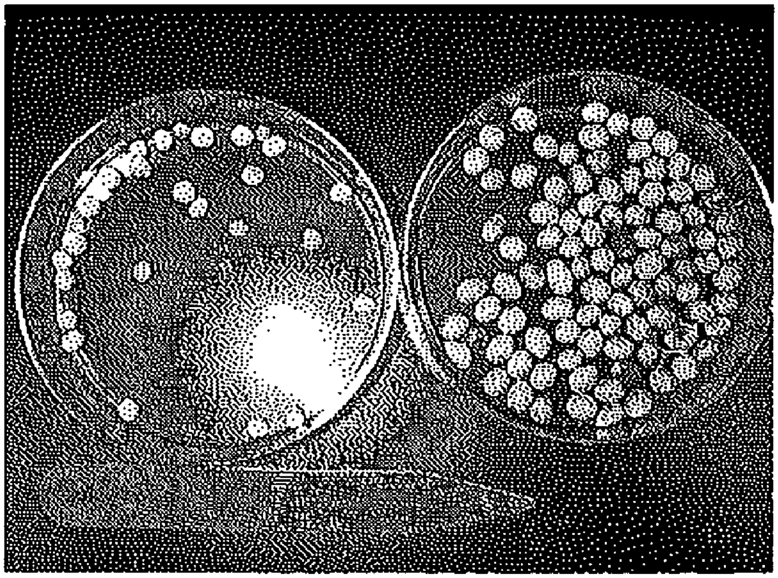

FIGURE 9 A-F (continued)
E F
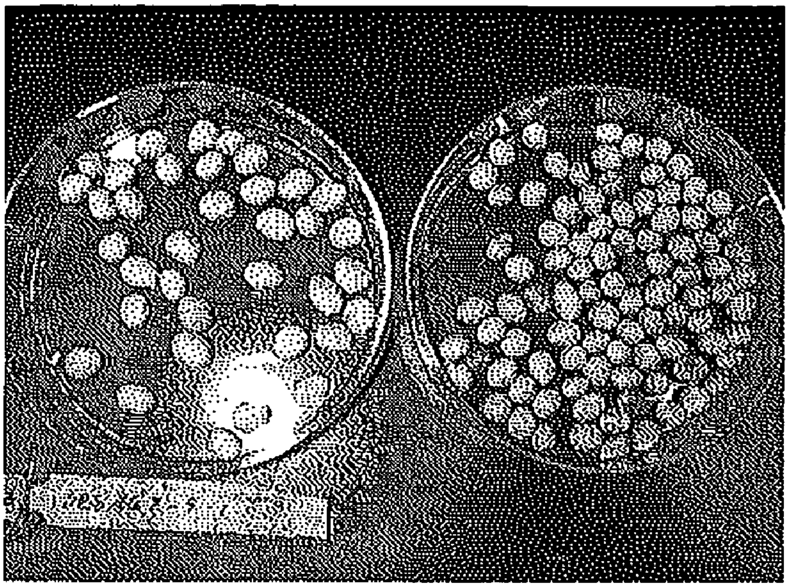

SEQUENCE LISTING

```
<160> NUMBER OF SEQ ID NOS: 128

<210> SEQ ID NO 1
<211> LENGTH: 1578
<212> TYPE: DNA
<213> ORGANISM: Oryza sativa

<400> SEQUENCE: 1

atggcgctct cctccatggc cgcggcgcaa gagagctccc tcctcctctt cctcctcccg      60

acgtcggccg cctccgtgtt cccgccgctc atctccgtgg tcgtcctcgc cgcgctcctc     120

ctgtggctct cgccgggtgg ccccgcgtgg gcgctgtccc gttgccgtgg cacgccgccg     180

ccgccgggcg tggcgggggg cgcggccagc gcgctgtccg gccctgccgc gcaccgcgtg     240

ctcgccggga tttcgcgcgc cgtcgagggc ggcgcggcgg tgatgtcgct ctccgtcggc     300

ctcacccgcc tcgtcgtggc gagccggccg gagacggcga gggagatcct cgtcagcccg     360

gcgttcggcg accgccccgt gaaggacgcg gcgaggcagc tgctgttcca ccgcgccatg     420

gggttcgccc cgtcgggcga cgcgcactgg cgcgggctcc gccgcgcctc cgcggcgcac     480
```

-continued

```
ctcttcggcc cgcgccgcgt ggccgggtcc gcgcccgagc gcgaggccat cggcgcccgc    540

atagtcggcg acgtcgcctc cctcatgtcc cgccgcggcg aggtccccct ccgccgcgtc    600

cttcacgccg cgtcgctcgg ccacgtcatg gcgaccgtct tcggcaagcg gcacggcgac    660

atctcgatcc aggacggcga gctcctggag gagatggtca ccgaagggta cgacctcctc    720

ggcaagttca actgggccga ccacctgcca ttgctcaggt ggctcgacct ccagggcatc    780

cgccgccggt gcaacaggct agtccagaag gtggaggtgt tcgtcggaaa gatcatacag    840

gagcacaagg cgaagcgagc tgccggaggc gtcgccgtcg ccgacggcgt cttgggcgac    900

ttcgtcgacg tcctcctcga cctccaggga gaggagaaga tgtcagactc cgacatgatc    960

gctgttcttt gggagatgat ctttagaggg acggacacgg tggcgatctt gatggagtgg   1020

gtgatggcga ggatggtgat gcacccggag atccaggcga aggcgcaggc ggaggtggac   1080

gccgccgtgg ggggacgccg cggcggcgtc gccgacggcg acgtggcgag cctcccctac   1140

atccagtcca tcgtgaagga gacgctgcgc atgcacccgc cgggcccgct cctgtcgtgg   1200

gcgcgcctcg ccgtgcacga cgcgcgcgtc ggtggccacg ccgtccccgc cgggacgacg   1260

gcgatggtga acatgtgggc gatcgcccac gacgccgccg tctggccgga gccggaggcg   1320

ttccgcccgg agcgcttctc ggagggggag gacgtcggcg tgctcggcgg cgacctccgc   1380

ctcgcgccgt tcggcgccgg ccgccgcgtc tgccctggca ggatgctggc gctcgccacc   1440

gcccacctct ggctcgccca gctgctgcac gccttcgact ggtcccccac cgccgccggc   1500

gtcgacctgt ccgagcgcct cggcatgtcg ctggagatgg cggcgccgct cgtgtgcaag   1560

gccgtggcta gggcctga                                                  1578
```

<210> SEQ ID NO 2
<211> LENGTH: 525
<212> TYPE: PRT
<213> ORGANISM: Oryza sativa

<400> SEQUENCE: 2

```
Met Ala Leu Ser Ser Met Ala Ala Ala Gln Glu Ser Ser Leu Leu Leu
1               5                   10                  15

Phe Leu Leu Pro Thr Ser Ala Ala Ser Val Phe Pro Pro Leu Ile Ser
            20                  25                  30

Val Val Val Leu Ala Ala Leu Leu Leu Trp Leu Ser Pro Gly Gly Pro
        35                  40                  45

Ala Trp Ala Leu Ser Arg Cys Arg Gly Thr Pro Pro Pro Pro Gly Val
    50                  55                  60

Ala Gly Gly Ala Ala Ser Ala Leu Ser Gly Pro Ala Ala His Arg Val
65                  70                  75                  80

Leu Ala Gly Ile Ser Arg Ala Val Glu Gly Gly Ala Ala Val Met Ser
                85                  90                  95

Leu Ser Val Gly Leu Thr Arg Leu Val Val Ala Ser Arg Pro Glu Thr
            100                 105                 110

Ala Arg Glu Ile Leu Val Ser Pro Ala Phe Gly Asp Arg Pro Val Lys
        115                 120                 125

Asp Ala Ala Arg Gln Leu Leu Phe His Arg Ala Met Gly Phe Ala Pro
    130                 135                 140

Ser Gly Asp Ala His Trp Arg Gly Leu Arg Arg Ala Ser Ala Ala His
145                 150                 155                 160

Leu Phe Gly Pro Arg Arg Val Ala Gly Ser Ala Pro Glu Arg Glu Ala
                165                 170                 175
```

-continued

```
Ile Gly Ala Arg Ile Val Gly Asp Val Ala Ser Leu Met Ser Arg Arg
            180                 185                 190

Gly Glu Val Pro Leu Arg Arg Val Leu His Ala Ala Ser Leu Gly His
        195                 200                 205

Val Met Ala Thr Val Phe Gly Lys Arg His Gly Asp Ile Ser Ile Gln
    210                 215                 220

Asp Gly Glu Leu Leu Glu Glu Met Val Thr Glu Gly Tyr Asp Leu Leu
225                 230                 235                 240

Gly Lys Phe Asn Trp Ala Asp His Leu Pro Leu Leu Arg Trp Leu Asp
                245                 250                 255

Leu Gln Gly Ile Arg Arg Arg Cys Asn Arg Leu Val Gln Lys Val Glu
            260                 265                 270

Val Phe Val Gly Lys Ile Ile Gln Glu His Lys Ala Lys Arg Ala Ala
        275                 280                 285

Gly Gly Val Ala Val Ala Asp Gly Val Leu Gly Asp Phe Val Asp Val
    290                 295                 300

Leu Leu Asp Leu Gln Gly Glu Glu Lys Met Ser Asp Ser Asp Met Ile
305                 310                 315                 320

Ala Val Leu Trp Glu Met Ile Phe Arg Gly Thr Asp Thr Val Ala Ile
                325                 330                 335

Leu Met Glu Trp Val Met Ala Arg Met Val Met His Pro Glu Ile Gln
            340                 345                 350

Ala Lys Ala Gln Ala Glu Val Asp Ala Ala Val Gly Gly Arg Arg Gly
        355                 360                 365

Gly Val Ala Asp Gly Asp Val Ala Ser Leu Pro Tyr Ile Gln Ser Ile
    370                 375                 380

Val Lys Glu Thr Leu Arg Met His Pro Pro Gly Pro Leu Leu Ser Trp
385                 390                 395                 400

Ala Arg Leu Ala Val His Asp Ala Arg Val Gly Gly His Ala Val Pro
                405                 410                 415

Ala Gly Thr Thr Ala Met Val Asn Met Trp Ala Ile Ala His Asp Ala
            420                 425                 430

Ala Val Trp Pro Glu Pro Glu Ala Phe Arg Pro Glu Arg Phe Ser Glu
        435                 440                 445

Gly Glu Asp Val Gly Val Leu Gly Gly Asp Leu Arg Leu Ala Pro Phe
    450                 455                 460

Gly Ala Gly Arg Arg Val Cys Pro Gly Arg Met Leu Ala Leu Ala Thr
465                 470                 475                 480

Ala His Leu Trp Leu Ala Gln Leu Leu His Ala Phe Asp Trp Ser Pro
                485                 490                 495

Thr Ala Ala Gly Val Asp Leu Ser Glu Arg Leu Gly Met Ser Leu Glu
            500                 505                 510

Met Ala Ala Pro Leu Val Cys Lys Ala Val Ala Arg Ala
        515                 520                 525
```

```
<210> SEQ ID NO 3
<211> LENGTH: 17201
<212> TYPE: DNA
<213> ORGANISM: Oryza sativa
<220> FEATURE:
<221> NAME/KEY: unsure
<222> LOCATION: (12598)
<223> OTHER INFORMATION: n = A, C, G, or T
<220> FEATURE:
<221> NAME/KEY: unsure
<222> LOCATION: (17041)
<223> OTHER INFORMATION: n = A, C, G, or T
```

-continued

<400> SEQUENCE: 3

```
agggaaattg tagtgttttg cttctcaaac cgctcctgtc ttccacttag acttgtaatt     60
tcacttctga ctttttcgat gtttctctgt accagtacct gtgcgatcta aacaattgtg    120
tcagtatgta gtgagcagcc ttaacaaaac tgttatcaca gtgtgacaca ttataattgt    180
cttcctttcc tgagtatatg tggtcttttg gtttgaatgt agaggtcaga tttaattcat    240
ttctaaagaa aatgtggtct tctagcaaca agctagttga gaaagatggt gaattaaagc    300
taattttcaa tctctcaaga aagtaaacca tatgatcatc cataatttcc tcttaatacg    360
atgatataaa tctccactta agcttctaaa tataccatta attatttatg agtactcatt    420
ttttgtttcg gccaattcat agccgctgct actcattatt tatgagagta tatatagcta    480
gcttgcatct agtgatatga tcgagctagc attcgagcca cagctcaaaa cgaggccaag    540
atcatacgcg tcgccggatc attcccacac gtgtgagaat tgaaccccaa aaaaaaaaga    600
gtacggtatt tgctagtgca gctaaaagct acgaattgaa tatgatatcg atattgtgta    660
gagtatggac gatacatgga atctcatctc atctgatcat catgatctcc tggatgaaaa    720
tacaatgtac atgaatagag agagggcttt tggttttggg tggagaaatg gagcaacact    780
ccttgacatt tgagccccat cttataatat gaattcaatg aaaaaaaaat ggaaaggaga    840
atagagccac gtggcaacac cgacttcgcg gaagaggctc gacgaaacga tcttgtgcgt    900
gcgcgtgcag cgatctagga acgctcttgc gtgcgtgagt gcacgggcca ccgggtgtcc    960
agaagtttct tcgtgaatat atcgatcgag caattaggcc catggaccat ggctcagcag   1020
gccgtgcgat ggcacaagaa catgttgggt gatttaggcc ttgtttagtt tctaaaacaa   1080
aaacttttca cccatcacat cgaatgttta gaaatatgtg tggagtatta aatgtgaaaa   1140
aaaaactcaa ttacacagtt tgcatgtaaa ttgcgagaca aatcttttaa tcctaattgc   1200
accatgattt gacaatgtgg tgctacagta aacatttgct aatgatggat taattaggct   1260
taataaattc gtctcgcggt ttcctgacgg aatctataat ttgtttaatt attagactac   1320
gtttaatact tcaaatgtgt gtccgtatat tcgatgtgac aatcaaaccc aatttttttc   1380
cccaactaaa caagccctta gagagaccaa actttacatg gatgaaatga gatattacgc   1440
atacatgtag gatgttctat atgcaaacac ccgttgcatg ctgatcgatg catgaacttt   1500
cacattcagt ggtccgtact ccctactttg tacgcacagc tccgattaat tatcactttc   1560
ctcgttccgc attataagat atttattaag cccttcaatc cctcgtctag attccctaat   1620
atccatatga atttaaacac atatatgaaa cacatacgtt gatccatgta tattttttt    1680
tcaaaaccca aaacgtatta tagtatgaaa cataaattta ttcaaaacct aaaacatctt   1740
atacacatac attgatgcat atatgaattt attaaaaccc taacaaaata gaaatttgtt   1800
caaaacccaa aagatcttct atccgattgt taccccaccg ggcccacgcc taggctcact   1860
aaaccatacg tggcttttgc catgcgcatg cgcttttcta gtaatgttaa agtcctagct   1920
tgacagtatt tgacatcgga agaaattgat gaactgtgtt tcgaactagt tccaccattt   1980
actcttatag cttattgtac gtagccaaaa tttaaatttt taaatttatt tttgggtttt   2040
gttccatcgt actttacttt ttttttcaac atttgctttt aaaccacaaa taacacacta   2100
taacatcata tatatatata tatatatata tgcctcctga ttaaaacccg gaaatatgat   2160
ttttgtattt aaatgtgtcc tattgatctc ctatgctaaa tgaatcgtgt tttaggctag   2220
atatctttta agatgttact aatttctaat atttaaccaa attttatcat aaattctaaa   2280
```

-continued

```
tatttatgac ataagataga gtagtttgat atagacaagt caaacccacg tgggataagt   2340
gaaagacaca tgagtcaaga taaactgtga aatcaataaa gggccaagtt ttacgtgatt   2400
atcagagatg atagcgggtt ttactaggtt aggcatagag aaaaaagaat tatacgatat   2460
atgtaacagt tttcaaagat tctttttatc aaaattcatt tattctattt aattatatat   2520
atatatagct caacttgtat tatcgctacc cgtcaataac attgctcatc gcaataacca   2580
agcagttatc accgataaag ttacaaccct agttaagaga caattagccg tagaatttca   2640
ctctcttttt gtccacacca cttccatcaa accttaattt ggcatctcaa ttgaaaagtt   2700
aataacctct ccctttttt ctgcatgcga tgcgttgcta cattgtacat atatacatct   2760
atagcaagtt caattggccc gaccgttacg tacgtagaga tcgtaataat taacgcacaa   2820
agacacaaaa tggagggtac agttaaccta tatatccagc atccaagcag ctggctggcc   2880
tggctatcaa ccacagctga cactaacagc taagctagct aaaagcagcc accggcgaac   2940
cgaaggttaa ccgtacgtcg gcgtcgcggt ctcgcggaga gccctgagaa tgtagagaaa   3000
ccgatcaccg atgtattatt ttcctattat gcacatacaa tttcagttct tacttgattc   3060
aaaattgttt actgcggcta tgttttacgg tggatagatg tgattacatt tttttatat   3120
atttgctctt ttgttttgaa aaagaaaatc ttttgcttac taaattctat aactctttcg   3180
gtggaaggcg acgtaccatt gatagcgaga cgtgtaggaa tttcgttaat cctaatacat   3240
gttgaccttt tctctaagaa gtggttatag gagtataagg tctgtatata ttcataaggg   3300
gtgagtatgc tttcgtatat gagcatatgc atttgtacta tgtttttttt taaaaaaagt   3360
ggaacattaa ttcctcgtga tcaaatgtgg gacattgact gacatatgga tttaataatt   3420
atttacttgt ccacaaataa cttaccttgt catttttact ggaggtagat gaactcaaac   3480
cattatttat aaataatctt ttataaatgt cggttccgta caagccatac gctacagttt   3540
cacgtcttag gagatgttag ctttttttgc atgcttgact tcacgtgagg aaatgcatga   3600
gttttataaa tgtatcgtac aagttacagg ttataaatgt ttattgtttt tgaagcggtt   3660
aaattaaacc acgtaacgac taaagtaagt tgcacaacta agatttgcat gcacacaatt   3720
tgacttgttc ctttaatggt gatacataaa aaaaaatcat ctgccttacc catgatgaaa   3780
ataattgaac cacatctaag aaagagtagg gattataatg ctatgcaatt gaattggatt   3840
gttcaaattc taaatcaaac tgttccactt ctatctacat gacctctttg tataaatttt   3900
ctcatggtga aatagtagca aggtggctaa attaacatag gctgctaggg aggtcgagtg   3960
aggggtatat agagaaaggt cgaggaggag gtagatcatt gcggtggacg acatggagat   4020
gatcccttct aaactctaaa cttgtttcaa tcctattcta tatagtgaaa gtatcatctt   4080
ttaaggaatc gaaaggttgg tctcttaaaa aaaagtttaa gataccacca cttttcatga   4140
aatttgactg aatgatgtgc tctatatcaa atatttgcat atatatgtcc caaatcaaga   4200
ccacatatgg caagtgaaca acacacgagt agttcaaaac aaccacggag tcagcggagg   4260
accaacttac acgtgattac agatagaaaa acgagtttta ctaggtttag atagagtgaa   4320
aattttcttt tataatgaat ctcgacagac agttagtggc gcaacacaca atttaagaga   4380
caatcaacaa tagaatttca cactcttttt tacccacacc acttcacttc cattatcgta   4440
aaaccatgat ttggcatctc atcaactaaa acgttaacac ctctcccctt ttcccggcga   4500
actgctcgcc tggccgatgc atgcaacccg ttgctataca ttgtacagta catctatagc   4560
aagctagctt ccactgctct gccgtttcaa ttcgcctgta acgtccagac cgtaataacg   4620
cacaaaggca caaaaatgaa ggccaaatgg ccaattagct agctgtcctg gattagtagc   4680
```

-continued

```
tgccacagtc cacagctaag cagccaccgg caaaccgaag gttagccgtc ggcgtcgcgt   4740
ctggtacgat cgagccctga gaacgtggag aaactgatgt gattatttcc tactccatgt   4800
atatggacat ataatttcag ttctttcttg attcaaaaat tgtttggtgg tgttgtgttt   4860
tacggtggat agagggttac atatatttat atttgtattt tcttgttttg caaaaaaaaa   4920
ctccctccat cccaaaatat aacaattttg gggtggatgg gacgtaccat agtactatga   4980
atttggacat aacccctatc cagattcata gtactagaat atgtcccatc tacccagaag   5040
ttgttatatt ttgagacggg aggagtattt ctttgcttat taaattatgg aattctttca   5100
atagtaaacg atgtacgtac cctcaagagg gagatgcctg tagtgatttt gttgatttca   5160
agatacgaca actcactcgg tcgaatgtgc ttataggggt aggatttgca tgcgttaata   5220
aaagtgagtg tgtctgcata tataagcgtc tacattagtt actatttcaa aaaaaaattg   5280
agacattgac tgacacgtgg atttacttaa ttatttactt gttcacatat aatttagctt   5340
gtcggttttt catcggaggt ggattaactt ggaccgttat ttattaaata atctttattt   5400
agaatatgtt ggttccgtac acatatggtt taacatctta ccagatgctt tacgtatact   5460
tgatttctac gtgaggaaat acatgagttt catatcttta taattaatgt atcgtacaag   5520
tagcatgtat gaaccgttta atgtttttgt ggcggttaaa ttaaaccaca taacgactaa   5580
aagtaagttg cattactaag attcgcatgc acataatttg gcttgttcct ttgatagtaa   5640
tacttaaaaa aaacattgat cgtcatctgc cttactcatg ttggaaataa ctaaattaca   5700
tctagaaaag ataagagcgt taaataggcc attcaaatct aaatcaaact gttccacttc   5760
tatctatatc tatatgacct ttatgaggca agttgtcgca tagtgaagat agtagcaagg   5820
tggctaaatt tacataggtg gtcagggagg aggagtttgt caacaatagg gtatagagga   5880
aggtcgagga gtaggtagat tgtggtagaa gatatggaga tgctcccttc taaactagtt   5940
ttaatcctat tctatatagt aaaaatatcc tcttttaagg aattgaaagg ttgatgtcca   6000
attcataata tttgattgaa tcatgtccta tatattaaac atttatgata agattttttt   6060
aaaaaaaata cacaagaaga gcatctttgt attaagagaa gtaaagttta tttacagata   6120
aaacgaaaaa tgttttacta cctctcttct aaaaagactt tattttcttt taccatgaat   6180
atacacagta cttaaagaaa caactcgttt attaccacaa cactctacca tcaacctttg   6240
atttggcatc tcaaataaaa aacgctaacc tctccccttt ccccgggcgc ctcttggccg   6300
ctgcatgcaa cccgttgcta gtacactgtg tactgctcca tctgtagcaa gctttcactg   6360
ctcttccgtt tcaattttgc ccgttgcatc cgtcgagact gaccgtaatg acgcacaaag   6420
ccaaattagc taagctgtgt cctgcctaag tagagttact accacagcta agcaagcatc   6480
gatcacagcc accggcgaaa tgaacggaat taaggttaag atgcagtcac cggcgagatg   6540
agtatcctga gaacttggaa caaaccgatg caaatctctc tggccccaac tggccatggc   6600
catgaattcg tgctcgattc cgtgtcattt tgcagtagcc acccaagagt taattctttc   6660
ggtttttatt ccagcctttt ttttgctttg tttttgtact agctagctag tattatgaga   6720
ctttgcaaag gcgccatact atgtgtattg caattcaatg cagttttttt tctgctgcat   6780
ttatatttca gttttaattt agcgccacat tttgttgctt tcctacgtaa agcctggacg   6840
cagttaacac agcagctagc ttgttagcct gtgacacaat agcaacagct ggtaattgta   6900
actgaaaatt tctgtttcaa agaagaaaaa aaaagaggta taactggaga aaaaaaagcc   6960
tggacgatgg ttttaatctt gttaggtgtg acttaattac cgaatacaca ccaaagattg   7020
```

-continued

```
aatgaacact acatgacagt gtcttcctgt gacaggcgtt gaaatcccta ttatggagat   7080
ggttttcttc cttaattcga aaattgtttg gtgccgtcaa ttagtgaaat tgtggacatg   7140
ttttacggtt gacagaggat tacatgtatt tatgttttat attttcttgt ttcacaaaag   7200
aatatatatt tctttgctta ctgaattgtg gaatattttt ggaaaaaaat acgggacatt   7260
gagtaatcga cgtgaatatc taattaatta tttactatct ccgtgcacga gtaacttagc   7320
ttgtcggttc tgactgagag gtagatgtcc tttggctgtt aattttttta aaaagcattt   7380
ctcttttta atgtcggttc cgtacaagct atacacgtgg tttcatgtct tggcgcttta   7440
tcttcgactt ccacgtaaca agctgcatga gttttgcgcg cgtctttaaa tgttatagta   7500
cgtttcatat tcgaaccgtt aacggtttct gaggcagtta aattaaacca cgtaacgact   7560
aaagctgagt tgcatgagta agacccacgc gcactcattt gccttgttta tctagtggta   7620
atacctaaaa gaaccgccaa tcaaccgcct tactcatgtt aaaaataatt aaattttatc   7680
gaggaaagat gaaagataag ggtgctatga tactttatat acaatttaat tagaccgcaa   7740
atcctagatc gaggtgacgc cactctatat cgttccacat ccgtctatat gatatcttta   7800
tatgtatgta gttccacatt cttatatact cccttccctc tggttagttc cattttgaac   7860
taaccaacgt caaatttaaa aaaaacagag gtatcatgat attttttagg tttaagttag   7920
attgaacgga atggaattga aatgttgttc tcttaatttt attttacact atcacatcat   7980
tacaaatttc aaactcttgt tctaaacagg caccatcttt ttcagttaca tctacactaa   8040
tttcaatagt aatgccatta ttatgtagtc caatatttaa ggaagaaact aatgatatat   8100
atatgcagat attgttaata atggcccttt gattacgcta tcattactga caatgacatg   8160
tggggccaga gtgtcagata attcgaggtc caaatttttg gagtggcaaa atggtctatt   8220
taaagcacca ggtgtttatt agcttctctc cacgtcttct tcctcccaag aaaactcctc   8280
tcacttcgcg aacgcttccc atggcgctct cctccatggc cgcggcgcaa gagagctccc   8340
tcctcctctt cctcctcccg acgtcggccg cctccgtgtt cccgccgctc atctccgtgg   8400
tcgtcctcgc cgcgctcctc ctgtggctct cgccgggtgg ccccgcgtgg gcgctgtccc   8460
gttgccgtgg cacgccgccg ccgccgggcg tggcgggggg cgcggccagc gcgctgtccg   8520
gccctgccgc gcaccgcgtg ctcgccggga tttcgcgcgc cgtcgagggc ggcgcggcgg   8580
tgatgtcgct ctccgtcggc ctcacccgcc tcgtcgtggc gagccggccg gagacggcga   8640
gggagatcct cgtcagcccg gcgttcggcg accgccccgt gaaggacgcg gcgaggcagc   8700
tgctgttcca ccgcgccatg gggttcgccc cgtcgggcga cgcgcactgg cgcgggctcc   8760
gccgcgcctc cgcggcgcac ctcttcggcc cgcgccgcgt ggccgggtcc gcgcccgagc   8820
gcgaggccat cggcgcccgc atagtcggcg acgtcgcctc cctcatgtcc cgccgcggcg   8880
aggtccccct ccgccgcgtc cttcacgccg cgtcgctcgg ccacgtcatg gcgaccgtct   8940
tcggcaagcg gcacggcgac atctcgatcc aggacggcga gctcctggag gagatggtca   9000
ccgaagggta cgacctcctc ggcaagttca actgggccga ccacctgcca ttgctcaggt   9060
ggctcgacct ccagggcatc cgccgccggt gcaacaggct agtccagaag gtggaggtgt   9120
tcgtcggaaa gatcatacag gagcacaagg cgaagcgagc tgccggaggc gtcgccgtcg   9180
ccgacggcgt cttgggcgac ttcgtcgacg tcctcctcga cctccaggga gaggagaaga   9240
tgtcagactc cgacatgatc gctgttcttt gggtaagtct cctcgtcgtc gtcttcgtcg   9300
taaagcttga gaaggaaacg tccatggcgt tttcatggat tggtttcttg ttttttttctt   9360
caggagatga tctttagagg gacggacacg gtggcgatct tgatggagtg ggtgatggcg   9420
```

-continued

```
aggatggtga tgcacccgga gatccaggcg aaggcgcagg cggaggtgga cgccgccgtg   9480
gggggacgcc gcggcggcgt cgccgacggc gacgtggcga gcctccccta catccagtcc   9540
atcgtgaagg agacgctgcg catgcacccg ccgggcccgc tcctgtcgtg ggcgcgcctc   9600
gccgtgcacg acgcgcgcgt cggtggccac gccgtccccg ccgggacgac ggcgatggtg   9660
aacatgtggg cgatcgccca cgacgccgcc gtctggccgg agccggaggc gttccgcccg   9720
gagcgcttct cggaggggga ggacgtcggc gtgctcggcg gcgacctccg cctcgcgccg   9780
ttcggcgccg gccgccgcgt ctgccctggc aggatgctgg cgctcgccac cgcccacctc   9840
tggctcgccc agctgctgca cgccttcgac tggtccccca ccgccgccgg cgtcgacctg   9900
tccgagcgcc tcggcatgtc gctggagatg gcggcgccgc tcgtgtgcaa ggccgtggct   9960
agggcctgag ccctagccgc cgccgccgcc attattgcca ttgatgtggc tagcgacgtt  10020
gtcgtgctcg catccatact cctccatagg caactcgtct agccaatgaa gaaagctact  10080
atctatctat ctatcaagct agctgctact atcacaaacc gcatttcggc atcatcttaa  10140
attagctctt aggggtgtag gcgattttgg tttcccccaa aaatttgctt tgccagtctt  10200
ttggtttaaa tcgaggcatt agttgtgaaa catcatgaga agttatttaa atctgaggaa  10260
ttttgtttga accttttctg gtgtgctaaa tggatcgtgc tttgagtatc ttattattct  10320
gaatgtgtta tgtagctaca ctctcctgaa tcatgtgtta accatgcaat atttctccag  10380
ttggctgtca gtttatcagc gtcttgtgaa tgccgttcat gagaaatctg accatcttcc  10440
aaatggtttc atcagtttgc tgtgataatt aggttatgtt tcatgtcagt attatctctg  10500
cactgtgttt gttttataca agtatactgc aacatatata acctttgtac accatgctag  10560
tactgtgaca ttttcaggtt gcatttcttt ccttttaaga ctatgaaaga ttgcgttatg  10620
taacaaacat tctattcttc taatatattg acgtgcaatc cttttgcgcg ttcgagaaaa  10680
aaaaaagact atgaaagatt aagttactga acttccacta agtatatggc catatggtct  10740
aacctatctc tagagattag tcacaaatct gttttgtttt gtcaagttga tatccttttt  10800
tctttctgaa tgaaatcaag attatgtcct tggaactgca ttttgatgct ggtctgcatt  10860
aggctaaatc tctgaatcta gagccattgc atgctcttgc ctgttgccta attgtagtgc  10920
tccgagcatc agattcatgt cagcatcaaa acttgcttct tatttcttat cgtcgactca  10980
tccttgatca atgtggccaa caaagatttg tgagcgctaa gttgcatcca cgtgttgatc  11040
atgcatataa acgcaaatgg gtcattttct ggaatcaaga ggatttggcc aactcgcttt  11100
tcgttgtcac aaggtctact actagggtct catccaaaag attcaaccta agaagatttg  11160
atagcaatgt gctgtcgctg ttatgttaag attgttagga tcacaatctg tttacagcat  11220
tacatcctga cagccattct cagtgggact ggaagtacaa aacgtggtgt tcagaacagt  11280
aattttcaag gtagagattg ctgatatata tgagaataat ttcttggcta tcatattaat  11340
gttaccaaca caaggtttgt accttaatct tcatagattt ttcatggtga ctcgctcatg  11400
ctagtcatga cttgatgaat atgcaaggag cagtcttcag ggatgttact gtcagacagg  11460
gccaggcatc tgaagaccat ctgtctaagt gacaggaagt cttcaggctt cagagaacag  11520
tcaagattca cttaattaag atggcctgtg gctgatctag gtagtcatta gtcaaccaaa  11580
tttcttcatg ttccttttct tttccttcct atcttacact aatatagtaa catccagaca  11640
gtcacgtatc ctcctacctt tgtgttatgg tgagactaac tgtgttctgg aaggtgtgaa  11700
atccctcacc aaaatggctg aagaattgag aattcagaag ccatggcaga agtgatcatg  11760
```

-continued

```
tgcatgatga attgatgata atatatcagg gggccctcat ctggtcatct cacctgcctc  11820
tctcttttct ctttttctga gacccaaatc ttgcataaga cttctgtgat tagacaggaa  11880
tcttgtatcc tttcccccta tggaaagaag cctccatttt gtgatatatg gctcacattt  11940
ttattcctga tcaggggcaa gatcacaaaa aggtgcttca ctgttgaccc atcactacca  12000
cttttgtgga tttgcttgat ggcgtgatgc ataatttctc tatagtcaaa agtcaagcat  12060
attttgatag tggttgagaa agtaccgtga ggtaaagtac cttatgctat atcacaagtc  12120
cataacaccg gaaacatata ggatgagttt ttttcttaac tttcccaact cacatctctc  12180
gtgttacccg cgcacgtatt ttaaactgct aaacgatata ttttttgcaa aagttttcta  12240
tacgaaagtt gctttaaaaa atcatattaa tccatttttc aaaaaaaaag ctaatactta  12300
attaatcata cgttaatgag ttgctctatt ttacgtgcat caaggattag ttcccaactg  12360
tgtatgccga acacagccat agttctcaag acacgtaaaa aacataataa acataataat  12420
tttttgagaa tctctacctt cttgaataat ctaaattatt gcctataatt cagcagccaa  12480
acgctaaaaa acttagactt ttcagatcct cagaagtttg ctactcacca tctacttcat  12540
acaatctcga gctctcttaa acagggcctc aaggataatt ttgcctccaa agcctcanaa  12600
aaagataccc aaatcctcct catggcgacc ttttgtcaac tcttggaaca gagaaaatgg  12660
tcaggtcgtt tgtcacacga tcaaacaaag tagagagaaa gaaaaaagaa ggaaagaaag  12720
gatgggattg ggttgttttt cccctggaca gaaaaagaac agggcccagc ccaactacca  12780
cgacggcacg acctgaattt gtggttagct gtagatgttt tcatggcaca ccttccacgt  12840
gcaaacttat atatatatat atatatatat atatatatat agagagagag agagagagag  12900
agagagagag agagagagag tacttgccac cagcagctta gtgtaattat atgctcgaat  12960
aataaactga agaaaaagtg aacaagtggt tggtgctgtg taacacagta ttagtgttct  13020
ttggttgaag attgaaggaa gatttagctc gcttttcatg tgcatatttt ccaaactatt  13080
aaacggtctt ttctaaaaaa tatttatata taaagtcgct ttaataaaac catacaagtc  13140
catttttcaa atctaaaatg attaatactt tattaatcgt atattaatgg ctaatctcgt  13200
tttgcgtatc tccccaatct ttttatttcc tttcaaacac tacgtcaact tgtattttgt  13260
ttttccttat ttagatggat aaacatgtac tatatactac aatcccctgt tgtcaactgg  13320
tttcatttga tcattggagg acaatgtaaa gaaagtacta ctttcttcag tcatctttat  13380
ttatcttcgg gatagctaat tttagggggg aggggggggg ggggttggag aaaattcaaa  13440
ggaaatttta taattcttag gaatattttc ttattagctc ctttggagaa aaggaatacg  13500
actgacaaat atcacatgaa tttagttctg atcactacaa caaaaatgct ttgtagagac  13560
atttttctag tactatagat acacttttca aatgccttta caatactata gaggcatttt  13620
aaaaaatgcc taataagtgc cttacggtga attgtctcta caaacgaaga ggcattttac  13680
aaaatgtcta aaagatggta gaggcatttt atagagacat taaattgtgt cacaaccata  13740
tgaaaccaat gtaaaaaaaa taaaatattt tcccttgttt ttgacaatcc ttgaactcat  13800
gatcaattgc acaattcatt cttatcttca aggcactaac caactcaacc ctaagtcatt  13860
acttatatgt tgttgtcttg agttatttat atttagtcat ttattacata cttttattct  13920
aagaagtgcc tttacagagt ttaaagtgtc tcaagaaaat gcctttacat atcaggcaca  13980
gtttaaagtg ccgaaagaat gcctctacaa tataaaatct aataaaatat gctgaaaata  14040
tttctaaagt gtctgtagag taaaagtttt ctaggcattt tttaaaatgc ctctataaaa  14100
tgtctctaca ctataaaact cctgatctaa gaggcaattt gcaaaacgcc tctacaaaag  14160
```

-continued

```
tgtctttata taaggttttt gttgtagtgg atgcctcagt tctacaggaa tataagtata  14220
aacttagacc tcatattttt atttttcttt gagaagtccg atgcattccc tcccctttc  14280
tctctagtat ttttcctcaa aataacttcc tccaaaatcc ctctgaaatt ccaatgtttt  14340
atttcctacg gacaatccaa atgcataaac tcttgaattc gcatgtttta aaatcactta  14400
ggaatccaaa gtatatatat gacatgatat tcatacattc tttttctatt tatgcgtttt  14460
gaaaacacta tattccaaag agaaaccctt agctctcccg acgtcaaata agagtgaccg  14520
ttctcgcatt cactccatcg cactacttca tgccgcaaaa tgtttccatt tgaaattatt  14580
gtttatttat acatacgacc cacgcccgac tcaactattg catagacact actgttattt  14640
tcctagaccc acatagagat aaactcagtg caaggattag tggatagaga tgcgatcgaa  14700
tgttagtcgt acgtcatggt cgtatatagt aggccgtcat gacattagtg gaacgtatgg  14760
caccctcaat atatattttt tctatgaaag ctgtcctctt tgggagcccg atgtgaagga  14820
aaaaatatca tgctagcttt ctttctgacc cattcctctc cctcctccta ctccactccc  14880
gtagcttgtg tcgcatgagg tggagctcat ttggttggca agggagacgt cgaccggact  14940
ttgtcctcgg aactaggatt ctctttttca ctaacatgtg agtccgataa atcctagacc  15000
cacatggtag tgacaaaaaa aaacatggca actttgaagg tagaggatct caatctttga  15060
tgagcttctt tctcatcctc tattgtcact agagctcatt tggttgggac gatgccatcc  15120
attagatttg gtgacatccc gagggacaaa agcggttagg gggtagggag gtcagacact  15180
agagatggta cggggcaatg gcgtggtggc tagcgtcagg gaaaataata tggagacaac  15240
accgtacgat gacatttacc ttgagccctc agatttaagg ctgcgtggat ttcctcggga  15300
ggacatcgtc acctcatcac cgggagcata caagagagaa gagtggatat gcgcgttgtg  15360
aattttcgat gtttcaggca gcacatacgg atgtttctcg tatttcgatc aaaatgttaa  15420
agtggggatt ttgatggcgt ttcttttttt tttttgtgg cacagttcct cagcaagaca  15480
agcgcacggc ttcacccact cacctactac ctctgcgttg tttcgccccg tctgctagcg  15540
cggcgggtcg ttgtcttctt catcaacagg aggcggcaag tagccaagta ggaggcatcc  15600
ccatagtcgc gcaaccttac ctccggatct tcgtattata ttgttttata ttgtttcttc  15660
ttcttcttct tcttcttctt cttcttcttc ttcttgtttg tgtagcaagt agcaacggag  15720
tctcagatca gattagccgc cacaggggag gggagaccat ggacgaggcc gccgccggcc  15780
aacgcgccag tcctcttctt gccaaggtac ggcgaaccgc ggaaactgct aatccccgca  15840
ggcgcctatc ctgacctttt cctcttgtat atatgtgtgt ttcttgcttt gctgccttat  15900
ggggtttcag gggaagcaga atagtatgat gcaaagattg tggctttacc gatcaagatt  15960
tggtttttac tacagttggg tgtggggatg tgagctggag taaatttttt tgttgttgtt  16020
ttttttttta aagaagaaaa tgcaaatcgt agtctgaaat tgagaaaaga aaaatgcgat  16080
gactgataac tgctacctgg atactgatct ttgatgttga taaggattat gaaaccccga  16140
agatgtctag tgcgtatttc attccgtcgg tggatttggt caaagaatgt tgagttttag  16200
attgttgtac cttgttttgg aacgcgaaat tttgcagatc gaataagctg ttttcgatct  16260
actcaatcac attgcggtgt ttatgctgac gtctggcctt ctgtcagaat gatggatcaa  16320
gctatggtga agaatcacag agtttattgg aagaacagga gccacaggtt aaaactaaac  16380
aatctggctg gagagcacca tcaatcattc tgggtgagcc ttgttatata agcataccct  16440
tcttctcgta aaatcaaaat cttctctcca tcgaaaactg tgtgaaaacc aattcatata  16500
```

-continued

```
tagagggatt ggagcaccca tcggtgcatc actatataaa cattctttac catgatgcca  16560
caactaatgc tcacaaatca tgcaggactt gaatgcttgg agagcatggc tttcaatggc  16620
attgccacaa atctagttgt gtatattcgc tcagttctcc atggtggcat cgcttccagt  16680
gcttcaactt cttctctttg gtacggtact agtttctttg tgcctatact tggagcaacc  16740
attgcagata cttactgggg aaactataag acagtcttga tctcctttat catgtattta  16800
cttgtaagat cagttttcct gctcaactgc tcaatcttat tcacatttca ttgaacaatt  16860
gaactactcc agagtcaaga tgatgcattt ttgttgtaga aaggtcataa tgaaataccg  16920
atgcacattt cagggtacgg tattcattac tgttggagct tttctgcctt ctgctccagc  16980
cttatgcaac acggaatcat gctcatcaat gaatgggact caacatctag tatacttctc  17040
naggcctgta tctcactgct attggttgtg gcggagtaag gtctgcgttg cttccgcttg  17100
gtgcagatca attcaacaac gatagcagtt tagatataca aaagagaagg aattcttcag  17160
tttattctac atttgtgtta tctttggtgt gatacttctg g                      17201
```

<210> SEQ ID NO 4
<211> LENGTH: 8300
<212> TYPE: DNA
<213> ORGANISM: Oryza sativa

<400> SEQUENCE: 4

```
agggaaattg tagtgttttg cttctcaaac cgctcctgtc ttccacttag acttgtaatt     60
tcacttctga ctttttcgat gtttctctgt accagtacct gtgcgatcta aacaattgtg    120
tcagtatgta gtgagcagcc ttaacaaaac tgttatcaca gtgtgacaca ttataattgt    180
cttcctttcc tgagtatatg tggtcttttg gtttgaatgt agaggtcaga tttaattcat    240
ttctaaagaa aatgtggtct tctagcaaca agctagttga gaaagatggt gaattaaagc    300
taattttcaa tctctcaaga aagtaaacca tatgatcatc cataatttcc tcttaatacg    360
atgatataaa tctccactta agcttctaaa tataccatta attatttatg agtactcatt    420
ttttgtttcg gccaattcat agccgctgct actcattatt tatgagagta tatatagcta    480
gcttgcatct agtgatatga tcgagctagc attcgagcca cagctcaaaa cgaggccaag    540
atcatacgcg tcgccggatc attcccacac gtgtgagaat tgaaccccaa aaaaaaaaga    600
gtacggtatt tgctagtgca gctaaaagct acgaattgaa tatgatatcg atattgtgta    660
gagtatggac gatacatgga atctcatctc atctgatcat catgatctcc tggatgaaaa    720
tacaatgtac atgaatagag agagggcttt tggttttggg tggagaaatg gagcaacact    780
ccttgacatt tgagccccat cttataatat gaattcaatg aaaaaaaaat ggaaaggaga    840
atagagccac gtggcaacac cgacttcgcg gaagaggctc gacgaaacga tcttgtgcgt    900
gcgcgtgcag cgatctagga acgctcttgc gtgcgtgagt gcacgggcca ccgggtgtcc    960
agaagtttct tcgtgaatat atcgatcgag caattaggcc catggaccat ggctcagcag   1020
gccgtgcgat ggcacaagaa catgttgggt gatttaggcc ttgtttagtt tctaaaacaa   1080
aaacttttca cccatcacat cgaatgttta gaaatatgtg tggagtatta aatgtgaaaa   1140
aaaaactcaa ttacacagtt tgcatgtaaa ttgcgagaca aatcttttaa tcctaattgc   1200
accatgattt gacaatgtgg tgctacagta aacatttgct aatgatggat taattaggct   1260
taataaattc gtctcgcggt ttcctgacgg aatctataat ttgtttaatt attagactac   1320
gtttaatact tcaaatgtgt gtccgtatat tcgatgtgac aatcaaaccc aatttttttc   1380
cccaactaaa caagccctta gagagaccaa actttacatg gatgaaatga gatattacgc   1440
```

-continued

```
atacatgtag gatgttctat atgcaaacac ccgttgcatg ctgatcgatg catgaacttt   1500
cacattcagt ggtccgtact ccctactttg tacgcacagc tccgattaat tatcactttc   1560
ctcgttccgc attataagat atttattaag cccttcaatc cctcgtctag attccctaat   1620
atccatatga atttaaacac atatatgaaa cacatacgtt gatccatgta tatttttttt   1680
tcaaaaccca aaacgtatta tagtatgaaa cataaattta ttcaaaacct aaaacatctt   1740
atacacatac attgatgcat atatgaattt attaaaaccc taacaaaata gaaatttgtt   1800
caaaacccaa aagatcttct atccgattgt taccccaccg ggcccacgcc taggctcact   1860
aaaccatacg tggcttttgc catgcgcatg cgcttttcta gtaatgttaa agtcctagct   1920
tgacagtatt tgacatcgga agaaattgat gaactgtgtt tcgaactagt tccaccattt   1980
actcttatag cttattgtac gtagccaaaa tttaaatttt taaatttatt tttgggtttt   2040
gttccatcgt actttacttt ttttttcaac atttgctttt aaaccacaaa taacacacta   2100
taacatcata tatatatata tatatatata tgcctcctga ttaaaacccg gaaatatgat   2160
ttttgtattt aaatgtgtcc tattgatctc ctatgctaaa tgaatcgtgt tttaggctag   2220
atatctttta agatgttact aatttctaat atttaaccaa attttatcat aaattctaaa   2280
tatttatgac ataagataga gtagtttgat atagacaagt caaacccacg tgggataagt   2340
gaaagacaca tgagtcaaga taaactgtga aatcaataaa gggccaagtt ttacgtgatt   2400
atcagagatg atagcgggtt ttactaggtt aggcatagag aaaaaagaat tatacgatat   2460
atgtaacagt tttcaaagat tctttttatc aaaattcatt tattctattt aattatatat   2520
atatatagct caacttgtat tatcgctacc cgtcaataac attgctcatc gcaataacca   2580
agcagttatc accgataaag ttacaaccct agttaagaga caattagccg tagaatttca   2640
ctctcttttt gtccacacca cttccatcaa accttaattt ggcatctcaa ttgaaaagtt   2700
aataacctct cccttttttt ctgcatgcga tgcgttgcta cattgtacat atatacatct   2760
atagcaagtt caattggccc gaccgttacg tacgtagaga tcgtaataat taacgcacaa   2820
agacacaaaa tggagggtac agttaaccta tatatccagc atccaagcag ctggctggcc   2880
tggctatcaa ccacagctga cactaacagc taagctagct aaaagcagcc accggcgaac   2940
cgaaggttaa ccgtacgtcg gcgtcgcggt ctcgcggaga gccctgagaa tgtagagaaa   3000
ccgatcaccg atgtattatt ttcctattat gcacatacaa tttcagttct tacttgattc   3060
aaaattgttt actgcggcta tgttttacgg tggatagatg tgattacatt ttttttatat   3120
atttgctctt ttgttttgaa aaagaaaatc ttttgcttac taaattctat aactctttcg   3180
gtggaaggcg acgtaccatt gatagcgaga cgtgtaggaa tttcgttaat cctaatacat   3240
gttgaccttt tctctaagaa gtggttatag gagtataagg tctgtatata ttcataaggg   3300
gtgagtatgc tttcgtatat gagcatatgc atttgtacta tgtttttttt taaaaaaagt   3360
ggaacattaa ttcctcgtga tcaaatgtgg gacattgact gacatatgga tttaataatt   3420
atttacttgt ccacaaataa cttaccttgt catttttact ggaggtagat gaactcaaac   3480
cattatttat aaataatctt ttataaatgt cggttccgta caagccatac gctacagttt   3540
cacgtcttag gagatgttag ctttttttgc atgcttgact tcacgtgagg aaatgcatga   3600
gttttataaa tgtatcgtac aagttacagg ttataaatgt ttattgtttt tgaagcggtt   3660
aaattaaacc acgtaacgac taaagtaagt tgcacaacta agatttgcat gcacacaatt   3720
tgacttgttc ctttaatggt gatacataaa aaaaaatcat ctgccttacc catgatgaaa   3780
```

-continued

```
ataattgaac cacatctaag aaagagtagg gattataatg ctatgcaatt gaattggatt   3840
gttcaaattc taaatcaaac tgttccactt ctatctacat gacctctttg tataaatttt   3900
ctcatggtga aatagtagca aggtggctaa attaacatag gctgctaggg aggtcgagtg   3960
aggggtatat agagaaaggt cgaggaggag gtagatcatt gcggtggacg acatggagat   4020
gatcccttct aaactctaaa cttgtttcaa tcctattcta tatagtgaaa gtatcatctt   4080
ttaaggaatc gaaaggttgg tctcttaaaa aaaagtttaa gataccacca cttttcatga   4140
aatttgactg aatgatgtgc tctatatcaa atatttgcat atatatgtcc caaatcaaga   4200
ccacatatgg caagtgaaca acacacgagt agttcaaaac aaccacggag tcagcggagg   4260
accaacttac acgtgattac agatagaaaa acgagtttta ctaggtttag atagagtgaa   4320
aattttcttt tataatgaat ctcgacagac agttagtggc gcaacacaca atttaagaga   4380
caatcaacaa tagaatttca cactcttttt tacccacacc acttcacttc cattatcgta   4440
aaaccatgat ttggcatctc atcaactaaa acgttaacac ctctcccctt ttcccggcga   4500
actgctcgcc tggccgatgc atgcaacccg ttgctataca ttgtacagta catctatagc   4560
aagctagctt ccactgctct gccgtttcaa ttcgcctgta acgtccagac cgtaataacg   4620
cacaaaggca caaaaatgaa ggccaaatgg ccaattagct agctgtcctg gattagtagc   4680
tgccacagtc cacagctaag cagccaccgg caaaccgaag gttagccgtc ggcgtcgcgt   4740
ctggtacgat cgagccctga gaacgtggag aaactgatgt gattatttcc tactccatgt   4800
atatggacat ataatttcag ttctttcttg attcaaaaat tgtttggtgg tgttgtgttt   4860
tacggtggat agagggttac atatatttat atttgtattt tcttgttttg caaaaaaaaa   4920
ctccctccat cccaaaatat aacaattttg gggtggatgg gacgtaccat agtactatga   4980
atttggacat aacccctatc cagattcata gtactagaat atgtcccatc tacccagaag   5040
ttgttatatt ttgagacggg aggagtattt ctttgcttat taaattatgg aattctttca   5100
atagtaaacg atgtacgtac cctcaagagg gagatgcctg tagtgatttt gttgatttca   5160
agatacgaca actcactcgg tcgaatgtgc ttataggggt aggatttgca tgcgttaata   5220
aaagtgagtg tgtctgcata tataagcgtc tacattagtt actatttcaa aaaaaaattg   5280
agacattgac tgacacgtgg atttacttaa ttatttactt gttcacatat aatttagctt   5340
gtcggttttt catcggaggt ggattaactt ggaccgttat ttattaaata atctttattt   5400
agaatatgtt ggttccgtac acatatggtt taacatctta ccagatgctt tacgtatact   5460
tgatttctac gtgaggaaat acatgagttt catatcttta taattaatgt atcgtacaag   5520
tagcatgtat gaaccgttta atgtttttgt ggcggttaaa ttaaaccaca taacgactaa   5580
aagtaagttg cattactaag attcgcatgc acataatttg gcttgttcct ttgatagtaa   5640
tacttaaaaa aaacattgat cgtcatctgc cttactcatg ttggaaataa ctaaattaca   5700
tctagaaaag ataagagcgt taaataggcc attcaaatct aaatcaaact gttccacttc   5760
tatctatatc tatatgacct ttatgaggca agttgtcgca tagtgaagat agtagcaagg   5820
tggctaaatt tacataggtg gtcagggagg aggagtttgt caacaatagg gtatagagga   5880
aggtcgagga gtaggtagat tgtggtagaa gatatggaga tgctcccttc taaactagtt   5940
ttaatcctat tctatatagt aaaaatatcc tcttttaagg aattgaaagg ttgatgtcca   6000
attcataata tttgattgaa tcatgtccta tatattaaac atttatgata agattttttt   6060
aaaaaaaata cacaagaaga gcatctttgt attaagagaa gtaaagttta tttacagata   6120
aaacgaaaaa tgttttacta cctctcttct aaaaagactt tattttcttt taccatgaat   6180
```

-continued

```
atacacagta cttaaagaaa caactcgttt attaccacaa cactctacca tcaacctttg   6240
atttggcatc tcaaataaaa aacgctaacc tctccccttt ccccgggcgc ctcttggccg   6300
ctgcatgcaa cccgttgcta gtacactgtg tactgctcca tctgtagcaa gctttcactg   6360
ctcttccgtt tcaattttgc ccgttgcatc cgtcgagact gaccgtaatg acgcacaaag   6420
ccaaattagc taagctgtgt cctgcctaag tagagttact accacagcta agcaagcatc   6480
gatcacagcc accggcgaaa tgaacggaat taaggttaag atgcagtcac cggcgagatg   6540
agtatcctga gaacttggaa caaaccgatg caaatctctc tggccccaac tggccatggc   6600
catgaattcg tgctcgattc cgtgtcattt tgcagtagcc acccaagagt taattctttc   6660
ggtttttatt ccagcctttt ttttgctttg tttttgtact agctagctag tattatgaga   6720
ctttgcaaag gcgccatact atgtgtattg caattcaatg cagttttttt tctgctgcat   6780
ttatatttca gttttaattt agcgccacat tttgttgctt tcctacgtaa agcctggacg   6840
cagttaacac agcagctagc ttgttagcct gtgacacaat agcaacagct ggtaattgta   6900
actgaaaatt tctgtttcaa agaagaaaaa aaaagaggta taactggaga aaaaaaagcc   6960
tggacgatgg ttttaatctt gttaggtgtg acttaattac cgaatacaca ccaaagattg   7020
aatgaacact acatgacagt gtcttcctgt gacaggcgtt gaaatcccta ttatggagat   7080
ggttttcttc cttaattcga aaattgtttg gtgccgtcaa ttagtgaaat tgtggacatg   7140
ttttacggtt gacagaggat tacatgtatt tatgttttat attttcttgt ttcacaaaag   7200
aatatatatt tctttgctta ctgaattgtg gaatattttt ggaaaaaaat acgggacatt   7260
gagtaatcga cgtgaatatc taattaatta tttactatct ccgtgcacga gtaacttagc   7320
ttgtcggttc tgactgagag gtagatgtcc tttggctgtt aatttttta aaaagcattt   7380
ctctttttta atgtcggttc cgtacaagct atacacgtgg tttcatgtct tggcgcttta   7440
tcttcgactt ccacgtaaca agctgcatga gttttgcgcg cgtctttaaa tgttatagta   7500
cgtttcatat tcgaaccgtt aacggtttct gaggcagtta aattaaacca cgtaacgact   7560
aaagctgagt tgcatgagta agacccacgc gcactcattt gccttgttta tctagtggta   7620
atacctaaaa gaaccgccaa tcaaccgcct tactcatgtt aaaaataatt aaattttatc   7680
gaggaaagat gaaagataag ggtgctatga tactttatat acaatttaat tagaccgcaa   7740
atcctagatc gaggtgacgc cactctatat cgttccacat ccgtctatat gatatcttta   7800
tatgtatgta gttccacatt cttatatact cccttccctc tggttagttc catttgaac   7860
taaccaacgt caaatttaaa aaaaacagag gtatcatgat attttttagg tttaagttag   7920
attgaacgga atggaattga aatgttgttc tcttaatttt attttacact atcacatcat   7980
tacaaatttc aaactcttgt tctaaacagg caccatcttt ttcagttaca tctacactaa   8040
tttcaatagt aatgccatta ttatgtagtc caatatttaa ggaagaaact aatgatatat   8100
atatgcagat attgttaata atggcccttt gattacgcta tcattactga caatgacatg   8160
tggggccaga gtgtcagata attcgaggtc caaatttttg gagtggcaaa atggtctatt   8220
taaagcacca ggtgtttatt agcttctctc cacgtcttct tcctcccaag aaaactcctc   8280
tcacttcgcg aacgcttccc                                                8300
```

<210> SEQ ID NO 5
<211> LENGTH: 7232
<212> TYPE: DNA
<213> ORGANISM: Oryza sativa
<220> FEATURE:

-continued

<221> NAME/KEY: unsure
<222> LOCATION: (2629)
<223> OTHER INFORMATION: n = A, C, G, or T
<220> FEATURE:
<221> NAME/KEY: unsure
<222> LOCATION: (7072)
<223> OTHER INFORMATION: n = A, C, G, or T

<400> SEQUENCE: 5
gccctagccg ccgccgccgc cattattgcc attgatgtgg ctagcgacgt tgtcgtgctc 60
gcatccatac tcctccatag gcaactcgtc tagccaatga agaaagctac tatctatcta 120
tctatcaagc tagctgctac tatcacaaac cgcatttcgg catcatctta aattagctct 180
taggggtgta ggcgattttg gtttccccca aaaatttgct ttgccagtct tttggtttaa 240
atcgaggcat tagttgtgaa acatcatgag aagttattta aatctgagga attttgtttg 300 aacctttttct ggtgtgctaa atggatcgtg ctttgagtat cttattattc tgaatgtgtt 360
atgtagctac actctcctga atcatgtgtt aaccatgcaa tatttctcca gttggctgtc 420
agtttatcag cgtcttgtga atgccgttca tgagaaatct gaccatcttc caaatggttt 480
catcagtttg ctgtgataat taggttatgt ttcatgtcag tattatctct gcactgtgtt 540
tgttttatac aagtatactg caacatatat aacctttgta caccatgcta gtactgtgac 600
attttcaggt tgcatttctt tccttttaag actatgaaag attgcgttat gtaacaaaca 660
ttctattctt ctaatatatt gacgtgcaat ccttttgcgc gttcgagaaa aaaaaaagac 720
tatgaaagat taagttactg aacttccact aagtatatgg ccatatggtc taacctatct 780
ctagagatta gtcacaaatc tgttttgttt tgtcaagttg atatcctttt ttctttctga 840
atgaaatcaa gattatgtcc ttggaactgc attttgatgc tggtctgcat taggctaaat 900
ctctgaatct agagccattg catgctcttg cctgttgcct aattgtagtg ctccgagcat 960
cagattcatg tcagcatcaa aacttgcttc ttatttctta tcgtcgactc atccttgatc 1020
aatgtggcca acaaagattt gtgagcgcta agttgcatcc acgtgttgat catgcatata 1080
aacgcaaatg ggtcattttc tggaatcaag aggatttggc caactcgctt ttcgttgtca 1140
caaggtctac tactagggtc tcatccaaaa gattcaacct aagaagattt gatagcaatg 1200
tgctgtcgct gttatgttaa gattgttagg atcacaatct gtttacagca ttacatcctg 1260
acagccattc tcagtgggac tggaagtaca aaacgtggtg ttcagaacag taattttcaa 1320
ggtagagatt gctgatatat atgagaataa tttcttggct atcatattaa tgttaccaac 1380
acaaggtttg taccttaatc ttcatagatt tttcatggtg actcgctcat gctagtcatg 1440
acttgatgaa tatgcaagga gcagtcttca gggatgttac tgtcagacag ggccaggcat 1500
ctgaagacca tctgtctaag tgacaggaag tcttcaggct tcagagaaca gtcaagattc 1560
acttaattaa gatggcctgt ggctgatcta ggtagtcatt agtcaaccaa atttcttcat 1620
gttccttttc ttttccttcc tatcttacac taatatagta acatccagac agtcacgtat 1680
cctcctacct ttgtgttatg gtgagactaa ctgtgttctg gaaggtgtga aatccctcac 1740
caaaatggct gaagaattga gaattcagaa gccatggcag aagtgatcat gtgcatgatg 1800
aattgatgat aatatatcag ggggccctca tctggtcatc tcacctgcct ctctcttttc 1860
tctttttctg agacccaaat cttgcataag acttctgtga ttagacagga atcttgtatc 1920 ctttcccccct atggaaagaa gcctccattt tgtgatatat ggctcacatt tttattcctg 1980
atcaggggca agatcacaaa aaggtgcttc actgttgacc catcactacc acttttgtgg 2040
atttgcttga tggcgtgatg cataatttct ctatagtcaa aagtcaagca tattttgata 2100

-continued gtggttgaga aagtaccgtg aggtaaagta ccttatgcta tatcacaagt ccataacacc 2160
ggaaacatat aggatgagtt tttttcttaa ctttcccaac tcacatctct cgtgttaccc 2220
gcgcacgtat tttaaactgc taaacgatat attttttgca aaagttttct atacgaaagt 2280
tgctttaaaa aatcatatta atccattttt caaaaaaaaa gctaatactt aattaatcat 2340
acgttaatga gttgctctat tttacgtgca tcaaggatta gttcccaact gtgtatgccg 2400
aacacagcca tagttctcaa gacacgtaaa aaacataata aacataataa ttttttgaga 2460
atctctacct tcttgaataa tctaaattat tgcctataat tcagcagcca aacgctaaaa 2520
aacttagact tttcagatcc tcagaagttt gctactcacc atctacttca tacaatctcg 2580
agctctctta aacagggcct caaggataat tttgcctcca aagcctcana aaaagatacc 2640
caaatcctcc tcatggcgac cttttgtcaa ctcttggaac agagaaaatg gtcaggtcgt 2700
ttgtcacacg atcaaacaaa gtagagagaa agaaaaaaga aggaaagaaa ggatgggatt 2760
gggttgtttt tcccctggac agaaaaagaa cagggcccag cccaactacc acgacggcac 2820
gacctgaatt tgtggttagc tgtagatgtt ttcatggcac accttccacg tgcaaactta 2880
tatatatata tatatatata tatatatata tagagagaga gagagagaga gagagagaga 2940
gagagagaga gtacttgcca ccagcagctt agtgtaatta tatgctcgaa taataaactg 3000
aagaaaaagt gaacaagtgg ttggtgctgt gtaacacagt attagtgttc tttggttgaa 3060
gattgaagga agatttagct cgcttttcat gtgcatattt tccaaactat taaacggtct 3120
tttctaaaaa atatttatat ataaagtcgc tttaataaaa ccatacaagt ccatttttca 3180
aatctaaaat gattaatact ttattaatcg tatattaatg gctaatctcg ttttgcgtat 3240
ctccccaatc tttttatttc ctttcaaaca ctacgtcaac ttgtattttg tttttcctta 3300
tttagatgga taaacatgta ctatatacta caatcccctg ttgtcaactg gtttcatttg 3360
atcattggag gacaatgtaa agaaagtact actttcttca gtcatcttta tttatcttcg 3420
ggatagctaa ttttaggggg gagggggggg gggggttgga gaaaattcaa aggaaatttt 3480
ataattctta ggaatatttt cttattagct cctttggaga aaaggaatac gactgacaaa 3540
tatcacatga atttagttct gatcactaca acaaaaatgc tttgtagaga catttttcta 3600
gtactataga tacacttttc aaatgccttt acaatactat agaggcattt taaaaaatgc 3660
ctaataagtg ccttacggtg aattgtctct acaaacgaag aggcatttta caaaatgtct 3720
aaaagatggt agaggcattt tatagagaca ttaaattgtg tcacaaccat atgaaaccaa 3780
tgtaaaaaaa ataaaatatt ttcccttgtt tttgacaatc cttgaactca tgatcaattg 3840
cacaattcat tcttatcttc aaggcactaa ccaactcaac cctaagtcat tacttatatg 3900
ttgttgtctt gagttattta tatttagtca tttattacat acttttattc taagaagtgc 3960
ctttacagag tttaaagtgt ctcaagaaaa tgcctttaca tatcaggcac agtttaaagt 4020
gccgaaagaa tgcctctaca atataaaatc taataaaata tgctgaaaat atttctaaag 4080
tgtctgtaga gtaaaagttt tctaggcatt ttttaaaatg cctctataaa atgtctctac 4140
actataaaac tcctgatcta agaggcaatt tgcaaaacgc ctctacaaaa gtgtctttat 4200
ataaggtttt tgttgtagtg gatgcctcag ttctacagga atataagtat aaacttagac 4260
ctcatatttt tatttttctt tgagaagtcc gatgcattcc ctccccttt ctctctagta 4320
tttttcctca aaataacttc ctccaaaatc cctctgaaat tccaatgttt tatttcctac 4380
ggacaatcca aatgcataaa ctcttgaatt cgcatgtttt aaaatcactt aggaatccaa 4440

-continued

```
agtatatata tgacatgata ttcatacatt ctttttctat ttatgcgttt tgaaaacact   4500
atattccaaa gagaaaccct tagctctccc gacgtcaaat aagagtgacc gttctcgcat   4560
tcactccatc gcactacttc atgccgcaaa atgtttccat ttgaaattat tgtttattta   4620
tacatacgac ccacgcccga ctcaactatt gcatagacac tactgttatt ttcctagacc   4680
cacatagaga taaactcagt gcaaggatta gtggatagag atgcgatcga atgttagtcg   4740
tacgtcatgg tcgtatatag taggccgtca tgacattagt ggaacgtatg gcaccctcaa   4800
tatatatttt ttctatgaaa gctgtcctct ttgggagccc gatgtgaagg aaaaaatatc   4860
atgctagctt tctttctgac ccattcctct ccctcctcct actccactcc cgtagcttgt   4920
gtcgcatgag gtggagctca tttggttggc aagggagacg tcgaccggac tttgtcctcg   4980
gaactaggat tctctttttc actaacatgt gagtccgata aatcctagac ccacatggta   5040
gtgacaaaaa aaaacatggc aactttgaag gtagaggatc tcaatctttg atgagcttct   5100
ttctcatcct ctattgtcac tagagctcat ttggttggga cgatgccatc cattagattt   5160
ggtgacatcc cgagggacaa aagcggttag gggtaggga ggtcagacac tagagatggt    5220
acggggcaat ggcgtggtgg ctagcgtcag ggaaaataat atggagacaa caccgtacga   5280
tgacatttac cttgagccct cagatttaag gctgcgtgga tttcctcggg aggacatcgt   5340
cacctcatca ccgggagcat acaagagaga agagtggata tgcgcgttgt gaattttcga   5400
tgtttcaggc agcacatacg gatgtttctc gtatttcgat caaaatgtta aagtggggat   5460
tttgatggcg tttctttttt tttttttgtg gcacagttcc tcagcaagac aagcgcacgg   5520
cttcacccac tcacctacta cctctgcgtt gtttcgcccc gtctgctagc gcggcgggtc   5580
gttgtcttct tcatcaacag gaggcggcaa gtagccaagt aggaggcatc cccatagtcg   5640
cgcaacctta cctccggatc ttcgtattat attgttttat attgtttctt cttcttcttc   5700
ttcttcttct tcttcttctt cttcttgttt gtgtagcaag tagcaacgga gtctcagatc   5760
agattagccg ccacagggga ggggagacca tggacgaggc cgccgccggc caacgcgcca   5820
gtcctcttct tgccaaggta cggcgaaccg cggaaactgc taatccccgc aggcgcctat   5880
cctgaccttt tcctcttgta tatatgtgtg tttcttgctt tgctgcctta tggggtttca   5940
ggggaagcag aatagtatga tgcaaagatt gtggctttac cgatcaagat ttggttttta   6000
ctacagttgg gtgtggggat gtgagctgga gtaaattttt ttgttgttgt tttttttttt   6060
aaagaagaaa atgcaaatcg tagtctgaaa ttgagaaaag aaaaatgcga tgactgataa   6120
ctgctacctg gatactgatc tttgatgttg ataaggatta tgaaaccccg aagatgtcta   6180
gtgcgtattt cattccgtcg gtggatttgg tcaaagaatg ttgagtttta gattgttgta   6240
ccttgttttg gaacgcgaaa ttttgcagat cgaataagct gttttcgatc tactcaatca   6300
cattgcggtg tttatgctga cgtctggcct tctgtcagaa tgatggatca agctatggtg   6360
aagaatcaca gagtttattg gaagaacagg agccacaggt taaaactaaa caatctggct   6420
ggagagcacc atcaatcatt ctgggtgagc cttgttatat aagcataccc ttcttctcgt   6480
aaaatcaaaa tcttctctcc atcgaaaact gtgtgaaaac caattcatat atagagggat   6540
tggagcaccc atcggtgcat cactatataa acattcttta ccatgatgcc acaactaatg   6600
ctcacaaatc atgcaggact tgaatgcttg gagagcatgg ctttcaatgg cattgccaca   6660
aatctagttg tgtatattcg ctcagttctc catggtggca tcgcttccag tgcttcaact   6720
tcttctcttt ggtacggtac tagtttcttt gtgcctatac ttggagcaac cattgcagat   6780
acttactggg gaaactataa gacagtcttg atctccttta tcatgtattt acttgtaaga   6840
```

-continued

```
tcagttttcc tgctcaactg ctcaatctta ttcacatttc attgaacaat tgaactactc   6900

cagagtcaag atgatgcatt tttgttgtag aaaggtcata atgaaatacc gatgcacatt   6960

tcagggtacg gtattcatta ctgttggagc ttttctgcct tctgctccag ccttatgcaa   7020

cacggaatca tgctcatcaa tgaatgggac tcaacatcta gtatacttct cnaggcctgt   7080

atctcactgc tattggttgt ggcggagtaa ggtctgcgtt gcttccgctt ggtgcagatc   7140

aattcaacaa cgatagcagt ttagatatac aaaagagaag gaattcttca gtttattcta   7200

catttgtgtt atctttggtg tgatacttct gg                                 7232
```

<210> SEQ ID NO 6
<211> LENGTH: 593
<212> TYPE: DNA
<213> ORGANISM: Oryza sativa

<400> SEQUENCE: 6

```
gcacgaggat cttgatggag tgggtgatgg cgaggatggt gatgcacccg gatgcgttcc     60

gcccggagcg cttctcggag ggggaggacg tcggcgtgct cggcggcgac ctccgcctcg    120

cgccgttcgg cgccggccgc cgcgtctgcc ctggcaggat gctggcgctc gccaccgccc    180

acctctggct cgcccagctg ctgcacgcct tcgactggtc ccccaccgcc gccggcgtcg    240

acctgtccga gcgcctcggc atgtcgctgg agatggcggc gccgctcgtg tgcaaggccg    300

tggctagggc ctgagcccta gccgccgccg ccgccattat tgccattgat gtggctagcg    360

acgttgtcgt gctcgcatcc atactcctcc ataggcaact cgtctagcca atgaagaaag    420

ctactatcta tctatctatc aagctagctg ctactatcac aaaccgcatt tcggcatcat    480

cttaaattag ctcttagggg tgtaggcgat tttggtttcc cccaaaaatt tgctttgcca    540

gtttttggt ttaaatcgag gcattagttg tgaaaaaaaa aaaaaaaaaa aaa           593
```

<210> SEQ ID NO 7
<211> LENGTH: 100
<212> TYPE: PRT
<213> ORGANISM: Oryza sativa

<400> SEQUENCE: 7

```
Leu Met Glu Trp Val Met Ala Arg Met Val Met His Pro Asp Ala Phe
  1               5                  10                  15

Arg Pro Glu Arg Phe Ser Glu Gly Glu Asp Val Gly Val Leu Gly Gly
             20                  25                  30

Asp Leu Arg Leu Ala Pro Phe Gly Ala Gly Arg Arg Val Cys Pro Gly
         35                  40                  45

Arg Met Leu Ala Leu Ala Thr Ala His Leu Trp Leu Ala Gln Leu Leu
     50                  55                  60

His Ala Phe Asp Trp Ser Pro Thr Ala Ala Gly Val Asp Leu Ser Glu
 65                  70                  75                  80

Arg Leu Gly Met Ser Leu Glu Met Ala Ala Pro Leu Val Cys Lys Ala
                 85                  90                  95

Val Ala Arg Ala
            100
```

<210> SEQ ID NO 8
<211> LENGTH: 1131
<212> TYPE: DNA
<213> ORGANISM: Oryza sativa

<400> SEQUENCE: 8

-continued

```
gcacgagctt tcgagggacg gacacggtgg cggtcctgat cgagtgggtg gcggcgaggc     60
tggtgctgca ccaggacgtg caggccaggg tccatgacga gctggaccga gtggtcgggt    120
cggaccgggc agtgaccgag tcggacgcgt ccaagctggt ctacctccaa gcggtgatca    180
aagaggtcct gcgcctccac ccgccgggcc cactgctctc gtgggcacgc ctcgccacgt    240
cggatgtaca cgtcggcggg ttcctcatac cctctgggac caccgccatg gtgaacatgt    300
gggccataac ccatgaccct gccgtttggc ccgacccgaa cgagttcaaa ccagagaggt    360
tcgtcgcagg gccctcgtcg gaccaggcca cggagtttcc gataatgggg tcggatctca    420
ggctcgcgcc gttcgggtca ggaaggcgaa gctgccccgg caagtcgctc gccatcgcca    480
ctgtcggatt ctgggttgcc acgttgctac acgagttcga ttggcttccc ttgtcagata    540
agtcgcgcgg cgtcgatctg tcggaggtgc tgaagctgtc gtgcgagatg gcaaccccgc    600
tggaggcaag gctaaggccg cgacgcaagg tgtgatgacg tgtcaccacc gtcacgtggg    660
actaagacga ggagagggaa gccgacttcc acttccttct agtgcttgtt gagatgtgta    720
aatgtcccta aatgtaaagt gttacgcttt gagtagaaat gcccctacgt tgtagtgcgt    780
agtattgtac acttgtagta tgtaatgctt gtatttttgt gtgttttgca cgtcctaagt    840
agtggagtag tagctgataa tagttagtta attactctgc tatttagtca tagttaacta    900
cctacctgca ggtgatgaga gtgacagttt ttttttgttt aattaactgc aggtgatgag    960
tgtagaatag ctcggtatgc ccatctctat cctaagtgca cgcgtgcgtg tgtaattatt   1020
gtcagatgta tgttgttttc aatgatagtg tacatatttt tggcgagctc gatcttccat   1080
taggaagtga tcgctgcatg cttacctcaa aaaaaaaaaa aaaaaaaaaa a            1131
```

<210> SEQ ID NO 9
<211> LENGTH: 208
<212> TYPE: PRT
<213> ORGANISM: Oryza sativa

<400> SEQUENCE: 9

```
Phe Arg Gly Thr Asp Thr Val Ala Val Leu Ile Glu Trp Val Ala Ala
  1               5                  10                  15

Arg Leu Val Leu His Gln Asp Val Gln Ala Arg Val His Asp Glu Leu
             20                  25                  30

Asp Arg Val Val Gly Ser Asp Arg Ala Val Thr Glu Ser Asp Ala Ser
         35                  40                  45

Lys Leu Val Tyr Leu Gln Ala Val Ile Lys Glu Val Leu Arg Leu His
     50                  55                  60

Pro Pro Gly Pro Leu Leu Ser Trp Ala Arg Leu Ala Thr Ser Asp Val
 65                  70                  75                  80

His Val Gly Gly Phe Leu Ile Pro Ser Gly Thr Thr Ala Met Val Asn
                 85                  90                  95

Met Trp Ala Ile Thr His Asp Pro Ala Val Trp Pro Asp Pro Asn Glu
            100                 105                 110

Phe Lys Pro Glu Arg Phe Val Ala Gly Pro Ser Ser Asp Gln Ala Thr
        115                 120                 125

Glu Phe Pro Ile Met Gly Ser Asp Leu Arg Leu Ala Pro Phe Gly Ser
    130                 135                 140

Gly Arg Arg Ser Cys Pro Gly Lys Ser Leu Ala Ile Ala Thr Val Gly
145                 150                 155                 160

Phe Trp Val Ala Thr Leu Leu His Glu Phe Asp Trp Leu Pro Leu Ser
                165                 170                 175
```

-continued

```
Asp Lys Ser Arg Gly Val Asp Leu Ser Glu Val Leu Lys Leu Ser Cys
            180                 185                 190

Glu Met Ala Thr Pro Leu Glu Ala Arg Leu Arg Pro Arg Arg Lys Val
        195                 200                 205


<210> SEQ ID NO 10
<211> LENGTH: 610
<212> TYPE: DNA
<213> ORGANISM: Oryza sativa

<400> SEQUENCE: 10

cttctccgga gcttcaggtg ggtcccgtcc ggcgaccgcg gcgtcgacat gagcgagcgc      60

ctcggcatgt ccctcgaaat ggagaagcca ttgatctgcc tcgcgcttcc aaggacctcg     120

tctacctagc tacacacaca agctgctacc aactttgcta agacctctac ttggaatctt     180

gtagattata tctgttaatt atgtataatt aagcttccgt aaaaaaatat atgtactccc     240

tttgtttcac aatataagtc attctagcat tttccacatt catattaatg ctaatgattc     300

attagcatta atatgaatgt gaaaaatact agaatgactt acattatgaa acggaggaag     360

tataataatt aagcatacgc atgttctaac ctatagatca attttcatgt gggtgcttgg     420

ttagaacttg aaataatccc aaggttttgt agcctgttct ttatataggg gttttttttt     480

tcatgctctc gtgatgcaag tatggggtgt ggtttgttct ctgggagaca tgagacgcta     540

ataagatgat tattgtactt ttttaaaaaa atggctgtgg accatatgtc ataaaaaaaa     600

aaaaaaaaaa                                                            610


<210> SEQ ID NO 11
<211> LENGTH: 42
<212> TYPE: PRT
<213> ORGANISM: Oryza sativa

<400> SEQUENCE: 11

Leu Leu Arg Ser Phe Arg Trp Val Pro Ser Gly Asp Arg Gly Val Asp
  1               5                  10                  15

Met Ser Glu Arg Leu Gly Met Ser Leu Glu Met Glu Lys Pro Leu Ile
            20                  25                  30

Cys Leu Ala Leu Pro Arg Thr Ser Ser Thr
        35                  40


<210> SEQ ID NO 12
<211> LENGTH: 1146
<212> TYPE: DNA
<213> ORGANISM: Zea mays

<400> SEQUENCE: 12

gcacgagcga cctgctcggc atgttcaact ggggtgacca cctgccgctg ctcaggtggc      60

tggacctgca gggcgtcagg aggcggtgca ggagcctggt gggcagagtc aacgtgttcg     120

tggccaggat catcgaagag cacaggcaca agaaggacga cgccattgga gagccggccg     180

ccgccggaga cttcgtcgac gtcttgctgg gactggatgg cgaggagaag ctgtcggact     240

ccgacatgat cgctgtcctc tgggagatga tctttcgagg gaccgacacg gtggcgatcc     300

tgctggagtg ggtgatggcg cggatggtgc tgcacccggg catccagtcc aaggcgcagg     360

cggagctgga cgccgtggtg ggccgcggcc gcgccgtttg cgacgccgac gtggcccgcc     420

tgccctacct gcagcgcgtc gtgaaggaga cgctccgcgt gcacccgccg ggtccgctgc     480

tctcgtgggc gcgcctggcc gtgcgcgacg cggtggtcgg cggccacgtg gtccccgcgg     540
```

-continued

```
gcaccacggc catggtcaac atgtgggcca tcgcgcacga ccccgcggtg tggccggagc    600

cctccgcgtt ccggcccgag cggttcgagg aggaggacgt gagcgtgctg ggcggcgacc    660

tccgcctcgc gcccttcggc gccggccggc gcgtgtgccc cggcaagacg ttggcgctcg    720

ccaccgtcca cctttggctc gcgcagctgc tgcaccgctt ccggtgggcg ccggccgacg    780

gccgcggcgt cgacctggcg gagcgcctcg gcatgtccct ggagatggag aagcccctcg    840

tgtgcaagcc cacgccgagg tggtgaatgg cgatcgctag agcgaaagcg caactacgct    900

acgcatggcg cgccatcgag ttccatgcaa aactatatta ttatactact attactagcg    960

tttcatattt tgcacttgtg gttttgttta cgttaattac cgttcgcgat cgatggaact   1020

gagtgaagtg tgcacagcat actccattgc tagaaagagg acgagatatg tgaaaacgcc   1080

tgatggctga tggcaaatta tatggagagc atgtttcagt aaaaaaaaaa aaaaaaaaaa   1140

aaaaaa                                                              1146


<210> SEQ ID NO 13
<211> LENGTH: 285
<212> TYPE: PRT
<213> ORGANISM: Zea mays

<400> SEQUENCE: 13

Asp Leu Leu Gly Met Phe Asn Trp Gly Asp His Leu Pro Leu Leu Arg
  1               5                  10                  15

Trp Leu Asp Leu Gln Gly Val Arg Arg Arg Cys Arg Ser Leu Val Gly
             20                  25                  30

Arg Val Asn Val Phe Val Ala Arg Ile Ile Glu Glu His Arg His Lys
         35                  40                  45

Lys Asp Asp Ala Ile Gly Glu Pro Ala Ala Ala Gly Asp Phe Val Asp
     50                  55                  60

Val Leu Leu Gly Leu Asp Gly Glu Glu Lys Leu Ser Asp Ser Asp Met
 65                  70                  75                  80

Ile Ala Val Leu Trp Glu Met Ile Phe Arg Gly Thr Asp Thr Val Ala
                 85                  90                  95

Ile Leu Leu Glu Trp Val Met Ala Arg Met Val Leu His Pro Gly Ile
            100                 105                 110

Gln Ser Lys Ala Gln Ala Glu Leu Asp Ala Val Val Gly Arg Gly Arg
        115                 120                 125

Ala Val Cys Asp Ala Asp Val Ala Arg Leu Pro Tyr Leu Gln Arg Val
    130                 135                 140

Val Lys Glu Thr Leu Arg Val His Pro Pro Gly Pro Leu Leu Ser Trp
145                 150                 155                 160

Ala Arg Leu Ala Val Arg Asp Ala Val Val Gly Gly His Val Val Pro
                165                 170                 175

Ala Gly Thr Thr Ala Met Val Asn Met Trp Ala Ile Ala His Asp Pro
            180                 185                 190

Ala Val Trp Pro Glu Pro Ser Ala Phe Arg Pro Glu Arg Phe Glu Glu
        195                 200                 205

Glu Asp Val Ser Val Leu Gly Gly Asp Leu Arg Leu Ala Pro Phe Gly
    210                 215                 220

Ala Gly Arg Arg Val Cys Pro Gly Lys Thr Leu Ala Leu Ala Thr Val
225                 230                 235                 240

His Leu Trp Leu Ala Gln Leu Leu His Arg Phe Arg Trp Ala Pro Ala
                245                 250                 255
```

-continued

```
Asp Gly Arg Gly Val Asp Leu Ala Glu Arg Leu Gly Met Ser Leu Glu
            260                 265                 270

Met Glu Lys Pro Leu Val Cys Lys Pro Thr Pro Arg Trp
        275                 280                 285


<210> SEQ ID NO 14
<211> LENGTH: 778
<212> TYPE: DNA
<213> ORGANISM: Zea mays

<400> SEQUENCE: 14

gcgaaggccc aggcggagct ggacggcgtc gtgggcatcg ggcgcggcgt ggcggacgcc      60

gacgtcgcca gcctacccta catccagtgc atcgtgaagg agacgctgcg catgcacccg     120

ccaggcccgc tcctgtcgtg ggcgcgcctc gccgtccacg acgcgcacgt cggaggccac     180

ctggtccccg ccggcaccac agccatggtc aacatgtggt ccatcgcgca cgaccccgcc     240

atctgggccg agccggagaa gttccgcccc gagcggttcc aggaggagga cgtgagcgtc     300

ctcgggagcg acctccgcct ggcccccttc ggcgccgggc gccgcgcctg ccccggcaag     360

atactggccc tcgccaccac ccacctctgg gtcgcccagc ttctgcacaa gttcgagtgg     420

gccgccggcg ggggcgtcga cctgtcggag cgcctgagca tgtcgctgga gatggccacg     480

ccgctggtgt gcaaggccgt acccagggtt cagggccaag cggcctccta gcctagcctc     540

catgcatgcc tgatgcctgg atgccgtagc gagagtggga gactgatgag tgtatgccgt     600

tatgtttgtg tgtccatgca tgcatgcatg cctcggctac tgtagctttt ggcttgcttg     660

ttgtgcatgt cctgcgtcga gaccttgcgt agtatgatgc agtataattt taataataat     720

attattatta aaggttaaag ttttgataat acagtaaaaa aaaaaaaaaa aaaaaaaa       778


<210> SEQ ID NO 15
<211> LENGTH: 177
<212> TYPE: PRT
<213> ORGANISM: Zea mays

<400> SEQUENCE: 15

Pro Ala Lys Ala Gln Ala Glu Leu Asp Gly Val Val Gly Ile Gly Arg
  1               5                  10                  15

Gly Val Ala Asp Ala Asp Val Ala Ser Leu Pro Tyr Ile Gln Cys Ile
             20                  25                  30

Val Lys Glu Thr Leu Arg Met His Pro Pro Gly Pro Leu Leu Ser Trp
         35                  40                  45

Ala Arg Leu Ala Val His Asp Ala His Val Gly Gly His Leu Val Pro
     50                  55                  60

Ala Gly Thr Thr Ala Met Val Asn Met Trp Ser Ile Ala His Asp Pro
 65                  70                  75                  80

Ala Ile Trp Ala Glu Pro Glu Lys Phe Arg Pro Glu Arg Phe Gln Glu
                 85                  90                  95

Glu Asp Val Ser Val Leu Gly Ser Asp Leu Arg Leu Ala Pro Phe Gly
            100                 105                 110

Ala Gly Arg Arg Ala Cys Pro Gly Lys Ile Leu Ala Leu Ala Thr Thr
        115                 120                 125

His Leu Trp Val Ala Gln Leu Leu His Lys Phe Glu Trp Ala Ala Gly
    130                 135                 140

Gly Gly Val Asp Leu Ser Glu Arg Leu Ser Met Ser Leu Glu Met Ala
145                 150                 155                 160

Thr Pro Leu Val Cys Lys Ala Val Pro Arg Val Gln Gly Gln Ala Ala
```

-continued 165 170 175

Ser

<210> SEQ ID NO 16
<211> LENGTH: 1597
<212> TYPE: DNA
<213> ORGANISM: Zea mays

<400> SEQUENCE: 16

```
ccacgcgtcc ggcgcaccgc accctggcgg cgctgtccca cgccgtagac ggcggcaagg     60
cactgatggc cttctcggtc gggctgaccc gtctcgtcgt gtcgagccag cccgatacgg    120
cgcgcgagat cctcgccagc cccgcgttcg gcgaccgccc catcaaggac gcggcgcgcc    180
acctgctctt ccaccacgcc atgggcttcg cgccctccgg agacgcgcac tggcgcgggc    240
tccgccgcct cgccgccaac cacctgttcg gcccgcgccg cgtggcgggt gccgcgcacc    300
accgcgcctc catcggcgag gccatggtcg ccgacgtcgc cgctgccatg gcgcgccacg    360
gcgaggtccc tctcaagcgc gtgctgcatg tcgcgtctct caaccacgtc atggccaccg    420
tgtttggcaa gcgctacgac atgggcagcc gagagggcgc cgttctggac gagatggtgg    480
ccgagggcta cgacctcctg ggcacgttca actgggctga ccacctgcca ttgctcaagc    540
atctcgaccc ccagggcgtg cgccgccggt gcaataggct ggtccaaaag gtcgaatcgt    600
tcgttggcaa gatcatcatg gagcacagga cgaggcgcgc aaatggagga gtcgtgggcg    660
atgagtgcat gggtgacttc gtcgacgtcc ttcttggcct cgagggagag gagaagctgt    720
cagatgagga catgatcgct gttctttggg agatgatctt cagaggcgcc gacaccgtgg    780
cgatcttgat ggagtgggtc atggcgagga tggcgctgca cccggacatc caggcgaagg    840
cccaggcgga gctggacggc gtcgtgggca tcgggcgcgg cgtggcggac gccgacgtcg    900
ccagcctacc ctacatccag tgcatcgtga aggagacgct gcgcatgcac ccgccaggcc    960
cgctcctgtc gtgggcgcgc ctcgccgtcc acgacgcgca cgtcggaggc cacctggtcc   1020
ccgccggcac cacagccatg gtcaacatgt ggtccatcgc gcacgacccc gccatctggg   1080
ccgagccgga gaagttccgc cccgagcggt tccaggagga ggacgtgagc gtcctcggga   1140
gcgacctccg cctggccccc ttcggggccg ggcgccgcgc ctgccccggc aagatactgg   1200
ccctcgccac cacccacctc tgggtcgccc agcttctgca caagttcgag tgggccgccg   1260
gcgggggcgt cgacctgtcg gagcgcctga gcatgtcgct ggagatggcc acgccgctgg   1320
tgtgcaaggc cgtacccagg gttcagggcc aagcggcctc ctagcctagc ctccatgcat   1380
gcctgatgcc tggatgccgt agcgagagtg ggagactgat gagtgtatgc cgttatgttt   1440
gtgtgtccat gcatgcatgc atgcctcggc tactgtagct tctggcttgc ttgttgtgca   1500
tgtcctgcgt cgagaccttg cgtagtatga tgcagtataa ttttaataat aatattatta   1560
ttaaaggtta aaaaaaaaaa aaaaaaaaaa aaaaaaa                            1597
```

<210> SEQ ID NO 17
<211> LENGTH: 451
<212> TYPE: PRT
<213> ORGANISM: Zea mays

<400> SEQUENCE: 17

```
Pro Ala His Arg Thr Leu Ala Ala Leu Ser His Ala Val Asp Gly Gly
  1               5                  10                  15

Lys Ala Leu Met Ala Phe Ser Val Gly Leu Thr Arg Leu Val Val Ser
             20                  25                  30
```

-continued

```
Ser Gln Pro Asp Thr Ala Arg Glu Ile Leu Ala Ser Pro Ala Phe Gly
        35                  40                  45

Asp Arg Pro Ile Lys Asp Ala Ala Arg His Leu Leu Phe His His Ala
    50                  55                  60

Met Gly Phe Ala Pro Ser Gly Asp Ala His Trp Arg Gly Leu Arg Arg
 65                  70                  75                  80

Leu Ala Ala Asn His Leu Phe Gly Pro Arg Arg Val Ala Gly Ala Ala
                85                  90                  95

His His Arg Ala Ser Ile Gly Glu Ala Met Val Ala Asp Val Ala Ala
            100                 105                 110

Ala Met Ala Arg His Gly Glu Val Pro Leu Lys Arg Val Leu His Val
        115                 120                 125

Ala Ser Leu Asn His Val Met Ala Thr Val Phe Gly Lys Arg Tyr Asp
    130                 135                 140

Met Gly Ser Arg Glu Gly Ala Val Leu Asp Glu Met Val Ala Glu Gly
145                 150                 155                 160

Tyr Asp Leu Leu Gly Thr Phe Asn Trp Ala Asp His Leu Pro Leu Leu
                165                 170                 175

Lys His Leu Asp Pro Gln Gly Val Arg Arg Arg Cys Asn Arg Leu Val
            180                 185                 190

Gln Lys Val Glu Ser Phe Val Gly Lys Ile Ile Met Glu His Arg Thr
        195                 200                 205

Arg Arg Ala Asn Gly Gly Val Val Gly Asp Glu Cys Met Gly Asp Phe
    210                 215                 220

Val Asp Val Leu Leu Gly Leu Glu Gly Glu Glu Lys Leu Ser Asp Glu
225                 230                 235                 240

Asp Met Ile Ala Val Leu Trp Glu Met Ile Phe Arg Gly Ala Asp Thr
                245                 250                 255

Val Ala Ile Leu Met Glu Trp Val Met Ala Arg Met Ala Leu His Pro
            260                 265                 270

Asp Ile Gln Ala Lys Ala Gln Ala Glu Leu Asp Gly Val Val Gly Ile
        275                 280                 285

Gly Arg Gly Val Ala Asp Ala Asp Val Ala Ser Leu Pro Tyr Ile Gln
    290                 295                 300

Cys Ile Val Lys Glu Thr Leu Arg Met His Pro Pro Gly Pro Leu Leu
305                 310                 315                 320

Ser Trp Ala Arg Leu Ala Val His Asp Ala His Val Gly Gly His Leu
                325                 330                 335

Val Pro Ala Gly Thr Thr Ala Met Val Asn Met Trp Ser Ile Ala His
            340                 345                 350

Asp Pro Ala Ile Trp Ala Glu Pro Glu Lys Phe Arg Pro Glu Arg Phe
        355                 360                 365

Gln Glu Glu Asp Val Ser Val Leu Gly Ser Asp Leu Arg Leu Ala Pro
    370                 375                 380

Phe Gly Ala Gly Arg Arg Ala Cys Pro Gly Lys Ile Leu Ala Leu Ala
385                 390                 395                 400

Thr Thr His Leu Trp Val Ala Gln Leu Leu His Lys Phe Glu Trp Ala
                405                 410                 415

Ala Gly Gly Gly Val Asp Leu Ser Glu Arg Leu Ser Met Ser Leu Glu
            420                 425                 430

Met Ala Thr Pro Leu Val Cys Lys Ala Val Pro Arg Val Gln Gly Gln
        435                 440                 445
```

-continued

```
Ala Ala Ser
    450


<210> SEQ ID NO 18
<211> LENGTH: 1539
<212> TYPE: DNA
<213> ORGANISM: Zea mays
<220> FEATURE:
<221> NAME/KEY: unsure
<222> LOCATION: (348)
<223> OTHER INFORMATION: n = A, C, G, or T

<400> SEQUENCE: 18

gcgctgcgcc gcgtggcgtc cacgcacctc ttctccccgc ggcaggtcgc cgcgtcggcc     60

gcgcagcgcg ccgtcatcgc gcgccagatg gtcggcgccg tcaaggagct gtcggcggcc    120

tcgccggggc ggcgcggcgg cgtcgaggtc cgccgcgtcc tgcgccgcgg ctccctgcac    180

agcgtcatgt ggtcggtgtt cggccggcgg tacgacctgg agctggaccc ggccagggag    240

agccccgaga cgcgggagct gaggcgactc gtggacgaag ggtacgacct gctgggccag    300

atcaactggt ccgaccacct ccccggcctc gcgtgcctcg acctgcanag caccagggcc    360

aggtgcgacc gcctcgtccc gctcgtgacc cgcttcgtcg gcggcatcgt cgacgagcac    420

cgcgcccgga accacctccg ctctgctccg cctgccgtcg tggacttcac cgacgtcctg    480

ctctcgctgc cggccgacga caggctcacc gacgctgaca tgatcgccgt cctctgggaa    540

atggtgttcc gtggaactga caccgtcgcc gtgctgatgg agtgggcgct ggccaggctc    600

gtgctgcacc ctgacgtgca ggcccgcgtc cacgacgagc tggaccgcgt ggtcggcccc    660

gaccgggccg tcaccgagtc cgacacggcg tcactggtct acctgcacgc cgtgatcaag    720

gaggtgctca ggatgcaccc gccgggcccg ctgctgtcgt gggcgcgctt ggccacgtca    780

gacgtgcacg tcgacgggca cctcatcccc gccgggacca ccgcgatggt gaacatgtgg    840

gccattacgc acgacccaga cgtgtgggcc gagccgacgg agttccagcc ggagaggttc    900

atggggtcca ccgagttccc gatcatgggg tcggacctca ggctcgcgcc gttcggggcg    960

ggccggcgca gctgccccgg gaagagcctc gccatggcca ccgtggcctt ctggctcgcg   1020

acgctgctgc acgagttcga gctgctcccc tcgcccgtcg acctgtcgga ggtgctcaag   1080

ctgtcgtgcg agatggccgt cccgctggcg ctggccgtga cggcgaggcc ccggcaagcg   1140

gttcagaagt cggttggggt atcagtctca ctgtgagcaa tagcatggcg ggctggcgct   1200

actgtacatg gaaagtgctt ctgcttgcag gttgctacta ctcggtcgac atgggtatat   1260

gcttttcatg ttactgtctt tgatgtgtat cgatcaggtg ccgaatgtga tactttggct   1320

tgtactgtta gctcttttcc tgggtgctct tttctttctt tttcttagta ctcgctgtaa   1380

gactcgtcaa atgtatatgc tggtttggat ggttttggat tgtagtcgca tactactagt   1440

agtattgcgc agttcaatgc ctaaatatgc tataatcaaa aaaaaaaaaa aaaaaaaaaa   1500

aaaaaaaaaa aaaaaaaaaa aaaaaaaaaa aaaaaaaaa                          1539


<210> SEQ ID NO 19
<211> LENGTH: 391
<212> TYPE: PRT
<213> ORGANISM: Zea mays
<220> FEATURE:
<221> NAME/KEY: UNSURE
<222> LOCATION: (116)
<223> OTHER INFORMATION: Xaa = any amino acid

<400> SEQUENCE: 19
```

-continued

```
Ala Leu Arg Arg Val Ala Ser Thr His Leu Phe Ser Pro Arg Gln Val
  1               5                  10                  15

Ala Ala Ser Ala Ala Gln Arg Ala Val Ile Ala Arg Gln Met Val Gly
             20                  25                  30

Ala Val Lys Glu Leu Ser Ala Ala Ser Pro Gly Arg Arg Gly Gly Val
         35                  40                  45

Glu Val Arg Arg Val Leu Arg Arg Gly Ser Leu His Ser Val Met Trp
     50                  55                  60

Ser Val Phe Gly Arg Arg Tyr Asp Leu Glu Leu Asp Pro Ala Arg Glu
 65                  70                  75                  80

Ser Pro Glu Thr Arg Glu Leu Arg Arg Leu Val Asp Glu Gly Tyr Asp
                 85                  90                  95

Leu Leu Gly Gln Ile Asn Trp Ser Asp His Leu Pro Gly Leu Ala Cys
            100                 105                 110

Leu Asp Leu Xaa Ser Thr Arg Ala Arg Cys Asp Arg Leu Val Pro Leu
        115                 120                 125

Val Thr Arg Phe Val Gly Gly Ile Val Asp Glu His Arg Ala Arg Asn
    130                 135                 140

His Leu Arg Ser Ala Pro Pro Ala Val Val Asp Phe Thr Asp Val Leu
145                 150                 155                 160

Leu Ser Leu Pro Ala Asp Asp Arg Leu Thr Asp Ala Asp Met Ile Ala
                165                 170                 175

Val Leu Trp Glu Met Val Phe Arg Gly Thr Asp Thr Val Ala Val Leu
            180                 185                 190

Met Glu Trp Ala Leu Ala Arg Leu Val Leu His Pro Asp Val Gln Ala
        195                 200                 205

Arg Val His Asp Glu Leu Asp Arg Val Val Gly Pro Asp Arg Ala Val
    210                 215                 220

Thr Glu Ser Asp Thr Ala Ser Leu Val Tyr Leu His Ala Val Ile Lys
225                 230                 235                 240

Glu Val Leu Arg Met His Pro Pro Gly Pro Leu Leu Ser Trp Ala Arg
                245                 250                 255

Leu Ala Thr Ser Asp Val His Val Asp Gly His Leu Ile Pro Ala Gly
            260                 265                 270

Thr Thr Ala Met Val Asn Met Trp Ala Ile Thr His Asp Pro Asp Val
        275                 280                 285

Trp Ala Glu Pro Thr Glu Phe Gln Pro Glu Arg Phe Met Gly Ser Thr
    290                 295                 300

Glu Phe Pro Ile Met Gly Ser Asp Leu Arg Leu Ala Pro Phe Gly Ala
305                 310                 315                 320

Gly Arg Arg Ser Cys Pro Gly Lys Ser Leu Ala Met Ala Thr Val Ala
                325                 330                 335

Phe Trp Leu Ala Thr Leu Leu His Glu Phe Glu Leu Leu Pro Ser Pro
            340                 345                 350

Val Asp Leu Ser Glu Val Leu Lys Leu Ser Cys Glu Met Ala Val Pro
        355                 360                 365

Leu Ala Leu Ala Val Thr Ala Arg Pro Arg Gln Ala Val Gln Lys Ser
    370                 375                 380

Val Gly Val Ser Val Ser Leu
385                 390
```

<210> SEQ ID NO 20
<211> LENGTH: 1764
<212> TYPE: DNA

-continued

<213> ORGANISM: Glycine max

<400> SEQUENCE: 20

```
gcacgaggtc ccttcttcct ctatctcttt ggctattagc aaacactctc atatttggtt     60
gttctagttc tcactaccat gtcaacccac attgaaagcc tgtgggtgtt ggccttagcc    120
tcaaaatgca ttcaagagaa cattgcatgg tcactcttga tcatcatggt cactctctgg    180
ctcaccatga ccttcttcta ctggtctcac cctggtggtc ctgcttgggg caaatactac    240
tactttaatt actggaaaaa aaccacctca accaacacaa acatcaacct taaaatgatt    300
atccctggtc ctagaggcta ccctttcatt gggagtatga gtctcatgac atccctcgca    360
caccaccgta ttgctgcggc gggggaagca tgcaacgcca ccaggctcat ggctttttcc    420
atgggtgaca cacgcgccat agtaacgtgc aaccccgatg tcgctaaaga gattctcaat    480
agttccactt ttgctgatcg tcccataaag gaatcagctt acagcctcat gttcaaccgc    540
gccatcggct tcgcccctta cggcgtctac tggcgtaccc tccgccgcat cgccgccacg    600
cacctcttct gccccaaaca aatcaaagcc tccgagctcc agcgcgctga aatcgccgcc    660
caaatgacaa actcattccg aaatcaccgt tgcagcggcg gtttcggaat ccgcagcgtg    720
ctcaagagag cgtcactgaa caacatgatg tggtcggtgt ttggacaaaa gtacaacctt    780
gacgagataa acaccgcaat ggacgagcta tccatgttgg tggaacaagg ctatgacttg    840
ttgggcaccc ttaattgggg agaccatatc cctttcctga aagactttga cctacagaaa    900
atccggttca cctgctccaa attagtccct caagtgaacc ggttcgttgg ttcaatcatc    960
gccgaccacc aggccgacac aacccaaacc aaccgcgatt tcgttcatgt tttgctctct   1020
ctccaaggtc ccgataaatt gtctcactcc gacatgattg ctgtcctctg ggaaatgata   1080
tttaggggga ccgacacggt ggcggttttg attgagtgga tactggcgag gatggtgctt   1140
catccggagg tgcaaaggaa ggtacaagag gagttggacg cggtggttag ggtggcgct    1200
ttgacggagg aggtcgtggc ggcgacggcg tatcttgcgg cggtggtgaa agaggttctg   1260
aggctgcacc cgccgggccc gcttctctcg tgggcccgct tggccatcac tgatacgacc   1320
attgatgggt atcacgtgcc tgcggggacc accgctatgg ttaatatgtg ggccatagca   1380
agggacccgg aggtgtggct ggacccactt gagttcaagc ccgagaggtt catgggtctg   1440
gaaaacgagt ttctgtttt  cgggtcggat ctgagactcg ctccattcgg ttcgggtcgg   1500
agaacatgcc ccgggaagac tttgggtttg agcaccgtaa ccttctgggt ggcttggctt   1560
ttgcatgagt ttgaatggct accgtctgat gaagccaagg ttgatctaac ggaggtgctg   1620
aggctctcgt gtgaaatggc taacccactc attgttaaag ttcgccctag gcatggatta   1680
agcacttaat gataaatataa ttaagcctat ctacgttatt aacttgaaat gttttaatgg  1740
gaaggaaaaa aaaaaaaaaa aaaa                                          1764
```

<210> SEQ ID NO 21
<211> LENGTH: 536
<212> TYPE: PRT
<213> ORGANISM: Glycine max

<400> SEQUENCE: 21

```
Met Ser Thr His Ile Glu Ser Leu Trp Val Leu Ala Leu Ala Ser Lys
  1               5                  10                  15

Cys Ile Gln Glu Asn Ile Ala Trp Ser Leu Leu Ile Ile Met Val Thr
             20                  25                  30

Leu Trp Leu Thr Met Thr Phe Phe Tyr Trp Ser His Pro Gly Gly Pro
```

-continued

```
        35                  40                  45

Ala Trp Gly Lys Tyr Tyr Tyr Phe Asn Tyr Trp Lys Lys Thr Thr Ser
     50                  55                  60

Thr Asn Thr Asn Ile Asn Leu Lys Met Ile Ile Pro Gly Pro Arg Gly
 65                  70                  75                  80

Tyr Pro Phe Ile Gly Ser Met Ser Leu Met Thr Ser Leu Ala His His
                 85                  90                  95

Arg Ile Ala Ala Ala Gly Glu Ala Cys Asn Ala Thr Arg Leu Met Ala
            100                 105                 110

Phe Ser Met Gly Asp Thr Arg Ala Ile Val Thr Cys Asn Pro Asp Val
        115                 120                 125

Ala Lys Glu Ile Leu Asn Ser Ser Thr Phe Ala Asp Arg Pro Ile Lys
    130                 135                 140

Glu Ser Ala Tyr Ser Leu Met Phe Asn Arg Ala Ile Gly Phe Ala Pro
145                 150                 155                 160

Tyr Gly Val Tyr Trp Arg Thr Leu Arg Arg Ile Ala Ala Thr His Leu
                165                 170                 175

Phe Cys Pro Lys Gln Ile Lys Ala Ser Glu Leu Gln Arg Ala Glu Ile
            180                 185                 190

Ala Ala Gln Met Thr Asn Ser Phe Arg Asn His Arg Cys Ser Gly Gly
        195                 200                 205

Phe Gly Ile Arg Ser Val Leu Lys Arg Ala Ser Leu Asn Asn Met Met
    210                 215                 220

Trp Ser Val Phe Gly Gln Lys Tyr Asn Leu Asp Glu Ile Asn Thr Ala
225                 230                 235                 240

Met Asp Glu Leu Ser Met Leu Val Glu Gln Gly Tyr Asp Leu Leu Gly
                245                 250                 255

Thr Leu Asn Trp Gly Asp His Ile Pro Phe Leu Lys Asp Phe Asp Leu
            260                 265                 270

Gln Lys Ile Arg Phe Thr Cys Ser Lys Leu Val Pro Gln Val Asn Arg
        275                 280                 285

Phe Val Gly Ser Ile Ile Ala Asp His Gln Ala Asp Thr Thr Gln Thr
    290                 295                 300

Asn Arg Asp Phe Val His Val Leu Leu Ser Leu Gln Gly Pro Asp Lys
305                 310                 315                 320

Leu Ser His Ser Asp Met Ile Ala Val Leu Trp Glu Met Ile Phe Arg
                325                 330                 335

Gly Thr Asp Thr Val Ala Val Leu Ile Glu Trp Ile Leu Ala Arg Met
            340                 345                 350

Val Leu His Pro Glu Val Gln Arg Lys Val Gln Glu Glu Leu Asp Ala
        355                 360                 365

Val Val Arg Gly Gly Ala Leu Thr Glu Glu Val Val Ala Ala Thr Ala
    370                 375                 380

Tyr Leu Ala Ala Val Val Lys Glu Val Leu Arg Leu His Pro Pro Gly
385                 390                 395                 400

Pro Leu Leu Ser Trp Ala Arg Leu Ala Ile Thr Asp Thr Thr Ile Asp
                405                 410                 415

Gly Tyr His Val Pro Ala Gly Thr Thr Ala Met Val Asn Met Trp Ala
            420                 425                 430

Ile Ala Arg Asp Pro Glu Val Trp Leu Asp Pro Leu Glu Phe Lys Pro
        435                 440                 445

Glu Arg Phe Met Gly Leu Glu Asn Glu Phe Ser Val Phe Gly Ser Asp
    450                 455                 460
```

-continued

```
Leu Arg Leu Ala Pro Phe Gly Ser Gly Arg Arg Thr Cys Pro Gly Lys
465                 470                 475                 480

Thr Leu Gly Leu Ser Thr Val Thr Phe Trp Val Ala Trp Leu Leu His
                485                 490                 495

Glu Phe Glu Trp Leu Pro Ser Asp Glu Ala Lys Val Asp Leu Thr Glu
            500                 505                 510

Val Leu Arg Leu Ser Cys Glu Met Ala Asn Pro Leu Ile Val Lys Val
        515                 520                 525

Arg Pro Arg His Gly Leu Ser Thr
    530                 535


<210> SEQ ID NO 22
<211> LENGTH: 1934
<212> TYPE: DNA
<213> ORGANISM: Glycine max

<400> SEQUENCE: 22

ctcttcttag ttccagcaca acaagctctt catttctccc acactttctt ttctttcacc     60

aaaaatgtca ccagatttca cacttttgtt cttcccggaa ctcatgcagt cccctatgat    120

cactttccaa gccaccctct gcgtccttct cttcaccctc atgttcacgc tgctcttcac    180

tcctggtggg cttccttggg cctgggcccg gcccagaccc atcatccctg gcccagtaac    240

tgccctgtta gggatcttta ctggctccac gcctcaccgt gctttatcca aactcgcccg    300

taattaccac gcggaaaaac tcatggcttt ctccatcggt ttaacccgtt tcgtcatctc    360

cagcgaaccg gagaccgcta aggagattct cggcagcccc agtttcgctg ataggccggt    420

gaaggaatcc gcctatgagc ttctcttcca ccgcgcaatg ggttttgcac cgtatgggga    480

gtactggagg aatttgagga gaatctcagc cctacatctc ttctccccga agagaatcac    540

cggctctgaa tccttcagga gcgaggttgg attaaaaatg gttgaacaag ttaagaaaac    600

catgagtgag aaccaacatg ttgaggttaa gaaaattcta cactttagtt cgttgaacaa    660

tgtgatgatg acggtgtttg gtaagtctta tgagttttac gagggtgagg gtttggagct    720

tgagggtttg gtgagtgaag ggtatgagtt gttgggtgtt tttaactgga gtgaccattt    780

tccggttttg ggtggttggg atttgcaggg tgtgaggaag aggtgtaggt gtttggttga    840

aaaggttaat gtttttgttg gaggggttat taaggagcat agggtgaaga gggagagggg    900

tgagtgtgtg aaggatgaag gaactgggga ttttgttgat gttttgcttg atttggagaa    960

ggaaaacagg ctcagtgaag ctgacatgat cgctgttctt tgggaaatga tatttagggg   1020

aactgacacg gtggcaattc tgctagagtg gactctggct cggatggttc tccaccctga   1080

aatccaagca aaggcacagc gcgaaataga cttcgtttgc ggatcctcca ggcccgtatc   1140

cgaagcagac attccgaacc tgcgctacct tcagtgcata gtaaaagaaa cccttcgtgt   1200

gcacccacca ggcccgctac tctcgtgggc tcgccttgct gtgcacgacg ttaccgtggg   1260

cggcaagcac gtgattccca agggcaccac cgcgatggtg aacatgtggg ccataaccca   1320

cgacgagagg gtgtgggccg agcccgagaa gtttaggccc gagcggtttg tggaggagga   1380

tgtgagcata atggggtctg atttgaggtt ggcacctttc gggtctggaa gaagagtgtg   1440

ccctgggaag gcccttggtt tggcctcggt tcatctttgg ctcgctcagt tgcttcaaaa   1500

ttttcattgg gtttcatctg atggtgtttc tgtggagttg gatgagtttc ttaagctttc   1560

tatggagatg aagaagccac tgtcttgcaa ggctgtgcct agggtttctg tttaggttta   1620

tgtgtgttgt tgggttgagt tggtttggtt tgtctgctta ggtttgtgga tgttgttccc   1680
```

-continued

```
aaggctgtgc ctagggtttc tgtttaggtt tatgtgtgtt gtttggtttg tctgtttagg   1740

tttatggatg ttgtttggtt gagttggttt ggtttgtgtt atctgctaag tttagttcaa   1800

gaaaagtagg gtttagagca cctttttatt aatcgctagg ggttgttatt ccgtgtacgg   1860

tttgtagtaa gttgtaaaag actagaagag aatgtaagag gttttgtttt gtgtgggtcg   1920

ttaaaaaaaa aaaa                                                      1934
```

```
<210> SEQ ID NO 23
<211> LENGTH: 516
<212> TYPE: PRT
<213> ORGANISM: Glycine max

<400> SEQUENCE: 23

Met Ser Pro Asp Phe Thr Leu Leu Phe Phe Pro Glu Leu Met Gln Ser
  1               5                  10                  15

Pro Met Ile Thr Phe Gln Ala Thr Leu Cys Val Leu Leu Phe Thr Leu
             20                  25                  30

Met Phe Thr Leu Leu Phe Thr Pro Gly Gly Leu Pro Trp Ala Trp Ala
         35                  40                  45

Arg Pro Arg Pro Ile Ile Pro Gly Pro Val Thr Ala Leu Leu Gly Ile
     50                  55                  60

Phe Thr Gly Ser Thr Pro His Arg Ala Leu Ser Lys Leu Ala Arg Asn
 65                  70                  75                  80

Tyr His Ala Glu Lys Leu Met Ala Phe Ser Ile Gly Leu Thr Arg Phe
                 85                  90                  95

Val Ile Ser Ser Glu Pro Glu Thr Ala Lys Glu Ile Leu Gly Ser Pro
            100                 105                 110

Ser Phe Ala Asp Arg Pro Val Lys Glu Ser Ala Tyr Glu Leu Leu Phe
        115                 120                 125

His Arg Ala Met Gly Phe Ala Pro Tyr Gly Glu Tyr Trp Arg Asn Leu
    130                 135                 140

Arg Arg Ile Ser Ala Leu His Leu Phe Ser Pro Lys Arg Ile Thr Gly
145                 150                 155                 160

Ser Glu Ser Phe Arg Ser Glu Val Gly Leu Lys Met Val Glu Gln Val
                165                 170                 175

Lys Lys Thr Met Ser Glu Asn Gln His Val Glu Val Lys Lys Ile Leu
            180                 185                 190

His Phe Ser Ser Leu Asn Asn Val Met Met Thr Val Phe Gly Lys Ser
        195                 200                 205

Tyr Glu Phe Tyr Glu Gly Glu Gly Leu Glu Leu Glu Gly Leu Val Ser
    210                 215                 220

Glu Gly Tyr Glu Leu Leu Gly Val Phe Asn Trp Ser Asp His Phe Pro
225                 230                 235                 240

Val Leu Gly Trp Leu Asp Leu Gln Gly Val Arg Lys Arg Cys Arg Cys
                245                 250                 255

Leu Val Glu Lys Val Asn Val Phe Val Gly Gly Val Ile Lys Glu His
            260                 265                 270

Arg Val Lys Arg Glu Arg Gly Glu Cys Val Lys Asp Glu Gly Thr Gly
        275                 280                 285

Asp Phe Val Asp Val Leu Leu Asp Leu Glu Lys Glu Asn Arg Leu Ser
    290                 295                 300

Glu Ala Asp Met Ile Ala Val Leu Trp Glu Met Ile Phe Arg Gly Thr
305                 310                 315                 320
```

-continued

```
Asp Thr Val Ala Ile Leu Leu Glu Trp Thr Leu Ala Arg Met Val Leu
                325                 330                 335

His Pro Glu Ile Gln Ala Lys Ala Gln Arg Glu Ile Asp Phe Val Cys
            340                 345                 350

Gly Ser Ser Arg Pro Val Ser Glu Ala Asp Ile Pro Asn Leu Arg Tyr
        355                 360                 365

Leu Gln Cys Ile Val Lys Glu Thr Leu Arg Val His Pro Pro Gly Pro
    370                 375                 380

Leu Leu Ser Trp Ala Arg Leu Ala Val His Asp Val Thr Val Gly Gly
385                 390                 395                 400

Lys His Val Ile Pro Lys Gly Thr Thr Ala Met Val Asn Met Trp Ala
                405                 410                 415

Ile Thr His Asp Glu Arg Val Trp Ala Glu Pro Glu Lys Phe Arg Pro
            420                 425                 430

Glu Arg Phe Val Glu Glu Asp Val Ser Ile Met Gly Ser Asp Leu Arg
        435                 440                 445

Leu Ala Pro Phe Gly Ser Gly Arg Arg Val Cys Pro Gly Lys Ala Leu
    450                 455                 460

Gly Leu Ala Ser Val His Leu Trp Leu Ala Gln Leu Leu Gln Asn Phe
465                 470                 475                 480

His Trp Val Ser Ser Asp Gly Val Ser Val Glu Leu Asp Glu Phe Leu
                485                 490                 495

Lys Leu Ser Met Glu Met Lys Lys Pro Leu Ser Cys Lys Ala Val Pro
            500                 505                 510

Arg Val Ser Val
        515
```

<210> SEQ ID NO 24
<211> LENGTH: 1905
<212> TYPE: DNA
<213> ORGANISM: Glycine max

<400> SEQUENCE: 24

```
gcacgagctt cctctttctc tctttaaata cacacacaca cacactcact ttcttgcttg     60

ttctaactac catgacaacc cacattgata acctgtgggt gttggccttg gtctcaaaat    120

gcacacaaga gaacattgca tggtcactct tgaccatcat ggtcactctc tggctctcca    180

tgaccttctt ctgctggtct catcccggtg gtcctgcttg gggcaagtac tactcctttc    240

attactggaa aaaaacaacc acaaccacaa cctcaacctc aaacaacaca aactccaaca    300

accttaaaat gattcccggt cccaaaggct atcctttcat tggaagcatg agcctcatga    360

catcccttgc acaccaccgt attgctgccg ctgctcaagc atgcaaagcc accaggctca    420

tggccttctc catgggtgac acgcgtgtca tcgtcacgtg ccaccccac gtggccaagg    480

agattcttaa cagctccgtc ttcgccgatc gtcccataaa ggaatcagcc tacagcctca    540

tgttcaaccg cgccatcggc tttgcccctt acggcgttta ctggcgcacc ctccgccgca    600

tcgccgccac gcacctcttc tgccccaaac aaatcaaggc ctcggagctc cagcgcgccg    660

aaatcgccgc ccagatgacc cactcgttcc gaaaccgccg cggcggtttc ggaatccgca    720

gcgttctcaa gagagcgtcg ctcaacaaca tgatgtggtc ggtgtttgga caaagatatg    780

accttgacga gacaaacact tcagtggacg agttatcccg gttagtggaa caaggctatg    840

acttgttggg taccccttaat tggggagacc atatcccttt tctgaaagac tttgaccttc    900

aaaaaatccg gtttacctgc tccaaactcg tcccccaagt gaaccggttc gtaggttcaa    960
```

-continued

```
tcatcgccga ccaccaaacc gacacaaccc aaaccaaccg cgatttcgtt catgttttgc   1020

tctctctcca aggtcccgat aaattgtctc actccgacat gattgctgtc ctctgggaaa   1080

tgatatttag ggggaccgac acggtggcgg ttttgattga gtggattatg gcaaggatgg   1140

tgcttcatcc ggaggtacaa aggagggtgc aagaggagct ggacgcggtg gttggaggtg   1200

gtgcgcgcgc tttgaaggag gaggacgtgg cggcgacggc gtatcttctg gcggtggtga   1260

aggaggttct gaggctgcac cctccaggcc cgcttctctc gtgggcccgc ttggccatca   1320

ccgatacgac cattgatggg tataacgtgc ccgcgggaac caccgccatg gttaatatgt   1380

gggccatagg aagggacccg gaggtgtggc tggacccact tgatttcaag cccgagaggt   1440

tcatgggcct ggaggcggag ttttctgttc tcgggtcgga tctgaggctg gctccattcg   1500

ggtcgggtag aagaacctgc cccggaaaga ctttgggttt gagcaccgtg actttctggg   1560

tggcgaggct tttgcacgag tttgaatggc taccatctga tgaggggaag gttgatctaa   1620

cggaggtgct gaggctctcg tgtgaaatgg ctaacccgct ctatgttaaa gttcgcccta   1680

ggcgtggatt aagtacttaa taataataat aataataata ataataataa taataatgtt   1740

aagtagcagg tgcatggccc tttggagcca ctaaatgtta agtgaatcca tgaatcaagg   1800

tagaaagttt gagttggctc tgtctctata atatgggtca acgggttttt gtttaaaaaa   1860

aaaaaaaaaa aaaaaaaaaa aaaaaaaaaa aaaaaaaaaa aaaaa                   1905


<210> SEQ ID NO 25
<211> LENGTH: 542
<212> TYPE: PRT
<213> ORGANISM: Glycine max

<400> SEQUENCE: 25

Met Thr Thr His Ile Asp Asn Leu Trp Val Leu Ala Leu Val Ser Lys
1               5                   10                  15

Cys Thr Gln Glu Asn Ile Ala Trp Ser Leu Leu Thr Ile Met Val Thr
            20                  25                  30

Leu Trp Leu Ser Met Thr Phe Phe Cys Trp Ser His Pro Gly Gly Pro
        35                  40                  45

Ala Trp Gly Lys Tyr Tyr Ser Phe His Tyr Trp Lys Lys Thr Thr Thr
    50                  55                  60

Thr Thr Thr Ser Thr Ser Asn Asn Thr Asn Ser Asn Asn Leu Lys Met
65                  70                  75                  80

Ile Pro Gly Pro Lys Gly Tyr Pro Phe Ile Gly Ser Met Ser Leu Met
                85                  90                  95

Thr Ser Leu Ala His His Arg Ile Ala Ala Ala Ala Gln Ala Cys Lys
            100                 105                 110

Ala Thr Arg Leu Met Ala Phe Ser Met Gly Asp Thr Arg Val Ile Val
        115                 120                 125

Thr Cys His Pro His Val Ala Lys Glu Ile Leu Asn Ser Ser Val Phe
    130                 135                 140

Ala Asp Arg Pro Ile Lys Glu Ser Ala Tyr Ser Leu Met Phe Asn Arg
145                 150                 155                 160

Ala Ile Gly Phe Ala Pro Tyr Gly Val Tyr Trp Arg Thr Leu Arg Arg
                165                 170                 175

Ile Ala Ala Thr His Leu Phe Cys Pro Lys Gln Ile Lys Ala Ser Glu
            180                 185                 190

Leu Gln Arg Ala Glu Ile Ala Ala Gln Met Thr His Ser Phe Arg Asn
        195                 200                 205
```

-continued

```
Arg Arg Gly Gly Phe Gly Ile Arg Ser Val Leu Lys Arg Ala Ser Leu
    210                 215                 220

Asn Asn Met Met Trp Ser Val Phe Gly Gln Arg Tyr Asp Leu Asp Glu
225                 230                 235                 240

Thr Asn Thr Ser Val Asp Glu Leu Ser Arg Leu Val Glu Gln Gly Tyr
                245                 250                 255

Asp Leu Leu Gly Thr Leu Asn Trp Gly Asp His Ile Pro Phe Leu Lys
            260                 265                 270

Asp Phe Asp Leu Gln Lys Ile Arg Phe Thr Cys Ser Lys Leu Val Pro
        275                 280                 285

Gln Val Asn Arg Phe Val Gly Ser Ile Ile Ala Asp His Gln Thr Asp
    290                 295                 300

Thr Thr Gln Thr Asn Arg Asp Phe Val His Val Leu Leu Ser Leu Gln
305                 310                 315                 320

Gly Pro Asp Lys Leu Ser His Ser Asp Met Ile Ala Val Leu Trp Glu
                325                 330                 335

Met Ile Phe Arg Gly Thr Asp Thr Val Ala Val Leu Ile Glu Trp Ile
            340                 345                 350

Met Ala Arg Met Val Leu His Pro Glu Val Gln Arg Arg Val Gln Glu
        355                 360                 365

Glu Leu Asp Ala Val Val Gly Gly Gly Ala Arg Ala Leu Lys Glu Glu
    370                 375                 380

Asp Val Ala Ala Thr Ala Tyr Leu Leu Ala Val Val Lys Glu Val Leu
385                 390                 395                 400

Arg Leu His Pro Pro Gly Pro Leu Leu Ser Trp Ala Arg Leu Ala Ile
                405                 410                 415

Thr Asp Thr Thr Ile Asp Gly Tyr Asn Val Pro Ala Gly Thr Thr Ala
            420                 425                 430

Met Val Asn Met Trp Ala Ile Gly Arg Asp Pro Glu Val Trp Leu Asp
        435                 440                 445

Pro Leu Asp Phe Lys Pro Glu Arg Phe Met Gly Leu Glu Ala Glu Phe
    450                 455                 460

Ser Val Leu Gly Ser Asp Leu Arg Leu Ala Pro Phe Gly Ser Gly Arg
465                 470                 475                 480

Arg Thr Cys Pro Gly Lys Thr Leu Gly Leu Ser Thr Val Thr Phe Trp
                485                 490                 495

Val Ala Arg Leu Leu His Glu Phe Glu Trp Leu Pro Ser Asp Glu Gly
            500                 505                 510

Lys Val Asp Leu Thr Glu Val Leu Arg Leu Ser Cys Glu Met Ala Asn
        515                 520                 525

Pro Leu Tyr Val Lys Val Arg Pro Arg Arg Gly Leu Ser Thr
    530                 535                 540
```

<210> SEQ ID NO 26
<211> LENGTH: 2924
<212> TYPE: DNA
<213> ORGANISM: Glycine max

<400> SEQUENCE: 26

```
gcacgagaaa aaagctcatg acattgagtc taggaacaaa tccagttgtt atcagcagtc      60

acccagaaac cgcaagagaa attctttgtg ggtcgaactt cgctgaccga cccgttaaag     120

aatcggcccg aatgctcatg tttgagcgtg ccattggatt tgctccatat gggacttatt     180

ggcgccacct acgtaaagtg gcaatcaccc acatgttctc tccaaggagg atttctgact     240
```

-continued

```
tggagagtct ccgacaacat gtggttggtg aaatggtgat gaggatatgg aaggagatgg    300
gggacaaagg ggtggtagag gttcgaggca tattgtatga agggtctttg agccacatgt    360
tggagtgtgt gtttggtatt aataattctc taggatcaca aacaaaggag gcgttgggtg    420
atatggttga ggaagggtat gacttgattg ccaagtttaa ttgggcagac tattttcctt    480
tcgggttttt ggactttcac ggggtcaaga gaaggtgtca caaattggca actaaggtca    540
atagtgtggt gggtaaaatt gtggaagaaa gaaaaaattc agggaagtac gttggacaaa    600
atgattttct tagtgccttg ttattgttgc ctaaagagga aagcataggt gattcagatg    660
tagtggctat cttatgggaa atgatatttc ggggaacaga cacaattgct atacttttag    720
aatggatcat ggccatgatg gttttacacc aagacgtaca aatgaaagct cgtcaagaga    780
tcgactcatg catcaagcaa aacggttaca tgcgagactc agacattcca aacctccctt    840
acctccaggc catagtgaag gaggttctcc gattgcaccc accaggccca ttactttcct    900
gggctcgcct cgcaatccat gatgtccacg tggacaaggt catcgtgcca gctggcacaa    960
ctgcaatggt taacatgtgg gctatatcac atgactcatc catttgggag gacccgtggg   1020
cctttaagcc cgaaagattc atgaaagaag atgtgtcgat catggggtcg gacatgagac   1080
ttgcaccatt tggtgcagga cgtagggtgt gcccaggaaa aacattaggc ttagccacag   1140
ttcatctatg gcttgcacaa cttcttcacc atttcatatg gattccagtg caacccgtgg   1200
atctttcaga atgcctaaag ctctcgctcg aaatgaaaaa gcctttacga tgccaagtga   1260
ttcgcaggtt caacaccata agctcttgaa ctcaacaaga taaattaatg cacaataaag   1320
gatatcatta tcgatgtaac tgttgtgata aaaaaaaatt aaagtctttg atttgggtgg   1380
aagttatgta atgttgtaaa aatatatcaa gtactgagag atcccctcat aatttcccca   1440
aagcgtaacc atgtgtgaat aaattttgag ctagtagggt tgcagccacg agtaagtctt   1500
cccttgttat tgtgtagcca gaatgccgca aaacttccat gcctaagcga actgttgaga   1560
gtacgtttcg atttctgact gtgttagcct ggaagtgctt gtcccaacct tgtttctgag   1620
catgaacgcc cgcaagccaa catgttagtt gaagcatcag ggcgattagc agcatgatat   1680
caaaacgctc tgagctgctc gttcggctat ggcgtaggcc tagtccgtag gcaggacttt   1740
tcaagtctcg gaaggtttct tcaatctgca ttcgcttcga atagatatta acaagttgtt   1800
tgggtgttcg aatttcaaca ggtaagttag ttgctagaac ccatggctcc tttgccgacg   1860
ctgagtagat tttaggtgac gggtggtgac aatgagtccg tgtcgagcgc tgattttttc   1920
ggcctttaga gcgagattta tacaatagaa tttggcatga gattggattg cttttagtca   1980
gcctcttata gcctaaagtc tttgagtgac tagatgacat atcatgtaag ttgctgatag   2040
gtttccagtt ttccgctcct aggtctgcat attgtacttt tcctcttact cgacttaacc   2100
agtaccaacc cagcttctca acggatttat accatggcac tttaaagcca gcatcactga   2160
caatgagcgg tgtggtgtta ctcggtagaa tgctcgcaag gtcggctaga aattggtcat   2220
gagctttctt tgaacattgc tctgaaagcg ggaacgcttt ctcataaaga gtaacagaac   2280
gaccgtgtag tgcgactgaa gctcgcaata ccataagtcg tttttgctca cgaatatcag   2340
accagtcaac aagtacaatg ggcatcgtat tgcccgaaca gataaagcta gcatgccaac   2400
ggtatacagc gagtcgctct ttgtggaggt gacgattacc taacaatcgg tcgattcgtt   2460
tgatgttatg ttttgttctc gctttggttg gcaggttacg gccaagttcg gtaagagtga   2520
gagttttaca gtcaagtaat gcgtggcaag ccaacgttaa gctgttgagt cgttttaagt   2580
gtaattcggg gcagaattgg taaagagagt cgtgtaaaat atcgagttcg cacatcttgt   2640
```

-continued

```
tgtctgatta ttgatttttc gcgaaaccat ttgatcatat gacaagatgt gtatccacct   2700

taacttaatg atttttacca aaatcattag gggattcatc agtatcaagt atgtagtatg   2760

cgttgagctc aagatagtcc aagaaatggg ctaatgaatg gattgatact atctctcttt   2820

gaaagtacac cacgtacaat attggatcta ataaagtcgc atggtttttg taaaaaaaaa   2880

aaaaaaaaaa aaaaaaaaaa aaaaaaaaaa aaaaaaaaaa aaaa                    2924


<210> SEQ ID NO 27
<211> LENGTH: 423
<212> TYPE: PRT
<213> ORGANISM: Glycine max

<400> SEQUENCE: 27

Met Thr Leu Ser Leu Gly Thr Asn Pro Val Val Ile Ser Ser His Pro
  1               5                  10                  15

Glu Thr Ala Arg Glu Ile Leu Cys Gly Ser Asn Phe Ala Asp Arg Pro
             20                  25                  30

Val Lys Glu Ser Ala Arg Met Leu Met Phe Glu Arg Ala Ile Gly Phe
         35                  40                  45

Ala Pro Tyr Gly Thr Tyr Trp Arg His Leu Arg Lys Val Ala Ile Thr
     50                  55                  60

His Met Phe Ser Pro Arg Arg Ile Ser Asp Leu Glu Ser Leu Arg Gln
 65                  70                  75                  80

His Val Val Gly Glu Met Val Met Arg Ile Trp Lys Glu Met Gly Asp
                 85                  90                  95

Lys Gly Val Val Glu Val Arg Gly Ile Leu Tyr Glu Gly Ser Leu Ser
            100                 105                 110

His Met Leu Glu Cys Val Phe Gly Ile Asn Asn Ser Leu Gly Ser Gln
        115                 120                 125

Thr Lys Glu Ala Leu Gly Asp Met Val Glu Glu Gly Tyr Asp Leu Ile
    130                 135                 140

Ala Lys Phe Asn Trp Ala Asp Tyr Phe Pro Phe Gly Phe Leu Asp Phe
145                 150                 155                 160

His Gly Val Lys Arg Arg Cys His Lys Leu Ala Thr Lys Val Asn Ser
                165                 170                 175

Val Val Gly Lys Ile Val Glu Glu Arg Lys Asn Ser Gly Lys Tyr Val
            180                 185                 190

Gly Gln Asn Asp Phe Leu Ser Ala Leu Leu Leu Leu Pro Lys Glu Glu
        195                 200                 205

Ser Ile Gly Asp Ser Asp Val Val Ala Ile Leu Trp Glu Met Ile Phe
    210                 215                 220

Arg Gly Thr Asp Thr Ile Ala Ile Leu Leu Glu Trp Ile Met Ala Met
225                 230                 235                 240

Met Val Leu His Gln Asp Val Gln Met Lys Ala Arg Gln Glu Ile Asp
                245                 250                 255

Ser Cys Ile Lys Gln Asn Gly Tyr Met Arg Asp Ser Asp Ile Pro Asn
            260                 265                 270

Leu Pro Tyr Leu Gln Ala Ile Val Lys Glu Val Leu Arg Leu His Pro
        275                 280                 285

Pro Gly Pro Leu Leu Ser Trp Ala Arg Leu Ala Ile His Asp Val His
    290                 295                 300

Val Asp Lys Val Ile Val Pro Ala Gly Thr Thr Ala Met Val Asn Met
305                 310                 315                 320
```

-continued

```
Trp Ala Ile Ser His Asp Ser Ser Ile Trp Glu Asp Pro Trp Ala Phe
                325                 330                 335

Lys Pro Glu Arg Phe Met Lys Glu Asp Val Ser Ile Met Gly Ser Asp
            340                 345                 350

Met Arg Leu Ala Pro Phe Gly Ala Gly Arg Arg Val Cys Pro Gly Lys
        355                 360                 365

Thr Leu Gly Leu Ala Thr Val His Leu Trp Leu Ala Gln Leu Leu His
    370                 375                 380

His Phe Ile Trp Ile Pro Val Gln Pro Val Asp Leu Ser Glu Cys Leu
385                 390                 395                 400

Lys Leu Ser Leu Glu Met Lys Lys Pro Leu Arg Cys Gln Val Ile Arg
                405                 410                 415

Arg Phe Asn Thr Ile Ser Ser
            420


<210> SEQ ID NO 28
<211> LENGTH: 528
<212> TYPE: DNA
<213> ORGANISM: Helianthus sp.
<220> FEATURE:
<221> NAME/KEY: unsure
<222> LOCATION: (476)
<223> OTHER INFORMATION: n = A, C, G, or T
<220> FEATURE:
<221> NAME/KEY: unsure
<222> LOCATION: (513)..(514)..(515)..(516)..(517)
<223> OTHER INFORMATION: n = A, C, G, or T
<220> FEATURE:
<221> NAME/KEY: unsure
<222> LOCATION: (519)..(520)..(521)
<223> OTHER INFORMATION: n = A, C, G, or T
<220> FEATURE:
<221> NAME/KEY: unsure
<222> LOCATION: (525)..(526)..(527)..(528)
<223> OTHER INFORMATION: n = A, C, G, or T

<400> SEQUENCE: 28

gcacgagtgg cattgcaaaa taggtgtgtc agatatgact gatgaaggtg ggaacccgat      60

ctggaagaac cgagttttga gtcaacagct ccgattttgc ggaccggccc attaaggaat     120

ctgcttatga actgttgttt caccgggcta tggggtttgc accctatggt gactactgga     180

ggagtttgag gagaatctcg gcgacccatt tgtttagccc gaaacgggtt gctgggtttg     240

gggtgtttcg tgaaactatt gggttgaaaa tggtgggtca ggttgtgtcc accatggaac     300

aaaacggtgt cgtggaggtt aaaaagattc ttcactttgg ttccttaaac aatgtcatga     360

tgtctgtgtt tggaaggttg tatgattttg gtgaaaatgg tggtgagggg tgtgagcttg     420

aggaacttgt gagtgaaggt tatgagttgt tggggatatt taactggagt gaccantttc     480

cggttgttag ttggtttgat ttgcaaggtg tcnnnnngnn ntgtnnnn                  528


<210> SEQ ID NO 29
<211> LENGTH: 144
<212> TYPE: PRT
<213> ORGANISM: Helianthus sp.
<220> FEATURE:
<221> NAME/KEY: UNSURE
<222> LOCATION: (132)
<223> OTHER INFORMATION: Xaa = any amino acid

<400> SEQUENCE: 29

Val Asn Ser Ser Asp Phe Ala Asp Arg Pro Ile Lys Glu Ser Ala Tyr
  1               5                  10                  15

Glu Leu Leu Phe His Arg Ala Met Gly Phe Ala Pro Tyr Gly Asp Tyr
```

-continued

```
            20                  25                  30

Trp Arg Ser Leu Arg Arg Ile Ser Ala Thr His Leu Phe Ser Pro Lys
        35                  40                  45

Arg Val Ala Gly Phe Gly Val Phe Arg Glu Thr Ile Gly Leu Lys Met
    50                  55                  60

Val Gly Gln Val Val Ser Thr Met Glu Gln Asn Gly Val Val Glu Val
 65                  70                  75                  80

Lys Lys Ile Leu His Phe Gly Ser Leu Asn Asn Val Met Met Ser Val
                85                  90                  95

Phe Gly Arg Leu Tyr Asp Phe Gly Glu Asn Gly Gly Glu Gly Cys Glu
            100                 105                 110

Leu Glu Glu Leu Val Ser Glu Gly Tyr Glu Leu Leu Gly Ile Phe Asn
        115                 120                 125

Trp Ser Asp Xaa Phe Pro Val Val Ser Trp Phe Asp Leu Gln Gly Val
    130                 135                 140
```

<210> SEQ ID NO 30
<211> LENGTH: 457
<212> TYPE: DNA
<213> ORGANISM: Helianthus sp.
<220> FEATURE:
<221> NAME/KEY: unsure
<222> LOCATION: (272)
<223> OTHER INFORMATION: n = A, C, G, or T
<220> FEATURE:
<221> NAME/KEY: unsure
<222> LOCATION: (447)
<223> OTHER INFORMATION: n = A, C, G, or T

<400> SEQUENCE: 30

```
gctatcgaaa gcccgatcga aaacaacaat tcccggccct tccggtatcc ctatactcgg     60

tctcatattt gccttcacat cttccatgac tcacagaacc cttgcaaaac tctctgtagc    120

atttaatgct acacatttaa tggcgttctc cgtcggattg actcgctttg ttatctcgag    180

tcacccggag accgccaaag agatcctcaa cagctctgcg ttcgcggacc ggcccgttaa    240

ggagtccgcg tacgagctgt tgtttcataa anccatgggg ttcgctccgt acggggaata    300

ttggcgaaac cttaggcgga tatcagctat tcatatgtta agcccgaaaa ggggtatccg    360

ggtcccggga ttttttttcgg ggctaaaaac aagggctgaa agtttgggtg aaatcaagat    420

tctcctaact ttccaatgaa aattgtnaaa gggttcc                             457
```

<210> SEQ ID NO 31
<211> LENGTH: 117
<212> TYPE: PRT
<213> ORGANISM: Helianthus sp.
<220> FEATURE:
<221> NAME/KEY: UNSURE
<222> LOCATION: (91)
<223> OTHER INFORMATION: Xaa = any amino acid

<400> SEQUENCE: 31

```
Leu Ser Lys Ala Arg Ser Lys Thr Thr Ile Pro Gly Pro Ser Gly Ile
  1               5                  10                  15

Pro Ile Leu Gly Leu Ile Phe Ala Phe Thr Ser Ser Met Thr His Arg
            20                  25                  30

Thr Leu Ala Lys Leu Ser Val Ala Phe Asn Ala Thr His Leu Met Ala
        35                  40                  45

Phe Ser Val Gly Leu Thr Arg Phe Val Ile Ser Ser His Pro Glu Thr
    50                  55                  60
```

-continued

```
Ala Lys Glu Ile Leu Asn Ser Ser Ala Phe Ala Asp Arg Pro Val Lys
 65                  70                  75                  80

Glu Ser Ala Tyr Glu Leu Leu Phe His Lys Xaa Met Gly Phe Ala Pro
                 85                  90                  95

Tyr Gly Glu Tyr Trp Arg Asn Leu Arg Arg Ile Ser Ala Ile His Met
            100                 105                 110

Leu Ser Pro Lys Arg
        115


<210> SEQ ID NO 32
<211> LENGTH: 615
<212> TYPE: DNA
<213> ORGANISM: Triticum aestivum
<220> FEATURE:
<221> NAME/KEY: unsure
<222> LOCATION: (24)
<223> OTHER INFORMATION: n = A, C, G, or T
<220> FEATURE:
<221> NAME/KEY: unsure
<222> LOCATION: (83)
<223> OTHER INFORMATION: n = A, C, G, or T
<220> FEATURE:
<221> NAME/KEY: unsure
<222> LOCATION: (492)
<223> OTHER INFORMATION: n = A, C, G, or T
<220> FEATURE:
<221> NAME/KEY: unsure
<222> LOCATION: (515)
<223> OTHER INFORMATION: n = A, C, G, or T
<220> FEATURE:
<221> NAME/KEY: unsure
<222> LOCATION: (543)
<223> OTHER INFORMATION: n = A, C, G, or T
<220> FEATURE:
<221> NAME/KEY: unsure
<222> LOCATION: (558)
<223> OTHER INFORMATION: n = A, C, G, or T
<220> FEATURE:
<221> NAME/KEY: unsure
<222> LOCATION: (578)
<223> OTHER INFORMATION: n = A, C, G, or T

<400> SEQUENCE: 32

gggacgcgcc gctcgagttc cggncggagc ggttcctggc cggcggggag gccccggacg     60

tgtccgtgct cggcgccgac ggncggctcg tgccgttcgg gtccggacgg aggagctgcc    120

cgggcaagtc cctggccatg accacggtga ccgcgtggat ggccaccctg ctgcacgagt    180

tcgagtgggc gccggcggcg cccggcgtcg acctgtcgga ggtgctccgc ctgtcgtgcg    240

agatggcggc gccgctccag gtccgggcgc gcccgaggcg cgacgcgtga tgtgctcgtc    300

gcgccatggc cggccggtcg actcgaccca ccgtccctac tacagtacgt agctcgtagc    360

ccgtgacccc gtgcttcacg aaagtgaata attaaagctg ccggcgtaaa atgtacgtgc    420

gccgagcgca gctcagtgtt gagtttcttt ctaacgtgtg tgatgtctgt gctatgtaat    480

gtaacccatc angtgtgagc gtgagagtga ctgantgagg ttcacatgtg tacaaaattg    540

canaacaaaa tctataanag atttttgcgg agtgtgcnat agtacacgtt ggggggggccc    600

ggtaccattc cccta                                                     615


<210> SEQ ID NO 33
<211> LENGTH: 95
<212> TYPE: PRT
<213> ORGANISM: Triticum aestivum
<220> FEATURE:
<221> NAME/KEY: UNSURE
<222> LOCATION: (8)
<223> OTHER INFORMATION: Xaa = any amino acid
```

-continued

<400> SEQUENCE: 33

```
Asp Ala Pro Leu Glu Phe Arg Xaa Glu Arg Phe Leu Ala Gly Gly Glu
  1               5                  10                  15

Ala Pro Asp Val Ser Val Leu Gly Ala Asp Gly Arg Leu Val Pro Phe
             20                  25                  30

Gly Ser Gly Arg Arg Ser Cys Pro Gly Lys Ser Leu Ala Met Thr Thr
         35                  40                  45

Val Thr Ala Trp Met Ala Thr Leu Leu His Glu Phe Glu Trp Ala Pro
     50                  55                  60

Ala Ala Pro Gly Val Asp Leu Ser Glu Val Leu Arg Leu Ser Cys Glu
 65                  70                  75                  80

Met Ala Ala Pro Leu Gln Val Arg Ala Arg Pro Arg Arg Asp Ala
                 85                  90                  95
```

<210> SEQ ID NO 34
<211> LENGTH: 1930
<212> TYPE: DNA
<213> ORGANISM: Aquilegia vulgaris

<400> SEQUENCE: 34

```
gcacgaggct ctctttcacg aaaaccacct ttctcttttt ctctctctac cttcaaaacc     60

actaataatg tcttcagaaa accttctttt ctttctccct tcatcaagct ttgaactttc    120

actctgtttt cttcttcttg tagccatttt tggcttttgg ttagcacctg gtggtttagc    180

ttgggctatt tcaaagactc attctcaagt tcaagctaaa accgccattc ctggaccatc    240

tgggtttcct ttattgggtt tggtctttgc ttttactggt tctactactc atagagtttt    300

agcaaatctt gctaaaacct ttaaagctat tcctttaatg gctttttctg ttggttttac    360

tcgttttatc atatcaagtt gtcctgatac agcaaaagag attcttaata gttcttcttt    420

tgctgatcga cctgttaagg aatctgctta tgaacttttg tttcacagag caatgggttt    480

tgctcctttt ggtgaatatt ggaggaatct gagaagaatc tcagctaccc atttattcag    540

tccaaagaga ataaccggtt ttgctacatt tcgaagtgaa ataggagaaa aaatgattaa    600

tgagattaaa tgtcaaatgg ggttaaatgg ggaagttgaa gttaaaaggg tattacactt    660

tgggtcttta aacaatgtga tgatgagtgt ttttggaacg ttttatgatt ttaaacaact    720

taatggtgat gggtttaaac ttgaagagtt ggtgagtgaa gggtatgagt tgcttgggat    780

ttttaactgg agtgatcact ttcctcttat gggctggttg gatttgcaag gagtaaggaa    840

gagaagcaga gtgttggttt ctaaggtgaa tatttttgtt ggaaaaatta ttgaagaaca    900

cagaaacaga aggattaatg gtgttttggg tcaagaatgt gttggtgact ttgttgatgt    960

cttgcttgat ttggagaaag aacatagtct cagtgactct gacatgattg ctgttctttg   1020

ggaaatgatc tttaggggca cagacacagt agcaatcctc ttagagtgga ttcttgcaag   1080

aatggcccta catccagata ttcaagcaaa agcccaatct gaaattgaca ctgtcgttgg   1140

cactaatcga ctagtatctg attctgactt acccaacctt ccttatctcc aagcagtagt   1200

gaaggaatcc ttaagggtgc accctcctgg ccccctcttg tcgtgggcac gactagctat   1260

ccatgatgtc catattggga agaactttat cccagctggg actactgcta tggtgaatat   1320

gtgggcaatc actcatgatg aaagtatttg gtctgagcca aatgaattta aacccgagcg   1380

attcatcgat gaagatgtga gcattatggg gtctgatctg aggttggcac cttttgggtc   1440

tggaaggagg gtttgtcctg gaaaggcttt gggtatggct actgtgcagc tatggttggg   1500
```

-continued

```
tcagttactt caaagtttca aatgggttcc ttctgaaggt ggtgtggact tgtctgagtg   1560

tcttaatctg tctctggaaa tgaagaagcc tttgatctgc aaggctattc caaggtttgc   1620

ctgaagttta cctatgatga tggggaggag tacttggttc ttaaaatttg ttttgttcct   1680

ctccttttag ttgtgttcta ggcttctagc taggatcata tggtttttac ttttgtgtct   1740

tttgtgtcct taaaggttta taggtgaaag taggattagt agtaatgcca gattcaggag   1800

ctaaaggttc tctcttttgt tgattatgat ctggttggta cttttgatat gtatacatta   1860

aagttatggt gccatgcata caacctttaa tatatatact ggatttctat aaaaaaaaaa   1920

aaaaaaaaaa                                                          1930
```

<210> SEQ ID NO 35
<211> LENGTH: 518
<212> TYPE: PRT
<213> ORGANISM: Aquilegia vulgaris

<400> SEQUENCE: 35

```
Met Ser Ser Glu Asn Leu Leu Phe Phe Leu Pro Ser Ser Ser Phe Glu
  1               5                  10                  15

Leu Ser Leu Cys Phe Leu Leu Leu Val Ala Ile Phe Gly Phe Trp Leu
             20                  25                  30

Ala Pro Gly Gly Leu Ala Trp Ala Ile Ser Lys Thr His Ser Gln Val
         35                  40                  45

Gln Ala Lys Thr Ala Ile Pro Gly Pro Ser Gly Phe Pro Leu Leu Gly
     50                  55                  60

Leu Val Phe Ala Phe Thr Gly Ser Thr Thr His Arg Val Leu Ala Asn
 65                  70                  75                  80

Leu Ala Lys Thr Phe Lys Ala Ile Pro Leu Met Ala Phe Ser Val Gly
                 85                  90                  95

Phe Thr Arg Phe Ile Ile Ser Ser Cys Pro Asp Thr Ala Lys Glu Ile
            100                 105                 110

Leu Asn Ser Ser Ser Phe Ala Asp Arg Pro Val Lys Glu Ser Ala Tyr
        115                 120                 125

Glu Leu Leu Phe His Arg Ala Met Gly Phe Ala Pro Phe Gly Glu Tyr
    130                 135                 140

Trp Arg Asn Leu Arg Arg Ile Ser Ala Thr His Leu Phe Ser Pro Lys
145                 150                 155                 160

Arg Ile Thr Gly Phe Ala Thr Phe Arg Ser Glu Ile Gly Glu Lys Met
                165                 170                 175

Ile Asn Glu Ile Lys Cys Gln Met Gly Leu Asn Gly Glu Val Glu Val
            180                 185                 190

Lys Arg Val Leu His Phe Gly Ser Leu Asn Asn Val Met Met Ser Val
        195                 200                 205

Phe Gly Thr Phe Tyr Asp Phe Lys Gln Leu Asn Gly Asp Gly Phe Lys
    210                 215                 220

Leu Glu Glu Leu Val Ser Glu Gly Tyr Glu Leu Leu Gly Ile Phe Asn
225                 230                 235                 240

Trp Ser Asp His Phe Pro Leu Met Gly Trp Leu Asp Leu Gln Gly Val
                245                 250                 255

Arg Lys Arg Ser Arg Val Leu Val Ser Lys Val Asn Ile Phe Val Gly
            260                 265                 270

Lys Ile Ile Glu Glu His Arg Asn Arg Arg Ile Asn Gly Val Leu Gly
        275                 280                 285

Gln Glu Cys Val Gly Asp Phe Val Asp Val Leu Leu Asp Leu Glu Lys
```

-continued

```
    290                 295                 300

Glu His Ser Leu Ser Asp Ser Asp Met Ile Ala Val Leu Trp Glu Met
305                 310                 315                 320

Ile Phe Arg Gly Thr Asp Thr Val Ala Ile Leu Leu Glu Trp Ile Leu
                325                 330                 335

Ala Arg Met Ala Leu His Pro Asp Ile Gln Ala Lys Ala Gln Ser Glu
            340                 345                 350

Ile Asp Thr Val Val Gly Thr Asn Arg Leu Val Ser Asp Ser Asp Leu
        355                 360                 365

Pro Asn Leu Pro Tyr Leu Gln Ala Val Val Lys Glu Ser Leu Arg Val
    370                 375                 380

His Pro Pro Gly Pro Leu Leu Ser Trp Ala Arg Leu Ala Ile His Asp
385                 390                 395                 400

Val His Ile Gly Lys Asn Phe Ile Pro Ala Gly Thr Thr Ala Met Val
                405                 410                 415

Asn Met Trp Ala Ile Thr His Asp Glu Ser Ile Trp Ser Glu Pro Asn
            420                 425                 430

Glu Phe Lys Pro Glu Arg Phe Ile Asp Glu Asp Val Ser Ile Met Gly
        435                 440                 445

Ser Asp Leu Arg Leu Ala Pro Phe Gly Ser Gly Arg Arg Val Cys Pro
    450                 455                 460

Gly Lys Ala Leu Gly Met Ala Thr Val Gln Leu Trp Leu Gly Gln Leu
465                 470                 475                 480

Leu Gln Ser Phe Lys Trp Val Pro Ser Glu Gly Gly Val Asp Leu Ser
                485                 490                 495

Glu Cys Leu Asn Leu Ser Leu Glu Met Lys Lys Pro Leu Ile Cys Lys
            500                 505                 510

Ala Ile Pro Arg Phe Ala
        515


<210> SEQ ID NO 36
<211> LENGTH: 884
<212> TYPE: DNA
<213> ORGANISM: Vitis sp.

<400> SEQUENCE: 36

ggaaaaggaa agcaggctca gcgactctga tatgattgct gttttatggg aaatgatctt     60

tagagggact gacacggtgg caattctgtt ggagtggatt cttgcaagaa tggttttaca    120

ccccgatatt caatccaaag cccaatctga aatagatgca gtggttggag ccacccgact    180

ggtgtctgat tcagacattc ataaactccc ttatctccat gccatagtaa aggaaactct    240

ccgcatgcat ccacctggcc cgctcctttc ctgggcacgc ctttccattc atgataccca    300

cattggttcg cacttcatcc ctgcaggcac cacagctatg gtgaatatgt gggcaataac    360

ccatgatgat gctgtgtggg atgagcctaa ggaattcaag ccaagtcgct ttatggagga    420

ggatgtgagc attttgggtt ctgatcttag gttggcacca tttggctctg gaagaagggt    480

ttgtcctggg aaagcaatgg gtttagcaac tgtgcaactg tggttggctc aattgctcca    540

aaacttcaaa tgggttgctt gtgactctgg tgtggacttg tctgagtgcc tcaagctctc    600

aatggagatg aaacagtcct tggtttgcaa ggctgttcct aggttctctt gaaatatgaa    660

ttgatgatgg ggtttgacaa tgatttgggt gtgatctcat ccatgatttt ggaagccttg    720

tatggtgagg tcaaacagat tacttactat ggttttcctt agcgttttaa tatccttgtt    780

ataagaacag taccgttgtt ggcttgaaag gtcgtggttg tgtaatgaaa gtgcttggct    840
```

ctggttaggt gcgaaaaaaa aaaaaaaaaa aaaaaaaaaa aaaa 884

<210> SEQ ID NO 37
<211> LENGTH: 216
<212> TYPE: PRT
<213> ORGANISM: Vitis sp.

<400> SEQUENCE: 37

```
Glu Lys Glu Ser Arg Leu Ser Asp Ser Asp Met Ile Ala Val Leu Trp
  1               5                  10                  15

Glu Met Ile Phe Arg Gly Thr Asp Thr Val Ala Ile Leu Leu Glu Trp
             20                  25                  30

Ile Leu Ala Arg Met Val Leu His Pro Asp Ile Gln Ser Lys Ala Gln
         35                  40                  45

Ser Glu Ile Asp Ala Val Val Gly Ala Thr Arg Leu Val Ser Asp Ser
     50                  55                  60

Asp Ile His Lys Leu Pro Tyr Leu His Ala Ile Val Lys Glu Thr Leu
 65                  70                  75                  80

Arg Met His Pro Pro Gly Pro Leu Leu Ser Trp Ala Arg Leu Ser Ile
                 85                  90                  95

His Asp Thr His Ile Gly Ser His Phe Ile Pro Ala Gly Thr Thr Ala
            100                 105                 110

Met Val Asn Met Trp Ala Ile Thr His Asp Asp Ala Val Trp Asp Glu
        115                 120                 125

Pro Lys Glu Phe Lys Pro Ser Arg Phe Met Glu Glu Asp Val Ser Ile
    130                 135                 140

Leu Gly Ser Asp Leu Arg Leu Ala Pro Phe Gly Ser Gly Arg Arg Val
145                 150                 155                 160

Cys Pro Gly Lys Ala Met Gly Leu Ala Thr Val Gln Leu Trp Leu Ala
                165                 170                 175

Gln Leu Leu Gln Asn Phe Lys Trp Val Ala Cys Asp Ser Gly Val Asp
            180                 185                 190

Leu Ser Glu Cys Leu Lys Leu Ser Met Glu Met Lys Gln Ser Leu Val
        195                 200                 205

Cys Lys Ala Val Pro Arg Phe Ser
    210                 215
```

<210> SEQ ID NO 38
<211> LENGTH: 442
<212> TYPE: DNA
<213> ORGANISM: Parthenium argentatum Grey
<220> FEATURE:
<221> NAME/KEY: unsure
<222> LOCATION: (340)
<223> OTHER INFORMATION: n = A, C, G, or T
<220> FEATURE:
<221> NAME/KEY: unsure
<222> LOCATION: (396)
<223> OTHER INFORMATION: n = A, C, G, or T
<220> FEATURE:
<221> NAME/KEY: unsure
<222> LOCATION: (407)
<223> OTHER INFORMATION: n = A, C, G, or T
<220> FEATURE:
<221> NAME/KEY: unsure
<222> LOCATION: (413)
<223> OTHER INFORMATION: n = A, C, G, or T
<220> FEATURE:
<221> NAME/KEY: unsure
<222> LOCATION: (418)
<223> OTHER INFORMATION: n = A, C, G, or T -continued

<400> SEQUENCE: 38

```
gtcgatgttt tgcttgattt ggaatccgag aacaagttta gcgaatccga tatgatcgca     60
gttctttggg aaatgatatt taggggaact gacacggtgg caattatgtt ggaatggatt    120
ctggctagga tggtgttaca cccggacata caagcaagag cgcaatccga aatcgatagt    180
gttgtcggct cgggtagacc catatccgat gcggatatcc cgaatctccc ttacctccat    240
gccattgtaa aagaaaccct acgtgtgcac ccaccaagcc cacttctgtc atgggcccgg    300
ctggcaatcc atgacaccca agtgggtccg cacatggtan cggccgggac aacggccaag    360
ggcaatatgt gggccaaaac ccatgatgat caaatnctgg ggtttgngcc cgnaaggntc    420
aacccaaatt ggtttaagaa cc                                             442
```

<210> SEQ ID NO 39
<211> LENGTH: 131
<212> TYPE: PRT
<213> ORGANISM: Parthenium argentatum Grey
<220> FEATURE:
<221> NAME/KEY: UNSURE
<222> LOCATION: (114)
<223> OTHER INFORMATION: Xaa = any amino acid

<400> SEQUENCE: 39

```
Val Asp Val Leu Leu Asp Leu Glu Ser Glu Asn Lys Phe Ser Glu Ser
  1               5                  10                  15

Asp Met Ile Ala Val Leu Trp Glu Met Ile Phe Arg Gly Thr Asp Thr
             20                  25                  30

Val Ala Ile Met Leu Glu Trp Ile Leu Ala Arg Met Val Leu His Pro
         35                  40                  45

Asp Ile Gln Ala Arg Ala Gln Ser Glu Ile Asp Ser Val Val Gly Ser
     50                  55                  60

Gly Arg Pro Ile Ser Asp Ala Asp Ile Pro Asn Leu Pro Tyr Leu His
 65                  70                  75                  80

Ala Ile Val Lys Glu Thr Leu Arg Val His Pro Pro Ser Pro Leu Leu
                 85                  90                  95

Ser Trp Ala Arg Leu Ala Ile His Asp Thr Gln Val Gly Pro His Met
            100                 105                 110

Val Xaa Ala Gly Thr Thr Ala Lys Gly Asn Met Trp Ala Lys Thr His
        115                 120                 125

Asp Asp Gln
    130
```

<210> SEQ ID NO 40
<211> LENGTH: 1687
<212> TYPE: DNA
<213> ORGANISM: Alstroemeria caryophylla

<400> SEQUENCE: 40

```
tgccaatgtc gccgccctca accctcgccg actccccct cccctacctc ccgacccca      60
tcatcgcctc ccctctcctc gccgtcctcg ccgccctact cttcgtcttc ctcgcccccg    120
gcggccccgc ctggtccctc tcccgctccc gccgccacgc catccccggc ccccctggct    180
tcctcctcgc tctctccggc ccctccgccc accgctccct cgccgccgtc tcctcctccc    240
tccgcgccct ccccctcctc tccttctccc tcggcctcac ccgcttcatt gtctcctccc    300
acccctccac cgccaaggac atcctctcca gctccgcctt cgccgaccgc cccatcaagg    360
actccgccta cggcctcctc ttccaccgcg ccatgggctt cgccccttc ggtgactact    420
```

-continued

```
ggcgcaacct ccgccgcatc tccgccaccc acctcttcag ccccaagcgc ctctccgcct    480

ccgcccccct ccgccgcgac atcggcctcc gcgccgtctc ccacgtcgcc tccctcatgg    540

ccacccacgg cgaggtcgag atcaagcgcc tcctccactt cgcctccctc aacaacgtca    600

tggccagcgt gttcggccgc gtctacgact tcgccacccg ggacggcctc gagctcgagg    660

ccttggtcag cgaggggtac gagctgctgg gcgtcttcaa ctggggcgac catttcccgc    720

ttgttgcctg gtttgacttc cagggggtca ggcggaggtg caaggccctc gtcagccgcg    780

tcaacgtctt tgtcggccgc ataatcgacg agcaccgcag caggcgggcg agcggctccg    840

tcagcgacgg cgccgtagac ttcgtcgacg tcctgctcga cgagaagctc tccgattccg    900

acatggtggc ggttctctgg gagatgatct ttcgcgggac ggatacggtg gccatcctgc    960

tggagtggat catggcgagg atggtgctgc acccggaaat ccaagccaaa gctcaagccg   1020

agatcgacgc cgttgtgggc ggtgagaggt cggtggccga cgccgacgtc gccaacctcc   1080

cttacctcca agccatcgtc aaggagtcgc tgaggatgca cccccccggc ccgctgctct   1140

cctgggctcg cctcgcagtc catgacgtgc acgtcggggg ccacttcgtc ccggccggca   1200

cgaccgcgat ggtgaacatg tgggccatag cgcacgacgg gaacatctgg ccggagccgg   1260

aggtgttcaa cccggagagg tttgtggagc aggatgtgag cattctgggc tcggatctcc   1320

ggctggcgcc gttcgggtcg gggaggaggg tgtgtcccgg caaggcgatg gggctggcca   1380

ccgcgcatct ctggctggct cagctgcttc agagcttcaa gtgggtggct tccgacaatg   1440

gcgttgatct ctcggaaaac ttgaagatgt cccttgagat gaaggtccct ctcgtgtgca   1500

aggctgttgc gaggcgctga atggtctggt tctctctctt taggttttag tgggttttta   1560

gctaactctg tggcttgttt gaactgcatc ttggaggtgg cggtgctgca ctcccctcca   1620

tggttttgta acttggtagt taaagcaatg gcctcccttt taacgcttaa aaaaaaaaaa   1680

aaaaaaa                                                             1687
```

<210> SEQ ID NO 41
<211> LENGTH: 504
<212> TYPE: PRT
<213> ORGANISM: Alstroemeria caryophylla

<400> SEQUENCE: 41

```
Met Ser Pro Pro Ser Thr Leu Ala Asp Ser Pro Leu Pro Tyr Leu Pro
  1               5                  10                  15

Thr Pro Ile Ile Ala Ser Pro Leu Leu Ala Val Leu Ala Ala Leu Leu
             20                  25                  30

Phe Val Phe Leu Ala Pro Gly Gly Pro Ala Trp Ser Leu Ser Arg Ser
         35                  40                  45

Arg Arg His Ala Ile Pro Gly Pro Pro Gly Phe Leu Leu Ala Leu Ser
     50                  55                  60

Gly Pro Ser Ala His Arg Ser Leu Ala Ala Val Ser Ser Ser Leu Arg
 65                  70                  75                  80

Ala Leu Pro Leu Leu Ser Phe Ser Leu Gly Leu Thr Arg Phe Ile Val
                 85                  90                  95

Ser Ser His Pro Ser Thr Ala Lys Asp Ile Leu Ser Ser Ser Ala Phe
            100                 105                 110

Ala Asp Arg Pro Ile Lys Asp Ser Ala Tyr Gly Leu Leu Phe His Arg
        115                 120                 125

Ala Met Gly Phe Ala Pro Phe Gly Asp Tyr Trp Arg Asn Leu Arg Arg
    130                 135                 140
```

-continued

```
Ile Ser Ala Thr His Leu Phe Ser Pro Lys Arg Leu Ser Ala Ser Ala
145                 150                 155                 160

Pro Leu Arg Arg Asp Ile Gly Leu Arg Ala Val Ser His Val Ala Ser
                165                 170                 175

Leu Met Ala Thr His Gly Glu Val Glu Ile Lys Arg Leu Leu His Phe
            180                 185                 190

Ala Ser Leu Asn Asn Val Met Ala Ser Val Phe Gly Arg Val Tyr Asp
        195                 200                 205

Phe Ala Thr Arg Asp Gly Leu Glu Leu Glu Ala Leu Val Ser Glu Gly
    210                 215                 220

Tyr Glu Leu Leu Gly Val Phe Asn Trp Gly Asp His Phe Pro Leu Val
225                 230                 235                 240

Ala Trp Phe Asp Phe Gln Gly Val Arg Arg Arg Cys Lys Ala Leu Val
                245                 250                 255

Ser Arg Val Asn Val Phe Val Gly Arg Ile Ile Asp Glu His Arg Ser
            260                 265                 270

Arg Arg Ala Ser Gly Ser Val Ser Asp Gly Ala Val Asp Phe Val Asp
        275                 280                 285

Val Leu Leu Asp Glu Lys Leu Ser Asp Ser Asp Met Val Ala Val Leu
    290                 295                 300

Trp Glu Met Ile Phe Arg Gly Thr Asp Thr Val Ala Ile Leu Leu Glu
305                 310                 315                 320

Trp Ile Met Ala Arg Met Val Leu His Pro Glu Ile Gln Ala Lys Ala
                325                 330                 335

Gln Ala Glu Ile Asp Ala Val Val Gly Gly Glu Arg Ser Val Ala Asp
            340                 345                 350

Ala Asp Val Ala Asn Leu Pro Tyr Leu Gln Ala Ile Val Lys Glu Ser
        355                 360                 365

Leu Arg Met His Pro Pro Gly Pro Leu Leu Ser Trp Ala Arg Leu Ala
    370                 375                 380

Val His Asp Val His Val Gly Gly His Phe Val Pro Ala Gly Thr Thr
385                 390                 395                 400

Ala Met Val Asn Met Trp Ala Ile Ala His Asp Gly Asn Ile Trp Pro
                405                 410                 415

Glu Pro Glu Val Phe Asn Pro Glu Arg Phe Val Glu Gln Asp Val Ser
            420                 425                 430

Ile Leu Gly Ser Asp Leu Arg Leu Ala Pro Phe Gly Ser Gly Arg Arg
        435                 440                 445

Val Cys Pro Gly Lys Ala Met Gly Leu Ala Thr Ala His Leu Trp Leu
    450                 455                 460

Ala Gln Leu Leu Gln Ser Phe Lys Trp Val Ala Ser Asp Asn Gly Val
465                 470                 475                 480

Asp Leu Ser Glu Asn Leu Lys Met Ser Leu Glu Met Lys Val Pro Leu
                485                 490                 495

Val Cys Lys Ala Val Ala Arg Arg
            500


<210> SEQ ID NO 42
<211> LENGTH: 537
<212> TYPE: PRT
<213> ORGANISM: Arabidopsis thaliana

<400> SEQUENCE: 42

Met Thr Ile Asp Met Tyr Leu Ser Phe Ala Ser Arg Ser Gly Ser Ser
  1               5                  10                  15
```

-continued

```
Pro Phe Pro Ser Leu Glu Leu Cys Leu Ser Ile Phe Leu Phe Ile Ser
            20                  25                  30

Leu Phe Val Phe Trp Leu Thr Pro Gly Gly Phe Ala Trp Ala Leu Tyr
        35                  40                  45

Lys Ala Arg Phe His Thr Arg Pro Glu Ser Lys Thr Gly Pro Ala Ile
    50                  55                  60

Pro Gly Pro Ser Gly Leu Pro Ile Phe Gly Leu Leu Leu Ala Phe Val
65                  70                  75                  80

Asn Asn Ala Leu Thr His Arg Ile Leu Ala Asn Ile Ala Asp Thr Cys
                85                  90                  95

Lys Ala Lys Ala Leu Met Ala Phe Ser Val Gly Ser Thr Arg Phe Val
            100                 105                 110

Ile Thr Ser Glu Pro Glu Thr Ala Lys Glu Leu Leu Asn Ser Ser Ala
        115                 120                 125

Phe Ala Asp Arg Pro Val Lys Glu Ser Ala Tyr Glu Leu Leu Phe Asp
    130                 135                 140

Arg Ala Met Gly Phe Ala Pro Phe Gly Asp Tyr Trp Arg Glu Leu Arg
145                 150                 155                 160

Arg Ile Ser Ser Thr His Leu Phe Ser Pro Lys Arg Ile Phe Ser Ser
                165                 170                 175

Gly Glu Ser Arg Arg Lys Ile Gly Gln Asn Met Val Gly Glu Ile Lys
            180                 185                 190

Asn Ala Met Glu Cys Tyr Gly Glu Val His Ile Lys Lys Ile Leu His
        195                 200                 205

Phe Gly Ser Leu Asn Asn Val Met Ser Ser Val Phe Gly Lys Thr Tyr
    210                 215                 220

Asn Phe Asn Glu Gly Ile Val Tyr Ser Lys Glu Ser Asn Glu Leu Glu
225                 230                 235                 240

His Leu Val Ser Glu Gly Tyr Glu Leu Leu Gly Ile Phe Asn Trp Ser
                245                 250                 255

Asp His Phe Pro Gly Met Arg Trp Leu Asp Leu Gln Gly Val Arg Arg
            260                 265                 270

Arg Cys Arg Ser Leu Val Gly Arg Val Asn Val Phe Val Gly Lys Ile
        275                 280                 285

Ile Asn Asp His Lys Ser Lys Arg Ser Leu Arg Asp Asn Pro Glu Glu
    290                 295                 300

Ser Thr Tyr Asp Asp Asp Phe Val Asp Val Leu Leu Gly Met His Gly
305                 310                 315                 320

Asn Ser Lys Leu Ser Asp Ser Asp Met Ile Ala Val Leu Trp Glu Met
                325                 330                 335

Ile Phe Arg Gly Thr Asp Thr Val Ala Ile Leu Leu Glu Trp Ile Leu
            340                 345                 350

Ala Arg Met Val Leu His Pro Asp Ile Gln Ala Lys Ala Gln Ala Glu
        355                 360                 365

Ile Asp Cys Ile Val Gly Asp Ser Gly Arg Gln Val Thr Asp Ser Asp
    370                 375                 380

Leu Pro Lys Leu Pro Tyr Val Arg Ala Ile Val Lys Glu Thr Leu Arg
385                 390                 395                 400

Met His Pro Pro Gly Pro Leu Leu Ser Trp Ala Arg Leu Ser Ile His
                405                 410                 415

Asp Thr Gln Ile Gly Thr His Phe Ile Pro Ala Gly Thr Thr Ala Met
            420                 425                 430
```

-continued

```
Val Asn Met Trp Ala Ile Thr His Asp Glu Lys Val Trp Pro Glu Ala
        435                 440                 445

His Glu Tyr Lys Pro Glu Arg Phe Leu Gly Ala Gln Glu Ser Asn Asn
    450                 455                 460

Phe Pro Ile Met Gly Ser Asp Leu Arg Leu Ala Pro Phe Gly Ala Gly
465                 470                 475                 480

Arg Arg Val Cys Pro Gly Lys Ser Met Gly Leu Ala Thr Val Glu Leu
                485                 490                 495

Trp Leu Ala Gln Leu Leu Gly Ser Tyr Lys Trp Val Ser Cys Gly Glu
            500                 505                 510

Val Asp Leu Ser Glu Thr Leu Lys Leu Ser Leu Glu Met Lys Asn Thr
        515                 520                 525

Leu Val Cys Lys Ala Ile Pro Arg Gly
    530                 535


<210> SEQ ID NO 43
<211> LENGTH: 426
<212> TYPE: PRT
<213> ORGANISM: Phalaenopsis sp. SM9108

<400> SEQUENCE: 43

Met Ala Phe Ser Val Gly Leu Thr Arg Phe Ile Val Ser Ser His Pro
  1               5                  10                  15

Lys Thr Ala Lys Glu Ile Leu Ser Ser Pro Ala Phe Ala Asp Arg Pro
            20                  25                  30

Ile Lys Glu Ser Ala Tyr Glu Leu Leu Phe Asn Arg Ala Met Gly Phe
        35                  40                  45

Ala Pro Phe Gly Asp Tyr Trp Arg Asn Leu Arg Arg Ile Ser Ser Thr
     50                  55                  60

Tyr Leu Phe Ser Pro Arg Arg Val Ser Ser Phe Glu Lys Gln Arg Ser
 65                  70                  75                  80

Glu Ile Gly Glu Gly Met Val Arg Asp Met Lys Arg Met Met Glu Arg
                85                  90                  95

Asn Gly Val Val Glu Val Arg Arg Met Leu His Tyr Gly Ser Leu Asn
            100                 105                 110

Asn Ile Met Leu Thr Val Phe Gly Lys Lys Phe Asp Phe Ala Lys Asp
        115                 120                 125

Glu Gly Leu Glu Leu Glu Leu Ile Leu Lys Glu Gly Tyr Glu Leu Leu
    130                 135                 140

Gly Ile Phe Asn Trp Gly Asp His Leu Pro Leu Leu Gly Trp Leu Asp
145                 150                 155                 160

Leu Gln Gly Val Arg Arg Arg Cys Arg Thr Leu Val Ala Lys Val Asn
                165                 170                 175

Val Phe Val Lys Lys Ile Ile Asp Glu His Lys Arg Arg Ala Asn Gly
            180                 185                 190

Val Gly Ile Asp Glu Gly Glu Gly Glu Asp Phe Val Asp Val Leu Leu
        195                 200                 205

Gly Leu Glu Glu Lys Asp Arg Leu Ser Glu Ser Asp Met Val Ala Val
    210                 215                 220

Leu Trp Glu Met Ile Phe Arg Gly Thr Asp Thr Val Ala Ile Leu Leu
225                 230                 235                 240

Glu Trp Thr Leu Ala Arg Met Val Leu His Pro Asp Ile Gln Ser Lys
                245                 250                 255

Ala Gln Val Glu Ile Asp Ser Val Val Asp Ser Ser Arg Pro Val Leu
            260                 265                 270
```

-continued

```
Asp Ser Asp Ile Gln Arg Leu Pro Tyr Leu Gln Ser Ile Val Lys Glu
        275                 280                 285

Thr Leu Arg Met His Pro Pro Gly Pro Leu Leu Ser Trp Ala Arg Leu
    290                 295                 300

Ala Ile His Asp Val Pro Val Asp Gly His Met Ile Pro Ala Gly Thr
305                 310                 315                 320

Thr Ala Met Val Asn Met Trp Ala Ile Thr His Asp Glu Cys Asn Trp
                325                 330                 335

Ala Glu Pro Asn Lys Phe Asn Pro Asp Arg Phe Ile Asp Glu Asp Val
            340                 345                 350

Asn Ile Leu Gly Ser Asp Leu Arg Leu Ala Pro Phe Gly Ser Gly Lys
        355                 360                 365

Arg Val Cys Pro Gly Lys Thr Met Ala Leu Ala Ala Val His Leu Trp
    370                 375                 380

Leu Ala Gln Leu Leu Lys Ser Phe Lys Leu Leu Pro Ser Arg Asn Gly
385                 390                 395                 400

Val Asp Leu Ser Glu Cys Leu Lys Met Ser Leu Glu Met Lys Asn Pro
                405                 410                 415

Leu Val Cys Val Ala Val Pro Arg Phe Glu
            420                 425


<210> SEQ ID NO 44
<211> LENGTH: 534
<212> TYPE: PRT
<213> ORGANISM: Arabidopsis thaliana

<400> SEQUENCE: 44

Met Ala Thr Lys Leu Asp Thr Ser Ser Leu Leu Leu Ala Leu Leu Ser
  1               5                  10                  15

Lys Cys Ser Leu Leu Thr Gln Thr Asn Leu Ala Leu Ser Leu Leu Val
             20                  25                  30

Ala Ser Leu Ala Ser Leu Ala Leu Ser Leu Phe Phe Trp Ser His Pro
         35                  40                  45

Gly Gly Pro Ala Trp Gly Lys Tyr Phe Leu His Arg Arg Arg Gln Thr
     50                  55                  60

Thr Val Ile Pro Gly Pro Arg Gly Leu Pro Phe Val Gly Ser Met Ser
 65                  70                  75                  80

Leu Met Ser Asn Thr Leu Ala His Arg Cys Ile Ala Ala Thr Ala Glu
                 85                  90                  95

Lys Phe Arg Ala Glu Arg Leu Met Ala Phe Ser Leu Gly Glu Thr Arg
            100                 105                 110

Val Ile Val Thr Cys Asn Pro Asp Val Ala Lys Glu Ile Leu Asn Ser
        115                 120                 125

Pro Val Phe Ala Asp Arg Pro Val Lys Glu Ser Ala Tyr Ser Leu Met
    130                 135                 140

Phe Asn Arg Ala Ile Gly Phe Ala Pro Tyr Gly Val Tyr Trp Arg Thr
145                 150                 155                 160

Leu Arg Lys Ile Ala Ser Asn His Leu Phe Ser Pro Lys Gln Ile Lys
                165                 170                 175

Arg Ser Glu Thr Gln Arg Ser Val Ile Ala Asn Gln Ile Val Lys Cys
            180                 185                 190

Leu Thr Lys Gln Ser Asn Thr Lys Gly Leu Cys Phe Ala Arg Asp Leu
        195                 200                 205

Ile Lys Thr Ala Ser Leu Asn Asn Met Met Cys Ser Val Phe Gly Lys
```

-continued

```
    210                 215                 220

Glu Tyr Glu Leu Glu Glu Glu His Glu Glu Val Ser Glu Leu Arg Glu
225                 230                 235                 240

Leu Val Glu Glu Gly Tyr Asp Leu Leu Gly Thr Leu Asn Trp Thr Asp
                245                 250                 255

His Leu Pro Trp Leu Ser Glu Phe Asp Pro Gln Arg Ile Arg Ser Arg
            260                 265                 270

Cys Ser Asn Leu Val Pro Lys Val Asn Arg Phe Val Asn Arg Ile Ile
        275                 280                 285

Ser Asp His Arg Glu Gln Thr Arg Asp Ser Pro Ser Asp Phe Val Asp
    290                 295                 300

Val Leu Leu Ser Leu Asp Gly Pro Asp Lys Leu Ser Asp Pro Asp Ile
305                 310                 315                 320

Ile Ala Val Leu Trp Glu Met Ile Phe Arg Gly Thr Asp Thr Val Ala
                325                 330                 335

Val Leu Ile Glu Trp Ile Leu Ala Arg Met Val Leu His Pro Asp Ile
            340                 345                 350

Gln Ser Thr Val His Asn Glu Leu Asp Gln Ile Val Gly Arg Ser Arg
        355                 360                 365

Ala Val Glu Glu Ser Asp Val Val Ser Leu Val Tyr Leu Thr Ala Val
    370                 375                 380

Val Lys Glu Val Leu Arg Leu His Pro Pro Gly Pro Leu Leu Ser Trp
385                 390                 395                 400

Ala Arg Leu Ala Ile Thr Asp Thr Ile Ile Asp Gly Arg Arg Val Pro
                405                 410                 415

Ala Gly Thr Thr Ala Met Val Asn Met Trp Ala Ile Ala His Asp Pro
            420                 425                 430

His Val Trp Glu Asn Pro Leu Glu Phe Lys Pro Glu Arg Phe Val Ala
        435                 440                 445

Lys Glu Gly Glu Val Glu Phe Ser Val Leu Gly Ser Asp Leu Arg Leu
    450                 455                 460

Ala Pro Phe Gly Ser Gly Arg Arg Val Cys Pro Gly Lys Asn Leu Gly
465                 470                 475                 480

Leu Thr Thr Val Thr Phe Trp Thr Ala Thr Leu Leu His Glu Phe Glu
                485                 490                 495

Trp Leu Thr Pro Ser Asp Glu Lys Thr Val Asp Leu Ser Glu Lys Leu
            500                 505                 510

Arg Leu Ser Cys Glu Met Ala Asn Pro Leu Ala Ala Lys Leu Arg Pro
        515                 520                 525

Arg Arg Ser Phe Ser Val
    530


<210> SEQ ID NO 45
<211> LENGTH: 523
<212> TYPE: PRT
<213> ORGANISM: Glycine max

<400> SEQUENCE: 45

Met Thr Ser His Ile Asp Asp Asn Leu Trp Ile Ile Ala Leu Thr Ser
  1               5                  10                  15

Lys Cys Thr Gln Glu Asn Leu Ala Trp Val Leu Leu Ile Met Gly Ser
             20                  25                  30

Leu Trp Leu Thr Met Thr Phe Tyr Tyr Trp Ser His Pro Gly Gly Pro
         35                  40                  45
```

-continued

```
Ala Trp Gly Lys Tyr Tyr Thr Tyr Ser Pro Pro Leu Ser Ile Ile Pro
     50                 55                  60

Gly Pro Lys Gly Phe Pro Leu Ile Gly Ser Met Gly Leu Met Thr Ser
 65                 70                  75                  80

Leu Ala His His Arg Ile Ala Ala Ala Ala Ala Thr Cys Arg Ala Lys
                85                  90                  95

Arg Leu Met Ala Phe Ser Leu Gly Asp Thr Arg Val Ile Val Thr Cys
            100                 105                 110

His Pro Asp Val Ala Lys Glu Ile Leu Asn Ser Ser Val Phe Ala Asp
        115                 120                 125

Arg Pro Val Lys Glu Ser Ala Tyr Ser Leu Met Phe Asn Arg Ala Ile
    130                 135                 140

Gly Phe Ala Ser Tyr Gly Val Tyr Trp Arg Ser Leu Arg Arg Ile Ala
145                 150                 155                 160

Ser Asn His Leu Phe Cys Pro Arg Gln Ile Lys Ala Ser Glu Leu Gln
                165                 170                 175

Arg Ser Gln Ile Ala Ala Gln Met Val His Ile Leu Asn Asn Lys Arg
            180                 185                 190

His Arg Ser Leu Arg Val Arg Gln Val Leu Lys Lys Ala Ser Leu Ser
        195                 200                 205

Asn Met Met Cys Ser Val Phe Gly Gln Glu Tyr Lys Leu His Asp Pro
    210                 215                 220

Asn Ser Gly Met Glu Asp Leu Gly Ile Leu Val Asp Gln Gly Tyr Asp
225                 230                 235                 240

Leu Leu Gly Leu Phe Asn Trp Ala Asp His Leu Pro Phe Leu Ala His
                245                 250                 255

Phe Asp Ala Gln Asn Ile Arg Phe Arg Cys Ser Asn Leu Val Pro Met
            260                 265                 270

Val Asn Arg Phe Val Gly Thr Ile Ile Ala Glu His Arg Ala Ser Lys
        275                 280                 285

Thr Glu Thr Asn Arg Asp Phe Val Asp Val Leu Leu Ser Leu Pro Glu
    290                 295                 300

Pro Asp Gln Leu Ser Asp Ser Asp Met Ile Ala Val Leu Trp Glu Met
305                 310                 315                 320

Ile Phe Arg Gly Thr Asp Thr Val Ala Val Leu Ile Glu Trp Ile Leu
                325                 330                 335

Ala Arg Met Ala Leu His Pro His Val Gln Ser Lys Val Gln Glu Glu
            340                 345                 350

Leu Asp Ala Val Val Gly Lys Ala Arg Ala Val Ala Glu Asp Asp Val
        355                 360                 365

Ala Val Met Thr Tyr Leu Pro Ala Val Val Lys Glu Val Leu Arg Leu
    370                 375                 380

His Pro Pro Gly Pro Leu Leu Ser Trp Ala Arg Leu Ser Ile Asn Asp
385                 390                 395                 400

Thr Thr Ile Asp Gly Tyr His Val Pro Ala Gly Thr Thr Ala Met Val
                405                 410                 415

Asn Thr Trp Ala Ile Cys Arg Asp Pro His Val Trp Lys Asp Pro Leu
            420                 425                 430

Glu Phe Met Pro Glu Arg Phe Val Thr Ala Gly Gly Asp Ala Glu Phe
        435                 440                 445

Ser Ile Leu Gly Ser Asp Pro Arg Leu Ala Pro Phe Gly Ser Gly Arg
    450                 455                 460

Arg Ala Cys Pro Gly Lys Thr Leu Gly Trp Ala Thr Val Asn Phe Trp
```

-continued

```
465                 470                 475                 480

Val Ala Ser Leu Leu His Glu Phe Glu Trp Val Pro Ser Asp Glu Lys
                485                 490                 495

Gly Val Asp Leu Thr Glu Val Leu Lys Leu Ser Ser Glu Met Ala Asn
            500                 505                 510

Pro Leu Thr Val Lys Val Arg Pro Arg Arg Gly
        515                 520


<210> SEQ ID NO 46
<211> LENGTH: 530
<212> TYPE: PRT
<213> ORGANISM: Arabidopsis thaliana

<400> SEQUENCE: 46

Met Ala Thr Lys Leu Glu Ser Ser Leu Ile Phe Ala Leu Leu Ser Lys
  1               5                  10                  15

Cys Ser Val Leu Ser Gln Thr Asn Leu Ala Phe Ser Leu Leu Ala Val
            20                  25                  30

Thr Ile Ile Trp Leu Ala Ile Ser Leu Phe Leu Trp Thr Tyr Pro Gly
        35                  40                  45

Gly Pro Ala Trp Gly Lys Tyr Leu Phe Gly Arg Leu Ile Ser Gly Ser
    50                  55                  60

Tyr Lys Thr Gly Asn Val Ile Pro Gly Pro Lys Gly Phe Pro Leu Val
 65                  70                  75                  80

Gly Ser Met Ser Leu Met Ser Ser Thr Leu Ala His Arg Arg Ile Ala
                 85                  90                  95

Asp Ala Ala Glu Lys Phe Gly Ala Lys Arg Leu Met Ala Phe Ser Leu
            100                 105                 110

Gly Glu Thr Arg Val Ile Val Thr Cys Asn Pro Asp Val Ala Lys Glu
        115                 120                 125

Ile Leu Asn Ser Pro Val Phe Ala Asp Arg Pro Val Lys Glu Ser Ala
    130                 135                 140

Tyr Ser Leu Met Phe Asn Arg Ala Ile Gly Phe Ala Pro His Gly Val
145                 150                 155                 160

Tyr Trp Arg Thr Leu Arg Arg Ile Ala Ser Asn His Leu Phe Ser Thr
                165                 170                 175

Lys Gln Ile Arg Arg Ala Glu Thr Gln Arg Arg Val Ile Ser Ser Gln
            180                 185                 190

Met Val Glu Phe Leu Glu Lys Gln Ser Ser Asn Glu Pro Cys Phe Val
        195                 200                 205

Arg Glu Leu Leu Lys Thr Ala Ser Leu Asn Asn Met Met Cys Ser Val
    210                 215                 220

Phe Gly Gln Glu Tyr Glu Leu Glu Lys Asn His Val Glu Leu Arg Glu
225                 230                 235                 240

Met Val Glu Glu Gly Tyr Asp Leu Leu Gly Thr Leu Asn Trp Thr Asp
                245                 250                 255

His Leu Pro Trp Leu Ser Glu Phe Asp Pro Gln Arg Leu Arg Ser Arg
            260                 265                 270

Cys Ser Thr Leu Val Pro Lys Val Asn Arg Phe Val Ser Arg Ile Ile
        275                 280                 285

Ser Glu His Arg Asn Gln Thr Gly Asp Leu Pro Arg Asp Phe Val Asp
    290                 295                 300

Val Leu Leu Ser Leu His Gly Ser Asp Lys Leu Ser Asp Pro Asp Ile
305                 310                 315                 320
```

-continued

```
Ile Ala Val Leu Trp Glu Met Ile Phe Arg Gly Thr Asp Thr Val Ala
                325                 330                 335

Val Leu Ile Glu Trp Ile Leu Ala Arg Met Val Leu His Pro Asp Met
            340                 345                 350

Gln Ser Thr Val Gln Asn Glu Leu Asp Gln Val Val Gly Lys Ser Arg
        355                 360                 365

Ala Leu Asp Glu Ser Asp Leu Ala Ser Leu Pro Tyr Leu Thr Ala Val
    370                 375                 380

Val Lys Glu Val Leu Arg Leu His Pro Pro Gly Pro Leu Leu Ser Trp
385                 390                 395                 400

Ala Arg Leu Ala Ile Thr Asp Thr Ile Val Asp Gly Arg Leu Val Pro
                405                 410                 415

Ala Gly Thr Thr Ala Met Val Asn Met Trp Ala Val Ser His Asp Pro
            420                 425                 430

His Val Trp Val Asp Pro Leu Glu Phe Lys Pro Glu Arg Phe Val Ala
        435                 440                 445

Lys Glu Gly Glu Val Glu Phe Ser Val Leu Gly Ser Asp Leu Arg Leu
    450                 455                 460

Ala Pro Phe Gly Ser Gly Arg Arg Ile Cys Pro Gly Lys Asn Leu Gly
465                 470                 475                 480

Phe Thr Thr Val Met Phe Trp Thr Ala Met Met Leu His Glu Phe Glu
                485                 490                 495

Trp Gly Pro Ser Asp Gly Asn Gly Val Asp Leu Ser Glu Lys Leu Arg
            500                 505                 510

Leu Ser Cys Glu Met Ala Asn Pro Leu Pro Ala Lys Leu Arg Arg Arg
        515                 520                 525

Arg Ser
    530


<210> SEQ ID NO 47
<211> LENGTH: 517
<212> TYPE: PRT
<213> ORGANISM: Arabidopsis thaliana

<400> SEQUENCE: 47

Met Ser Pro Glu Ala Tyr Val Leu Phe Phe Asn Ser Phe Asn Leu Val
  1               5                  10                  15

Thr Phe Glu Ala Phe Ala Ser Val Ser Leu Ile Ile Ala Thr Val Ala
            20                  25                  30

Phe Leu Leu Ser Pro Gly Gly Leu Ala Trp Ala Trp Thr Gly Ser Ser
         35                  40                  45

Lys Ser Arg Val Ser Ile Pro Gly Pro Ser Gly Ser Leu Ser Val Phe
     50                  55                  60

Ser Gly Ser Asn Pro His Arg Val Leu Ala Ala Leu Ala Lys Arg Phe
 65                  70                  75                  80

Lys Ala Ser Pro Leu Met Ala Phe Ser Val Gly Phe Ser Arg Phe Val
                 85                  90                  95

Ile Ser Ser Glu Pro Glu Thr Ala Lys Glu Ile Leu Ser Ser Ser Ala
            100                 105                 110

Phe Ala Asp Arg Pro Val Lys Glu Ser Ala Tyr Glu Leu Leu Phe His
        115                 120                 125

Arg Ala Met Gly Phe Ala Pro Tyr Gly Glu Tyr Trp Arg Asn Leu Arg
    130                 135                 140

Arg Ile Ser Ser Thr His Leu Phe Ser Pro Arg Arg Ile Ala Ser Phe
145                 150                 155                 160
```

-continued

```
Glu Gly Val Arg Val Gly Ile Gly Met Lys Met Val Lys Lys Ile Lys
                165                 170                 175

Ser Leu Val Thr Ser Asp Ala Cys Gly Glu Val Glu Val Lys Lys Ile
            180                 185                 190

Val His Phe Gly Ser Leu Asn Asn Val Met Thr Thr Val Phe Gly Glu
        195                 200                 205

Ser Tyr Asp Phe Asp Glu Val Asn Gly Lys Gly Cys Phe Leu Glu Arg
    210                 215                 220

Leu Val Ser Glu Gly Tyr Glu Leu Leu Gly Ile Phe Asn Trp Ser Asp
225                 230                 235                 240

His Phe Trp Phe Leu Arg Trp Phe Asp Phe Gln Gly Val Arg Lys Arg
                245                 250                 255

Cys Arg Ala Leu Val Ser Glu Val Asn Thr Phe Val Gly Gly Ile Ile
            260                 265                 270

Glu Lys His Lys Met Lys Lys Gly Asn Asn Leu Asn Gly Glu Glu Asn
        275                 280                 285

Asp Phe Val Asp Val Leu Leu Gly Leu Gln Lys Asp Glu Lys Leu Ser
    290                 295                 300

Asp Ser Asp Met Ile Ala Val Leu Trp Glu Met Ile Phe Arg Gly Thr
305                 310                 315                 320

Asp Thr Val Ala Ile Leu Val Glu Trp Val Leu Ala Arg Met Val Leu
                325                 330                 335

His Gln Asp Ile Gln Asp Lys Leu Tyr Arg Glu Ile Ala Ser Ala Thr
            340                 345                 350

Ser Asn Asn Ile Arg Ser Leu Ser Asp Ser Asp Ile Pro Lys Leu Pro
        355                 360                 365

Tyr Leu Gln Ala Ile Val Lys Glu Thr Leu Arg Leu His Pro Pro Gly
    370                 375                 380

Pro Leu Leu Ser Trp Ala Arg Leu Ala Ile His Asp Val His Val Gly
385                 390                 395                 400

Pro Asn Leu Val Pro Ala Gly Thr Ile Ala Met Val Asn Met Trp Ser
                405                 410                 415

Ile Thr His Asn Ala Lys Ile Trp Thr Asp Pro Glu Ala Phe Met Pro
            420                 425                 430

Glu Arg Phe Ile Ser Glu Asp Val Ser Ile Met Gly Ser Asp Leu Arg
        435                 440                 445

Leu Ala Pro Phe Gly Ser Gly Arg Arg Val Cys Pro Gly Lys Ala Met
    450                 455                 460

Gly Leu Ala Thr Val His Leu Trp Ile Gly Gln Leu Ile Gln Asn Phe
465                 470                 475                 480

Glu Trp Val Lys Gly Ser Cys Asp Val Glu Leu Ala Glu Val Leu Lys
                485                 490                 495

Leu Ser Met Glu Met Lys Asn Pro Leu Lys Cys Lys Ala Val Pro Arg
            500                 505                 510

Asn Val Gly Phe Ala
        515
```

<210> SEQ ID NO 48
<211> LENGTH: 29
<212> TYPE: DNA
<213> ORGANISM: synthetic construct

<400> SEQUENCE: 48
agaattcttc ccatggcgct ctcctccat                                         29

<210> SEQ ID NO 49
<211> LENGTH: 28
<212> TYPE: DNA
<213> ORGANISM: synthetic construct

<400> SEQUENCE: 49
agaattctag gccctagcca cggccttg 28

<210> SEQ ID NO 50
<211> LENGTH: 26
<212> TYPE: DNA
<213> ORGANISM: synthetic construct

<400> SEQUENCE: 50
aggtctccca tggcgctctc ctccat 26

<210> SEQ ID NO 51
<211> LENGTH: 30
<212> TYPE: DNA
<213> ORGANISM: synthetic construct

<400> SEQUENCE: 51
atcatgatct aggccctagc cacggccttg 30

<210> SEQ ID NO 52
<211> LENGTH: 27
<212> TYPE: DNA
<213> ORGANISM: synthetic construst

<400> SEQUENCE: 52
agcggccgct tcccatggcg ctctcct 27

<210> SEQ ID NO 53
<211> LENGTH: 27
<212> TYPE: DNA
<213> ORGANISM: synthetic construct

<400> SEQUENCE: 53
agcggccgct caggccctag ccacggc 27

<210> SEQ ID NO 54
<211> LENGTH: 32
<212> TYPE: DNA
<213> ORGANISM: synthetic construct

<400> SEQUENCE: 54
gtttcataat gaaattgact ctttttcagt aa 32

<210> SEQ ID NO 55
<211> LENGTH: 31
<212> TYPE: DNA
<213> ORGANISM: synthetic construct

<400> SEQUENCE: 55
gcaaataatt atttctatat acaggacagg c 31

<210> SEQ ID NO 56
<211> LENGTH: 31
<212> TYPE: DNA
<213> ORGANISM: synthetic construct

<400> SEQUENCE: 56

-continued tagctttaga gtacatttct tagatacggc a 31

<210> SEQ ID NO 57
<211> LENGTH: 32
<212> TYPE: DNA
<213> ORGANISM: synthetic construct

<400> SEQUENCE: 57
ttactttgag cgtgccaagc agtataattt ct 32

<210> SEQ ID NO 58
<211> LENGTH: 48
<212> TYPE: DNA
<213> ORGANISM: synthetic construct

<400> SEQUENCE: 58
aaggagagga cgctgtctgt cgaaggtaag gaacggacga gagaaggg 48

<210> SEQ ID NO 59
<211> LENGTH: 52
<212> TYPE: DNA
<213> ORGANISM: synthetic construct

<400> SEQUENCE: 59
ctctcccttc tcgaatcgta accgttcgta cgagaatcgc tgtcctctcc tt 52

<210> SEQ ID NO 60
<211> LENGTH: 29
<212> TYPE: DNA
<213> ORGANISM: synthetic construct

<400> SEQUENCE: 60
cacccgttct cggagcactg tccgaccgc 29

<210> SEQ ID NO 61
<211> LENGTH: 30
<212> TYPE: DNA
<213> ORGANISM: synthetic construct

<400> SEQUENCE: 61
atataggcgc cagcaaccgc acctgtggcg 30

<210> SEQ ID NO 62
<211> LENGTH: 30
<212> TYPE: DNA
<213> ORGANISM: synthetic construct

<400> SEQUENCE: 62
cgaatcgtaa ccgttcgtac gagaatcgct 30

<210> SEQ ID NO 63
<211> LENGTH: 20
<212> TYPE: DNA
<213> ORGANISM: synthetic construct

<400> SEQUENCE: 63
ctgaaccatc ttggaaggac 20

<210> SEQ ID NO 64
<211> LENGTH: 20
<212> TYPE: DNA
<213> ORGANISM: synthetic construct

<400> SEQUENCE: 64

-continued

```
acttgcaagt ctgggaagtg                                                20


<210> SEQ ID NO 65
<211> LENGTH: 21
<212> TYPE: DNA
<213> ORGANISM: synthetic construct

<400> SEQUENCE: 65

attcaggctg cgcaactgtt g                                              21


<210> SEQ ID NO 66
<211> LENGTH: 20
<212> TYPE: DNA
<213> ORGANISM: synthetic construct

<400> SEQUENCE: 66

ctgcaaggcg attaagttgg                                                20


<210> SEQ ID NO 67
<211> LENGTH: 19
<212> TYPE: DNA
<213> ORGANISM: synthetic construct

<400> SEQUENCE: 67

gggttttccc agtcacgac                                                 19


<210> SEQ ID NO 68
<211> LENGTH: 24
<212> TYPE: DNA
<213> ORGANISM: synthetic construct

<400> SEQUENCE: 68

tgagttagct cactcattag ggac                                           24


<210> SEQ ID NO 69
<211> LENGTH: 21
<212> TYPE: DNA
<213> ORGANISM: synthetic construct

<400> SEQUENCE: 69

gcttccggct cgtatgttgt g                                              21


<210> SEQ ID NO 70
<211> LENGTH: 19
<212> TYPE: DNA
<213> ORGANISM: synthetic construct

<400> SEQUENCE: 70

gaccatgatt acgccaagc                                                 19


<210> SEQ ID NO 71
<211> LENGTH: 16
<212> TYPE: DNA
<213> ORGANISM: synthetic construct
<220> FEATURE:
<221> NAME/KEY: misc_feature
<222> LOCATION: (3)..(3)
<223> OTHER INFORMATION: w = a or t
<220> FEATURE:
<221> NAME/KEY: misc_feature
<222> LOCATION: (8)..(8)
<223> OTHER INFORMATION: w = a or t
<220> FEATURE:
<221> NAME/KEY: misc_feature
<222> LOCATION: (13)..(13)
```

-continued

<223> OTHER INFORMATION: s = c or g
<220> FEATURE:
<221> NAME/KEY: Unsure
<222> LOCATION: (5)..(5)
<223> OTHER INFORMATION: n = a, c, g, or t
<220> FEATURE:
<221> NAME/KEY: Unsure
<222> LOCATION: (10)..(10)
<223> OTHER INFORMATION: n = a, c, g, or t

<400> SEQUENCE: 71
tgwgnagwan casaga 16

<210> SEQ ID NO 72
<211> LENGTH: 16
<212> TYPE: DNA
<213> ORGANISM: synthetic construct
<220> FEATURE:
<221> NAME/KEY: misc_feature
<222> LOCATION: (3)..(3)
<223> OTHER INFORMATION: w = a or t
<220> FEATURE:
<221> NAME/KEY: misc_feature
<222> LOCATION: (8)..(8)
<223> OTHER INFORMATION: w = a or t
<220> FEATURE:
<221> NAME/KEY: misc_feature
<222> LOCATION: (13)..(13)
<223> OTHER INFORMATION: w = a or t
<220> FEATURE:
<221> NAME/KEY: Unsure
<222> LOCATION: (5)..(5)
<223> OTHER INFORMATION: n = a, c, g, or t
<220> FEATURE:
<221> NAME/KEY: Unsure
<222> LOCATION: (10)..(10)
<223> OTHER INFORMATION: n = a, c, g, or t

<400> SEQUENCE: 72
agwgnagwan cawagg 16

<210> SEQ ID NO 73
<211> LENGTH: 16
<212> TYPE: DNA
<213> ORGANISM: synthetic construct
<220> FEATURE:
<221> NAME/KEY: misc_feature
<222> LOCATION: (3)..(3)
<223> OTHER INFORMATION: w = a or t
<220> FEATURE:
<221> NAME/KEY: modified_base
<222> LOCATION: (6)..(6)
<223> OTHER INFORMATION: n = inosine
<220> FEATURE:
<221> NAME/KEY: modified_base
<222> LOCATION: (11)..(11)
<223> OTHER INFORMATION: n = inosine
<220> FEATURE:
<221> NAME/KEY: misc_feature
<222> LOCATION: (13)..(13)
<223> OTHER INFORMATION: s= c or g
<220> FEATURE:
<221> NAME/KEY: Unsure
<222> LOCATION: (8)..(8)
<223> OTHER INFORMATION: n = a, c, g, or t

<400> SEQUENCE: 73
cawcgncnga nasgaa 16

<210> SEQ ID NO 74
<211> LENGTH: 16
<212> TYPE: DNA
<213> ORGANISM: synthetic construct -continued
<220> FEATURE:
<221> NAME/KEY: misc_feature
<222> LOCATION: (3)..(3)
<223> OTHER INFORMATION: s = c or g
<220> FEATURE:
<221> NAME/KEY: modified_base
<222> LOCATION: (5)..(5)
<223> OTHER INFORMATION: n = inosine
<220> FEATURE:
<221> NAME/KEY: modified_base
<222> LOCATION: (11)..(11)
<223> OTHER INFORMATION: n = inosine
<220> FEATURE:
<221> NAME/KEY: misc_feature
<222> LOCATION: (13)..(13)
<223> OTHER INFORMATION: w= a or t
<220> FEATURE:
<221> NAME/KEY: Unsure
<222> LOCATION: (8)..(8)
<223> OTHER INFORMATION: n = a, c, g, or t

<400> SEQUENCE: 74
tcstncgnac ntwgga 16

<210> SEQ ID NO 75
<211> LENGTH: 16
<212> TYPE: DNA
<213> ORGANISM: synthetic construct
<220> FEATURE:
<221> NAME/KEY: Unsure
<222> LOCATION: (1)..(1)
<223> OTHER INFORMATION: n = a, c, g, or t
<220> FEATURE:
<221> NAME/KEY: Unsure
<222> LOCATION: (11)..(11)
<223> OTHER INFORMATION: n = a, c, g, or t
<220> FEATURE:
<221> NAME/KEY: misc_feature
<222> LOCATION: (7)..(7)
<223> OTHER INFORMATION: s = c or g
<220> FEATURE:
<221> NAME/KEY: misc_feature
<222> LOCATION: (8)..(8)
<223> OTHER INFORMATION: w = a or t
<220> FEATURE:
<221> NAME/KEY: misc_feature
<222> LOCATION: (13)..(13)
<223> OTHER INFORMATION: w = a or t

<400> SEQUENCE: 75
ngtcgaswga nawgaa 16

<210> SEQ ID NO 76
<211> LENGTH: 16
<212> TYPE: DNA
<213> ORGANISM: synthetic construct
<220> FEATURE:
<221> NAME/KEY: Unsure
<222> LOCATION: (3)..(3)
<223> OTHER INFORMATION: n = a, c, g, or t
<220> FEATURE:
<221> NAME/KEY: Unsure
<222> LOCATION: (11)..(11)
<223> OTHER INFORMATION: n = a, c, g, or t
<220> FEATURE:
<221> NAME/KEY: misc_feature
<222> LOCATION: (7)..(7)
<223> OTHER INFORMATION: s = c or g
<220> FEATURE:
<221> NAME/KEY: misc_feature
<222> LOCATION: (8)..(8)
<223> OTHER INFORMATION: w = a or t
<220> FEATURE:
<221> NAME/KEY: misc_feature
<222> LOCATION: (13)..(13)

<223> OTHER INFORMATION: w = a or t

<400> SEQUENCE: 76
gtncgaswca nawgtt 16

<210> SEQ ID NO 77
<211> LENGTH: 16
<212> TYPE: DNA
<213> ORGANISM: synthetic construct
<220> FEATURE:
<221> NAME/KEY: misc_feature
<222> LOCATION: (1)..(1)
<223> OTHER INFORMATION: w = a or t
<220> FEATURE:
<221> NAME/KEY: misc_feature
<222> LOCATION: (8)..(8)
<223> OTHER INFORMATION: w = a or t
<220> FEATURE:
<221> NAME/KEY: Unsure
<222> LOCATION: (5)..(5)
<223> OTHER INFORMATION: n = a, c, g, or t
<220> FEATURE:
<221> NAME/KEY: Unsure
<222> LOCATION: (10)..(10)
<223> OTHER INFORMATION: n = a, c, g, or t
<220> FEATURE:
<221> NAME/KEY: Unsure
<222> LOCATION: (13)..(13)
<223> OTHER INFORMATION: n = a, c, g, or t

<400> SEQUENCE: 77
wgtgnagwan canaga 16

<210> SEQ ID NO 78
<211> LENGTH: 21
<212> TYPE: DNA
<213> ORGANISM: synthetic construct

<400> SEQUENCE: 78
gggaagcgtt cgcgaagtga g 21

<210> SEQ ID NO 79
<211> LENGTH: 23
<212> TYPE: DNA
<213> ORGANISM: synthetic construct

<400> SEQUENCE: 79
agcggataac aatttcacac agg 23

<210> SEQ ID NO 80
<211> LENGTH: 6
<212> TYPE: PRT
<213> ORGANISM: conserved sequence motif
<220> FEATURE:
<221> NAME/KEY: UNSURE
<222> LOCATION: (2)..(2)
<223> OTHER INFORMATION: Xaa = any amino acid

<400> SEQUENCE: 80

Ser Xaa Gly Leu Thr Arg
1 5

<210> SEQ ID NO 81
<211> LENGTH: 11
<212> TYPE: PRT
<213> ORGANISM: conserved sequence motif
<220> FEATURE:
<221> NAME/KEY: UNSURE
<222> LOCATION: (5)..(5)

-continued

<223> OTHER INFORMATION: Xaa = any amino acid

<400> SEQUENCE: 81

Leu Leu Phe His Xaa Ala Met Gly Phe Ala Pro
1               5                   10

<210> SEQ ID NO 82
<211> LENGTH: 7
<212> TYPE: PRT
<213> ORGANISM: conserved sequence motif
<220> FEATURE:
<221> NAME/KEY: UNSURE
<222> LOCATION: (3)..(3)
<223> OTHER INFORMATION: Xaa = any amino acid

<400> SEQUENCE: 82

Met Xaa Thr Val Phe Gly Lys
1               5

<210> SEQ ID NO 83
<211> LENGTH: 48
<212> TYPE: PRT
<213> ORGANISM: conserved sequence motif
<220> FEATURE:
<221> NAME/KEY: UNSURE
<222> LOCATION: (4)..(4)
<223> OTHER INFORMATION: Xaa = any amino acid
<220> FEATURE:
<221> NAME/KEY: UNSURE
<222> LOCATION: (8)..(8)
<223> OTHER INFORMATION: Xaa = any amino acid
<220> FEATURE:
<221> NAME/KEY: UNSURE
<222> LOCATION: (12)..(12)
<223> OTHER INFORMATION: Xaa = any amino acid
<220> FEATURE:
<221> NAME/KEY: UNSURE
<222> LOCATION: (15)..(15)
<223> OTHER INFORMATION: Xaa = any amino acid
<220> FEATURE:
<221> NAME/KEY: UNSURE
<222> LOCATION: (17)..(17)
<223> OTHER INFORMATION: Xaa = any amino acid
<220> FEATURE:
<221> NAME/KEY: UNSURE
<222> LOCATION: (19)..(20)
<223> OTHER INFORMATION: Xaa = any amino acid
<220> FEATURE:
<221> NAME/KEY: UNSURE
<222> LOCATION: (23)..(23)
<223> OTHER INFORMATION: Xaa = any amino acid
<220> FEATURE:
<221> NAME/KEY: UNSURE
<222> LOCATION: (26)..(26)
<223> OTHER INFORMATION: Xaa = any amino acid
<220> FEATURE:
<221> NAME/KEY: UNSURE
<222> LOCATION: (28)..(28)
<223> OTHER INFORMATION: Xaa = any amino acid
<220> FEATURE:
<221> NAME/KEY: UNSURE
<222> LOCATION: (31)..(32)
<223> OTHER INFORMATION: Xaa = any amino acid
<220> FEATURE:
<221> NAME/KEY: UNSURE
<222> LOCATION: (35)..(35)
<223> OTHER INFORMATION: Xaa = any amino acid
<220> FEATURE:
<221> NAME/KEY: UNSURE
<222> LOCATION: (38)..(39)
<223> OTHER INFORMATION: Xaa = any amino acid
<220> FEATURE:
<221> NAME/KEY: UNSURE
<222> LOCATION: (43)..(44)
<223> OTHER INFORMATION: Xaa = any amino acid -continued
<220> FEATURE:
<221> NAME/KEY: UNSURE
<222> LOCATION: (46)..(46)
<223> OTHER INFORMATION: Xaa = any amino acid

<400> SEQUENCE: 83

Glu Gly Tyr Xaa Leu Leu Gly Xaa Phe Asn Trp Xaa Asp His Xaa Pro
1               5                   10                  15

Xaa Leu Xaa Xaa Leu Asp Xaa Gln Gly Xaa Arg Xaa Arg Cys Xaa Xaa
            20                  25                  30

Leu Val Xaa Lys Val Xaa Xaa Phe Val Gly Xaa Xaa Ile Xaa Glu His
        35                  40                  45

<210> SEQ ID NO 84
<211> LENGTH: 7
<212> TYPE: PRT
<213> ORGANISM: conserved sequence motif

<400> SEQUENCE: 84

Asp Phe Val Asp Val Leu Leu
1               5

<210> SEQ ID NO 85
<211> LENGTH: 15
<212> TYPE: PRT
<213> ORGANISM: conserved sequence motif

<400> SEQUENCE: 85

Ala Val Leu Trp Glu Met Ile Phe Arg Gly Thr Asp Thr Val Ala
1               5                   10                  15

<210> SEQ ID NO 86
<211> LENGTH: 4
<212> TYPE: PRT
<213> ORGANISM: conserved sequence motif

<400> SEQUENCE: 86

Met Ala Arg Met
1

<210> SEQ ID NO 87
<211> LENGTH: 6
<212> TYPE: PRT
<213> ORGANISM: conserved sequence motif

<400> SEQUENCE: 87

Ile Gln Ala Lys Ala Gln
1               5

<210> SEQ ID NO 88
<211> LENGTH: 19
<212> TYPE: PRT
<213> ORGANISM: conserved sequence motif
<220> FEATURE:
<221> NAME/KEY: UNSURE
<222> LOCATION: (7)..(7)
<223> OTHER INFORMATION: Xaa = any amino acid

<400> SEQUENCE: 88

Val Lys Glu Thr Leu Arg Xaa His Pro Pro Gly Pro Leu Leu Ser Trp
1               5                   10                  15

Ala Arg Leu

<210> SEQ ID NO 89

-continued

<211> LENGTH: 9
<212> TYPE: PRT
<213> ORGANISM: conserved sequence motif

<400> SEQUENCE: 89

Gly Thr Thr Ala Met Val Asn Met Trp
1 5

<210> SEQ ID NO 90
<211> LENGTH: 16
<212> TYPE: PRT
<213> ORGANISM: conserved sequence motif
<220> FEATURE:
<221> NAME/KEY: UNSURE
<222> LOCATION: (9)..(9)
<223> OTHER INFORMATION: Xaa = any amino acid
<220> FEATURE:
<221> NAME/KEY: UNSURE
<222> LOCATION: (13)..(13)
<223> OTHER INFORMATION: Xaa = any amino acid

<400> SEQUENCE: 90

Asp Leu Arg Leu Ala Pro Phe Gly Xaa Gly Arg Arg Xaa Cys Pro Gly
1 5 10 15

<210> SEQ ID NO 91
<211> LENGTH: 7
<212> TYPE: PRT
<213> ORGANISM: conserved sequence motif
<220> FEATURE:
<221> NAME/KEY: UNSURE
<222> LOCATION: (3)..(3)
<223> OTHER INFORMATION: Xaa = any amino acid

<400> SEQUENCE: 91

Pro Leu Xaa Cys Lys Ala Val
1 5

<210> SEQ ID NO 92
<211> LENGTH: 1585
<212> TYPE: DNA
<213> ORGANISM: Hordeum vulgare

<400> SEQUENCE: 92
gcggccgcga gctcaattaa ccctcactaa agggagtcga ctcgatcttt ccatggttac 60
cggcccggag gactccctcc tcttgctctt cctcccggct accaccctgc tcccacccct 120
tctcgccgtg ctcctcctcg ccgcctccct cctgtggctg tcaccgggcg gtccggcgtg 180
ggctttgtca ctctgccgtc gcccgccgcc aggcccaccg ggcgtggtca ccgcgctctc 240
cagccccgtg gcgcaccgcg tcatggctac gctgtcacgc tccgtccgcg gcggcgcggc 300
attgatgtcc ttctccgtcg gcctcacccg cgtcgtcgtg tcgagcaggc aagatacggc 360
gcgtgagata ctcgtcaacc cggcgttcgg cgaccggccg gtgaaggacg cggcgcgcca 420
cctcctcttc caccgcgcca tgggttttgc cccgtcgggc gacgcgcact ggcgtgcgct 480
gcgccgtctc gccgcggcgc acctcttcgg ccctcgccgt gtggcggcct ccgcaccccca 540 ccgttcctct attggggcgc gcatgctcgg cgacgtcgcc tccatcatgg cccgccacgg 600
cgaggtcgct cctcggaggt tcctgcacgc ggcgtccctc aaccacgtca tggccgtcgt 660
cttcggcaag cgctacgacg acttcacaag ccaagaagga gtcgttgtgg aggagatggt 720
aaacgaaggg tacgacctcc tcggcacgtt caactgggca gatcacctgc cattcctcaa 780
gtgcctcgat ctccagggcg tgcggcgccg gtgcaacagg ttagtccggc aagtggaggc 840

-continued

```
gtacgtcggt aacatcatac aggagcacaa ggcgaggcgc gacagtgcat caggcattgc    900

ggatgagctc tccggcgact tcgtcgatgt gctcctcggc ctcgacggag aagacaagat    960

gtcagagtcc gacatgatcg ccgttctttg ggagatgatc tttagaggga cggacacggt   1020

ggcgatcttg atggagtgga ttatggcgag gatggtgctg cacccggaga tccagtcgaa   1080

ggcccgggcg gagcttgacg ccgtggtggg ccggggcagg gccgtgacgg acgaggacgt   1140

gtcgaggctc ccctacatcc agtgcatcgt caaggagacg ctgcgcatgc acccgccggg   1200

cccgctcctc tcatgggcgc ggctggccgt gcacgacgcg cacgtcggcg gccacctcgt   1260

gccggccggc acgacggcga tggtgaacat gtgggccatc gcgcacgacg cggcggtgtg   1320

gcccgagccg gagctgttcc ggccggagcg gttcatggag gaggacgtga gcgtgctggg   1380

cagcgacctc cgcctggccc cgttcggcgc cgggcggcgc gtgtgccccg ggaagatgct   1440

ggccctcgcc accgtccacc tctggctcgc gcagctgctt caccggttcg agtgggctcc   1500

ctcggggagc gtcgacctgt cagagcgcct caagatgtca ctggagatgg ccacgccgct   1560

ggtctgcaag gccgtcgctc gctag                                         1585
```

<210> SEQ ID NO 93
<211> LENGTH: 510
<212> TYPE: PRT
<213> ORGANISM: Hordeum vulgare

<400> SEQUENCE: 93

```
Met Val Thr Gly Pro Glu Asp Ser Leu Leu Leu Leu Phe Leu Pro Ala
1               5                   10                  15

Thr Thr Leu Leu Pro Pro Leu Leu Ala Val Leu Leu Leu Ala Ala Ser
            20                  25                  30

Leu Leu Trp Leu Ser Pro Gly Gly Pro Ala Trp Ala Leu Ser Leu Cys
        35                  40                  45

Arg Arg Pro Pro Pro Gly Pro Pro Gly Val Val Thr Ala Leu Ser Ser
    50                  55                  60

Pro Val Ala His Arg Val Met Ala Thr Leu Ser Arg Ser Val Arg Gly
65                  70                  75                  80

Gly Ala Ala Leu Met Ser Phe Ser Val Gly Leu Thr Arg Val Val Val
                85                  90                  95

Ser Ser Arg Gln Asp Thr Ala Arg Glu Ile Leu Val Asn Pro Ala Phe
            100                 105                 110

Gly Asp Arg Pro Val Lys Asp Ala Ala Arg His Leu Leu Phe His Arg
        115                 120                 125

Ala Met Gly Phe Ala Pro Ser Gly Asp Ala His Trp Arg Ala Leu Arg
    130                 135                 140

Arg Leu Ala Ala Ala His Leu Phe Gly Pro Arg Arg Val Ala Ala Ser
145                 150                 155                 160

Ala Pro His Arg Ser Ser Ile Gly Ala Arg Met Leu Gly Asp Val Ala
                165                 170                 175

Ser Ile Met Ala Arg His Gly Glu Val Ala Pro Arg Arg Phe Leu His
            180                 185                 190

Ala Ala Ser Leu Asn His Val Met Ala Val Val Phe Gly Lys Arg Tyr
        195                 200                 205

Asp Asp Phe Thr Ser Gln Glu Gly Val Val Val Glu Glu Met Val Asn
    210                 215                 220

Glu Gly Tyr Asp Leu Leu Gly Thr Phe Asn Trp Ala Asp His Leu Pro
225                 230                 235                 240
```

-continued

Phe Leu Lys Cys Leu Asp Leu Gln Gly Val Arg Arg Arg Cys Asn Arg
                245                 250                 255

Leu Val Arg Gln Val Glu Ala Tyr Val Gly Asn Ile Ile Gln Glu His
            260                 265                 270

Lys Ala Arg Arg Asp Ser Ala Ser Gly Ile Ala Asp Glu Leu Ser Gly
        275                 280                 285

Asp Phe Val Asp Val Leu Leu Gly Leu Asp Gly Glu Asp Lys Met Ser
    290                 295                 300

Glu Ser Asp Met Ile Ala Val Leu Trp Glu Met Ile Phe Arg Gly Thr
305                 310                 315                 320

Asp Thr Val Ala Ile Leu Met Glu Trp Ile Met Ala Arg Met Val Leu
                325                 330                 335

His Pro Glu Ile Gln Ser Lys Ala Arg Ala Glu Leu Asp Ala Val Val
            340                 345                 350

Gly Arg Gly Arg Ala Val Thr Asp Glu Asp Val Ser Arg Leu Pro Tyr
        355                 360                 365

Ile Gln Cys Ile Val Lys Glu Thr Leu Arg Met His Pro Pro Gly Pro
    370                 375                 380

Leu Leu Ser Trp Ala Arg Leu Ala Val His Asp Ala His Val Gly Gly
385                 390                 395                 400

His Leu Val Pro Ala Gly Thr Thr Ala Met Val Asn Met Trp Ala Ile
                405                 410                 415

Ala His Asp Ala Ala Val Trp Pro Glu Pro Glu Leu Phe Arg Pro Glu
            420                 425                 430

Arg Phe Met Glu Glu Asp Val Ser Val Leu Gly Ser Asp Leu Arg Leu
        435                 440                 445

Ala Pro Phe Gly Ala Gly Arg Arg Val Cys Pro Gly Lys Met Leu Ala
    450                 455                 460

Leu Ala Thr Val His Leu Trp Leu Ala Gln Leu Leu His Arg Phe Glu
465                 470                 475                 480

Trp Ala Pro Ser Gly Ser Val Asp Leu Ser Glu Arg Leu Lys Met Ser
                485                 490                 495

Leu Glu Met Ala Thr Pro Leu Val Cys Lys Ala Val Ala Arg
            500                 505                 510

<210> SEQ ID NO 94
<211> LENGTH: 1758
<212> TYPE: DNA
<213> ORGANISM: Zea mays

<400> SEQUENCE: 94
atgcagttat taggactgcc aaatacctac ctgcgattta aactgcaaac agtaaattat 60
ttggcgtgca gttgccagat cagcagccat tttcaccgca ctccccccgc cccttttaaa 120
agctccctcc ctctcaacac tctacacaca ccagctccac tgcatcaaaa cccctcatca 180
ccctgcagcc tgcactcatc agacatggtg ctcaccatgg ccagcggcca agaggactcg 240
ctcctcctcc cgaccacctc cccactgccg cccctcatgg cagtgttcat cctagccgcc 300
gtcctcctgt ggctctcccc cggcggtcct gcgtgggcgc tctcccgctg ccgccgcccg 360
ccgcccgggc caacgggcgt ggtcaccgcg ctctccagcc ccgtggcgca ccgcaccctg 420
gcggcgctgt cccacgccgt agacggcggc aaggcactga tggccttctc ggtcgggctg 480
acccgtctcg tcgtgtcgag ccagcccgat acggcgcgcg agatcctcgc cagcccccgcg 540 ttcggcgacc gccccgtcaa ggacgcggcg cgccacctgc tcttccaccg cgccatgggc 600

-continued

```
ttcgcgccct ccggagacgc gcactggcgc gggctccgcc gcctcgccgc caaccacctg    660

ttcggcccgc gccgcgtggc gggtgccgcg caccaccgcg cctccatcgg cgaggccatg    720

gtcgccgacg tcgccgctgc catggcgcgc cacggcgagg tccctctcaa gcgcgtgctg    780

catgtcgcat ctctcaacca cgtcatggcc accgtgtttg gcaagcgcta cgacatgggc    840

agccgagagg gcgcccttct ggacgagatg gtggccgagg gctacgacct cctgggcacg    900

ttcaactggg ctgaccacct gccattgctc aagcatctcg acccccaggg cgtgcgccgc    960

cggtgcaaca ggctggtccg aaaggtcgaa tcgttcgttg gcaagatcat cttggagcac   1020

agggcgcggc gcgcaaatgg aggagtcgtg ggcgatgagt gcatgggtga cttcgtcgac   1080

gtccttcttg gcctcgaggg agaggagaag ctgtcagatg cggacatgat cgctgttctt   1140

tgggagatgg tcttcagagg cgccgacacc gtggcgatct tgatggagtg ggtcatggcg   1200

aggatggcgc tgcacccgga catccaggcg aaggcccagg cggagctgga cggcgtcgtg   1260

ggcatcgggc gcggcgtggc ggacgccgac gtcgccagcc taccctacat ccagtgcatc   1320

gtgaaggaga cgctgcgcat gcacccgcca ggcccgctcc tgtcgtgggc gcgcctcgcc   1380

gtccacgacg cgcacgtcgg cggccacctg gtccccgccg gcaccacagc catggtgaac   1440

atgtggtcca tcgcgcacga ccccgccatc tgggccgagc cggagaagtt ccgccccgag   1500

cggttccagg aggaggacgt gagcgtcctc gggagcgacc tccgcctggc cccccttcggc   1560

gccgggcgcc gcgcctgccc cggcaagata ctggccctcg ccaccaccca cctctgggtc   1620

gcccagcttc tgcacaagtt cgagtgggcc gccggcgggg gcgtcgacct gtcggagcgc   1680

ctgagcatgt cgctggagat ggccacgccg ctggtgtgca aggccgtacc cagggttcag   1740

ggccaagcgg cctcctag                                                 1758
```

<210> SEQ ID NO 95
<211> LENGTH: 585
<212> TYPE: PRT
<213> ORGANISM: Zea mays

<400> SEQUENCE: 95

```
Met Gln Leu Leu Gly Leu Pro Asn Thr Tyr Leu Arg Phe Lys Leu Gln
  1               5                  10                  15

Thr Val Asn Tyr Leu Ala Cys Ser Cys Gln Ile Ser Ser His Phe His
             20                  25                  30

Arg Thr Pro Pro Ala Pro Phe Lys Ser Ser Leu Pro Leu Asn Thr Leu
         35                  40                  45

His Thr Pro Ala Pro Leu His Gln Asn Pro Ser Ser Pro Cys Ser Leu
     50                  55                  60

His Ser Ser Asp Met Val Leu Thr Met Ala Ser Gly Gln Glu Asp Ser
 65                  70                  75                  80

Leu Leu Leu Pro Thr Thr Ser Pro Leu Pro Pro Leu Met Ala Val Phe
                 85                  90                  95

Ile Leu Ala Ala Val Leu Leu Trp Leu Ser Pro Gly Gly Pro Ala Trp
            100                 105                 110

Ala Leu Ser Arg Cys Arg Arg Pro Pro Pro Gly Pro Thr Gly Val Val
        115                 120                 125

Thr Ala Leu Ser Ser Pro Val Ala His Arg Thr Leu Ala Ala Leu Ser
    130                 135                 140

His Ala Val Asp Gly Gly Lys Ala Leu Met Ala Phe Ser Val Gly Leu
145                 150                 155                 160

Thr Arg Leu Val Val Ser Ser Gln Pro Asp Thr Ala Arg Glu Ile Leu
```

-continued

```
                165                 170                 175

Ala Ser Pro Ala Phe Gly Asp Arg Pro Val Lys Asp Ala Ala Arg His
            180                 185                 190

Leu Leu Phe His Arg Ala Met Gly Phe Ala Pro Ser Gly Asp Ala His
        195                 200                 205

Trp Arg Gly Leu Arg Arg Leu Ala Ala Asn His Leu Phe Gly Pro Arg
    210                 215                 220

Arg Val Ala Gly Ala Ala His His Arg Ala Ser Ile Gly Glu Ala Met
225                 230                 235                 240

Val Ala Asp Val Ala Ala Ala Met Ala Arg His Gly Glu Val Pro Leu
                245                 250                 255

Lys Arg Val Leu His Val Ala Ser Leu Asn His Val Met Ala Thr Val
            260                 265                 270

Phe Gly Lys Arg Tyr Asp Met Gly Ser Arg Glu Gly Ala Leu Leu Asp
        275                 280                 285

Glu Met Val Ala Glu Gly Tyr Asp Leu Leu Gly Thr Phe Asn Trp Ala
    290                 295                 300

Asp His Leu Pro Leu Leu Lys His Leu Asp Pro Gln Gly Val Arg Arg
305                 310                 315                 320

Arg Cys Asn Arg Leu Val Arg Lys Val Glu Ser Phe Val Gly Lys Ile
                325                 330                 335

Ile Leu Glu His Arg Ala Arg Arg Ala Asn Gly Gly Val Val Gly Asp
            340                 345                 350

Glu Cys Met Gly Asp Phe Val Asp Val Leu Leu Gly Leu Glu Gly Glu
        355                 360                 365

Glu Lys Leu Ser Asp Ala Asp Met Ile Ala Val Leu Trp Glu Met Val
    370                 375                 380

Phe Arg Gly Ala Asp Thr Val Ala Ile Leu Met Glu Trp Val Met Ala
385                 390                 395                 400

Arg Met Ala Leu His Pro Asp Ile Gln Ala Lys Ala Gln Ala Glu Leu
                405                 410                 415

Asp Gly Val Val Gly Ile Gly Arg Gly Val Ala Asp Ala Asp Val Ala
            420                 425                 430

Ser Leu Pro Tyr Ile Gln Cys Ile Val Lys Glu Thr Leu Arg Met His
        435                 440                 445

Pro Pro Gly Pro Leu Leu Ser Trp Ala Arg Leu Ala Val His Asp Ala
    450                 455                 460

His Val Gly Gly His Leu Val Pro Ala Gly Thr Thr Ala Met Val Asn
465                 470                 475                 480

Met Trp Ser Ile Ala His Asp Pro Ala Ile Trp Ala Glu Pro Glu Lys
                485                 490                 495

Phe Arg Pro Glu Arg Phe Gln Glu Glu Asp Val Ser Val Leu Gly Ser
            500                 505                 510

Asp Leu Arg Leu Ala Pro Phe Gly Ala Gly Arg Arg Ala Cys Pro Gly
        515                 520                 525

Lys Ile Leu Ala Leu Ala Thr Thr His Leu Trp Val Ala Gln Leu Leu
    530                 535                 540

His Lys Phe Glu Trp Ala Ala Gly Gly Gly Val Asp Leu Ser Glu Arg
545                 550                 555                 560

Leu Ser Met Ser Leu Glu Met Ala Thr Pro Leu Val Cys Lys Ala Val
                565                 570                 575

Pro Arg Val Gln Gly Gln Ala Ala Ser
            580                 585
```

-continued

<210> SEQ ID NO 96
<211> LENGTH: 1545
<212> TYPE: DNA
<213> ORGANISM: Zea mays

<400> SEQUENCE: 96

```
atggacgcca ccctcagcac cacgaccacc caggactccc tactcttcct cctcccttca     60
gccgccacct tgctctcccc gctcctgacc gtgctcctcg tagccgtctc gctgctctgg    120
ctcttcccgg gcgggcccgc gtgggcgttc gtctccaggt cccgcgcgac gccgccgggc    180
gcgccgggcc tggtcaccgc gctcgcgggc cccgcggcgc accgcgccct cgcgtcgctg    240
tcccggtccc ttcccggcgg cgccgcgctg tcggccttct ccgtcggcct cacgcgcctc    300
gtcgtagcga gccagccgga cacggcgcgg gagctcctgg ccagcgccgc cttcgccgac    360
cgccccgtga aggacgcggc gcgggggctc ctcttccacc gcgccatggg ctttgccccg    420
tcgggcgact actggcgcgc gcttcggcgc atcagctccg cgtacctctt cagcccgcgc    480
agcgtggccg cggcgggccc gcgccgcgcc gccatcggcg agcgcatgct gcgggacctc    540
tccggcgcgg ccggacgaga ggtcgtcatg cggcgcgtgc tccacgcggc atccctggac    600
cacgtcatgg ccaccgtgtt cggcgcgcgc tacgacgccg ccagcccgga gggcgcggag    660
ctggaggaga tggtgaagga agggtacgac ctgctcggca tgttcaactg ggcgaccac    720
ctgccgctgc tcaggtggct ggacctgcag ggcgtcagga ggcggtgcag gagcctggtg    780
ggcagagtca acgtgttcgt ggccaggatc atcgaagagc acaggcagaa gaaggacgac    840
gccattggag agccggcggc cgccggagac ttcgtcgacg tcttgctggg actggagggc    900
gaggagaagc tgtcggactc cgacatgatc gctgtcctct gggagatgat ctttcgaggg    960
accgacacgg tggcgatcct gctggagtgg gtgatggcgc ggatggtgct gcacccgggc   1020
atccagtcca aggcgcaggc ggagctggac gccgtggtgg gccgcggccg cgccgtttgc   1080
gacgccgacg tggcccgcct gccctacctg cagcgcgtcg tgaaggagac gctccgcgtg   1140
cacccgccgg gcccgctgct ctcgtgggcg cgcctggccg tgcgcgacgc ggtggtcggc   1200
ggccacgtgg tccccgcggg caccacggcc atggtcaaca tgtgggccat cgcgcacgac   1260
cccgcggtgt ggccggagcc ctccgctttc cggcccgagc ggttcgaggt ggaggacgtg   1320
agcgtgctgg gcggcgacct ccgcctcgcg cccttcggcg ccggccggcg cgtgtgcccg   1380
ggcaagacgc tggcgctcgc cactgtccac ctctggctcg cgcagctgct gcaccgcttc   1440
cggtgggcgc cggccgacgg ccgcggcgtc gacctggcgg agcgcctcgg catgtccctg   1500
gagatggaga agcccctcgt gtgcaagccc acgccgaggt ggtga                   1545
```

<210> SEQ ID NO 97
<211> LENGTH: 514
<212> TYPE: PRT
<213> ORGANISM: Zea mays

<400> SEQUENCE: 97

```
Met Asp Ala Thr Leu Ser Thr Thr Thr Thr Gln Asp Ser Leu Leu Phe
  1               5                  10                  15

Leu Leu Pro Ser Ala Ala Thr Leu Leu Ser Pro Leu Leu Thr Val Leu
             20                  25                  30

Leu Val Ala Val Ser Leu Leu Trp Leu Phe Pro Gly Gly Pro Ala Trp
         35                  40                  45

Ala Phe Val Ser Arg Ser Arg Ala Thr Pro Pro Gly Ala Pro Gly Leu
```

-continued

```
        50                  55                  60

Val Thr Ala Leu Ala Gly Pro Ala Ala His Arg Ala Leu Ala Ser Leu
 65                  70                  75                  80

Ser Arg Ser Leu Pro Gly Gly Ala Ala Leu Ser Ala Phe Ser Val Gly
                 85                  90                  95

Leu Thr Arg Leu Val Val Ala Ser Gln Pro Asp Thr Ala Arg Glu Leu
            100                 105                 110

Leu Ala Ser Ala Ala Phe Ala Asp Arg Pro Val Lys Asp Ala Ala Arg
        115                 120                 125

Gly Leu Leu Phe His Arg Ala Met Gly Phe Ala Pro Ser Gly Asp Tyr
    130                 135                 140

Trp Arg Ala Leu Arg Arg Ile Ser Ser Ala Tyr Leu Phe Ser Pro Arg
145                 150                 155                 160

Ser Val Ala Ala Ala Gly Pro Arg Arg Ala Ala Ile Gly Glu Arg Met
                165                 170                 175

Leu Arg Asp Leu Ser Gly Ala Ala Gly Arg Glu Val Val Met Arg Arg
            180                 185                 190

Val Leu His Ala Ala Ser Leu Asp His Val Met Ala Thr Val Phe Gly
        195                 200                 205

Ala Arg Tyr Asp Ala Ala Ser Pro Glu Gly Ala Glu Leu Glu Glu Met
    210                 215                 220

Val Lys Glu Gly Tyr Asp Leu Leu Gly Met Phe Asn Trp Gly Asp His
225                 230                 235                 240

Leu Pro Leu Leu Arg Trp Leu Asp Leu Gln Gly Val Arg Arg Arg Cys
                245                 250                 255

Arg Ser Leu Val Gly Arg Val Asn Val Phe Val Ala Arg Ile Ile Glu
            260                 265                 270

Glu His Arg Gln Lys Lys Asp Asp Ala Ile Gly Glu Pro Ala Ala Ala
        275                 280                 285

Gly Asp Phe Val Asp Val Leu Leu Gly Leu Glu Gly Glu Glu Lys Leu
    290                 295                 300

Ser Asp Ser Asp Met Ile Ala Val Leu Trp Glu Met Ile Phe Arg Gly
305                 310                 315                 320

Thr Asp Thr Val Ala Ile Leu Leu Glu Trp Val Met Ala Arg Met Val
                325                 330                 335

Leu His Pro Gly Ile Gln Ser Lys Ala Gln Ala Glu Leu Asp Ala Val
            340                 345                 350

Val Gly Arg Gly Arg Ala Val Cys Asp Ala Asp Val Ala Arg Leu Pro
        355                 360                 365

Tyr Leu Gln Arg Val Val Lys Glu Thr Leu Arg Val His Pro Pro Gly
    370                 375                 380

Pro Leu Leu Ser Trp Ala Arg Leu Ala Val Arg Asp Ala Val Val Gly
385                 390                 395                 400

Gly His Val Val Pro Ala Gly Thr Thr Ala Met Val Asn Met Trp Ala
                405                 410                 415

Ile Ala His Asp Pro Ala Val Trp Pro Glu Pro Ser Ala Phe Arg Pro
            420                 425                 430

Glu Arg Phe Glu Val Glu Asp Val Ser Val Leu Gly Gly Asp Leu Arg
        435                 440                 445

Leu Ala Pro Phe Gly Ala Gly Arg Arg Val Cys Pro Gly Lys Thr Leu
    450                 455                 460

Ala Leu Ala Thr Val His Leu Trp Leu Ala Gln Leu Leu His Arg Phe
465                 470                 475                 480
```

-continued

Arg Trp Ala Pro Ala Asp Gly Arg Gly Val Asp Leu Ala Glu Arg Leu
485 490 495

Gly Met Ser Leu Glu Met Glu Lys Pro Leu Val Cys Lys Pro Thr Pro
500 505 510

Arg Trp

<210> SEQ ID NO 98
<211> LENGTH: 1557
<212> TYPE: DNA
<213> ORGANISM: Zea mays

<400> SEQUENCE: 98
atggacgcca cccaggactc cctcctcttc ctcttcccgg ccgccgccac cttactctcc 60
ccgctccttg ccgtgctcct cgcagctctc tcgctgctct ggctctaccc gggcggtccc 120
gcgtgggcgc tcatctctag gtcccgcgcg acgccgcccg gcacgccgga cgtggtcacc 180
gcgctcgcgg gtcccgccgc gcaccgcgcc ctggcgtcgc tgtcgcagtc gctgcccggc 240
cgcgccgcgc tgtcggcctt ctccgtaggt ctcacgcgcc ttgtcgtggc cagccagccg 300
gacacggtgc gggagctcct ggccagcgcc gccttcgccg accgccccat caaggacgcg 360
gcgcgggggc tcctcttcca ccgcgccatg ggcttcgccc cctccggcga ctactggcgc 420
gcgctgcggc gcatcagctc cgcgtacctc ttcagcccgc gcagcgtgtc cgcaacggcc 480
ccgcgtcgtg tcgccatcgg cgagcgcatg ctgcgggacc tctcggccgc gcccggcggc 540
gaggtcgtca tgcggcgcgt gctccacgcg gcctccctcg accacgtcat ggccaccgtg 600
ttcggcgcgc actacgacgc cgccagcccg gagagcgcgg agctggagga gatggtgaag 660
gaagggtacg acctgctcgg cttgttcaac tggggcgacc acctgccgtt gctcaggtgg 720
ctggacctgc aaggcgtcag gaggaggtgc aggagcctgg tgagcagagt gaacgtgttc 780
gtggcgagga tcatcgaaga gcacaggcgg aagaagaagg aggccgccag tggcgagtcg 840
gtcgccggag acttcgtcga cgtcttgctg ggattgcagg gcgaggagaa gctgtcggac 900
tttgagagtt gtgttaacac ggactccgac atgatcgctg tcctctggga gatgatcttt 960
cgaggcaccg acacggtcgc gatcctgctg gagtgggtga tggcgcggat ggtgctgcac 1020
ccgggcatcc agtccaaggc gcaggcggag ctggacgccg tcgtgggtcg cggccgcgtg 1080
tccgacgccg atgtggtccg cctgccctac ctccagcgcg tcgtaaagga gacgctccgc 1140
gtgcacccgc ccggcccgct gctgtcgtgg gcgcgcctgg ccgtgcacga cgcggtggtc 1200
ggcggccacc tggtccccgc cggcaccacg gccatggtga acatgtgggc gatcgcgcac 1260
gaccccgcgg tgtggccgga gccctccgcg ttccgccccg agcggttcga ggaggagtac 1320
gtgagcgtgc tgggcggcga cctccggttc ggcgccggcc ggcgcgtgtg ccccggcaag 1380
acgctggcac tcgccactgt ccacctctgg ctcgcgcagc tgctgcaccg cttccagtgg 1440
gcggcgtcga cctggcggag cgactcggca ttgggcggcg tcgacctggc ggagcgactc 1500
ggcatgtcgc tggagatgga gaagcccctc gtgtgcaagc ccacgccgag gtggtaa 1557

<210> SEQ ID NO 99
<211> LENGTH: 518
<212> TYPE: PRT
<213> ORGANISM: Zea mays

<400> SEQUENCE: 99

Met Asp Ala Thr Gln Asp Ser Leu Leu Phe Leu Phe Pro Ala Ala Ala
1 5 10 15

-continued

```
Thr Leu Leu Ser Pro Leu Leu Ala Val Leu Leu Ala Ala Leu Ser Leu
            20                  25                  30

Leu Trp Leu Tyr Pro Gly Gly Pro Ala Trp Ala Leu Ile Ser Arg Ser
        35                  40                  45

Arg Ala Thr Pro Pro Gly Thr Pro Asp Val Val Thr Ala Leu Ala Gly
    50                  55                  60

Pro Ala Ala His Arg Ala Leu Ala Ser Leu Ser Gln Ser Leu Pro Gly
65                  70                  75                  80

Arg Ala Ala Leu Ser Ala Phe Ser Val Gly Leu Thr Arg Leu Val Val
                85                  90                  95

Ala Ser Gln Pro Asp Thr Val Arg Glu Leu Leu Ala Ser Ala Ala Phe
            100                 105                 110

Ala Asp Arg Pro Ile Lys Asp Ala Ala Arg Gly Leu Leu Phe His Arg
        115                 120                 125

Ala Met Gly Phe Ala Pro Ser Gly Asp Tyr Trp Arg Ala Leu Arg Arg
    130                 135                 140

Ile Ser Ser Ala Tyr Leu Phe Ser Pro Arg Ser Val Ser Ala Thr Ala
145                 150                 155                 160

Pro Arg Arg Val Ala Ile Gly Glu Arg Met Leu Arg Asp Leu Ser Ala
                165                 170                 175

Ala Pro Gly Gly Glu Val Val Met Arg Arg Val Leu His Ala Ala Ser
            180                 185                 190

Leu Asp His Val Met Ala Thr Val Phe Gly Ala His Tyr Asp Ala Ala
        195                 200                 205

Ser Pro Glu Ser Ala Glu Leu Glu Glu Met Val Lys Glu Gly Tyr Asp
    210                 215                 220

Leu Leu Gly Leu Phe Asn Trp Gly Asp His Leu Pro Leu Leu Arg Trp
225                 230                 235                 240

Leu Asp Leu Gln Gly Val Arg Arg Arg Cys Arg Ser Leu Val Ser Arg
                245                 250                 255

Val Asn Val Phe Val Ala Arg Ile Ile Glu Glu His Arg Arg Lys Lys
            260                 265                 270

Lys Glu Ala Ala Ser Gly Glu Ser Val Ala Gly Asp Phe Val Asp Val
        275                 280                 285

Leu Leu Gly Leu Gln Gly Glu Glu Lys Leu Ser Asp Phe Glu Ser Cys
    290                 295                 300

Val Asn Thr Asp Ser Asp Met Ile Ala Val Leu Trp Glu Met Ile Phe
305                 310                 315                 320

Arg Gly Thr Asp Thr Val Ala Ile Leu Leu Glu Trp Val Met Ala Arg
                325                 330                 335

Met Val Leu His Pro Gly Ile Gln Ser Lys Ala Gln Ala Glu Leu Asp
            340                 345                 350

Ala Val Val Gly Arg Gly Arg Val Ser Asp Ala Asp Val Val Arg Leu
        355                 360                 365

Pro Tyr Leu Gln Arg Val Val Lys Glu Thr Leu Arg Val His Pro Pro
    370                 375                 380

Gly Pro Leu Leu Ser Trp Ala Arg Leu Ala Val His Asp Ala Val Val
385                 390                 395                 400

Gly Gly His Leu Val Pro Ala Gly Thr Thr Ala Met Val Asn Met Trp
                405                 410                 415

Ala Ile Ala His Asp Pro Ala Val Trp Pro Glu Pro Ser Ala Phe Arg
            420                 425                 430
```

-continued

```
Pro Glu Arg Phe Glu Glu Glu Tyr Val Ser Val Leu Gly Gly Asp Leu
        435                 440                 445

Arg Phe Gly Ala Gly Arg Arg Val Cys Pro Gly Lys Thr Leu Ala Leu
    450                 455                 460

Ala Thr Val His Leu Trp Leu Ala Gln Leu Leu His Arg Phe Gln Trp
465                 470                 475                 480

Ala Ala Ser Thr Trp Arg Ser Asp Ser Ala Leu Gly Gly Val Asp Leu
                485                 490                 495

Ala Glu Arg Leu Gly Met Ser Leu Glu Met Glu Lys Pro Leu Val Cys
            500                 505                 510

Lys Pro Thr Pro Arg Trp
        515


<210> SEQ ID NO 100
<211> LENGTH: 1155
<212> TYPE: DNA
<213> ORGANISM: Oryza sativa

<400> SEQUENCE: 100

atggggtcgc tgatgtcctg catctccggg caggcaccgt cggcgtcgcc gccgccggtg      60

gcgaagcggc ggtcatccgt gtcgtcgcgc cgcggcggcg gcggcggagg cgccaaggcg     120

gtggccatcg acgaggaggc gctggcggcg gcggcggcgc tggtgctggg gcagaggagc     180

tcgttcggcg gaggcggggg tggaggcgga ggcgcgttcg agcggtcggc gtcggtgcgg     240

tacgcggcga ggcggcagca gcagcagcag ggcccgccgc tgccgaggag ctccagcacg     300

cgcccccgct ccctcgccga cccggagctc cacccgcagc agcttctcgc caaggatttg     360

aacactaaag atcttgaaac caacatcatt gttcttgttc atggaggagg ttttggtgct     420

tggtgttggt acaagactat agcacttctt gaggatagtg ggttcagagt caatgctatt     480

gacttaacag gttccgggat tcattcgtat gatacaaaca agattagcag tctcacgcag     540

tatgctgagc cgcttacatc ttaccttaaa agcctaggtg acaacgaaaa ggtgattttg     600

gttggacatg attttggtgg tgcttgtata tcctacgcaa tggagatgtt tccatcaaaa     660

gttgcgaagg ctgttttcct ttgtgcagca atgctgaaaa atgggcatag tactcttgat     720

atgtttcaac aacagatgga tacaaatggt acactccaaa gggcgcagga atttgtatat     780

tccaatggca aggagcagcc tcccaccgct atcaatatag agaagtcttt actgaaacat     840

ttgttgttca accaaagccc ctctaaggat gtatctttgg cttcagtgtc catgagacct     900

atcccctttg ctcctgtgct ggagaagctg gtcctaacag aagagaagta cggatcggtg     960

cggcgattct acgtcgaaac cacagaagac aatgccattc cacttcatct tcagcaaggt    1020

atgtgcgaca tgaacccgcc cgagaaggtt cttcggttga aaggctcgga tcatgcccca    1080

ttcttctcca agccacaagc tctgcacaag acccttgtag agatagcaac catgccacca    1140

gtcaaggcat catga                                                     1155


<210> SEQ ID NO 101
<211> LENGTH: 384
<212> TYPE: PRT
<213> ORGANISM: Oryza sativa

<400> SEQUENCE: 101

Met Gly Ser Leu Met Ser Cys Ile Ser Gly Gln Ala Pro Ser Ala Ser
  1               5                  10                  15

Pro Pro Pro Val Ala Lys Arg Arg Ser Ser Val Ser Ser Arg Arg Gly
            20                  25                  30
```

-continued

```
Gly Gly Gly Gly Gly Ala Lys Ala Val Ala Ile Asp Glu Glu Ala Leu
        35                  40                  45

Ala Ala Ala Ala Ala Leu Val Leu Gly Gln Arg Ser Ser Phe Gly Gly
    50                  55                  60

Gly Gly Gly Gly Gly Gly Gly Ala Phe Glu Arg Ser Ala Ser Val Arg
 65                  70                  75                  80

Tyr Ala Ala Arg Arg Gln Gln Gln Gln Gln Gly Pro Pro Leu Pro Arg
                85                  90                  95

Ser Ser Ser Thr Arg Pro Arg Ser Leu Ala Asp Pro Glu Leu His Pro
            100                 105                 110

Gln Gln Leu Leu Ala Lys Asp Leu Asn Thr Lys Asp Leu Glu Thr Asn
        115                 120                 125

Ile Ile Val Leu Val His Gly Gly Gly Phe Gly Ala Trp Cys Trp Tyr
    130                 135                 140

Lys Thr Ile Ala Leu Leu Glu Asp Ser Gly Phe Arg Val Asn Ala Ile
145                 150                 155                 160

Asp Leu Thr Gly Ser Gly Ile His Ser Tyr Asp Thr Asn Lys Ile Ser
                165                 170                 175

Ser Leu Thr Gln Tyr Ala Glu Pro Leu Thr Ser Tyr Leu Lys Ser Leu
            180                 185                 190

Gly Asp Asn Glu Lys Val Ile Leu Val Gly His Asp Phe Gly Gly Ala
        195                 200                 205

Cys Ile Ser Tyr Ala Met Glu Met Phe Pro Ser Lys Val Ala Lys Ala
    210                 215                 220

Val Phe Leu Cys Ala Ala Met Leu Lys Asn Gly His Ser Thr Leu Asp
225                 230                 235                 240

Met Phe Gln Gln Gln Met Asp Thr Asn Gly Thr Leu Gln Arg Ala Gln
                245                 250                 255

Glu Phe Val Tyr Ser Asn Gly Lys Glu Gln Pro Pro Thr Ala Ile Asn
            260                 265                 270

Ile Glu Lys Ser Leu Leu Lys His Leu Leu Phe Asn Gln Ser Pro Ser
        275                 280                 285

Lys Asp Val Ser Leu Ala Ser Val Ser Met Arg Pro Ile Pro Phe Ala
    290                 295                 300

Pro Val Leu Glu Lys Leu Val Leu Thr Glu Glu Lys Tyr Gly Ser Val
305                 310                 315                 320

Arg Arg Phe Tyr Val Glu Thr Thr Glu Asp Asn Ala Ile Pro Leu His
                325                 330                 335

Leu Gln Gln Gly Met Cys Asp Met Asn Pro Pro Glu Lys Val Leu Arg
            340                 345                 350

Leu Lys Gly Ser Asp His Ala Pro Phe Phe Ser Lys Pro Gln Ala Leu
        355                 360                 365

His Lys Thr Leu Val Glu Ile Ala Thr Met Pro Pro Val Lys Ala Ser
    370                 375                 380
```

<210> SEQ ID NO 102
<211> LENGTH: 1149
<212> TYPE: DNA
<213> ORGANISM: Zea mays

<400> SEQUENCE: 102

```
atgggttcgc tggtgtcctg cctctccgac ccctgccagt cggggaacgg gtccccgccg      60

ccgcaggcga ggcggcgctc ctccacctcc tcccgcggcg gccgtggcgg cggcgggagg     120
```

-continued

```
gactccgcca aggcgtcggt gaccatagac gaggaggcgc tggccgcggc ggcggcgctc    180

gtgctggggc agcggggcgc cgccgccgtt ggcgcgttcg agcggtccgc gtcggtgcgg    240

tacgcggcca agcggcacgg ccagggcccg ccgctgcccc gcagctgcag cacgcgcccc    300

aggtcgctcg ctgaccccga gctccagccg cagcagctcc tcgccaagga tttgaacacc    360

aaggatttgg aaaccagcgt cattgttctc gttcatggag gcggattcgg cgcgtggtgt    420

tggtacaaga ctatatcgct tcttgaagac agtgggttca gagttaacgc catcgacttg    480

acaggctccg ggatccattc ttatgacacg aacaagatta gcagtctttc agagtacgct    540

gaaccgctta cgtcttacct tgaaggctta ggtgatgctg aaaaggtaat cttggtggct    600

catgatcttg gtggtgcctg tgtatcctac gcaatggaga tgttcccatc caaagttgcc    660

aaggccgttt tcctctgtgc agcgatgctg acgaacggaa acagtgccct tgacatgttc    720

cagcagcaga tggacacaaa cggtacgctc caaaaggcgc aggcattcgt ctactccaac    780

ggcaaggacc ggcccccgac cgccatcaac gtcgacaggg cattgcttag agacttgttg    840

ttcaaccaga gcccttccaa ggacgtgtcg ctggcctcgg tgtccatgag gcccatcccc    900

ttcgcccctg tgctggagaa gctcgtgctc accgccgaga actacggctc ggtgcggcgg    960

ttctacgtgg agaccacgga ggacaacgcg atccctctgc ccctccagca gagcatgtgt   1020

ggcgccaacc caccggagaa ggtgctgcgg ctgaaagggg ccgaccacgc acccttcttc   1080

tccaagccgc aggcgctgca caagaccctc gtcgagatcg ccgccatgcc gccggtcggg   1140

gcttcgtga                                                           1149


<210> SEQ ID NO 103
<211> LENGTH: 382
<212> TYPE: PRT
<213> ORGANISM: Zea mays

<400> SEQUENCE: 103

Met Gly Ser Leu Val Ser Cys Leu Ser Asp Pro Cys Gln Ser Gly Asn
  1               5                  10                  15

Gly Ser Pro Pro Pro Gln Ala Arg Arg Arg Ser Ser Thr Ser Ser Arg
             20                  25                  30

Gly Gly Arg Gly Gly Gly Gly Arg Asp Ser Ala Lys Ala Ser Val Thr
         35                  40                  45

Ile Asp Glu Glu Ala Leu Ala Ala Ala Ala Ala Leu Val Leu Gly Gln
     50                  55                  60

Arg Gly Ala Ala Ala Val Gly Ala Phe Glu Arg Ser Ala Ser Val Arg
 65                  70                  75                  80

Tyr Ala Ala Lys Arg His Gly Gln Gly Pro Pro Leu Pro Arg Ser Cys
                 85                  90                  95

Ser Thr Arg Pro Arg Ser Leu Ala Asp Pro Glu Leu Gln Pro Gln Gln
            100                 105                 110

Leu Leu Ala Lys Asp Leu Asn Thr Lys Asp Leu Glu Thr Ser Val Ile
        115                 120                 125

Val Leu Val His Gly Gly Gly Phe Gly Ala Trp Cys Trp Tyr Lys Thr
    130                 135                 140

Ile Ser Leu Leu Glu Asp Ser Gly Phe Arg Val Asn Ala Ile Asp Leu
145                 150                 155                 160

Thr Gly Ser Gly Ile His Ser Tyr Asp Thr Asn Lys Ile Ser Ser Leu
                165                 170                 175

Ser Glu Tyr Ala Glu Pro Leu Thr Ser Tyr Leu Glu Gly Leu Gly Asp
            180                 185                 190
```

-continued

```
Ala Glu Lys Val Ile Leu Val Ala His Asp Leu Gly Gly Ala Cys Val
        195                 200                 205

Ser Tyr Ala Met Glu Met Phe Pro Ser Lys Val Ala Lys Ala Val Phe
    210                 215                 220

Leu Cys Ala Ala Met Leu Thr Asn Gly Asn Ser Ala Leu Asp Met Phe
225                 230                 235                 240

Gln Gln Gln Met Asp Thr Asn Gly Thr Leu Gln Lys Ala Gln Ala Phe
                245                 250                 255

Val Tyr Ser Asn Gly Lys Asp Arg Pro Pro Thr Ala Ile Asn Val Asp
            260                 265                 270

Arg Ala Leu Leu Arg Asp Leu Leu Phe Asn Gln Ser Pro Ser Lys Asp
        275                 280                 285

Val Ser Leu Ala Ser Val Ser Met Arg Pro Ile Pro Phe Ala Pro Val
    290                 295                 300

Leu Glu Lys Leu Val Leu Thr Ala Glu Asn Tyr Gly Ser Val Arg Arg
305                 310                 315                 320

Phe Tyr Val Glu Thr Thr Glu Asp Asn Ala Ile Pro Leu Pro Leu Gln
                325                 330                 335

Gln Ser Met Cys Gly Ala Asn Pro Pro Glu Lys Val Leu Arg Leu Lys
            340                 345                 350

Gly Ala Asp His Ala Pro Phe Phe Ser Lys Pro Gln Ala Leu His Lys
        355                 360                 365

Thr Leu Val Glu Ile Ala Ala Met Pro Pro Val Gly Ala Ser
    370                 375                 380
```

<210> SEQ ID NO 104
<211> LENGTH: 2022
<212> TYPE: DNA
<213> ORGANISM: Zea mays

<400> SEQUENCE: 104

```
atcaacaaga attaaatttt ttattcttaa tataatctat gatggcttca gtgatctatt      60

ctgtacaagt gttacacaat tccttttgag tagatggtct gttgcctacg aacgttagtt     120

ggtccagaat actcggccgc tactgaagat aggattgctg gggctgggg ctgaggctgg     180

gtgatgccgt ggctgtggat aaactgacga gaggattgga ggacttggaa cgggtgaaag     240

agtcatacgt acacggtaca cgaccccaat aacccccagc cggccctata tgtacacgta     300

cacgatacac cgtgtcatgc gctggaaaaa ccgaaactct tgcgacgctg gaaagtggaa     360

cccaccaaaa cgaaggctgg cagtatgtgt acgctacagg gctcctacag caatggccaa     420

tgagaccacg agctcgctgg catgcatcgc agcagcaccg gtgccgtttt ggtgggtcgg     480

aggagttacc gctttcggat cgtttttatg cccgggttcg cgggtgtatc gaaccgctaa     540

agcatgacac gacgccacga cgatggtttc ttgggtattg ctcgcacacc acgcacggct     600

ttgatgatac tgtgtctttt tattgacttc acggtaaatt ttaccatttg agccgatctt     660

ttatttttct tattacgatt aatatctatc atggattgtt aataagaact ctcgttcttt     720

tttcgaaaga tatttcctgt cttgtttttt tagtttacta gtcagatata gtttctaaat     780

atcatatggc taattttttta aataaaacac aaaaatatat gtaatctatt agttagatga     840

gtataaatat atagccaaca actaagtttc aaaccaccgc taaattgtta catccatcgc     900

cgtggtcgtg ggccgcctca cccatcaacc gtcggaccag cctagagcca atgcgtggtc     960

gagcggccac gtgagagcgc gactatcgca aaagctcttt gtgcatgtca ctcatttata    1020
```

-continued

```
tatattggaa gatttttttt cccgagatcc aacttctatt cgaagtatgt cttgcttgca   1080

tgcaccaccg catatccgct agcattattt cacatagtgt tgcgcttgcc tttcgcttta   1140

gttctaacta gcatttgtat gttgtaacgt aactcattac gcgctaaagt ttagtccata   1200

ttatattgaa tgtttggttg tcaactatga gtattaaata tagactaatt aaaaactaat   1260

tacatagatt agactaaacg gcgagataag tctcttggtt tgatattatt ggtctgtcta   1320

tatatttact taaacacttt ttctaatggt caaatgctga tttttatctt ctctttaaga   1380

aataaaatat ccgccgtctt atttgatttt ttttttctgc aaatcaaggt gactctcaac   1440

tttagaacat ctccaagtga ctttttattt attagctctc tatttaactt tctatttatc   1500

atcccataac gattattact ctatatgtag catctcactc aaacagacta tctatctagt   1560

ttgactagtt aaagtggtta gccaagtttg actagttaca tagacaattt ggagtcgaat   1620

atcttggcaa gttagataac taatctgttg gagagttatt ttgctgttga gtagccaaaa   1680

tttggcttca tgagccattt ggctagtcta ttgaaaatgc tcttacatgt tcatagacta   1740

atggtaaaaa atcgttgttt gaaaatatta ctcttttcgt tctttttat ttgtcaccga   1800

ttaattcaaa aataaattaa cgagccacaa atattcgaga acagagttag gcaattgaaa   1860

tatagcaagt ctacatagga tcttatcggt tattgcccac acataaatca taatgcgttt   1920

cacctggata aaaaatcaag gcatttatat caaaggtaac atgctaatgc gtcattactg   1980

ttgaaaaagc aggctctcga tcacgatttg attgataata ta                       2022
```

<210> SEQ ID NO 105
<211> LENGTH: 2000
<212> TYPE: DNA
<213> ORGANISM: Zea mays

<400> SEQUENCE: 105

```
cgacaaaact atcaacaggt atatttacta aatgttcttc aaactggctt tagaggctag     60

aggtgtagcc aaggggatgt ttgtttgtga ttataatttg tctatattat ataatctaac    120

aaatttattt taaattagtt gttagtttaa tatttattgg attatataat ctgaatagat    180

tataatttca gacaaacacc ctaaaatgtt ttccaaaata gctttagaga ccattttgtt    240

aaaacagcta gtagatggta cgctccatat tccacaaggc cggtgatagc ggctagaaaa    300

ataattgttg ctccttccca aaacatgagt tatattagtt tttgtaaagt taatatacct    360

caaattataa gttattttaa ccttttttaaa atcaaagcat cttaagttta atcaaattcg    420

aataataaaa caatactata tataatatta aataaatatc attattttgt cattaattat    480

atttagtata cctattcaat gttataaatc ttataatttc attctatgat tttaaccgac    540

aaatttgaga agctttgatt ccttagaaaa aacaaaatgg tttataattt taaacggagt    600

gagcctgtgg cttgattgca aatgtggtcg tggaaagccg tcggccgatc ggtccccgtc    660

cgtattctct tgcatcgttg cgtgcgatgg aaaggctact agtgagagct gttggagcgg    720

cgggcggcgg aagtctagct acggggtccc cgccgtcggc gcaagtaccg cgcgtgtagg    780

tggcggcggc gcagacgcac tttatacacg ggcgggacgg ggaccgggga cgaggactag    840

ccagggaggc cgcgccgcgc cgccgcggcc cgcagtcgcc tggcgctcgt ctgtccgtgt    900

ccggtacccc cacctgcagc ctgcagtata tattagcagc aagtttaaat ttcagcggcc    960

tcacggttaa cgctaataat aaccgccacg ccgtcgaacg aaatgtgatc gcaggcgagt   1020

aatttgtcac tgatagtggc ctgctgcggc catgcagcga ttcctcgaag cacttgctga   1080

atccaaccat tctctctcga atcttcctac ttgtactttt catatgtaaa tacctcttta   1140
```

-continued

```
ttcttcgtat ccgtttgacc gtttctaact attctccgta ttcagctttc ctatacactt   1200

caacttagct atttaacttt ttacataagt ttttagagtt tttaaaaaaa atactacatt   1260

atttatgtaa tgcaatacac attgttttta gttaattaaa ctagaaaaag attgatttcc   1320

tagttaaaat cactgattaa tgaaaagggt gagattagag ctttccctaa cagagaaaaa   1380

tattcaaggc tcagtgacca gacatacatt aaattcacgc gggaaaaggt cgagtgaacc   1440

gttggacact gtcttagggc atgtacaatc tttaaccatc gaatcggttt tctaagtatg   1500

gcatcaattt attattcttg tttaagtata tatatagaaa taacggtaga ttgtctttat   1560

gtcattacag accagatttt gttgaatttg tgatttcatc taacatattc ttttattctt   1620

agaaccaaaa agtatataat atttttataa attacaacga actaaagttt tagttttagt   1680

gtaaaacata tgcgataacc gtagcctaaa aagctaaaat tagtaccagc agaatttaaa   1740

agagtcccat tctttttacg agaacttctc gttaaaagct gaacgccagt tgcaaaagcg   1800

gctacattct ctcctttaat cagggaatca gtacaatgcg tttccatttc tcctccagcc   1860

gttactagtg tcatgctctc agcacactgg tctgctcgtc tgcctccttt gccttcctct   1920

atttaaaccc tctccgcccc cccggaccca aaacccacac catccagcct tcccacctcc   1980

ctcccccccca cgccgtcgtc                                              2000
```

<210> SEQ ID NO 106
<211> LENGTH: 21
<212> TYPE: DNA
<213> ORGANISM: synthetic construct

<400> SEQUENCE: 106
tcgtgtgcaa ggccgtggct a 21

<210> SEQ ID NO 107
<211> LENGTH: 23
<212> TYPE: DNA
<213> ORGANISM: synthetic construct

<400> SEQUENCE: 107
gcacgatcca tttagcacac cag 23

<210> SEQ ID NO 108
<211> LENGTH: 38
<212> TYPE: DNA
<213> ORGANISM: synthetic construct

<400> SEQUENCE: 108
aattaaccct cactaaaggg cacctgctct tccaccac 38

<210> SEQ ID NO 109
<211> LENGTH: 40
<212> TYPE: DNA
<213> ORGANISM: synthetic construct

<400> SEQUENCE: 109
gtaatacgac tcactatagg gcgactgccc atttcgtagc 40

<210> SEQ ID NO 110
<211> LENGTH: 346
<212> TYPE: DNA
<213> ORGANISM: synthetic construct
<220> FEATURE:
<221> NAME/KEY: misc_feature
<222> LOCATION: (39)..(39)

-continued

<223> OTHER INFORMATION: s = c or g
<220> FEATURE:
<221> NAME/KEY: misc_feature
<222> LOCATION: (73)..(73)
<223> OTHER INFORMATION: k = g or t

<400> SEQUENCE: 110
cacctgctct tccaccacgc catgggcttc gcgccctcsg gagacgcgca ctggcgcggg 60
ctccgccgcc tckccgccaa ccacctgttc ggcccgcgcc gcgtggcggg tgccgcgcac 120
caccgcgcct ccatcggcga ggccatggtc gccgacgtcg ccgctgccat ggcgcgccac 180
ggcgaggtcc ctctcaagcg cgtgctgcat gtcgcgtctc tcaaccacgt catggccacc 240
gtgtttggca agcgctacga catgggcagc cgagagggcg cccttctgga cgagatggtg 300
gccgagggct acgacctcct gggcacgttc aactgggctg atcaac 346

<210> SEQ ID NO 111
<211> LENGTH: 17
<212> TYPE: DNA
<213> ORGANISM: synthetic construct

<400> SEQUENCE: 111
gatcgatgga actgagt 17

<210> SEQ ID NO 112
<211> LENGTH: 49
<212> TYPE: DNA
<213> ORGANISM: Artificial Sequence
<220> FEATURE:
<223> OTHER INFORMATION: PCR primer: GE-ORF1

<400> SEQUENCE: 112
acaccaggtg ctcgagaatt cggtctccca tggcgctctc ctccatggc 49

<210> SEQ ID NO 113
<211> LENGTH: 20
<212> TYPE: DNA
<213> ORGANISM: Artificial Sequence
<220> FEATURE:
<223> OTHER INFORMATION: PCR Primer: GE-ORF2

<400> SEQUENCE: 113
gccgacggag agcgacatca 20

<210> SEQ ID NO 114
<211> LENGTH: 31
<212> TYPE: DNA
<213> ORGANISM: Artificial Sequence
<220> FEATURE:
<223> OTHER INFORMATION: PCR Primer: Construct 5'

<400> SEQUENCE: 114
caccaggtgc tcgagaattc ggtctcccat g 31

<210> SEQ ID NO 115
<211> LENGTH: 47
<212> TYPE: DNA
<213> ORGANISM: Artificial Sequence
<220> FEATURE:
<223> OTHER INFORMATION: PCR Primer: Construct 3'

<400> SEQUENCE: 115
ttcatgggag acctcgagct gcagtcaggc cctagccacg gccttgc 47

-continued

<210> SEQ ID NO 116
<211> LENGTH: 2034
<212> TYPE: DNA
<213> ORGANISM: Zea mays
<220> FEATURE:
<221> NAME/KEY: misc_feature
<223> OTHER INFORMATION: ubiquitin promoter

<400> SEQUENCE: 116

```
tgcagaagat aacttcgtat aatgtatgct atacgaagtt atgtaacacc aaacaacagg     60

gtgagcatcg acaaaagaaa cagtaccaag caaataaata gcgtatgaag gcagggctaa    120

aaaaatccac atatagctgc tgcatatgcc atcatccaag tatatcaaga tcaaaataat    180

tataaaacat acttgtttat tataatagat aggtactcaa ggttagagca tatgaataga    240

tgctgcatat gccatcatgt atatgcatca gtaaaaccca catcaacatg tatacctatc    300

ctagatcgat atttccatcc atcttaaact cgtaactatg aagatgtatg acacacacat    360

acagttccaa aattaataaa tacaccaggt agtttgaaac agtattctac tccgatctag    420

aacgaatgaa cgaccgccca accacaccac atcatcacaa ccaagcgaac aaaaagcatc    480

tctgtatatg catcagtaaa acccgcatca acatgtatac ctatcctaga tcgatatttc    540

catccatcat cttcaattcg taactatgaa tatgtatggc acacacatac agatccaaaa    600

ttaataaatc caccaggtag tttgaaacag aattctactc cgatctagaa cgaccgccca    660

accagaccac atcatcacaa ccaagacaaa aaaaagcatg aaaagatgac ccgacaaaca    720

agtgcacggc atatattgaa ataaaggaaa agggcaaacc aaaccctatg caacgaaaca    780

aaaaaaatca tgcatgaaat cgatcccgtc tgcggaacgg ctagagccat cccaggattc    840

cccaaagaga aacactggca agttagcaat cagaacgtgt ctgacgtaca ggtcgcatcc    900

gtgtacgaac gctagcagca cggatctaac acaaacacgg atctaacaca aacatgaaca    960

gaagtagaac taccgggccc taaccatgga ccggaacgcc gatctagaga aggtagagag   1020

gggggggggg ggaggacgag cggcgtacct tgaagcggag gtgccgacgg gtggatttgg   1080

gggagatctg gttgtgtgtg tgtgcgctcc gaacaacacg aggttgggga aagagggtgt   1140

ggcgggggtg tctatttatt acggcgggcg aggaagggaa agcgaaggag cggtgggaaa   1200

ggaatccccc gtagctgccg tgccgtgaga ggaggaggag gccgcctgcc gtgccggctc   1260

acgtctgccg ctccgccacg caatttctgg atgccgacag cggagcaagt ccaacggtgg   1320

agcggaactc tcgagagggg tccagaggca gcgacagaga tgccgtgccg tctgcttcgc   1380

ttggcccgac gcgacgctgc tggttcgctg gttggtgtcc gttagactcg tcgatcgacg   1440

gcgtttaaca ggctggcatt atctactcga aacaagaaaa atgtttcctt agttttttta   1500

atttcttaaa gggtatttgt ttaattttta gtcactttat tttattctat tttatatcta   1560

aattattaaa taaaaaaact aaaatagagt tttagttttc ttaatttaga ggctaaaata   1620

gaataaaata gatgtactaa aaaaattagt ctataaaaac cattaaccct aaaccctaaa   1680

tggatgtact aataaaatgg atgaagtatt atataggtga agctatttgc aaaaaaaaag   1740

gagaacacat gcacactaaa aagataaaac tgtagagtcc tgttgtcaaa atactcaatt   1800

gtcctttaga ccatgtctaa ctgttcattt atatgattct ctaaaacact gatattattg   1860

tagtactata gattatatta ttcgtagagt aaagtttaaa tatatgtata aagatagata   1920

aactgcactt caaacaagtg tgacaaaaaa aatatgtggt aatttttttat aacttagaca   1980

tgcaatgctc attatctcta gagaggggca cgaccgggtc acgctgcact gcag         2034
```

-continued

<210> SEQ ID NO 117
<211> LENGTH: 441
<212> TYPE: DNA
<213> ORGANISM: Zea mays
<220> FEATURE:
<221> NAME/KEY: misc_feature
<223> OTHER INFORMATION: 2-1A terminator

<400> SEQUENCE: 117
gcggccgtac cgctctctct ctcccttgcc taagtttctg tgcacgtaaa taattattag 60
tagaaaaaaa ttggaaggta catgagttag gtgaagatga aagtatataa tattgttgtg 120
gtggggtata gaggtttgat ataggtggaa ctgctgtaga gcgtggagat ataggggaaa 180
gagaacgctg atgtgacaag tgagtgagat atagggggag aaatttaggg ggaacgccga 240
acacagtcta aagaagcttg ggacccaaag cactctgttc gggggttttt ttttttgtct 300
ttcaactttt tgctgtaatg ttattcaaaa taagaaaagc acttggcatg gctaagaaat 360
agagttcaac aactgaacag tacagtgtat tatcaatggc ataaaaaaca acccttacag 420
cattgccgta ttttattgat c 441

<210> SEQ ID NO 118
<211> LENGTH: 8969
<212> TYPE: DNA
<213> ORGANISM: Artificial Sequence
<220> FEATURE:
<223> OTHER INFORMATION: Plasmid vector PHP 18422
<220> FEATURE:
<221> NAME/KEY: misc_feature
<222> LOCATION: (1373)..(1373)
<223> OTHER INFORMATION: n is a, c, g, or t

<400> SEQUENCE: 118
aagctggtac gattgtaata cgactcacta tagggcgaat tgagcgctgt ttaaacgctc 60
ttcaactgga agagcggtta ccagagctgg tcacctttgt ccaccaagat ggaactgcgg 120
ccgctcatta attaagtcag gcgcgcctct agttgaagac acgttcatgt cttcatcgta 180
agaagacact cagtagtctt cggccagaat ggccatctgg attcagcagg cctagaaggc 240
catttaaatc ctgaggatct ggtcttccta aggacccggg cggtccgatt aaactttaat 300
tcggaccgaa gcttctgcag gaattcctgc agtgcagcgt gacccggtcg tgcccctctc 360
tagtggatct gagcttctag aaatccgtca acatggtgga gcacgacact ctcgtctact 420
ccaagaatat caaagataca gtctcagaag accaaagggc tattgagact tttcaacaaa 480
gggtaatatc gggaaacctc ctcggattcc attgcccagc tatctgtcac ttcatcaaaa 540
ggacagtaga aaaggaaggt ggcacctaca aatgccatca ttgcgataaa ggaaaggcta 600
tcgttcaaga tgcctctgcc gacagtggtc ccaaagatgg acccccaccc acgaggagca 660
tcgtggaaaa agaagacgtt ccaaccacgt cttcaaagca agtggattga tgtgatgctc 720
tagaaatccg tcaacatggt ggagcacgac actctcgtct actccaagaa tatcaaagat 780
acagtctcag aagaccaaag ggctattgag acttttcaac aaagggtaat atcgggaaac 840
ctcctcggat tccattgccc agctatctgt cacttcatca aaaggacagt agaaaaggaa 900
ggtggcacct acaaatgcca tcattgcgat aaaggaaagg ctatcgttca agatgcctct 960
gccgacagtg gtcccaaaga tggaccccca cccacgagga gcatcgtgga aaaagaagac 1020
gttccaacca cgtcttcaaa gcaagtggat tgatgtgata tctccactga cgtaagggat 1080
gacgcacaat cccactatcc ttcgcaagac ccttcctcta tataaggaag ttcatttcat 1140
ttggagagga cgagctgcag gtcgacggat caagtgcaaa ggtccgcctt gtttctcctc 1200

-continued

```
tgtctcttga tctgactaat cttggtttat gattcgttga gtaattttgg ggaaagcttc   1260
gtccacagtt tttttttcga tgaacagtgc cgcagtggcg ctgatcttgt atgctatcct   1320
gcaatcgtgg tgaacttatg tcttttatat ccttcactac catgaaaaga ctngtaatct   1380
ttctcgatgt aacatcgtcc agcactgcta ttaccgtgtg gtccatccga cagtctggct   1440
gaacacatca tacgatattg agcaaagatc gatctatctt ccctgttctt taatgaaaga   1500
cgtcattttc atcagtatga tctaagaatg ttgcaacttg caaggaggcg tttctttctt   1560
tgaatttaac taactcgttg agtggccctg tttctcggac gtaaggcctt tgctgctcca   1620
cacatgtcca ttcgaatttt accgtgttta gcaagggcga aaagtttgca tcttgatgat   1680
ttagcttgac tatgcgattg ctttcctgga cccgtgcagc tgcggacgga tccaccatga   1740
gcccagaacg acgcccggcc gacatccgcc gtgccaccga ggcggacatg ccggcggtct   1800
gcaccatcgt caaccactac atcgagacaa gcacggtcaa cttccgtacc gagccgcagg   1860
aaccgcagga ctggacggac gacctcgtcc gtctgcggga gcgctatccc tggctcgtcg   1920
ccgaggtgga cggcgaggtc gccggcatcg cctacgcggg cccctggaag gcacgcaacg   1980
cctacgactg gacggccgag tcgaccgtgt acgtctcccc ccgccaccag cggacgggac   2040
tgggctccac gctctacacc cacctgctga agtccctgga ggcacagggc ttcaagagcg   2100
tggtcgctgt catcgggctg cccaacgacc cgagcgtgcg catgcacgag gcgctcggat   2160
atgccccccg cggcatgctg cgggcggccg gcttcaagca cgggaactgg catgacgtgg   2220
gtttctggca gctggacttc agcctgccgg taccgccccg tccggtcctg cccgtcaccg   2280
agatctgatc cgtcgaccaa cctagacttg tccatcttct ggattggcca acttaattaa   2340
tgtatgaaat aaaaggatgc acacatagtg acatgctaat cactataatg tgggcatcaa   2400
agttgtgtgt tatgtgtaat tactagttat ctgaataaaa gagaaagaga tcatccatat   2460
ttcttatcct aaatgaatgt cacgtgtctt tataattctt tgatgaacca gatgcatttc   2520
attaaccaaa tccatataca tataaatatt aatcatatat aattaatatc aattgggtta   2580
gcaaaacaaa tctagtctag gtgtgttttg cgaattcatt ccgattaatc gtggcctctt   2640
gctcttcagg atgaagagct atgtttaaac gtgcaagcgc tactagacaa ttcagtacat   2700
taaaaacgtc cgcaatgtgt tattaagttg tctaagcgtc aatttgttta caccacaata   2760
tatcctgcca ccagccagcc aacagctccc cgaccggcag ctcggcacaa aatcaccact   2820
cgatacaggc agcccatcag tccgggacgg cgtcagcggg agagccgttg taaggcggca   2880
gactttgctc atgttaccga tgctattcgg aagaacggca actaagctgc cgggtttgaa   2940
acacggatga tctcgcggag ggtagcatgt tgattgtaac gatgacagag cgttgctgcc   3000
tgtgatcaaa tatcatctcc ctcgcagaga tccgaattat cagccttctt attcatttct   3060
cgcttaaccg tgacaggctg tcgatcttga gaactatgcc gacataatag gaaatcgctg   3120
gataaagccg ctgaggaagc tgagtggcgc tatttcttta gaagtgaacg ttgacgatcg   3180
tcgaccgtac cccgatgaat taattcggac gtacgttctg aacacagctg gatacttact   3240
tgggcgattg tcatacatga catcaacaat gtacccgttt gtgtaaccgt ctcttggagg   3300
ttcgtatgac actagtggtt cccctcagct tgcgactaga tgttgaggcc taacatttta   3360
ttagagagca ggctagttgc ttagatacat gatcttcagg ccgttatctg tcagggcaag   3420
cgaaaattgg ccatttatga cgaccaatgc cccgcagaag ctcccatctt tgccgccata   3480
gacgccgcgc cccccttttg gggtgtagaa catccttttg ccagatgtgg aaaagaagtt   3540
```

-continued

```
cgttgtccca ttgttggcaa tgacgtagta gccggcgaaa gtgcgagacc catttgcgct   3600
atatataagc ctacgatttc cgttgcgact attgtcgtaa ttggatgaac tattatcgta   3660
gttgctctca gagttgtcgt aatttgatgg actattgtcg taattgctta tggagttgtc   3720
gtagttgctt ggagaaatgt cgtagttgga tggggagtag tcatagggaa gacgagcttc   3780
atccactaaa acaattggca ggtcagcaag tgcctgcccc gatgccatcg caagtacgag   3840
gcttagaacc accttcaaca gatcgcgcat agtcttcccc agctctctaa cgcttgagtt   3900
aagccgcgcc gcgaagcggc gtcggcttga acgaattgtt agacattatt tgccgactac   3960
cttggtgatc tcgcctttca cgtagtgaac aaattcttcc aactgatctg cgcgcgaggc   4020
caagcgatct tcttgtccaa gataagcctg cctagcttca agtatgacgg gctgatactg   4080
ggccggcagg cgctccattg cccagtcggc agcgacatcc ttcggcgcga ttttgccggt   4140
tactgcgctg taccaaatgc gggacaacgt aagcactaca tttcgctcat cgccagccca   4200
gtcgggcggc gagttccata gcgttaaggt ttcatttagc gcctcaaata gatcctgttc   4260
aggaaccgga tcaaagagtt cctccgccgc tggacctacc aaggcaacgc tatgttctct   4320
tgcttttgtc agcaagatag ccagatcaat gtcgatcgtg gctggctcga agatacctgc   4380
aagaatgtca ttgcgctgcc attctccaaa ttgcagttcg cgcttagctg gataacgcca   4440
cggaatgatg tcgtcgtgca caacaatggt gacttctaca gcgcggagaa tctcgctctc   4500
tccaggggaa gccgaagttt ccaaaaggtc gttgatcaaa gctcgccgcg ttgtttcatc   4560
aagccttaca gtcaccgtaa ccagcaaatc aatatcactg tgtggcttca ggccgccatc   4620
cactgcggag ccgtacaaat gtacggccag caacgtcggt tcgagatggc gctcgatgac   4680
gccaactacc tctgatagtt gagtcgatac ttcggcgatc accgcttccc tcatgatgtt   4740
taactcctga attaagccgc gccgcgaagc ggtgtcggct tgaatgaatt gttaggcgtc   4800
atcctgtgct cccgagaacc agtaccagta catcgctgtt tcgttcgaga cttgaggtct   4860
agttttatac gtgaacaggt caatgccgcc gagagtaaag ccacattttg cgtacaaatt   4920
gcaggcaggt acattgttcg tttgtgtctc taatcgtatg ccaaggagct gtctgcttag   4980
tgcccacttt ttcgcaaatt cgatgagact gtgcgcgact cctttgcctc ggtgcgtgtg   5040
cgacacaaca atgtgttcga tagaggctag atcgttccat gttgagttga gttcaatctt   5100
cccgacaagc tcttggtcga tgaatgcgcc atagcaagca gagtcttcat cagagtcatc   5160
atccgagatg taatccttcc ggtaggggct cacacttctg gtagatagtt caaagccttg   5220
gtcggatagg tgcacatcga acacttcacg aacaatgaaa tggttctcag catccaatgt   5280
ttccgccacc tgctcaggga tcaccgaaat cttcatatga cgcctaacgc ctggcacagc   5340
ggatcgcaaa cctggcgcgg cttttggcac aaaaggcgtg acaggtttgc gaatccgttg   5400
ctgccacttg ttaacccttt tgccagattt ggtaactata atttatgtta gaggcgaagt   5460
cttgggtaaa aactggccta aaattgctgg ggatttcagg aaagtaaaca tcaccttccg   5520
gctcgatgtc tattgtagat atatgtagtg tatctacttg atcgggggat ctgctgcctc   5580
gcgcgtttcg gtgatgacgg tgaaaacctc tgacacatgc agctcccgga gacggtcaca   5640
gcttgtctgt aagcggatgc cgggagcaga caagcccgtc agggcgcgtc agcgggtgtt   5700
ggcgggtgtc ggggcgcagc catgacccag tcacgtagcg atagcggagt gtatactggc   5760
ttaactatgc ggcatcagag cagattgtac tgagagtgca ccatatgcgg tgtgaaatac   5820
cgcacagatg cgtaaggaga aaataccgca tcaggcgctc ttccgcttcc tcgctcactg   5880
actcgctgcg ctcggtcgtt cggctgcggc gagcggtatc agctcactca aaggcggtaa   5940
```

-continued

```
tacggttatc cacagaatca ggggataacg caggaaagaa catgtgagca aaaggccagc   6000
aaaaggccag gaaccgtaaa aaggccgcgt tgctggcgtt tttccatagg ctccgccccc   6060
ctgacgagca tcacaaaaat cgacgctcaa gtcagaggtg gcgaaacccg acaggactat   6120
aaagatacca ggcgtttccc cctggaagct ccctcgtgcg ctctcctgtt ccgaccctgc   6180
cgcttaccgg atacctgtcc gcctttctcc cttcgggaag cgtggcgctt tctcatagct   6240
cacgctgtag gtatctcagt tcggtgtagg tcgttcgctc caagctgggc tgtgtgcacg   6300
aaccccccgt tcagcccgac cgctgcgcct tatccggtaa ctatcgtctt gagtccaacc   6360
cggtaagaca cgacttatcg ccactggcag cagccactgg taacaggatt agcagagcga   6420
ggtatgtagg cggtgctaca gagttcttga agtggtggcc taactacggc tacactagaa   6480
ggacagtatt tggtatctgc gctctgctga agccagttac cttcggaaaa agagttggta   6540
gctcttgatc cggcaaacaa accaccgctg gtagcggtgg tttttttgtt tgcaagcagc   6600
agattacgcg cagaaaaaaa ggatctcaag aagatccttt gatcttttct acggggtctg   6660
acgctcagtg gaacgaaaac tcacgttaag ggattttggt catgagatta tcaaaaagga   6720
tcttcaccta gatcctttta aattaaaaat gaagttttaa atcaatctaa agtatatatg   6780
agtaaacttg gtctgacagt taccaatgct taatcagtga ggcacctatc tcagcgatct   6840
gtctatttcg ttcatccata gttgcctgac tccccgtcgt gtagataact acgatacggg   6900
agggcttacc atctggcccc agtgctgcaa tgataccgcg agacccacgc tcaccggctc   6960
cagatttatc agcaataaac cagccagccg gaagggccga gcgcagaagt ggtcctgcaa   7020
ctttatccgc ctccatccag tctattaatt gttgccggga agctagagta agtagttcgc   7080
cagttaatag tttgcgcaac gttgttgcca ttgctgcagg gggggggggg ggggggggact   7140
tccattgttc attccacgga caaaaacaga gaaaggaaac gacagaggcc aaaaagcctc   7200
gctttcagca cctgtcgttt cctttctttt cagagggtat tttaaataaa aacattaagt   7260
tatgacgaag aagaacggaa acgccttaaa ccggaaaatt ttcataaata gcgaaaaccc   7320
gcgaggtcgc cgccccgtaa cctgtcggat caccggaaag gacccgtaaa gtgataatga   7380
ttatcatcta catatcacaa cgtgcgtgga ggccatcaaa ccacgtcaaa taatcaatta   7440
tgacgcaggt atcgtattaa ttgatctgca tcaacttaac gtaaaaacaa cttcagacaa   7500
tacaaatcag cgacactgaa tacggggcaa cctcatgtcc cccccccccc cccccctgca   7560
ggcatcgtgg tgtcacgctc gtcgtttggt atggcttcat tcagctccgg ttcccaacga   7620
tcaaggcgag ttacatgatc ccccatgttg tgcaaaaaag cggttagctc cttcggtcct   7680
ccgatcgttg tcagaagtaa gttggccgca gtgttatcac tcatggttat ggcagcactg   7740
cataattctc ttactgtcat gccatccgta agatgctttt ctgtgactgg tgagtactca   7800
accaagtcat tctgagaata gtgtatgcgg cgaccgagtt gctcttgccc ggcgtcaaca   7860
cgggataata ccgcgccaca tagcagaact ttaaaagtgc tcatcattgg aaaacgttct   7920
tcggggcgaa aactctcaag gatcttaccg ctgttgagat ccagttcgat gtaacccact   7980
cgtgcaccca actgatcttc agcatctttt actttcacca gcgtttctgg gtgagcaaaa   8040
acaggaaggc aaaatgccgc aaaaaaggga ataagggcga cacggaaatg ttgaatactc   8100
atactcttcc tttttcaata ttattgaagc atttatcagg gttattgtct catgagcgga   8160
tacatatttg aatgtattta gaaaaataaa caaatagggg ttccgcgcac atttccccga   8220
aaagtgccac ctgacgtcta agaaaccatt attatcatga cattaaccta taaaaatagg   8280
```

-continued

```
cgtatcacga ggccctttcg tcttcaagaa ttggtcgacg atcttgctgc gttcggatat   8340

tttcgtggag ttcccgccac agacccggat tgaaggcgag atccagcaac tcgcgccaga   8400

tcatcctgtg acggaacttt ggcgcgtgat gactggccag gacgtcggcc gaaagagcga   8460

caagcagatc acgcttttcg acagcgtcgg atttgcgatc gaggattttt cggcgctgcg   8520

ctacgtccgc gaccgcgttg agggatcaag ccacagcagc ccactcgacc ttctagccga   8580

cccagacgag ccaagggatc tttttggaat gctgctccgt cgtcaggctt tccgacgttt   8640

gggtggttga acagaagtca ttatcgtacg gaatgccaag cactcccgag gggaaccctg   8700

tggttggcat gcacatacaa atggacgaac ggataaacct tttcacgccc ttttaaatat   8760

ccgttattct aataaacgct cttttctctt aggtttaccc gccaatatat cctgtcaaac   8820

actgatagtt taaactgaag gcgggaaacg acaatctgat catgagcgga gaattaaggg   8880

agtcacgtta tgacccccgc cgatgacgcg ggacaagccg ttttacgttt ggaactgaca   8940

gaaccgcaac gttgaaggag ccactcagc                                     8969
```

```
<210> SEQ ID NO 119
<211> LENGTH: 32
<212> TYPE: DNA
<213> ORGANISM: Artificial Sequence
<220> FEATURE:
<223> OTHER INFORMATION: PCR Primer: GE AscI F

<400> SEQUENCE: 119

gcccgctcct gtcgtgggcg cgcctcgccg tg                                   32
```

```
<210> SEQ ID NO 120
<211> LENGTH: 70
<212> TYPE: DNA
<213> ORGANISM: Artificial Sequence
<220> FEATURE:
<223> OTHER INFORMATION: PCR Primer: gemycR

<400> SEQUENCE: 120

ggcgcgccct actcgaggtc ctcctccgag atgagcttct gctcggccct agccacggcc     60

ttgcacacga                                                            70
```

```
<210> SEQ ID NO 121
<211> LENGTH: 420
<212> TYPE: DNA
<213> ORGANISM: Artificial Sequence
<220> FEATURE:
<223> OTHER INFORMATION: AscI fragment 1xMyc

<400> SEQUENCE: 121

ggcgcgcctc gccgtgcacg acgcgcgcgt cggtggccac gccgtccccg ccgggacgac     60

ggcgatggtg aacatgtggg cgatcgccca cgacgccgcc gtctggccgg agccggaggc    120

gttccgcccg gagcgcttct cggaggggga ggacgtcggc gtgctcggcg gcgacctccg    180

cctcgcgccg ttcggcgccg gccgccgcgt ctgccctggc aggatgctgg cgctcgccac    240

cgcccacctc tggctcgccc agctgctgca cgccttcgac tggtccccca ccgccgccgg    300

cgtcgacctg tccgagcgcc tcggcatgtc gctggagatg gcggcgccgc tcgtgtgcaa    360

ggccgtggct agggccgagc agaagctcat ctcggaggag gacctcgagt agggcgcgcc    420
```

```
<210> SEQ ID NO 122
<211> LENGTH: 69
<212> TYPE: DNA
<213> ORGANISM: Artificial Sequence
```

-continued

<220> FEATURE:
<223> OTHER INFORMATION: cmyc2XGD

<400> SEQUENCE: 122
ctcgagcaga agctcatctc ggaggaggac ctcggcgagc agaagctcat ctcggaggag 60
gacctcgag 69

<210> SEQ ID NO 123
<211> LENGTH: 69
<212> TYPE: DNA
<213> ORGANISM: Artificial Sequence
<220> FEATURE:
<223> OTHER INFORMATION: cmyc2XDC

<400> SEQUENCE: 123
ctcgaggtcc tcctccgaga tgagcttctg ctcgccgagg tcctcctccg agatgagctt 60
ctgctcgag 69

<210> SEQ ID NO 124
<211> LENGTH: 8
<212> TYPE: DNA
<213> ORGANISM: Artificial Sequence
<220> FEATURE:
<223> OTHER INFORMATION: Adaptor Pst BsphI

<400> SEQUENCE: 124 catgtgca 8

<210> SEQ ID NO 125
<211> LENGTH: 24
<212> TYPE: DNA
<213> ORGANISM: Artificial Sequence
<220> FEATURE:
<223> OTHER INFORMATION: mutagenesis primer GE_ATG-TTG-1

<400> SEQUENCE: 125
gagtggcaaa ttggtctatt taaa 24

<210> SEQ ID NO 126
<211> LENGTH: 28
<212> TYPE: DNA
<213> ORGANISM: Artificial Sequence
<220> FEATURE:
<223> OTHER INFORMATION: PCR Primer: XhoIORF5'

<400> SEQUENCE: 126
aactcgagat ggcgctctcc tccatggc 28

<210> SEQ ID NO 127
<211> LENGTH: 27
<212> TYPE: DNA
<213> ORGANISM: Artificial Sequence
<220> FEATURE:
<223> OTHER INFORMATION: PCR Primer: XhoIORF3'

<400> SEQUENCE: 127
aactcgagtc aggccctagc cacggcc 27

<210> SEQ ID NO 128
<211> LENGTH: 8831
<212> TYPE: DNA
<213> ORGANISM: Artificial Sequence
<220> FEATURE:
<223> OTHER INFORMATION: Plasmid vector pKS59

-continued

<400> SEQUENCE: 128
gaactcgagc agctgaagct tcccgggtct agaggatcca attccaatcc cacaaaaatc 60
tgagcttaac agcacagttg ctcctctcag agcagaatcg ggtattcaac accctcatat 120
caactactac gttgtgtata acggtccaca tgccggtata tacgatgact ggggttgtac 180
aaaggcggca acaaacggcg ttcccggagt tgcacacaag aaatttgcca ctattacaga 240
ggcaagagca gcagctgacg cgtacacaac aagtcagcaa acagacaggt tgaacttcat 300
ccccaaagga gaagctcaac tcaagcccaa gagctttgct aaggccctaa caagcccacc 360
aaagcaaaaa gcccactggc tcacgctagg aaccaaaagg cccagcagtg atccagcccc 420
aaaagagatc tcctttgccc cggagattac aatggacgat ttcctctatc tttacgatct 480
aggaaggaag ttcgaaggtg aaggtgacga cactatgttc accactgata atgagaaggt 540
tagcctcttc aatttcagaa agaatgctga cccacagatg gttagagagg cctacgcagc 600
aggtctcatc aagacgatct acccgagtaa caatctccag gagatcaaat accttcccaa 660
gaaggttaaa gatgcagtca aaagattcag gactaattgc atcaagaaca cagagaaaga 720
catatttctc aagatcagaa gtactattcc agtatggacg attcaaggct tgcttcataa 780
accaaggcaa gtaatagaga ttggagtctc taaaaaggta gttcctactg aatctaaggc 840
catgcatgga gtctaagatt caaatcgagg atctaacaga actcgccgtg aagactggcg 900
aacagttcat acagagtctt ttacgactca atgacaagaa gaaaatcttc gtcaacatgg 960
tggagcacga cactctggtc tactccaaaa atgtcaaaga tacagtctca gaagaccaaa 1020
gggctattga gacttttcaa caaaggataa tttcgggaaa cctcctcgga ttccattgcc 1080
cagctatctg tcacttcatc gaaaggacag tagaaaagga aggtggctcc tacaaatgcc 1140
atcattgcga taaaggaaag gctatcattc aagatgcctc tgccgacagt ggtcccaaag 1200
atggaccccc acccacgagg agcatcgtgg aaaaagaaga cgttccaacc acgtcttcaa 1260
agcaagtgga ttgatgtgac atctccactg acgtaaggga tgacgcacaa tcccactatc 1320
cttcgcaaga cccttcctct atataaggaa gttcatttca tttggagagg acacgctcga 1380
gctcatttct ctattacttc agccataaca aaagaactct tttctcttct tattaaacca 1440
tgaaaaagcc tgaactcacc gcgacgtctg tcgagaagtt tctgatcgaa aagttcgaca 1500
gcgtctccga cctgatgcag ctctcggagg gcgaagaatc tcgtgctttc agcttcgatg 1560
taggagggcg tggatatgtc ctgcgggtaa atagctgcgc cgatggtttc tacaaagatc 1620
gttatgttta tcggcacttt gcatcggccg cgctcccgat tccggaagtg cttgacattg 1680
gggaattcag cgagagcctg acctattgca tctcccgccg tgcacagggt gtcacgttgc 1740
aagacctgcc tgaaaccgaa ctgcccgctg ttctgcagcc ggtcgcggag gccatggatg 1800
cgatcgctgc ggccgatctt agccagacga gcgggttcgg cccattcgga ccgcaaggaa 1860
tcggtcaata cactacatgg cgtgatttca tatgcgcgat tgctgatccc catgtgtatc 1920
actggcaaac tgtgatggac gacaccgtca gtgcgtccgt cgcgcaggct ctcgatgagc 1980
tgatgctttg ggccgaggac tgccccgaag tccggcacct cgtgcacgcg gatttcggct 2040
ccaacaatgt cctgacggac aatggccgca taacagcggt cattgactgg agcgaggcga 2100
tgttcgggga ttcccaatac gaggtcgcca acatcttctt ctggaggccg tggttggctt 2160
gtatggagca gcagacgcgc tacttcgagc ggaggcatcc ggagcttgca ggatcgccgc 2220
ggctccgggc gtatatgctc cgcattggtc ttgaccaact ctatcagagc ttggttgacg 2280
gcaatttcga tgatgcagct tgggcgcagg gtcgatgcga cgcaatcgtc cgatccggag 2340

-continued

```
ccgggactgt cgggcgtaca caaatcgccc gcagaagcgc ggccgtctgg accgatggct   2400
gtgtagaagt actcgccgat agtggaaacc gacgccccag cactcgtccg agggcaaagg   2460
aatagtgagg tacctaaaga aggagtgcgt cgaagcagat cgttcaaaca tttggcaata   2520
aagtttctta agattgaatc ctgttgccgg tcttgcgatg attatcatat aatttctgtt   2580
gaattacgtt aagcatgtaa taattaacat gtaatgcatg acgttattta tgagatgggt   2640
ttttatgatt agagtcccgc aattatacat ttaatacgcg atagaaaaca aaatatagcg   2700
cgcaaactag gataaattat cgcgcgcggt gtcatctatg ttactagatc gatgtcgact   2760
ctagaggatc caattccaat cccacaaaaa tctgagctta acagcacagt tgctcctctc   2820
agagcagaat cgggtattca acaccctcat atcaactact acgttgtgta taacggtcca   2880
catgccggta tatacgatga ctggggttgt acaaaggcgg caacaaacgg cgttcccgga   2940
gttgcacaca agaaatttgc cactattaca gaggcaagag cagcagctga cgcgtacaca   3000
acaagtcagc aaacagacag gttgaacttc atccccaaag gagaagctca actcaagccc   3060
aagagctttg ctaaggccct aacaagccca ccaaagcaaa aagcccactg gctcacgcta   3120
ggaaccaaaa ggcccagcag tgatccagcc ccaaaagaga tctcctttgc cccggagatt   3180
acaatggacg atttcctcta tctttacgat ctaggaagga agttcgaagg tgaaggtgac   3240
gacactatgt tcaccactga taatgagaag gttagcctct tcaatttcag aaagaatgct   3300
gacccacaga tggttagaga ggcctacgca gcaggtctca tcaagacgat ctacccgagt   3360
aacaatctcc aggagatcaa ataccttccc aagaaggtta aagatgcagt caaaagattc   3420
aggactaatt gcatcaagaa cacagagaaa gacatatttc tcaagatcag aagtactatt   3480
ccagtatgga cgattcaagg cttgcttcat aaaccaaggc aagtaataga gattggagtc   3540
tctaaaaagg tagttcctac tgaatctaag gccatgcatg gagtctaaga ttcaaatcga   3600
ggatctaaca gaactcgccg tgaagactgg cgaacagttc atacagagtc ttttacgact   3660
caatgacaag aagaaaatct tcgtcaacat ggtggagcac gacactctgg tctactccaa   3720
aaatgtcaaa gatacagtct cagaagacca aagggctatt gagacttttc aacaaaggat   3780
aatttcggga aacctcctcg gattccattg cccagctatc tgtcacttca tcgaaaggac   3840
agtagaaaag gaaggtggct cctacaaatg ccatcattgc gataaaggaa aggctatcat   3900
tcaagatgcc tctgccgaca gtggtcccaa agatggaccc ccacccacga ggagcatcgt   3960
ggaaaaagaa gacgttccaa ccacgtcttc aaagcaagtg gattgatgtg acatctccac   4020
tgacgtaagg gatgacgcac aatcccacta tccttcgcaa gacccttcct ctatataagg   4080
aagttcattt catttggaga ggacacgctc gagctcattt ctctattact tcagccataa   4140
caaaagaact cttttctctt cttattaaac catggtacgt cctgtagaaa ccccaacccg   4200
tgaaatcaaa aaactcgacg gcctgtgggc attcagtctg gatcgcgaaa actgtggaat   4260
tgatcagcgt tggtgggaaa gcgcgttaca agaaagccgg gcaattgctg tgccaggcag   4320
ttttaacgat cagttcgccg atgcagatat tcgtaattat gcgggcaacg tctggtatca   4380
gcgcgaagtc tttataccga aaggttgggc aggccagcgt atcgtgctgc gtttcgatgc   4440
ggtcactcat tacggcaaag tgtgggtcaa taatcaggaa gtgatggagc atcagggcgg   4500
ctatacgcca tttgaagccg atgtcacgcc gtatgttatt gccgggaaaa gtgtacgtat   4560
caccgtttgt gtgaacaacg aactgaactg gcagactatc ccgccgggaa tggtgattac   4620
cgacgaaaac ggcaagaaaa agcagtctta cttccatgat ttctttaact atgccggaat   4680
```

-continued

```
ccatcgcagc gtaatgctct acaccacgcc gaacacctgg gtggacgata tcaccgtggt   4740
gacgcatgtc gcgcaagact gtaaccacgc gtctgttgac tggcaggtgg tggccaatgg   4800
tgatgtcagc gttgaactgc gtgatgcgga tcaacaggtg gttgcaactg gacaaggcac   4860
tagcgggact ttgcaagtgg tgaatccgca cctctggcaa ccgggtgaag gttatctcta   4920
tgaactgtgc gtcacagcca aaagccagac agagtgtgat atctacccgc ttcgcgtcgg   4980
catccggtca gtggcagtga agggccaaca gttcctgatt aaccacaaac cgttctactt   5040
tactggcttt ggtcgtcatg aagatgcgga cttacgtggc aaaggattcg ataacgtgct   5100
gatggtgcac gaccacgcat taatggactg gattggggcc aactcctacc gtacctcgca   5160
ttacccttac gctgaagaga tgctcgactg ggcagatgaa catggcatcg tggtgattga   5220
tgaaactgct gctgtcggct ttaacctctc tttaggcatt ggtttcgaag cgggcaacaa   5280
gccgaaagaa ctgtacagcg aagaggcagt caacggggaa actcagcaag cgcacttaca   5340
ggcgattaaa gagctgatag cgcgtgacaa aaaccaccca agcgtggtga tgtggagtat   5400
tgccaacgaa ccggataccc gtccgcaagt gcacgggaat atttcgccac tggcggaagc   5460
aacgcgtaaa ctcgacccga cgcgtccgat cacctgcgtc aatgtaatgt tctgcgacgc   5520
tcacaccgat accatcagcg atctctttga tgtgctgtgc ctgaaccgtt attacggatg   5580
gtatgtccaa agcggcgatt tggaaacggc agagaaggta ctggaaaaag aacttctggc   5640
ctggcaggag aaactgcatc agccgattat catcaccgaa tacggcgtgg atacgttagc   5700
cgggctgcac tcaatgtaca ccgacatgtg gagtgaagag tatcagtgtg catggctgga   5760
tatgtatcac cgcgtctttg atcgcgtcag cgccgtcgtc ggtgaacagg tatggaattt   5820
cgccgatttt gcgacctcgc aaggcatatt gcgcgttggc ggtaacaaga aagggatctt   5880
cactcgcgac cgcaaaccga agtcggcggc ttttctgctg caaaaacgct ggactggcat   5940
gaacttcggt gaaaaaccgc agcagggagg caaacaatga atcaacaact ctcctggcgc   6000
accatcgtcg gctacagcct cggtggggaa ttccccgggg gtacctaaag aaggagtgcg   6060
tcgaagcaga tcgttcaaac atttggcaat aaagtttctt aagattgaat cctgttgccg   6120
gtcttgcgat gattatcata taatttctgt tgaattacgt taagcatgta ataattaaca   6180
tgtaatgcat gacgttattt atgagatggg tttttatgat tagagtcccg caattataca   6240
tttaatacgc gatagaaaac aaaatatagc gcgcaaacta ggataaatta tcgcgcgcgg   6300
tgtcatctat gttactagat cgatgtcgac gatcatccgg atatagttcc tcctttcagc   6360
aaaaaacccc tcaagacccg tttagaggcc ccaaggggtt atgctagtta ttgctcagcg   6420
gtggcagcag ccaactcagc ttcctttcgg gctttgttag cagccggatc gatccaagct   6480
gtacctcact attcctttgc cctcggacga gtgctggggc gtcggtttcc actatcggcg   6540
agtacttcta cacagccatc ggtccagacg gccgcgcttc tgcgggcgat ttgtgtacgc   6600
ccgacagtcc cggctccgga tcggacgatt gcgtcgcatc gaccctgcgc ccaagctgca   6660
tcatcgaaat tgccgtcaac caagctctga tagagttggt caagaccaat gcggagcata   6720
tacgcccgga gccgcggcga tcctgcaagc tccggatgcc tccgctcgaa gtagcgcgtc   6780
tgctgctcca tacaagccaa ccacggcctc cagaagaaga tgttggcgac ctcgtattgg   6840
gaatccccga acatcgcctc gctccagtca atgaccgctg ttatgcggcc attgtccgtc   6900
aggacattgt tggagccgaa atccgcgtgc acgaggtgcc ggacttcggg gcagtcctcg   6960
gcccaaagca tcagctcatc gagagcctgc gcgacggacg cactgacggt gtcgtccatc   7020
acagtttgcc agtgatacac atggggatca gcaatcgcgc atatgaaatc acgccatgta   7080
```

-continued

```
gtgtattgac cgattccttg cggtccgaat gggccgaacc cgctcgtctg gctaagatcg   7140

gccgcagcga tcgcatccat agcctccgcg accggctgca gaacagcggg cagttcggtt   7200

tcaggcaggt cttgcaacgt gacaccctgt gcacggcggg agatgcaata ggtcaggctc   7260

tcgctgaatt ccccaatgtc aagcacttcc ggaatcggga gcgcggccga tgcaaagtgc   7320

cgataaacat aacgatcttt gtagaaacca tcggcgcagc tatttacccg caggacatat   7380

ccacgccctc ctacatcgaa gctgaaagca cgagattctt cgccctccga gagctgcatc   7440

aggtcggaga cgctgtcgaa cttttcgatc agaaacttct cgacagacgt cgcggtgagt   7500

tcaggctttt ccatgggtat atctccttct taaagttaaa caaaattatt tctagaggga   7560

aaccgttgtg gtctccctat agtgagtcgt attaatttcg cgggatcgag atctgatcaa   7620

cctgcattaa tgaatcggcc aacgcgcggg gagaggcggt ttgcgtattg ggcgctcttc   7680

cgcttcctcg ctcactgact cgctgcgctc ggtcgttcgg ctgcggcgag cggtatcagc   7740

tcactcaaag gcggtaatac ggttatccac agaatcaggg gataacgcag gaaagaacat   7800

gtgagcaaaa ggccagcaaa aggccaggaa ccgtaaaaag gccgcgttgc tggcgttttt   7860

ccataggctc cgcccccctg acgagcatca caaaaatcga cgctcaagtc agaggtggcg   7920

aaacccgaca ggactataaa gataccaggc gtttccccct ggaagctccc tcgtgcgctc   7980

tcctgttccg accctgccgc ttaccggata cctgtccgcc tttctccctt cgggaagcgt   8040

ggcgctttct caatgctcac gctgtaggta tctcagttcg gtgtaggtcg ttcgctccaa   8100

gctgggctgt gtgcacgaac cccccgttca gcccgaccgc tgcgccttat ccggtaacta   8160

tcgtcttgag tccaacccgg taagacacga cttatcgcca ctggcagcag ccactggtaa   8220

caggattagc agagcgaggt atgtaggcgg tgctacagag ttcttgaagt ggtggcctaa   8280

ctacggctac actagaagga cagtatttgg tatctgcgct ctgctgaagc cagttacctt   8340

cggaaaaaga gttggtagct cttgatccgg caaacaaacc accgctggta gcggtggttt   8400

ttttgtttgc aagcagcaga ttacgcgcag aaaaaaagga tctcaagaag atcctttgat   8460

cttttctacg gggtctgacg ctcagtggaa cgaaaactca cgttaaggga ttttggtcat   8520

gacattaacc tataaaaata ggcgtatcac gaggcccttt cgtctcgcgc gtttcggtga   8580

tgacggtgaa aacctctgac acatgcagct cccggagacg gtcacagctt gtctgtaagc   8640

ggatgccggg agcagacaag cccgtcaggg cgcgtcagcg ggtgttggcg ggtgtcgggg   8700

ctggcttaac tatgcggcat cagagcagat tgtactgaga gtgcaccata tggacatatt   8760

gtcgttagaa cgcggctaca attaatacat aaccttatgt atcatacaca tacgatttag   8820

gtgacactat a                                                        8831
```

ALTERATION OF EMBRYO/ENDOSPERM SIZE DURING SEED DEVELOPMENT

This application is a continuation-in-part of U.S. patent application Ser. No. 10/163,198, filed Jun. 5, 2002 and now abandoned, the entire contents of which are hereby incorporated by reference, which claims the benefit of U.S. Provisional Application No. 60/295,921, filed Jun. 5, 2001, the entire contents of which are hereby incorporated by reference, and U.S. Provisional Application No. 60/334,317, filed Nov. 28, 2001, the entire contents of which are hereby incorporated by reference.

FIELD OF THE INVENTION

The present invention is in the field of plant breeding and genetics and, in particular, relates to recombinant constructs useful for altering embryo/endosperm size during seed development.

BACKGROUND OF THE INVENTION

Elucidation of how the size of a developing embryo is genetically regulated is important because the final volume of endosperm as a storage organ of starch and proteins is affected by embryo size in cereal crops. Researchers have found that embryo size-related genes contribute to the regulation of endosperm development Investigation of these genes is important for agriculture because cereal endosperms are the staple diet in many countries. Also, it is important for agriculture because embryos of various crop grains are the source of many valuable nutrients including oil.

The giant embryo (ge) mutation was first described by Satoh and Omura (1981) *Jap. J. Breed.* 31:316-326. The giant embryo mutant is a potentially useful character for quality improvement in cereals because increased embryo size will result in increased embryo oil and nutrient traits that are desirable for human consumption. Also, the enlargement of embryos would result in increased embryo-related enzymatic activities, which are often important features in the processing of grains. The mutation was genetically mapped to chromosome 7 (Iwata and Omura (1984) *Japan. J. Genet.* 59:199-204; Satoh and Iwata (1990) *Japan. J. Breed.* 40 (Suppl. 2): 268-269), with additional ge alleles also localized to chromosome 7 (Koh et al. (1996) *Theor. Appl. Genet.* 93:257-261). The ge mutations were analyzed at the morphologic and genetic level by Hong et al. (1994) *Development* 122:2051-2058. This publication linked the GE gene as being required for proper endosperm development. Since both endosperm and embryo size are affected by the mutation, GE appears to control coordinated proliferation of the endosperm and embryo during development. Beside the morphological change of embryo and endosperm in ge, it was also shown that the ge seed accumulates more oil compared to the wild type (Matsuo et al. (1987) *Japan. J. Breed.* 37:185-191; Okuno (1997) In "Science of the Rice Plant" Vol. III, Matsuo et al. eds., Food and agriculture policy research center, Tokyo, Japan, pp 433-435).

It has been found that loss-of-function of the GE gene leads to an enlargement of embryonic tissue at the expense of endosperm tissue. This developmental change may be useful in increasing the amount of embryo-specific metabolites such as oil in seed-bearing plants. Despite the extensive genetic and morphological characterization of the GE gene there has been no molecular analysis of the nucleic acid encoding this protein. Indeed, the identity of the protein encoded by GE has not been reported. A better understanding of the GE gene, and the protein it encodes, will be required for a complete understanding of the process controlling embryo size in rice.

SUMMARY OF THE INVENTION

This invention concerns an isolated nucleotide fragment comprising a nucleic acid sequence selected from the group consisting of:

(a) a nucleic acid sequence encoding a cytochrome P450 polypeptide associated with controlling embryo/endosperm size during seed development having an amino acid identity of at least 61% based on the Clustal method of alignment when compared to a second polypeptide selected from the group consisting of SEQ ID NO:2, 7, 11, 19, 27, or 33; or (b) a nucleic acid sequence encoding a cytochrome P450 polypeptide associated with controlling embryo/endosperm size during seed development having an amino acid identity of at least 65% based on the Clustal method of alignment when compared to a third polypeptide selected from the group consisting of SEQ ID NO:15, 17, 31, 93, 95, 97, or 99; or (c) a nucleic acid sequence encoding a cytochrome P450 polypeptide associated with controlling embryo/endosperm size during seed development having an amino acid identity of at least 70% based on the Clustal method of alignment when compared to a fourth polypeptide selected from the group consisting of SEQ ID NO:9, 13, 23, 29, 35, or 41; or (d) a nucleic acid sequence encoding a cytochrome P450 polypeptide associated with controlling embryo/endosperm size during seed development having an amino acid identity of at least 77% based on the Clustal method of alignment when compared to a second polypeptide selected from the group consisting of SEQ ID NO:21, 25, 37, or 39.

Also of interest is the complement of such isolated nucleotide fragment.

In a second embodiment, this invention concerns such isolated nucleotide sequence or its complement which comprises at least one motif corresponding substantially to any of the amino acid sequences set forth in SEQ ID NOs:2, 7, 9, 11, 13, 15, 17, 19, 21, 23, 25, 27, 29, 31, 33, 35, 37, 39, 41, 93, 95, 97, or 99 wherein said motif is a conserved subsequence. Examples of such motifs, among others that can be identified, are shown in SEQ ID NOs:80-91. Also of interest is the use of such fragment or a part thereof in antisense inhibition or co-suppression of cytochrome P450 activity in a transformed plant.

In a third embodiment this invention concerns such isolated nucleotide fragment of Claim 1 complement thereof wherein the fragment or a part thereof is useful in antisense inhibition or co-suppression of cytochrome P450 activity in a transformed plant.

In a fourth embodiment this invention concerns an isolated nucleotide sequence fragment comprising a nucleic acid sequence encoding a first polypeptide associated with controlling embryo/endosperm size during seed development wherein said polypeptide has an amino acid identity of at least 50%, 55%, 60%, 61%, 65%, 70%, 75%, 77%, 80%, 85%, 90%, 95%, or 100% based on the Clustal method of alignment when compared to a second polypeptide selected from the group consisting of SEQ ID NO:2, 7, 9, 11, 13, 15, 17, 19, 21, 23, 25, 27, 29, 31, 33, 35, 37, 39, 41, 42, 43, 44, 45, 46, 47, 93, 95, 97, or 99. Also of interest is the complement of such sequence.

In a fifth embodiment, this invention concerns this isolated nucleotide sequence of or its complement which comprises at least one motif corresponding substantially to any of the amino acid sequences set forth in SEQ ID NOs:2, 7, 9, 11, 13, 15, 17, 19, 21, 23, 25, 27, 29, 31, 33, 35, 37, 39, 41, 42, 43, 44, 45, 46, 47, 93, 95, 97, or 99, wherein said motif is a conserved subsequence. Any of these fragments or complements or part of either can be useful in antisense inhibition or co-suppression of cytochrome P450 activity in a transformed plant.

In a sixth embodiment, this invention concerns an isolated nucleic acid fragment comprising a promoter wherein said promoter consists essentially of the nucleotide sequence set forth in SEQ ID NOs:3, 4, 104, or 105, or said promoter consists essentially of a fragment or subfragment that is substantially similar and functionally equivalent to the nucleotide sequence set forth in SEQ ID NOs:3, 4, 104, or 105.

In a seventh embodiment, this invention concerns chimeric constructs comprising any of the foregoing nucleic acid fragment or complement thereof or part of either operably linked to at least one regulatory sequence. Also, of interest are plants comprising such chimeric constructs in their genome, plant tissue or cells obtained from such plants, seeds obtained from these plants and oil obtained from such seeds.

In an eighth embodiment, this invention concerns a method of controlling embryo/endosperm size during seed development in plants which comprises:

(a) transforming a plant with a chimeric construct of the invention;

(b) growing the transformed plant under conditions suitable for the expression of the chimeric construct; and (c) selecting those transformed plants which produce seeds having an altered embryo/endosperm size.

In a ninth embodiment, this invention concerns a method to isolate nucleic acid fragments encoding polypeptides associated with controlling embryo/endosperm size during seed development which comprises:

(a) comparing SEQ ID NOs:2, 7, 9, 11, 13, 15, 17, 19, 21, 23, 25, 27, 29, 31, 33, 35, 37, 39, 41, 42, 43, 44, 45, 46, 47, 93, 95, 97, or 99, with other polypeptide sequences associated with controlling embryo/endosperm size during seed development;

(b) identifying the conserved sequences(s) or 4 or more amino acids obtained in step (a);

(c) making region-specific nucleotide probe(s) or oligomer(s) based on the conserved sequences identified in step (b); and (d) using the nucleotide probe(s) or oligomer(s) of step (c) to isolate sequences associated with controlling embryo/endosperm size during seed development by sequence dependent protocols.

In a tenth embodiment, this invention also concerns a method of mapping genetic variations related to controlling embryo/endosperm size during seed development and/or altering oil phenotypes in plants comprising:

(a) crossing two plant varieties; and (b) evaluating genetic variations with respect to:

(i) a nucleic acid sequence selected from the group consisting of SEQ ID NO:1, 3, 4, 5, 6, 8, 10, 12, 14, 16, 18, 20, 22, 24, 26, 28, 30, 32, 34, 36, 38, 40, 92, 94, 96, 98, 100, 102, 104, or 105; or (ii) a nucleic acid sequence encoding a polypeptide selected from the group consisting of SEQ ID NO:2, 7, 9, 11, 13, 15, 17, 19, 21, 23, 25, 27, 29, 31, 33, 35, 37, 39, 41, 42, 43, 44, 45, 46, 47, 80-91, 93, 95, 97, or 99;

in progeny plants resulting from the cross of step (a) wherein the evaluation is made using a method selected from the group consisting of: RFLP analysis, SNP analysis, and PCR-based analysis.

In an eleventh embodiment, this invention concerns a method of molecular breeding to obtain altered embryo/endosperm size during seed development and/or altered oil phenotypes in plants comprising:

(a) crossing two plant varieties; and (b) evaluating genetic variations with respect to:

(i) a nucleic acid sequence selected from the group consisting of SEQ ID NO:1, 3, 4, 5, 6, 8, 10, 12, 14, 16, 18, 20, 22, 24, 26, 28, 30, 32, 34, 36, 38, 40, 92, 94, 96, 98, 100, 102, 104, or 105; or (ii) a nucleic acid sequence encoding a polypeptide selected from the group consisting of SEQ ID NO:2, 7, 9, 11, 13, 15, 17, 19, 21, 23, 25, 27, 29, 31, 33, 35, 37, 39, 41, 42, 43, 44, 45, 46, 47, 80-91, 93, 95, 97, or 99;

in progeny plants resulting from the cross of step (a) wherein the evaluation is made using a method selected from the group consisting of: RFLP analysis, SNP analysis, and PCR-based analysis.

BRIEF DESCRIPTION OF THE FIGURES AND SEQUENCE LISTINGS

The invention can be more fully understood from the following detailed description and the accompanying drawings and Sequence Listing which form a part of this application.

FIG. 1 shows an alignment of the sequence of the GE gene (SEQ ID NO:1) and ge mutant alleles. The allelic mutations resulting in a giant embryo phenotype are noted by a "*" on the complementary strand. Each mutation is labeled and the base change is shown (the corresponding complementary base changes on the coding strand are noted below) and the resulting amino acid change is noted parenthetically (i.e. wild-type->mutant). The ge-1 mutant had a mutation that alters the G at nucleotide 1482 to an A, changing the corresponding Trp residue to a premature translational stop (UGG codon to UGA). In ge-2, the G at nucleotide 1451 was altered to A, again changing the encoded Trp to a premature translational stop (UAG). In ge-3 and ge-9, the C at nucleotide 1177 was altered to T, changing a Pro residue, which is highly conserved among cytochrome P450 proteins, into Ser. In ge-4, the C at nucleotide 1388 was altered to G, changing a Pro residue into Ala. In ge-5, the C at nucleotide 28 was altered to T, causing a premature translational stop (UAA). In ge-6, the A at nucleotide 1067 was altered to C, causing the change of Gln, which is conserved among the CYP78 group, into Pro. In ge-8, we found two mutations: the T at nucleotide 559 was altered to C, causing the change of Ser to Pro, and the C at nucleotide 1328 was altered to T, causing the change of Pro to Leu. One 91 nucleotide-long intron was found between nucleotides 972 and 973.

FIG. 2 shows an alignment of the rice GE (SEQ ID NO:2), barley GE-homolog (SEQ ID NO:93), maize GE1-homolog (SEQ ID NO:95), maize GE2-homolog (SEQ ID NO:97), maize GE3-homolog (SEQ ID NO:99), lily GE-homolog (SEQ ID NO:41), orchid gi 1173624 (SEQ ID NO:43), *Arabidopsis* gi 1235138 (SEQ ID NO:42), *Arabidopsis* gi 8920576 (SEQ ID NO:47), columbine GE-homolog (SEQ ID NO:35), soybean GE-homolog (SEQ ID NO:23), *Arabidopsis* gi 11249511 (SEQ ID NO:44), soybean gi 5921926 (SEQ ID NO:45), soybean GE-homolog (SEQ ID NO:25), soybean GE-homolog (SEQ ID NO:21), and *Arabidopsis* gi 3831440 (SEQ ID NO:46). The boxed residues are predicted helical regions identified by the Bioscout DSC program (King and Sternberg (1996) *Protein Sci* 5:2298-2310). Other boxed elements include "SRS" or substrate-recognition-sites which are hypervariable sequences in the cytochrome P450 structure, "PPP" clusters of prolines often Pro-Pro-Gly-Pro in cytochrome P450s, "F-G loop" which is the substrate access channel (part of the conserved sequence motif of SEQ ID NO:83), the conserved "GXDT" the proton transfer groove involved in heme interaction and enzyme catalysis (part of the conserved sequence motif of SEQ ID NO:85), "EXXR" the K-helix motif conserved in all cytochrome P450s necessary for heme stabilization and core structure stability (part of conserved sequence motif of SEQ ID NO:88), and "FXXGXRXCXG" the conserved heme binding site with the cysteine that contacts the heme (part of the conserved sequence motif of SEQ ID NO:90).

FIG. 3 shows GE ectopic expression leads to a reduced embryo and enlarged endosperm phenotype in maize.

FIG. 4A-B shows the oil content analysis of segregating Ubi::GE seeds. F1 kernels of a Ubi::GE backcrossed to wild type were analyzed for seed oil content (3797701). The transgenic construct segregated in a 1:1 fashion. FIG. 4B shows the percent oil distribution of a control transgenic line that does not affect embryo/endosperm size.

FIG. 5A-C shows A) wild type (T65) seed, B) ge-3 mutant seed in T65 background, and C) ge-3 mutant with the complementing EcoRI 5.1 kb fragment.

Figure 2A:
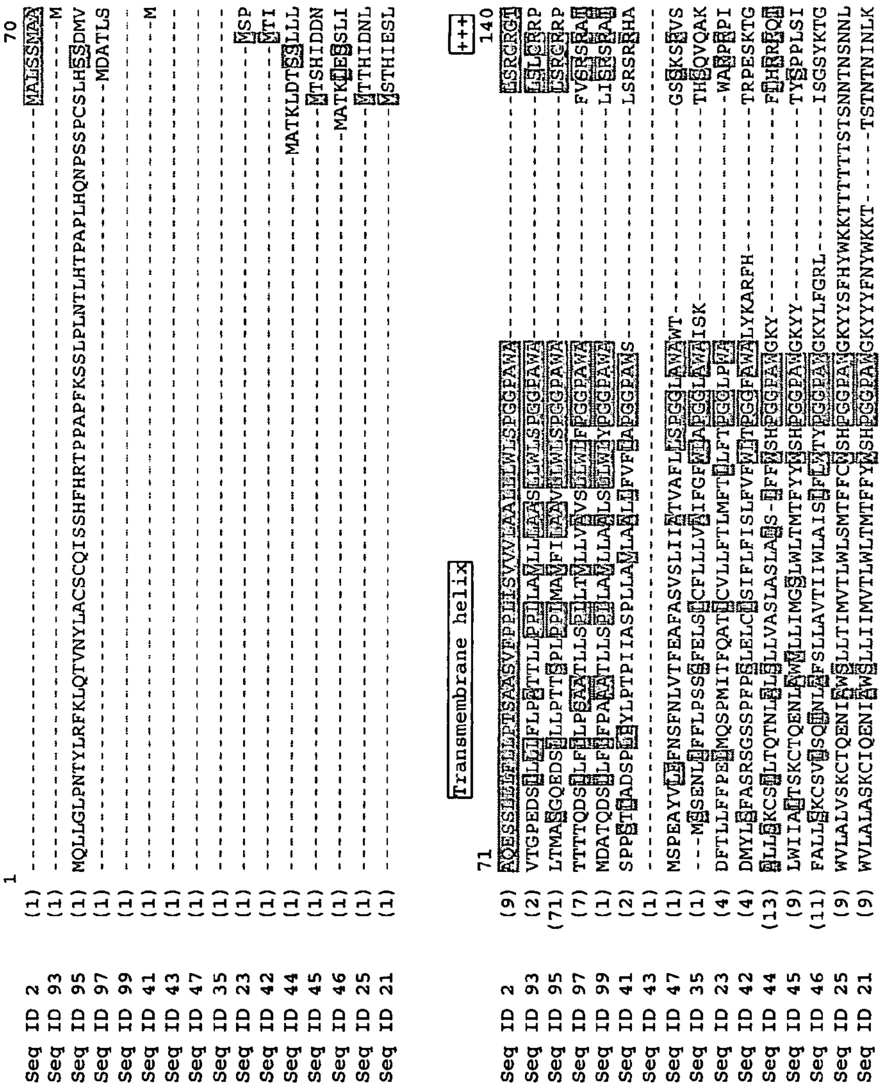
Figure 2B:
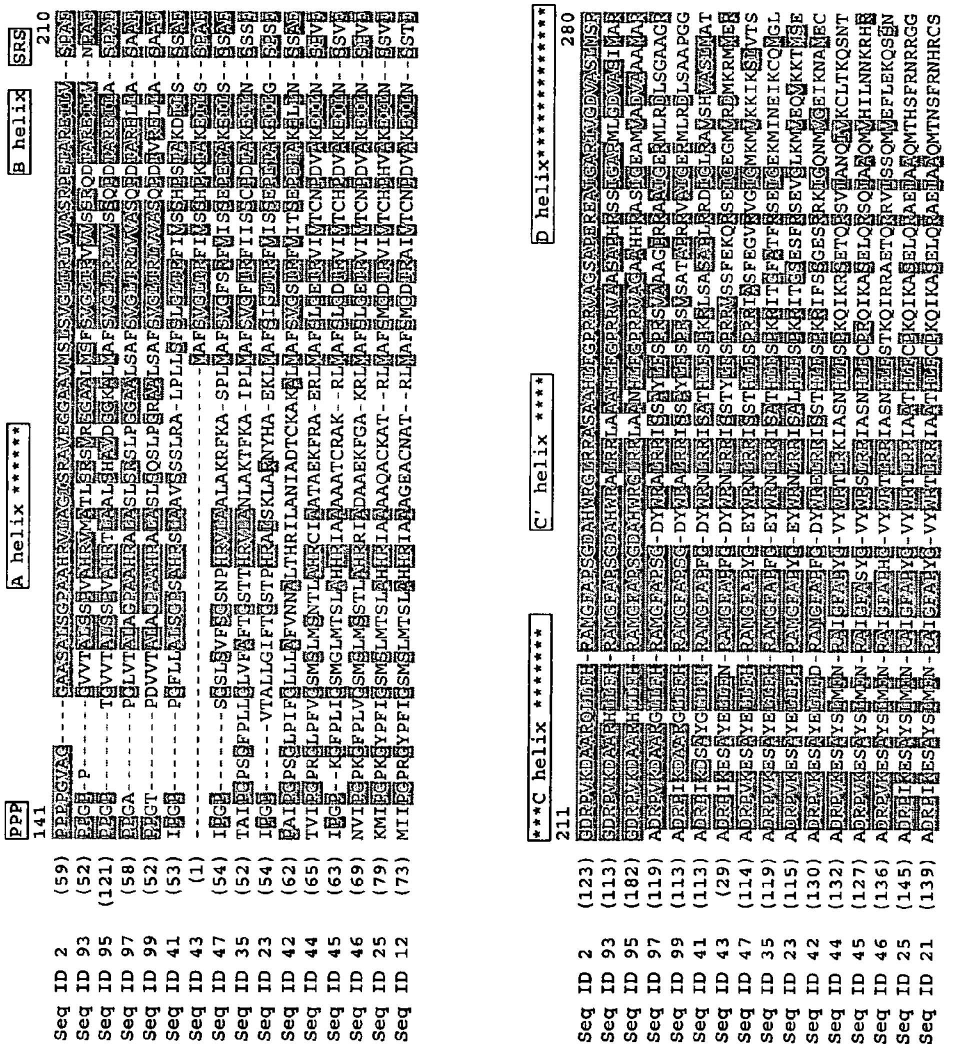
Figure 2C:
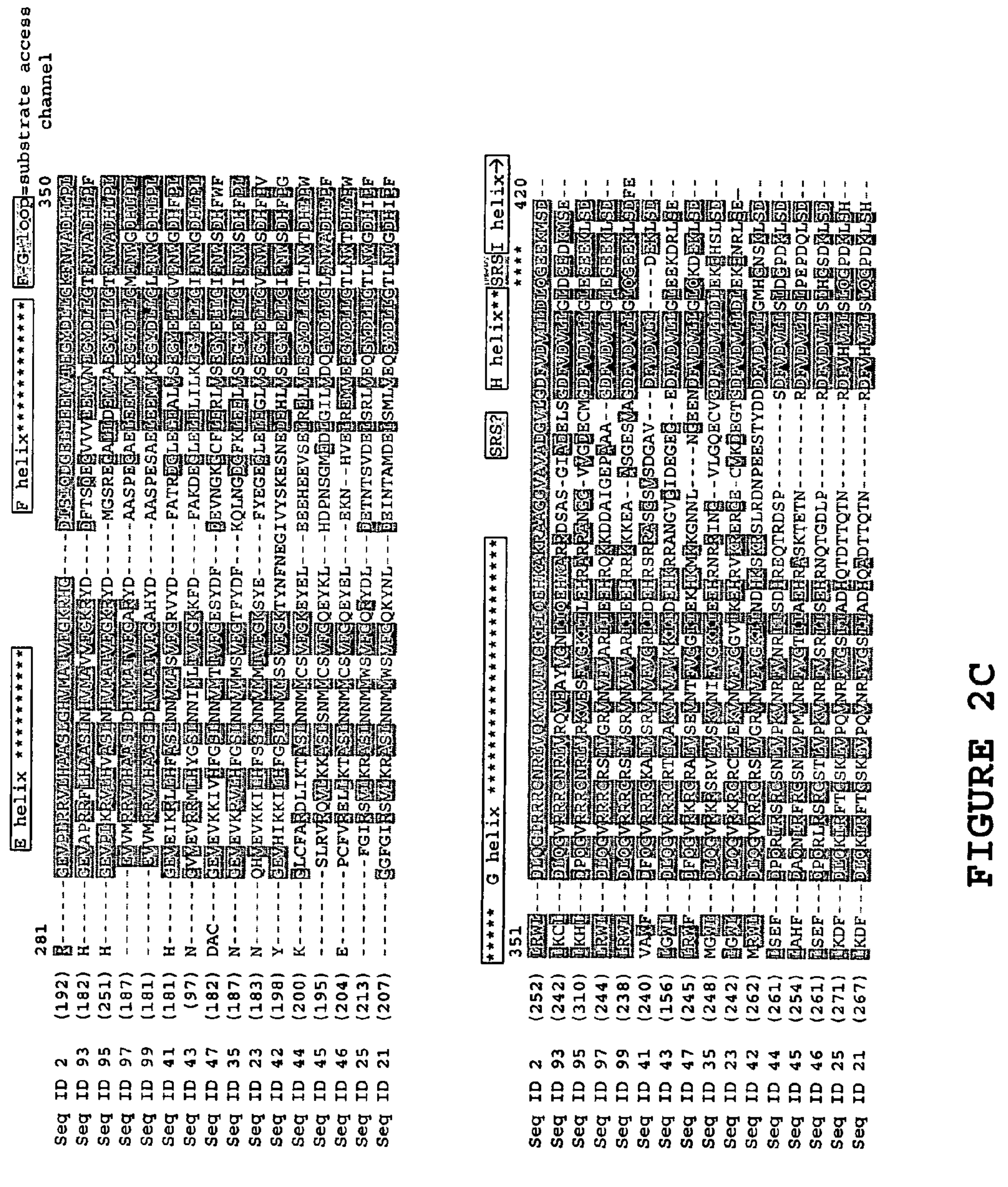
Figure 2D:
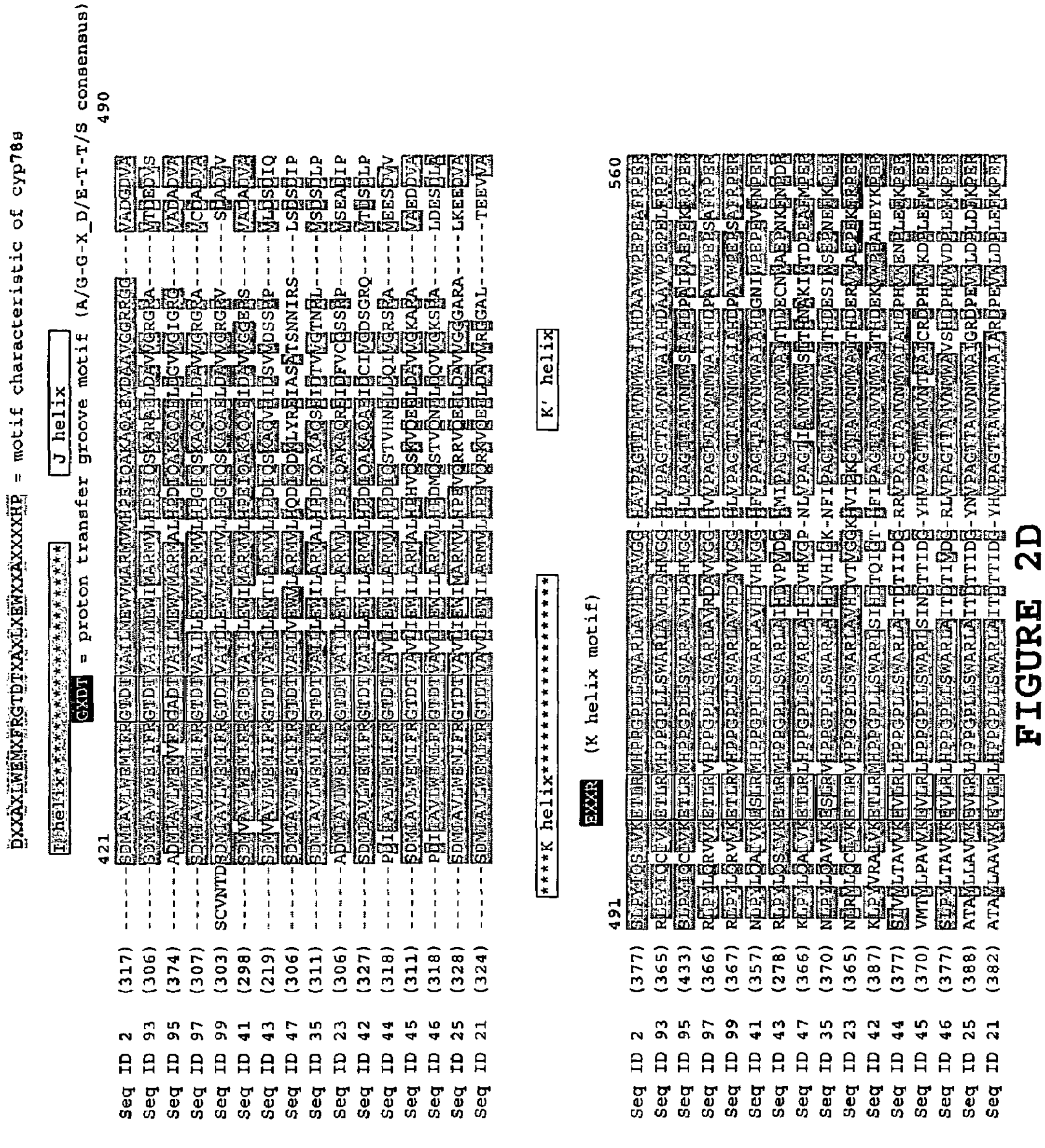
Figure 2E:
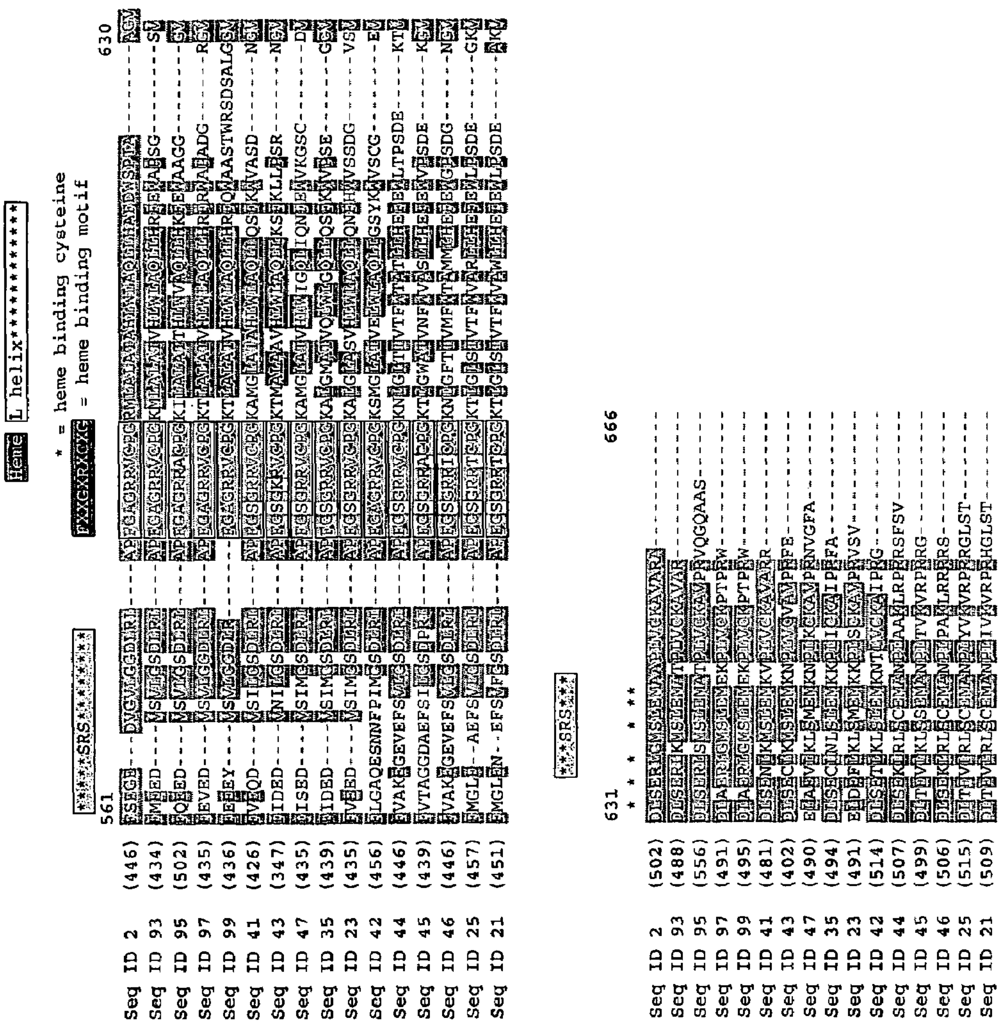

FIG. 8A-D shows GE ectopic expression leads to enlarged flowers and seed in *Arabidopsis*. A and C show a wild type flower and seed, respectively; and B and D show a 35S::GE expressing flower and seed.

FIG. 9A-F shows GE ectopic expression in soybean under 35S promoter.

A: HygR Control event (SRS 163-3-1-1); B: Jack wild-type seed;

C: An event with small seed (SRS 103-3-1-3; D: Jack wild-type seed;

E: An event with large seed (SRS 162-9-1); F: Jack wild-type seed.

Table 1 lists the polypeptides that are described herein, the designation of the genomic or cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Genes Encoding Enzymes Associated With Altering Embryo/Endosperm Size During Seed Development

| Cytochrome P450 Enzymes | Clone Designation | SEQ ID NO: (Nucleotide) | SEQ ID NO: (Amino Acid) |
|---|---|---|---|
| Rice (*Oryza sativa*) | bac4d1g.pk001.l12.f | 1 | 2 |
| Rice (*Oryza sativa*) | bac1i1g.pk001.d18 | 3 | |
| Rice (*Oryza sativa*) | bac4d1g.pk001.o6 | 4 | |
| Rice (*Oryza sativa*) | bac4d1g.pk001.k21 | 5 | |
| Rice (*Oryza sativa*) | rca1c.pk007.n11:fis | 6 | 7 |
| Rice (*Oryza sativa*) | rls2.pk0022.b12:fis | 8 | 9 |
| Rice (*Oryza sativa*) | rr1.pk0044.e7 | 10 | 11 |
| Maize (*Zea mays*) | cbn10.pk0034.f8:fis | 12 | 13 |
| Maize (*Zea mays*) | p0037.crwbn23r | 14 | 15 |

TABLE 1-continued

Genes Encoding Enzymes Associated With Altering Embryo/Endosperm Size During Seed Development

| Cytochrome P450 Enzymes | Clone Designation | SEQ ID NO: (Nucleotide) | SEQ ID NO: (Amino Acid) |
|---|---|---|---|
| Maize (*Zea mays*) | p0121.cfrmn62r:fis | 16 | 17 |
| Maize (*Zea mays*) | contig of: p0014.ctusi51r p0014.ctutw92r:fis p0022.cglnh53r p0122.ckama19r p9998.cmrne01rb | 18 | 19 |
| Soybean (*Glycine max*) | sdp2c.pk042.p12:fis | 20 | 21 |
| Soybean (*Glycine max*) | contig of: se1.20e06 se4.pk0009.e9 | 22 | 23 |
| Soybean (*Glycine max*) | sfl1.pk0010.a2:fis | 24 | 25 |
| Soybean (*Glycine max*) | src3c.pk009.k13 | 26 | 27 |
| Sunflower (*Helianthus* sp.) | hso1c.pk003.n10 | 28 | 29 |
| Sunflower (*Helianthus* sp.) | hss1c.pk004.b24 | 30 | 31 |
| Wheat (*Triticum aestivum*) | contig of: wdk2c.pk013.c20 wre1n.pk0056.b6 | 32 | 33 |
| Columbine (*Aquilegia vulgaris*) | eav1c.pk006.n4:fis | 34 | 35 |
| Grape (*Vitis* sp.) | veb1c.pk001.k11:fis | 36 | 37 |
| Guayule (*Parthenium argentatum* Grey) | epb3c.pk005.d14 | 38 | 39 |
| Lily (*Astroemeria caryophylla*) | eae1s.pk003.b24:fis | 40 | 41 |
| Barley (*Hordeum vulgare*) | bdl1c.pk003.h16 | 92 | 93 |
| Maize (*Zea mays*) | p0037.crwbn23r:fis | 94 | 95 |
| Maize (*Zea mays*) | cbn10.pk0034.f8.f | 96 | 97 |
| Maize (*Zea mays*) | cpls1s.pk001.m19 | 98 | 99 |

SEQ ID NO:1 and 2 represent the wild-type open-reading-frame (ORF) DNA sequence and the translated amino acid sequence, respectively, for the rice cytochrome P450 gene, which is responsible for the giant embryo phenotype when mutated. SEQ ID NO:3 represents 17 kb of genomic DNA sequence containing the GE ORF (nucleotides 8301 to 9969) which is interrupted by a 91 nucleotide intron (9273 to 9363). SEQ ID NO:4 represents the 8300 nucleotides upstream of the GE ORF that contains the promoter for the gene and the 5' untranslated (UTR) portion of the GE mRNA. SEQ ID NO:5 represents the 7224 nucleotides downstream of the GE ORF that contains the 3'-UTR and polyadenylation sequences for the gene. There were no other genes, besides GE, detected by BLAST homology that were contained within this 17 kb region of the rice genome. SEQ ID NOs:80-91 are conserved sequence motifs that re useful in identifying cytochrome P450 genes that are functional homologs of GE. SEQ ID NOs:104 and 105 are upstream promoter sequences for maize homologs zmGE1 and zmGE2, respectively (see Example 13 for more detail). The remaining sequences are PCR primers, adaptors, mutagenesis primers, promoter sequences, terminator sequences, or plasmid vector sequences that were used in making the recombinant DNA/chimeric constructs used in the examples described herein.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 1×SSC, 0.1% SDS, 60° C.) with the sequences exemplified herein, or to any portion of the nucleotide sequences reported herein and which are functionally equivalent to the gene or the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length; and should be at least 80% identical, preferably at least 85% identical, more preferably at least 90% identical, and most preferably at least 95% identical.

Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of an isolated nucleic acid fragment in different tissues or cell types, or at different stages of development, or in response to different environmental conditions. Promoters which cause an isolated nucleic acid fragment to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA fragments of some variation may have identical promoter activity.

Specific examples of promoters that may be useful in expressing the nucleic acid fragments of the invention include, but are not limited to, the GE promoter disclosed in this application (SEQ ID NO:4), oleosin promoter (PCT Publication WO99/65479, published on Dec. 12, 1999), maize 27 kD zein promoter (Ueda et al (1994) *Mol Cell Bio* 14:4350-4359), ubiquitin promoter (Christensen et al (1992) *Plant Mol Biol* 18:675-680), SAM synthetase promoter (PCT Publication WO00/37662, published on Jun. 29, 2000), or CaMV 35S (Odell et al (1985) *Nature* 313:810-812).

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of an isolated nucleic acid fragment involves transcription of the isolated nucleic acid fragment and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature* (*London*) 327:70-73; U.S. Pat. No. 4,945,050), or an *Agrobacterium*-mediated method using an appropriate Ti plasmid containing the transgene (Ishida Y. et al., 1996, Nature Biotech. 14:745-750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263-273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) *Plant Cell* 10:1747-1757).

Plant cytochrome P450 enzymes are NADPH-dependent monooxygenases that are responsible for the oxidative metabolism of a variety of compounds in plants. The cytochrome P450s contain iron-sulfur ligands, termed haem-thiolate complexes, that are responsible for a distinctive absorption spectrum with a maximum at 450 nm in the presence of carbon monoxide. In animal systems P450 enzymes are responsible for detoxification pathways in the liver, inactivation and activation of certain carcinogenic compounds, and drug and hormone metabolism. In plants, the cytochrome P450 family is responsible for, but not limited to, herbicide metabolism, secondary metabolism, and wounding responses.

Surprisingly, it has been found that a single mutation of a cytochrome P450 gene in rice can lead to an alteration of embryo/endosperm size during seed development. This gene is named Giant Embryo (GE). Inhibition of the function of the gene leads to enlargement of embryonic tissue at the expense of part of the endosperm tissue. Thus, the GE gene and protein product can regulate proliferation both negatively and positively depending on the tissue. Enlargement of the embryo will result in seeds with high content of valuable components such as oils. A search of GenBank with the rice GE sequence uncovers a number of genes from plants that appear to be homologous.

"Giant embryo-like cytochrome P450" polypeptides would encompass those enzymes from other plants that share sequence and/or functional similarity to the rice GE polypeptide. It is believed that such a polypeptide would comprise a subset of the cytochrome P450 family, and that alteration in the expression of this member would affect embryo-size.

"Motifs" or "subsequences" refer to short regions of conserved sequences of nucleic acids or amino acids that comprise part of a longer sequence. For example, it is expected that such conserved subsequences (for example SEQ ID NOs: 80-91) would be important for function, and could be used to identify new homologues of GE-like cytochrome P450s in plants. It is expected that some or all of the elements may be found in a GE-homologue. Also, it is expected that one or two of the conserved amino acids in any given motif may differ in a true GE-homologue.

Thus, in one aspect, this invention concerns an isolated nucleotide fragment comprising a nucleic acid sequence selected from the group consisting of:

(a) a nucleic acid sequence encoding a cytochrome P450 polypeptide associated with controlling embryo/endosperm size during seed development having an amino acid identity of at least 61% based on the Clustal method of alignment when compared to a second polypeptide selected from the group consisting of SEQ ID NO:2, 7, 11, 19, 27, or 33; or (b) a nucleic acid sequence encoding a cytochrome P450 polypeptide associated with controlling embryo/endosperm size during seed development having an amino acid identity of at least 65% based on the Clustal method of alignment when compared to a third polypeptide selected from the group consisting of SEQ ID NOs:15, 17, 31, 93, 95, 97, or 99; or (c) a nucleic acid sequence encoding a cytochrome P450 polypeptide associated with controlling embryo/endosperm size during seed development having an amino acid identity of at least 70% based on the Clustal method of alignment when compared to a third polypeptide selected from the group consisting of SEQ ID NOs:9, 13, 23, 29, 35, or 41; or (d) a nucleic acid sequence encoding a cytochrome P450 polypeptide associated with controlling embryo/endosperm size during seed development having an amino acid identity of at least 77% based on the Clustal method of alignment when compared to a second polypeptide selected from the group consisting of SEQ ID NOs:21, 25, 37, or 39.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%.

Also, of interest is the complement of this isolated nucleotide fragment.

The isolated nucleotide sequence or its complement can also comprise at least one, two, three, four, five, six, seven, eight, nine, ten, or eleven motif(s) corresponding substantially to any of the amino acid sequences set forth in SEQ ID NOs:80-91 wherein said motif is a conserved subsequence. In another aspect, this isolated nucleotide fragment or its complement (whether they comprise the aforementioned motif or not) or a part of the fragment or its complement can be used in antisense inhibition or co-suppression of cytochrome P450 activity in a transformed plant. It is appreciated that further embodiments would include at least one, two, three, four, five, six, seven, eight, nine, ten, or eleven motif(s) corresponding substantially to any of the amino acid sequences set forth in SEQ ID NOs:80-91 being used to identify cytochrome P450 polypeptides associated with controlling embryo/endosperm size during seed development.

Protocols for antisense inhibition or co-suppression are well known to those skilled in the art and are described above.

In still a further aspect, this invention concerns an isolated nucleic acid fragment comprising a promoter wherein said promoter consists essentially of the nucleotide sequence set forth in SEQ ID NOs:3, 4, 104, or 105, or said promoter consists essentially of a fragment or subfragment that is substantially similar and functionally equivalent to the nucleotide sequence set forth in SEQ ID NOs:3, 4, 104, or 105.

Also of interest are chimeric constructs comprising any of the above-identified isolated nucleic acid fragments or complements thereof or parts of such fragments or complements operably linked to at least one regulatory sequence.

Plants, plant tissue or plant cells comprising such chimeric constructs in their genome are also within the scope of this invention. Transformation methods are well known to those skilled in the art and are described above. Any plant, dicot or monocot can be transformed with such chimeric constructs.

Examples of monocots include, but are not limited to, corn, wheat, rice, sorghum, millet, barley, palm, lily, *Alstroemeria*, rye, and oat. Examples of dicots include, but are not limited to, soybean, rape, sunflower, canola, grape, guayule, columbine, cotton, tobacco, peas, beans, flax, safflower, alfalfa.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue. The plant tissue may in plant or in organ, tissue or cell culture.

Also within the scope of this invention are seeds obtained from such plants and oil obtained from these seeds.

In another aspect, this invention concerns a method of controlling embryo/endosperm size during seed development in plants which comprises:

(a) transforming a plant with a chimeric construct of the invention;

(b) growing the transformed plant under conditions suitable for the expression of the chimeric construct; and (c) selecting those transformed plants which produce seeds having an altered embryo/endosperm size.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue.

The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *Bio/Technology* 6:923 (1988), Christou et al., *Plant Physiol.* 87:671-674 (1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (*USA*) 84:5354, (1987)); barley (Wan and Lemaux, *Plant*

*Physiol* 104:37 (1994)); *Zea mays* (Rhodes et al., *Science* 240:204 (1988), Gordon-Kamm et al., *Plant Cell* 2:603-618 (1990), Fromm et al., *Bio/Technology* 8:833 (1990), Koziel et al., *Bio/Technology* 11: 194, (1993), Armstrong et al., *Crop Science* 35:550-557 (1995)); oat (Somers et al., *Bio/Technology* 10: 15 89 (1992)); orchard grass (Horn et al., *Plant Cell Rep.* 7:469 (1988)); rice (Toriyama et al., *Theor Appl. Genet.* 205:34, (1986); Part et al., *Plant Mol. Biol.* 32:1135-1148, (1996); Abedinia et al., *Aust. J. Plant Physiol.* 24:133-141 (1997); Zhang and Wu, *Theor. Appl. Genet.* 76:835 (1988); Zhang et al. *Plant Cell Rep.* 7:379, (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect isolated nucleic acid fragment constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

In a still further aspect this invention concerns a method to isolate nucleic acid fragments encoding polypeptides associated with controlling embryo/endosperm size during seed development which comprises:

(a) comparing SEQ ID NOs:2, 7, 9, 11, 13, 15, 17, 19, 21, 23, 25, 27, 29, 31, 33, 35, 37, 39, 41, 42, 43, 44, 45, 46, 47, 93, 95, 97, or 99, with other polypeptide sequences associated with controlling embryo/endosperm size during seed development;

(b) identifying the conserved sequences(s) or 4 or more amino acids obtained in step (a);

(c) making region-specific nucleotide probe(s) or oligomer(s) based on the conserved sequences identified in step (b); and (d) using the nucleotide probe(s) or oligomer(s) of step (c) to isolate sequences associated with controlling embryo/endosperm size during seed development by sequence dependent protocols.

Examples of conserved sequence elements that would be useful in identifying other plant sequences associated with controlling embryo/endosperm size during seed development can be found in the group comprising, but not limited to, the nucleotides encoding the polypeptides of SEQ ID NO:80, 81, 82, 83, 84, 85, 86, 87, 88, 89, 90, or 91.

In another aspect, this invention also concerns a method of mapping genetic variations related to controlling embryo/endosperm size during seed development and/or altering oil phenotypes in plants comprising:

(a) crossing two plant varieties; and (b) evaluating genetic variations with respect to:

(i) a nucleic acid sequence selected from the group consisting of SEQ ID NO:1, 3, 4, 5, 6, 8, 10, 12, 14, 16, 18, 20, 22, 24, 26, 28, 30, 32, 34, 36, 38, 40, 92, 94, 96, 98, 100, 102, 104, or 105; or (ii) a nucleic acid sequence encoding a polypeptide selected from the group consisting of SEQ ID NO:2, 7, 9, 11, 13, 15, 17, 19, 21, 23, 25, 27, 29, 31, 33, 35, 37, 39, 41, 42, 43, 44, 45, 46, 47, 80-91, 93, 95, 97, or 99;

in progeny plants resulting from the cross of step (a) wherein the evaluation is made using a method selected from the group consisting of: RFLP analysis, SNP analysis, and PCR-based analysis.

In another embodiment, this invention concerns a method of molecular breeding to obtain altered embryo/endosperm size during seed development and/or altered oil phenotypes in plants comprising:

(a) crossing two plant varieties; and (b) evaluating genetic variations with respect to:

(i) a nucleic acid sequence selected from the group consisting of SEQ ID NO:1, 3, 4, 5, 6, 8, 10, 12, 14, 16, 18, 20, 22, 24, 26, 28, 30, 32, 34, 36, 38, 40, 92, 94, 96, 98, 100, 102, 104, or 105; or (ii) a nucleic acid sequence encoding a polypeptide selected from the group consisting of SEQ ID NO:2, 7, 9, 11, 13, 15, 17, 19, 21, 23, 25, 27, 29, 31, 33, 35, 37, 39, 41, 42, 43, 44, 45, 46, 47, 80-91, 93, 95, 97, or 99;

in progeny plants resulting from the cross of step (a) wherein the evaluation is made using a method selected from the group consisting of: RFLP analysis, SNP analysis, and PCR-based analysis.

The terms "mapping genetic variation" or "mapping genetic variability" are used interchangeably and define the process of identifying changes in DNA sequence, whether from natural or induced causes, within a genetic region that differentiates between different plant lines, cultivars, varieties, families, or species. The genetic variability at a particular locus (gene) due to even minor base changes can alter the pattern of restriction enzyme digestion fragments that can be generated. Pathogenic alterations to the genotype can be due to deletions or insertions within the gene being analyzed or even single nucleotide substitutions that can create or delete a restriction enzyme recognition site. RFLP analysis takes advantage of this and utilizes Southern blotting with a probe corresponding to the isolated nucleic acid fragment of interest.

Thus, if a polymorphism (i.e., a commonly occurring variation in a gene or segment of DNA; also, the existence of several forms of a gene (alleles) in the same species) creates or destroys a restriction endonuclease cleavage site, or if it results in the loss or insertion of DNA (e.g., a variable nucleotide tandem repeat (VNTR) polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms: ("RFLPs"). RFLPs have been widely used in human and plant genetic analyses (Glassberg, UK Patent Application 2135774; Skolnick et al, Cytogen. *Cell Genet.* 32:58-67 (1982); Botstein et al, *Ann. J. Hum. Genet.* 32:314-331 (1980); Fischer et al (PCT Application WO 90/13668; Uhlen, PCT Application WO 90/11369).

A central attribute of "single nucleotide polymorphisms" or "SNPs" is that the site of the polymorphism is at a single nucleotide. SNPs have certain reported advantages over RFLPs or VNTRs. First, SNPs are more stable than other classes of polymorphisms. Their spontaneous mutation rate is approximately $10^{-9}$ (Kornberg, DNA Replication, W.H. Freeman & Co., San Francisco, 1980), approximately, 1,000 times less frequent than VNTRs (U.S. Pat. No. 5,679,524). Second, SNPs occur at greater frequency, and with greater uniformity than RFLPs and VNTRs. As SNPs result from sequence variation, new polymorphisms can be identified by sequencing random genomic or cDNA molecules. SNPs can also result from deletions, point mutations and insertions. Any single base alteration, whatever the cause, can be a SNP. The greater frequency of SNPs means that they can be more readily identified than the other classes of polymorphisms.

SNPs can be characterized using any of a variety of methods. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism or by other biochemical interpretation. SNPs can be sequenced by a number of methods. Two basic methods may be used for DNA sequencing, the chain termination method of Sanger et al, *Proc. Natl. Acad. Sci.* (U.S.A.) 74:5463-5467 (1977), and the chemical degradation method of Maxam and Gilbert, *Proc. Natl. Acad. Sci.* (U.S.A.) 74: 560-564 (1977).

Furthermore, single point mutations can be detected by modified PCR techniques such as the ligase chain reaction ("LCR") and PCR-single strand conformational polymorphisms ("PCR-SSCP") analysis. The PCR technique can also be used to identify the level of expression of genes in extremely small samples of material, e.g., tissues or cells from a body. The technique is termed reverse transcription-PCR ("RT-PCR").

The term "molecular breeding" defines the process of tracking molecular markers during the breeding process. It is common for the molecular markers to be linked to phenotypic traits that are desirable. By following the segregation of the molecular marker or genetic trait, instead of scoring for a phenotype, the breeding process can be accelerated by growing fewer plants and eliminating assaying or visual inspection for phenotypic variation. The molecular markers useful in this process include, but are not limited to, any marker useful in identifying mapable genetic variations previously mentioned, as well as any closely linked genes that display synteny across plant species. The term "synteny" refers to the conservation of gene placement/order on chromosomes between different organisms. This means that two or more genetic loci, that may or may not be closely linked, are found on the same chromosome among different species. Another term for synteny is "genome colinearity".

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various rice, columbine, grape, guayule, Peruvian lily, corn, soybean, sunflower, and wheat tissues were prepared as described below. The characteristics of the libraries are described below in Table 2.

TABLE 2

Genomic and cDNA Libraries from Rice, Columbine, Grape, Guayule, Peruvian lily, Corn, Soybean, Sunflower, and Wheat

| Library | Tissue | Clone |
|---|---|---|
| bac1i1g | The BAC clone, 1I, is derived from the Texas A&M library. The insert is 100 kb long. This BAC clone covers the Giant Embryo region. The average insertion length of this library is 1-2 kb. | bac1i1g.pk001.d18 |
| bac4d1g | The BAC clone, 4D, is derived from the Texas A&M library. The insert is 80 kb long. This BAC clone covers part of the Giant Embryo region. The average insertion length of this library is 1-2 kb. | bac4d1g.pk001.o6<br>bac4d1g.pk001.k21<br>bac4d1g.pk001.l12.f |
| bac1i1g | The BAC clone 1I is derived from the Texas A&M library. The insert is 100 kb long. This BAC clone covers the Giant Embryo region. The average insertion length of this library is 1-2 kb. | bac1i1g.pk001.p23 |
| Bacm | Maize BAC fingerprinting | bacm.pk015.d18.f<br>bacm.pk019.j23 |
| bdl1c | Barley (*Hordeum vulgaris*) leaf tissues infected with *M grisea* (6043) for 48 hours | bdl1c.pk003h16 |
| eav1c | Columbine (*Aquilegia vulgaris*) developing seeds (looking for delta 5 desaturase genes) | eav1c.pk006.n4:fis |
| veb1c | Grape (*Vitis* sp.) early berries | veb1c.pk001.k11:fis |
| epb3c | Guayule (*Parthenium argentatum*, 11591) stem bark harvested at Dec. 28, 1993-high activity for rubber biosynthesis | epb3c.pk005.d14 |
| eae1s | *Alstroemeria cayophylla* emerging leaf from mature stem | eae1s.pk003.b24:fis |
| cbn10 | Corn Developing Kernel (Embryo and Endosperm); 10 Days After Pollination | cbn10.pk0034.f8:fis |
| cpe1c | Corn (*Zea mays L.*) pooled BMS treated with chemicals related to phosphatase | cpe1c.pk011.m11 |
| cpf1c | Corn (*Zea mays L.*) pooled BMS treated with chemicals related to protein synthesis | cpf1c.pk001.c2 |
| cpj1c | Corn (*Zea mays L.*) pooled BMS treated with chemicals related to membrane ionic force | cpj1c.pk002.d2 |
| cpls1s | Maize, leaf sheath, pulvinus region. Identify genes that are expressed in the pulvinus region of the leaf sheath | cpls1s.pk001.m19 |
| p0022 | Green leaves treated with JA 24 hr before collection [JA] = 1 mg/ml in 0.02% Tween 20 middle ¾ of the 3rd leaf blade and mid rib only (normalized P0012) | p0022.cglnh53rb |

TABLE 2-continued

| Genomic and cDNA Libraries from Rice, Columbine, Grape, Guayule, Peruvian lily, Corn, Soybean, Sunflower, and Wheat | | |
|---|---|---|
| Library | Tissue | Clone |
| p0037 | corn Root Worm infested V5 roots | p0037.crwbn23r |
| p0083 | 7 DAP whole kernels | p0083.cldaq05r<br>p0083.cldaq05ra |
| p0121 | shank tissue collected from ears 5DAP, | p0121.cfrmn62r:fis |
| p9998 | Screened 1 Clone confirmations that did not match expected clone | p9998.cmrne01rb |
| rca1c | Rice Nipponbare Callus. | rca1c.pk007.n11:fis |
| rls2 | Rice Leaf 15 Days After Germination, 2 Hours After Infection of Strain *Magnaporthe grisea* 4360-R-67 (AVR2-YAMO); Susceptible | rls2.pk0022.b12:fis |
| rr1 | Rice Root of Two Week Old Developing Seedling | rr1.pk0044.e7 |
| sdp2c | Soybean (*Glycine max L.*) developing pods 6-7 mm | sdp2c.pk042.p12:fis |
| se4 | Soybean Embryo, 19 Days After Flowering | se4.pk0009.e9 |
| sfl1 | Soybean Immature Flower | sfl1.pk0010.a2:fis |
| src3c | Soybean 8 Day Old Root Infected With Cyst Nematode | src3c.pk009.k13 |
| hso1c | oxalate oxidase-transgenic sunflower plants | hso1c.pk003.n10 |
| hss1c | Sclerotinia infected sunflower plants, purpose isolation of full length Sclerotinia induced cDNAs | hss1c.pk004.b24 |
| wdk2c | Wheat Developing Kernel, 7 Days After Anthesis. | wdk2c.pk013.c20 |

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones

Clones for cDNAs encoding GE-like cytochrome P450 proteins were identified by conducting BLAST searches. (Basic Local Alignment Search Tool; Altschul et al. (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding GE-like Cytochrome P450 Proteins

The BLASTX search using the EST sequences from clones listed in Table 3 revealed similarity of the polypeptides encoded by the cDNAs to cytochrome P450 proteins from *Arabidopsis [Arabidopsis thaliana*] (NCBI General Identifier Nos. gi, [SEQ ID NO:42] which is identical to gi 12325138 and gi 15221132; and gi 11249511, [SEQ ID NO:44]; and gi 3831440, [SEQ ID NO:46]; and gi 8920576, [SEQ ID NO:47]), and a cytochrome P450 protein from orchid [*Phalaenopsis* sp.SM9108] (NCBI General Identifier No. gi 1173624, [SEQ ID NO:43]), and a cytochrome P450 protein from soybean [*Glycine max*] (NCBI General Identifier No. gi 5921926, [SEQ ID NO:45]). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding the Rice Giant Embryo Cytochrome P450 and Polypeptides Homologous To GE

| | | BLAST pLog Score | | | | | |
|---|---|---|---|---|---|---|---|
| clone | Status | 7109461 | 1173624 | 11249511 | 5921926 | 3831440 | 8920576 |
| bac4d1g.pk001.l12.fis | CGS | 155.0 | | | | | |
| rca1c.pk007.n11:fis | FIS | | 24.0 | | | | |
| ris2.pk0022.b12:fis | FIS | | | 78.3 | | | |
| rr1.pk0044.e7 | EST | | | | 3.5 | | |
| cbn10.pk0034.f8:fis | FIS | | 114.0 | | | | |
| p0037.crwbn23r | EST | | 63.2 | | | | |
| p0121.cfrmn62r:fis | FIS | | 156.0 | | | | |
| Contig of:<br>p0014.ctusi51r<br>p0014.ctutw92r:fis<br>p0022.cglnh53r<br>p0122.ckama19r<br>p9998.cmrne01rb | CON | | | | | 126.0 | |
| sdp2c.pk042.p12:fis | FIS | | | | 180.0 | | |
| Contig of:<br>se1.20e06<br>se4.pk0009.e9 | CON | | | | | | 180.0 |
| sfl1.pk0010.a2:fis | FIS | | | | 180.0 | | |
| src3c.pk009.k13 | EST | | 32.5 | | | | |
| hso1c.pk003.n10 | EST | 58.1 | | | | | |
| hss1c.pk004.b24 | EST | | | | | | 42.0 |
| contig of:<br>wdk2c.pk013.c20<br>wre1n.pk0056.b6 | CON | | | | 27.7 | | |
| eav1c.pk006.n4:fis | FIS | 180.0 | | | | | |
| veb1c.pk001.k11:fis | FIS | 92.4 | | | | | |
| epb3c.pk005.d14 | EST | | 60.7 | | | | |
| eae1s.pk003.b24:fis | FIS | | | | | | 176.0 |
| bdl1c.pk003.h16 | CGS | 154.0 | | | | | |
| p0037.crwbn23r:fis | GCS | 155.0 | | | | | |
| cbn10.pk0034.f8.f | CGS | | 160.0 | | | | |
| cpls1s.pk001.m19 | CGS | | 152.0 | | | | |

The data in Table 4 represents a calculation of the percent identity of the amino acid sequences set forth in SEQ ID NOs:2, 7, 9, 11, 13, 15, 17, 19, 21, 23, 25, 27, 29, 31, 33, 35, 37, 39, and 41, and the cytochrome P450 proteins from *Arabidopsis [Arabidopsis thaliana*] (NCBI General Identifier Nos. gi 7109461, [SEQ ID NO:42] which is identical to gi 12325138 and gi 15221132; and gi 11249511, [SEQ ID NO:44]; and gi 3831440, [SEQ ID NO:46]; and gi 8920576, [SEQ ID NO:47]), and a cytochrome P450 protein from orchid [*Phalaenopsis* sp.SM9108] (NCBI General Identifier No. gi 1173624, [SEQ ID NO:43]), and a cytochrome P450 protein from soybean [*Glycine max*] (NCBI General Identifier No. gi 5921926, [SEQ ID NO:45]).

TABLE 4

Percent Identity of Amino Acid Sequences Deduced From the Nucleotide Sequences of cDNA Clones Encoding Rice Giant Embryo Cytochrome P450 and Polypeptides Homologous To GE

| | Percent Identity to | | | | | |
|---|---|---|---|---|---|---|
| SEQ ID NO. | 7109461 | 1173624 | 11249511 | 5921926 | 3831440 | 8920576 |
| 2 | 49.1 | 59.6 | | | | |
| 7 | | 59.0 | | | | |
| 9 | | | 65.9 | | | |
| 11 | | 47.6 | | | | |
| 13 | | 67.0 | | | | |
| 15 | | 63.3 | | | | |
| 17 | | 62.0 | | | | |
| 19 | | | 53.2 | | 52.2% | |
| 21 | | | | 71.1 | | |
| 23 | | 67.1 | | | | |
| 25 | | | | 72.7 | | |
| 27 | | 53.4 | | | | |
| 29 | 68.1 | | | | | 68.8 |
| 31 | | | | | | 63.2 |
| 33 | | | 60.0 | | | |
| 35 | 62.7 | 68.8 | | | | |
| 37 | 73.6 | 75.0 | | | | |
| 39 | | 74.0 | | | | |
| 41 | | 67.1 | | | | |
| 93 | 49.6 | 61.3 | | | | |
| 95 | 47.5 | 61.7 | | | | |
| 97 | | 63.8 | | | | |
| 99 | | 61.3 | | | | |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a plant cytochrome P450 protein that shares homology with the rice protein that gives rise to the giant embryo phenotype when mutated.

Example 4

Expression of Chimeric Constructs in Monocot Cells

A chimeric construct comprising a plant cDNA encoding the instant polypeptides in sense orientation with respect to promoter from the maize 27 kD zein, ubiquitin, or CaMV 35S, gene that is located 5' to the cDNA fragment can be constructed. The 3' fragment from the 10 kD zein gene [Kirihara et al. (1988) *Gene* 71:359-370] can be placed 3' to the cDNA fragment. Such constructs are used to overexpress or cosuppress the gene(s) homologous to GE. It is realized that one skilled in the art could employ different promoters and/or 3'-end sequences to achieve comparable expression results. The construct with the CaMV 35S promoter is made as follows: the transcription termination element is released from the clone, In2-1 A, by BglII and Asp718 digestion. The fragment is ligated to SphI and Asp718 restriction sites of pML141 [PCT Application No. WO 00/08162, published Feb. 17, 2000], which carries the 35S promoter, using the linker (GATCCATG) to connect BglII and SphI ends. The DNA containing the GE ORF is amplified through PCR by using a primer set (5'-AGAATTCTTCCCATGGCGCTCTCCTCCAT-3', SEQ ID NO:48; and 5'-AGAATTCTAGGCCCTAGCCACGGCCTTG-3', SEQ ID NO:49) and the cDNA as a template. The fragment is then digested with EcoRI and inserted to the EcoRI site of the vector between the 35S promoter and the transcription terminator. The appropriate orientation of the insert is confirmed by sequencing.

The construct with the ubiquitin promoter is made as follows: the transcription termination element is released from the clone, In2-1 A, by BclI and KpnI digestion. The fragment is ligated to BamHI and NotI restriction sites of SK-ubi (BbsI), which carries the ubiquitin promoter (maize Ubi-1 promoter, Christensen and Quail (1996) *Transgenic Res.* 5: 213-218), using the linker (GGCCGTAC) to connect NotI and KpnI ends. The DNA containing the GE ORF is amplified through PCR by using a primer set (5'-AGGTCTCCCATGGCGCTCTCCTCCAT-3', SEQ ID NO:50; and 5'-ATCATGATCTAGGCCCTAGCCACGGCCTTG-3', SEQ ID NO:51) and the cDNA as a template. The fragment is then digested with BspHI and BsaI and inserted into the BbsI site between the ubiquitin promoter and the transcription terminator.

Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene [Prat et al. (1987) *Gene* 52:51-49; Gallardo et al. (1988) *Plant Sci.* 54:211-2811] and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric construct encoding, in the 5' to 3' direction, the maize 27 kD zein promoter, a cDNA fragment encoding the instant polypeptides, and the 10 kD zein 3' region.

The chimeric construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Constructs in Dicot Cells

The 35S promoter of CaMV can be used to over-express and co-suppress the genes homologous to GE in dicot cells. For GE overexpression, the vector KS50 can be used to fuse the GE ORF to the 35S promoter. The GE ORF is amplified by PCR using the primer set with the NotI site at the 3' end, AGCGGCCGCTTCCCATGGCGCTCTCCT, SEQ ID NO:52, and AGCGGCCGCTCAGGCCCTAGCCACGGC, SEQ ID NO:53. The amplified DNA fragment is digested with NotI and ligated into the NotI site of KS50. The correct orientation of the insert is determined by sequencing. KS50 (7,453 bp) is a derivative of pKS18HH (U.S. Pat. No. 5,846,784) which contains a T7 promoter/T7 terminator controlling the expression of a hygromycin phosphotransferase (HPT) gene, as well as a 35S promoter/NOS terminator controlling the expression of a second HPT gene. KS50 has an insert at the Sal I site consisting of a 35S promoter (960 bp)/NOS terminator (700 bp) cassette taken from pAW28, with a NotI cloning site between the promoter and terminator.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric construct composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Fine Mapping of the ge Locus

The ge locus was mapped to the region around 85 cM on chromosome 7 using microsatellite and RFLP markers (Koh et al. (1996) *Theor. Appl. Genet.* 93:257-261). Although numerous RFLP markers and YAC contigs have been mapped to rice chromosomes (Harushima et al. (1998) *Genetics* 148: 479-494; http://rgp.dna.affrc.go.jp), the ge region was located in a 5 cM-long region where no physical markers were found so far. In order to map the ge locus, we made two mapping populations. The ge-3 (*Japonica* rice cv. Taichung 65) and ge-5 (*Japonica* rice cv. Kinmaze) homozygous mutant plants were chosen as female parents and *Indica* rice cultivar Kasalath as a male parent. The resulted F1 plants were selfed to obtain the F2 population. The ge F2 progeny (homozygous for ge) was selected from the F2 population.

To obtain F2 plants that carry recombinations near the ge locus, PCR-based DNA markers were developed. Several known RFLP markers were selected based on their map positions published by the Rice Genome Project Group (RGP) (Harushima et al. (1998) *Genetics* 148:479-494). The RFLP markers, R1245, R2677 and B2F2, were chosen for the distal markers and the markers, S1848 and C847, were chosen for the proximal markers. Primers were designed to amplify the genomic DNA corresponding to these markers, whose sequences were available from Genbank. For B2F2, which is a barley EST clone, rice homologues were obtained from the DuPont EST database as well as RGP EST database. The primers were designed based on the corresponding rice EST sequence.

A PCR reaction was carried out with 2 pmole primers of two dominant marker sets together, which were specific to the Kasalath sequence of C847 and B2F2. Young leaf tissues obtained from germinated ge F2 plants on N6 medium plates containing 0.3% gelrite were subjected to direct PCR reactions as described in Klimyuk et al. (1993) *Plant J.* 3:493-494 with modification of extending the sample boiling time to four minutes at the neutralization step. One 30 ul PCR reaction contained 2 ul 2.5 mM dNTPs, 2 ul 25 mM $MgCl_2$, 2 ul DNA extracted from leaf, 0.3 ul Amplitaq gold (Perkin Elmer) and 3 ul PCR buffer. The thermal cycle condition was 95° C. 10 min, 94° C. 30 sec, 56° C. 30 sec, 72° C. 30 sec, 72° C. 5 min repeating step 2 to 4 40 times. Amplification of Kasalath DNA was examined on 2.5 or 3% agarose gels.

By amplifying the marker regions from the parental *Japonica* and *Indica* cultivars, several single nucleotide polymorphisms (SNPs) were found. To develop a dominant PCR-based DNA marker from the distal side, one SNP found in C847 was chosen. At this SNP the *Japonica* sequence had an A residue, whereas the *Indica* sequence had T. The primer (5'GTTTCATAATGAAATTGACTCTTTTTCAGTAA3'; SEQ ID NO:54) was designed in a way that the *Indica*-specific base was complementary to its 3' end. Using this and the other primer (5'GCAAATAAATTTCTATATACAGGACAGGC3'; SEQ ID NO:55) as a set, the corresponding DNA could be amplified only from the *Indica*. For the proximal side, the B2F2 rice homologue was chosen, which carried a SNP between *Japonica* (A) and *Indica* cultivars (T). The designed primer (5'TAGCTTTAGAGTACATTTCTTAGATACGGCA3'; SEQ ID NO:56) was complementary to the *Indica* sequence at its 3' end. In combination with another primer (5'TTACTTTGAGCGTGCCAAGCAGTATAATTTCT3'; SEQ ID NO:57), DNA was amplified only from *Indica* but not from *Japonica*.

By using these *Indica*-specific primer pairs, 1290 ge homozygous F2 were screened, and 33 recombinants in total were obtained, 15 from the proximal and 18 from the distal ge region.

Example 7

Man-Based Cloning of GE

To obtain the closest physical marker which could serve as a starting point of the chromosome walk toward GE, DNA was isolated from the ends of three YAC clones, Y1931, Y4052 and Y4566. These clones were previously mapped to the region relatively close to the ge locus by RGP. Using a PCR-based method, we recovered and sequenced the both ends of Y4052 and Y1931 and left end of Y4566 (see Methods and Materials). By using primer sets specific to each isolated end, the orientation and overlaps of these YAC clones were analyzed and it was established that the Y4052 left end is the far-most end of the contig of Y4052 and Y4566. To determine which end of Y4052 is close to the ge locus, RFLP was developed for each end. The segregation analysis of ten recombinants from the distal region showed that the Y4052 left end was closer to ge than the right end, leaving 3 and 9 recombination breakpoints, respectively.

Total DNA from yeast YAC strains was extracted. 100 ng DNA was digested by AluI, HaeIII and RsaI, and ligated with the vectorette adaptor (5'AAGGAGAGGACGCTGTCTGTCGAAGGTAAGGAACGGACGAGAGAAGGG3'; SEQ ID NO:58; and 5'CTCTCCCTTCTCGAATCGTAACCGTTCGTACGAGAATCGCTGTCCTCTCCTT3'; SEQ ID NO:59). 10 ng of ligated DNA was used as PCR template to amplify YAC ends. One PCR reaction contained 20 pmole of the primer specific to the left YAC arm (5'CACCCGTTCTCGGAGCACTGTCCGACCGC3'; SEQ ID NO:60; or the primer specific to the right arm (5'ATATAGGCGCCAGCAACCGCACCTGTGGCG3'; SEQ ID NO:61) with 1.6 mM $MgCl_2$, 50 mM KCl, 10 mM Tris-HCl (pH9.0), 0.01% gelatin and 2.5 mM dNTPs. The cycle condition was 95° C. 10 min, 92° C. 1 min, 60° C. 1 min, 72° C. 1 min. After completing 10 cycles of step 2 through 4, the vectorette specific primer was (5'CGMTCGTAACCGTTCGTACGAGAATCGCT3'; SEQ ID NO:62) was added to the reaction and further amplified in the condition of 92° C. 1 min, 60° C. 1 min and 72° C. 3 min for 30 cycles. The PCR products were separated on agarose gels and amplified DNA was extracted for the second PCR amplification. The second PCR was carried out with the presence of 16 pmole the primer specific to the vectorette unit and 30 pmole the nested primer specific to the YAC left end (5'CTGAACCATCTTGGAAGGAC3'; SEQ ID NO:63) or the primer specific to the right end (5'ACTTGCAAGTCTGGGAAGTG3'; SEQ ID NO:64). The cycling condition was 95° C. 10 min, 94° C. 1 min, 58° C. 1 min, 72° C. 1 min, repeating step 2 to step 4 20 times. The recovered ends were cloned into pGEM-T Easy (Promega) and sequenced. The primers derived from the end sequences were used for analyzing the overlapped structure of the YAC contig. Also, these DNA fragments were used to find RFLP to map them with respect to the ge locus.

Based on these results, we initiated a chromosome walk from the Y4052 left end. Two Texas A&M BAC libraries made from the genomic DNA of Taquiq (TQ *Indica* rice) and Lemont (LM *Japonica* rice) were used to screen corresponding clones by DNA blot hybridization. Two BAC clones were recovered, TQ1-19L and TQ22-7E, using the Y4052 left end as a probe. The ends of BAC clones were recovered by TAIL PCR and the recovered DNA fragments were cloned into pGEM-T Easy for sequencing (see Materials Methods). Using these sequences, BAC end-specific primer sets were designed and the orientation of these BAC clones in the; contig was determined. The data of the PCR analysis showed that the right end (the SP6 side) of TQ1-19L was the new closest end to ge, not present in TQ22-7E and the YAC clones.

The right end of TQ1-19L was used for the second screening of overlapping BAC clones. Three BACs were obtained, LM10-22N, LM10-11O and LM15-7P. The process of recovering BAC ends and mapping per PCR was repeated. For the third screen, the left end was used (the T7 side) of LM15-7P and LM3-6B was obtained. For the fourth screen, the left end of LM3-6B was used and LM20-4D, LM17-3H were obtained. The left end of LM20-4D was mapped to the end of the contig. For the fifth screen, this end was not used as a probe to obtain overlapping BAC clones because of the presence of a repetitive sequence. To obtain an appropriate DNA probe from LM20-4D, the BAC clone was digested by restriction enzyme HindIII and subcloned into pUC18. By DNA blot analysis, one 1.6 kb-long fragment was found not present on the other overlapping clone, LM3-6B, indicating that the fragment was localized toward the end the BAC contig. The 1.6 kb HindIII fragment was used as a probe for the fifth screen and TQ18-1I and LM2-15J were isolated as the overlapping clones. In the sixth screening, the left end of TQ18-1I was used as a probe and two BAC clones, LM4-12E and LM15-20J, were isolated.

The blots of two Texas A&M BAC libraries made from Taquiq, *Indica* rice; and Lemont, *Japonica* rice were hybridized with DNA probes using standard DNA hybridization conditions (Sambrook et al. (1989) "Molecular Cloning" Cold Spring Harbor Laboratory Press, New York). The ends of BAC clones, which were made using the pBeloBAC11 vector, were recovered by TAIL PCR. A typical TAIL PCR reaction was carried out in 20 ul, containing a BAC vector specific primer (4 pmole) and arbitrary degenerated (AD) primers (50 pmole) with 0.2 ul expand hi fidelity Taq polymerase (Roche). Six nested primers specific to the BAC vector were designed:

| | | |
|---|---|---|
| BACL1; | ATTCAGGCTGCGCAACTGTTG | SEQ ID NO:65 |
| BACL2; | CTGCAAGGCGATTAAGTTGG | SEQ ID NO:66 |
| BACL3; | GGGTTTTCCCAGTCACGAC | SEQ ID NO:67 |
| BACR1; | TGAGTTAGCTCACTCATTAGGGAC | SEQ ID NO:68 |
| BACR2; | GCTTCCGGCTCGTATGTTGTG | SEQ ID NO:69 |
| BACR3; | GACCATGATTACGCCAAGC | SEQ ID NO:70 |

Seven different AD primers (AD1-7) were used as designed by Liu and Whittier (1995) *Genomics* 25:674-681, and Liu et al. (1995) *Plant J.* 8:457-463:

| | | |
|---|---|---|
| AD1; | TGWGNAGWANCASAGA | SEQ ID NO:71 |
| AD2; | AGWGNAGWANCAWAGG | SEQ ID NO:72 |
| AD3; | CAWCGICNGAIASGAA | SEQ ID NO:73 |
| AD4; | TCSTICGNACITWGGA | SEQ ID NO:74 |
| AD5; | NGTCGASWGANAWGAA | SEQ ID NO:75 |
| AD6; | GTNCGASWCANAWGTT | SEQ ID NO:76 |
| AD7; | WGTGNAGWANCANAGA | SEQ ID NO:77 |

The condition of the first-round PCR was as described by Liu and Whittier 1995, and Liu et al. 1995 with modification of the annealing temperatures changing to 65° C. for the first 5 cycles and 61° C. for the last 15 cycles. In the second PCR, we used 1 ul 1/30 diluted $1^{st}$ PCR product as a template. The 20 ul reaction contained 8 pmole $2^{nd}$ BAC vector specific primer, 25 pmole AD primer, and 0.2 ul expand hi fidelity Taq polymerase. The condition of thermal cycle was as described by Liu and Whittier 1995, and Liu et al. 1995 with modification of the annealing temperatures changing to 60° C. for the first two cycles.

$3^{rd}$ PCR was carried out with a normal PCR thermal cycle steps. The reaction contained the $3^{rd}$ BAC vector specific primer and AD primers. PCR product was cloned into pGEM-T easy vector (Promega) and their DNA sequence was determined by conventional sequencing methods.

Several DNA fragments isolated from these BAC clones that showed polymorphisms between the *Japonica* and *Indica* cultivars were used to map recombination break points of the isolated recombinants. As a result, the 1.6 kb HindIII fragment LM20-4D gave three recombination break points, whereas a 950 bp HindIII fragment of TQ18-1I gave no break point among the fifteen distal recombinants. Since the same fragment of TQ18-1I gave one break point among the proximal recombinants, the ge locus was mapped between two makers, 1.6 kb HindIII of LM20-4D and 950 bp HindIII of TQ18-1I, i.e. on the two BAC clones, LM20-4D and TQ18-1I.

Example 8

Identification of the GE Gene

In order to identify the GE gene that was mapped to the region comprising two BAC clones, LM20-4D and TQ18-1I, the whole genomic insert of these BAC clones was sequenced. For the purpose, BAC DNA was nebulized using high-pressure nitrogen gas as described in Roe et al. 1996 (Roe et al. (1996) "DNA isolation and Sequencing" John Wiley and Sons, New York). DNA fragments with the length of 1-2 kb were recovered from agarose gels and cloned into pUC18. 686 clones derived from LM20-4D were randomly isolated and sequenced. Likewise, 700 clones derived from TQ1I-18 were isolated and sequenced. Twelve groups of contiguous sequences were obtained from LM20-4D and 16 from TQ1I-18. Most gaps were filled by PCR and also by obtaining other subclones derived from HindIII or EcoRI fragments of LM20 4D and LM4-12E. This resulted in the construction of a 90 kb-long continuous sequence between two DNA markers, 1.6 kb HindIII LM20-4D and 950 bp HindIII TQ18-1I.

Within the 90 kb sequence, more than ten regions showing certain similarities to genes filed in Genbank as well as in our EST database were identified. Judging from the number of recombinants at the end of the region and the location of these ORFs, one ORF encoding a protein similar to CYP78 proteins, a subfamily of P450 proteins, was found to be a candidate for the GE gene. To confirm the correlation between GE and the P450 gene, the genomic region from mutants and wild type were amplified by PCR. Comparing these sequences, mutations of nine different alleles were identified, all of which were found in the ORF of the P450 gene; three nonsense and six mis-sense mutations were found (see FIG. 1). These data confirm that this rice cytochrome P450 gene is the GE gene, and that mutations within this gene can result in a GE phenotype.

There are a number of P450 genes from GenBank shown to be homologous to GE. Some of them are also expressed in ovules or shoot meristems (Nadeau et al. (1996) *Plant Cell* 8:213-239; Zondlo and Irish (1999) *Plant J.* 19:259-268). However, the function of these genes remains largely unknown. In one case, an *Arabidopsis* gene homologous to GE was overexpressed and the resulting fruit, or pericarp, became enlarged while forming few, if any, seeds or embryos (Ito and Meyerowitz (2000) *Plant Cell* 12:1541-1550). However, the disruption of this *Arabidopsis* gene caused no phenotype. It is believed that the characterization, in the present invention, of the rice cytochrome P450 gene as "giant embryo" represents the first example of a plant gene directly controlling embryo size.

Example 9

Cloning the cDNA Encoding Cytochrome P450 Protein Associated with the Giant Embryo Phenotype Total RNA was extracted from developing rice seeds harvested 2-5 days after pollination, using a TRIazol® Reagent obtained from Life Technologies Inc., Rockville, Md., 20849 (GIBCO-BRL) which contains phenol and guanidine thiocyanate. Poly A mRNA was purified from total RNA with mRNA Purification kits obtained from Amersham Pharmacia Biotech Inc., Piscataway, N.J., 08855, which consists of oligo (dT)-cellulose spin columns. To make the cDNA library, 5.5 ug of polyA RNA was used for cDNA synthesis kits obtained from Stratagene, La Jolla, Calif., 92037. Superscript® reverse transcriptase obtained from Life Technologies Inc., Rockville, Md., 20849 (GIBCO-BRL) was substituted for the MMLV reverse transcriptase in the first step. BRL cDNA Size Fraction Columns (GIBCO-BRL) were used to fractionate the cDNA by size, fraction 1 to 13 were precipitated, resuspended and ligated with 1 ug of the Uni-ZAP XR vector. After two days of ligation it was packaged in Gigapack III Gold® packaging extract obtained from Stratagene, La Jolla, Calif., 92037. The unamplified library titer was approximately 780,000 plaques per ml. The entire amount was used for amplification purposes and the procedure produced 150 mls of an amplified cDNA library with a titer of $5.5\times10^8$ pfu/ml.

Screening for the GE cDNA followed standard protocols well known to those skilled in the art (Ausubel et al. 1993, "Current Protocols in Molecular Biology" John Wiley & Sons, USA, or Sambrook et al. 1989. Molecular Cloning: A Laboratory Manual. Cold Spring Harbor Laboratory Press). Briefly, $1.5\times10^6$ phage clones were plated, then transferred to nylon membranes, which were then subjected to hybridization with radioactively labeled GE probe. More than five positives were detected per 50,000 plaques. Approximately 125 positives were isolated and examined for their identity as GE cDNAs through PCR with GE-specific primers. One primer specific to the 5' end of the isolated nucleic acid fragment (GGGAAGCGTTCGCGAAGTGAG, SEQ ID NO:78) and the other specific to the cloning vector next to the 5' end of the cDNA insert (AGCGGATAACCAATTTCACACAGG, SEQ ID NO:79). Six of the longest cDNA clones that gave positive results from the PCR reaction were isolated and sequenced. All six clones have nearly the same length, the longest cDNA being 28 nucleotides upstream of the ATG start codon predicted from the genomic sequence.

Example 10

Genetic Confirmation of the GE Gene

The genetic confirmation that the rice cytochrome P450 isolated nucleic acid fragment encoded the polypeptide responsible for the giant embryo phenotype was accomplished by transforming ge mutants with the isolated cytochrome P450 cloned sequence. This experiment confirmed that the cytochrome P450 is the GE gene, and that the genomic region used in the transformation contained the complete set of regulatory elements necessary for normal GE expression. The genomic DNA used for the transformation covered 1.7 kb upstream of the coding region, the coding region of GE, and 1.6 kb downstream of the coding region.

GE homologs from other crop species can also be tested in this system by obtaining full-gene sequences, and complementing the rice GE mutant.

In order to confirm possible tissue-specific expression of the GE gene, the presence of the GE transcript in various tissues was analyzed by RNA blot analysis and in situ hybridization (see Example 11).

One method for transforming DNA into cells of higher plants that is available to those skilled in the art is high-velocity ballistic bombardment using metal particles coated with the nucleic acid constructs of interest (see Klein et al. *Nature* (1987) (London) 327:70-73, and see U.S. Pat. No. 4,945,050). A Biolistic PDS-1000/He (BioRAD Laboratories, Hercules, Calif.) was used for these complementation experiments see Example 4 for further details). The particle bombardment technique was used to transform the ge mutant with a 5.1 kb EcoRI fragment from wild type (nucleotides 6604-11735 of SEQ ID NO:3) that includes 1.7 kb upstream of the GE coding region, the GE coding region plus intron, and 1.6 kb downstream of the GE coding region.

The bacterial hygromycin B phosphotransferase (Hpt II) gene from *Streptomyces hygroscopicus* that confers resistance to the antibiotic hygromycin was used as the selectable marker for the rice transformation. In the vector, pML18, the Hpt II gene was engineered with the 35S promoter from Cauliflower Mosaic Virus and the termination and polyadenylation signals from the octopine synthase gene of *Agrobacterium tumefaciens*. pML18 was described in WO 97/47731, which was published on Dec. 18, 1997, the disclosure of which is hereby incorporated by reference.

Embryogenic callus cultures derived from the scutellum of germinating rice seeds serve as source material for transformation experiments. This material was generated by germinating sterile rice seeds on a callus initiation media (MS salts, Nitsch and Nitsch vitamins, 1.0 mg/l 2,4-D and 10 μM $AgNO_3$) in the dark at 27-28° C. Embryogenic callus proliferating from the scutellum of the embryos was then transferred to CM media (N6 salts, Nitsch and Nitsch vitamins, 1 mg/l 2,4-D, Chu et al., 1985, *Sci. Sinica* 18: 659-668). Callus cultures were maintained on CM by routine sub-culture at two week intervals and used for transformation within 10 weeks of initiation.

Callus was prepared for transformation by subculturing 0.5-1.0 mm pieces approximately 1 mm apart, arranged in a circular area of about 4 cm in diameter, in the center of a circle of Whatman #541 paper placed on CM media. The plates with callus were incubated in the dark at 27-28° C. for 3-5 days. Prior to bombardment, the filters with callus were transferred to CM supplemented with 0.25 M mannitol and 0.25 M sorbitol for 3 hr in the dark. The petri dish lids were then left ajar for 20-45 minutes in a sterile hood to allow moisture on tissue to dissipate.

Each genomic DNA fragment was co-precipitated with pML18 containing the selectable marker for rice transformation onto the surface of gold particles. To accomplish this, a total of 10 μg of DNA at a 2:1 ratio of trait:selectable marker DNAs were added to 50 μl aliquot of gold particles that were resuspended at a concentration of 60 mg $ml^{-1}$. Calcium chloride (50 μl of a 2.5 M solution) and spermidine (20 μl of a 0.1 M solution) were then added to the gold-DNA suspension as the tube was vortexed for 3 min. The gold particles were centrifuged in a microfuge for 1 sec and the supernatant removed. The gold particles were then washed twice with 1 ml of absolute ethanol and then resuspended in 50 μl of absolute ethanol and sonicated (bath sonicator) for one second to disperse the gold particles. The gold suspension was incubated at −70° C. for five minutes and sonicated (bath sonicator) if needed to disperse the particles. Six μl of the DNA-coated gold particles were then loaded onto mylar macrocarrier disks and the ethanol was allowed to evaporate.

At the end of the drying period, a petri dish containing the tissue was placed in the chamber of the PDS-1000/He. The air in the chamber was then evacuated to a vacuum of 28-29 inches Hg. The macrocarrier was accelerated with a helium shock wave using a rupture membrane that bursts when the He pressure in the shock tube reaches 1080-1100 psi. The tissue was placed approximately 8 cm from the stopping screen and the callus was bombarded two times. Two to four plates of tissue were bombarded in this way with the DNA-coated gold particles. Following bombardment, the callus tissue was transferred to CM media without supplemental sorbitol or mannitol.

Within 3-5 days after bombardment the callus tissue was transferred to SM media (CM medium containing 50 mg/l hygromycin). To accomplish this, callus tissue was transferred from plates to sterile 50 ml conical tubes and weighed. Molten top-agar at 40° C. was added using 2.5 ml of top agar/100 mg of callus. Callus clumps were broken into fragments of less than 2 mm diameter by repeated dispensing through a 10 ml pipet. Three ml aliquots of the callus suspension were plated onto fresh SM media and the plates were incubated in the dark for 4 weeks at 27-28° C. After 4 weeks, transgenic callus events were identified, transferred to fresh SM plates and grown for an additional 2 weeks in the dark at 27-28° C.

Growing callus was transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus was transferred to RM2 media (MS salts, Nitsch and Nitsch vitamins, 3% sucrose, 0.4% gelrite+50 ppm hyg B) and placed under cool white light (~40 $\mu Em^{-2}s^{-1}$) with a 12 hr photoperiod at 25° C. and 30-40% humidity. After 2-4 weeks in the light, callus began to organize, and form shoots. Shoots were removed from surrounding callus/media and gently transferred to RM3 media (½× MS salts, Nitsch and Nitsch vitamins, 1% sucrose+50 ppm hygromycin B) in phytatrays (Sigma Chemical Co., St. Louis, Mo.) and incubation was continued using the same conditions as described in the previous step.

Plants were transferred from RM3 to 4" pots containing Metro mix 350 after 2-3 weeks, when sufficient root and shoot growth had occurred. The seed obtained from the transgenic plants was examined for genetic complementation of the ge mutation with the wild-type genomic DNA containing the GE gene. The mutant GE line transformed with the 5.1 kb EcoRI fragment containing the wild-type GE isolated nucleic acid fragment yielded rice grains with normal embryos.

This result confirms that the 5.1 kb EcoRI fragment containing the cytochrome P450 coding region is sufficient to complement the ge mutant phenotype. Furthermore, all regulatory elements necessary for "wild-type" expression of the gene are apparently present within the 5.1 kb EcoRI fragment, since this region completely complements the ge mutation.

Example 11

Characterization of the GE Promoter

The 5.1 kb EcoRI genomic fragment described in Example 10 was sufficient to complement the ge mutation. This demonstrated that the promoter, required for the proper GE expression, was encoded in this genomic region. Two corn homologs of the rice GE are described in Example 13. The 2 kb upstream sequences from both of these genes, zmGE1 and zmGE2, are shown in SEQ ID NOs: 104 and 105, respectively. It is believed that the regulatory elements necessary for normal maize GE expression are contained within SEQ ID NO:104 or 105 and the coding regions for zmGE1 and zmGE2.

In order to investigate the expression pattern necessary for GE function, the accumulation of GE RNA in tissues was analyzed by means of in situ hybridization. To obtain detailed data of weak GE expression, a radioactive method following the protocol of Sakai et al. (1995) *Nature* 378:199-203) was employed. Plant materials were fix and embedded in paraplast according to Jackson, D. P. (1991) In Situ Hybridization in Plants. In: "Molecular Plant Pathology: A Practical Approach", (Bowles, D. J., Gurr, S. J. and McPhereson, M.

eds), Oxford University Press. The sections were prepared in 8-μm thickness using a rotary microtome. To detect GE-specific sense RNA, the region containing the 3'UTR was amplified by PCR and cloned into pGEM-T (Promega). The primers used to amplify the region for the probe were GE3'RVQ: TCGTGTGCAAGGCCGTGGCTA (SEQ ID NO:106) and GE3'LVC: GCACGATCCATTTAGCACACCAG (SEQ ID NO:107). The amplified sequence was from nucleotide 9941 to 10300 of SEQ ID NO:3.

The antisense RNA probe to detect sense GE RNA was synthesized by linearizing the clone by digesting with SpeI and transcribing with T7 RNA polymerase. The sense RNA for control was synthesized by linearizing the clone by digesting with NcoI and transcribing with SP6 RNA polymerase.

After three weeks of exposure on NBT2 Kodak autoradiography emulsion film, the result was analyzed through dark field microscopy using a compound microscope (Nikon, Eclipse E800). GE RNA accumulation was detected in the developing embryo as well as endosperm tissues. The earliest expression detected was at two day after pollination. GE expression detected in embryos was restricted to the apical region at the globular stage and to the epidermal layer of scutellum facing to the endosperm tissue at coleopilar and late stages. In the developing endosperm before the cellular stage, GE RNA was detected in the entire region with some concentration in the area close to the embryonic tissue. Later, the GE expression pattern shifted, with more expression seen in the area facing the embryo. Furthermore, GE expression was also detected in very young leaf tissues.

Example 12

Identification of the Barley GE Homolog

In order to identify the gene, a barley genomic library (Stratagene, Catalogue No. 946104) was screened by hybridizing a DNA probe made from the entire GE isolated nucleic acid fragment at 65° C. and washing at a medium stringency (5×SSPE, 0.5% SDS at 65° C. followed by 1×SSPE, 0.5× SDS, 65° C.). Five positively hybridizing lambda clones were isolated. Mapping of these clones via restriction enzyme digestion confirmed that all five were overlapping clones from the same genomic region. The DNA fragment that contained the region homologous to rice GE was further subcloned and sequenced.

The deduced coding sequence and the deduced translation product of the barley GE homolog are shown in SEQ ID NO:92 and 93, respectively. The barley GE homolog has a high degree of conservation to the rice GE protein (72.9% identity based on the Clustal method of alignment). Furthermore, the 91 nucleotide intron found in the rice GE gene is conserved in its placement within the barley gene (between nucleotides 991 and 992 of SEQ ID NO:92, the barley intron is 125 nucleotides). This conservation of intron placement is also found in zmGE1, zmGE2, and zmGE3 (see Example 13).

Example 13

Identification of Maize GE Homologs

Maize GE homologs were identified by analysis of EST clones with strong homologies to GE (see EXAMPLE 3). Two genes represented by ESTs, cbn10.pk0034.f8, maize GE2 (zmGE2, SEQ ID NO:96 for the nucleotide coding sequence, and SEQ ID NO:97 for the putative translation product) and p0121.cformn62r, maize GE1 (zmGE1, SEQ ID NO:94 for the nucleotide coding sequence, and SEQ ID NO:95 for the putative translation product), were shown to be the most homologous genes in the maize genome by the cross-hybridization analysis. A third clone cpls1s.pk001.m19 (zmGE3, SEQ ID NO:98 for the nucleotide coding sequence, and SEQ ID NO:99 for the putative translation product) has also been identified by analyzing BAC genomic clones (see below). There is a single intron contained within each of the three maize genes, and its placement is conserved with respect to the rice and barley genes discussed in Example 12. The intron for zmGE1 is 122 nucleotides and is found between nucleotides 1143 and 1144 of SEQ ID NO:94, the intron for zmGE2 is 193 nucleotides and is found between nucleotides 942 and 943 of SEQ ID NO:96, and the size of the intron for zmGE3 has not yet been determined, although it is considerably larger than the other four.

For the cross-hybridization analysis, as described below, maize DNA was digested with several different restriction enzymes and separated on 0.7% agarose gel. DNA was transferred to a nylon membrane filter, HyBond N (Amersham), and hybridized at 50° C. with the $^{32}P$-labeled probe made from the whole coding region of the rice GE gene. After washing the filter at 1×SSPE, 0.5% SDS at 65° C., it was exposed on the Phospho Imager screen (Molecular Dynamics) and signals were detected by using Phospho Imager scanner (Molecular Dynamics). The signals were detected from more than one band, indicating the possibility that there was more than one maize genes very homologous to rice GE.

To identify the homologous genes in the maize genome, the maize genomic library (Stratagene, Catalog No. 946102) was screened at the medium stringency condition starting at 2×SSPE, 0.5% SDS, 50° C. and then at 1×SSPE, 0.5% SDS 65° C., and obtained nine lambda clones that gave distinct positive signals. PCR analysis showed these clones were shown to have sequences specific to either cbn10.pk0034.f8 or p0121.cformn62r, proving that these EST clones encoded the corn genes most homologous to rice GE.

In order to obtain further information on the structure of these genes represented by two EST clones, maize genomic BAC clones were screened. The clone, p0121.cformn62r, hybridized to BAC clones that belonged to one contig. The clone, cbn10.pk0034.f8, hybridized to BAC clones that derived from two distinct contigs. One BAC clone from each contig was chosen and subclones for sequencing were made of whole BAC inserts. These BACs were BAC b94d.b2 for p0121.cformn62r (zmGE1) and BACs b153c.j17 and b37c.f1 for cbn10.pk0034.f8 contigs (zmGE2). The sequence of each BAC revealed the genomic structure of maize GE homologs. The BAC b37c.f1 contained ORF nearly identical but distinct sequence to the gene represented by cbn10.pk0034.f8 and BAC b153c.j17. The third corn homolog was named zmGE3.

Example 14

Identification of a GE Homolog by Genomic Synteny Analysis

Synteny analysis, or the conservation of gene placement on chromosomes between different organisms, is known to be a useful tool for identifying homologous genes or genomic regions from one species by comparison to a known genomic region from another closely related species. For instance, GeneA from corn is known to possess a unique activity but is related to a large multigene family. Chromosomal analysis of GeneA shows that it is closely linked to GeneB. If one wanted to find the homolog of GeneA in rice (GeneA-r), it is likely that the member of the GeneA-r family will be closely linked to GeneB-r. Rice and maize are known to exhibit conservation of chromosomal structures, i.e. gene orders, to a large extent (Ahn and Tanksley PNAS (1993)90:7980-7984). In order to make use of such synteny relationships to identify homologs among closely related species, the genomic sequence of the three BACs described in EXAMPLE 13 were compared to the 100 kb-long, rice GE genomic sequence described in EXAMPLE 1. The analysis revealed ORFs in BAC b94d.b2, showing a similarity to a hydrolase, a gene closely linked to the rice GE (the rice hydrolase gene is shown in SEQ ID NO:100 and 101, nucleotide and polypeptide, respectively; and the maize hydrolase is shown in SEQ ID NO:102 and 103). Therefore, zmGE1 is closely linked to a hydrolase gene, just like the rice GE gene. This demonstrated that rice genes closely linked to GE could be used as tags to isolate GE homologs from plant species that have conserved chromosomal structures by using synteny.

Example 15

Identification of Protein Sequences Specific to GE and GE Homologs

Cytochrome P450 proteins comprise a superfamily of genes with a variety of functions (Werck-Reichhart and Feyereisen (2000) *Genome Biology* 1:reviews 3003.1-3003.9). FIG. 2 shows an alignment of the rice GE (SEQ ID NO:2), barley GE-homolog (SEQ ID NO:93), maize GE1-homolog (SEQ ID NO:95), maize GE2-homolog (SEQ ID NO:97), maize GE3-homolog (SEQ ID NO:99), lily GE-homolog (SEQ ID NO:41), orchid gi 1173624 (SEQ ID NO:43), *Arabidopsis* gi 1235138 (SEQ ID NO:42), *Arabidopsis* gi 8920576 (SEQ ID NO:47), columbine GE-homolog (SEQ ID NO:35), soybean GE-homolog (SEQ ID NO:23), *Arabidopsis* gi 11249511 (SEQ ID NO:44), soybean gi 5921926 (SEQ ID NO:45), soybean GE-homolog (SEQ ID NO:25), soybean GE-homolog (SEQ ID NO:21), and *Arabidopsis* gi 3831440 (SEQ ID NO:46). The boxed residues are predicted helical regions identified by the Bioscout DSC program (King and Sternberg (1996) *Protein Sci* 5:2298-2310). Other boxed elements include "SRS" or substrate-recognition-sites which are hypervariable sequences in the cytochrome P450 structure, "PPP" clusters of prolines often Pro-Pro-Gly-Pro in cytochrome P450s, "F-G loop" which is the substrate access channel (part of the conserved sequence motif of SEQ ID NO:83), the conserved "GXDT" the proton transfer groove involved in heme interaction and enzyme catalysis (part of the conserved sequence motif of SEQ ID NO:85), "EXXR" the K-helix motif conserved in all cytochrome P450s necessary for heme stabilization and core structure stability (part of conserved sequence motif of SEQ ID NO:88), and "FXXGXRXCXG" the conserved heme binding site with the cysteine that contacts the heme (part of the conserved sequence motif of SEQ ID NO:90).

The alignment of the sequences and comparison to related cytochrome P450 sequences provides a useful method for identifying motifs that are unique to GE-like cytochrome P450s. Many of the conserved sequence motifs found in SEQ ID NOs:80-91 are found at the edge of helical domains, or in SRS regions.

Example 16

Genetic Mapping of Maize GE Homolog to Loci Related to High Oil Seed Trait

High oil corn cultivars and rice giant embryo mutants share extensive similarities in their phenotypes. GE homologs were mapped to investigate the possible correlation between maize GE homologs and loci controlling high oil traits. Mapping was performed by finding polymorphic nucleotide sequences (SNPs) in the 3'UTR region. Gene specific primers were made to PCR amplify the gene from the genomic DNA of the mapping parents. The following primers were used for the amplification: 90F: AATTAACCCTCACTAAAGGGCACCTGCTCTTCCACCAC (SEQ ID NO:108) and 91R: GTAATACGACTCACTATAGGGCGACTGCCCATTTCGTAGC (SEQ ID NO:109). The PCR products were directly sequenced by dye terminator chemistry, and the sequences were then aligned and analyzed for polymorphisms.

For the isolated nucleic acid fragment represented by zmGE1 (p0121.cfrmn62r), a polymorphism between the mapping parents G61/G39 was found at consensus position 73 with the nucleotide T in G61, but G in G39.

The location of polymorphisms are shown below (S corresponds to C or G, and K corresponds to G or T):

```
                                         (SEQ ID NO:110)
CACCTGCTCTTCCACCACGCCATGGGCTTCGCGCCCTCSGGAGACGCGCA
CTGGCGCGGGCTCCGCCGCCTCKCCGCCAACCACCTGTTCGGCCCGCGCC
GCGTGGCGGGTGCCGCGCACCACCGCGCCTCCATCGGCGAGGCCATGGTC
GCCGACGTCGCCGCTGCCATGGCGCGCCACGGCGAGGTCCCTCTCAAGCG
CGTGCTGCATGTCGCGTCTCTCAACCACGTCATGGCCACCGTGTTTGGCA
AGCGCTACGACATGGGCAGCCGAGAGGGCGCCCTTCTGGACGAGATGGTG
GCCGAGGGCTACGACCTCCTGGGCACGTTCAACTGGGCTGATCAAC.
```

A sequencing primer close to the polymorphism was made in order to genotype 94 individuals in the mapping population by Pyrosequencing™ (Uppsala, Sweden; Rickert et al. (2002) *BioTechniques* 32:592-603). The sequencing primer, PY90R, was GGGCCGAACAGGTGGTTG (complementary sequence of positions 77-95 in SEQ ID NO:110, underlined above). The heritage score were then used to place the gene onto a core maize genetic map using MAPMAKER™ or JOINMAP™. Clone p0121.cfrmn62r was mapped onto the bottom of Chromosome 7, in the vicinity of the marker bnl8.39 in bin 7.04.

This map position was overlapped with one of the quantitative trait loci (QTL) that were associated with high seed oil.

The materials for QTL mapping were developed by crossing two lines, 49.007 and H31. 49.007 was a high oil inbred lined (about 20% kernel oil) developed from the ASKC28 population (Wang, S M. Lin Y H and Huang A H C, 1984. Plant Phys., 76:837). H31 is a public line derived from the Illinois Low Oil (ILO) population that has very low kernel oil content (about 1%) (Quackenbush F W, Firch J G, Brunson A M and House L R. 1963. Cereal Chem. 40:250). From this cross, 180 F2:3 families were developed through two selfing generations. The F3 grain from individual F2 plants was evaluated for germ weight and other oil-related traits. One hundred kernels were shelled from the middle of each ear, dried to ~5% moisture (40 C for 4 d), weighed and oil content determined by NMR. Twenty germs were dissected from a random subsample of the 100 kernels to determine germ weight. Twenty seedlings of each F3 family were grown in greenhouse and the leaves of the seedlings were bulked on individual family basis. The leaf samples were lyophilized, ground into powder and used for DNA extraction. Genomic DNA was extracted by mini-CTAB method in a 96-well format. SSR markers were used in this mapping study. All genotypes were detected using ABI PRISM systems, which include the use of fluorescent end-label primers, gel electrophoresis on ABI377 DNA sequencer, peak detection and allele identification on GeneScan™ and Genotyper™ software. A total of 89 polymorphic SSRs were used in mapping analysis. The linkage map was assembled by MAPMAKER and confirmed by MAPMANAGER. QTL analysis was carried out on mean value of each trait through composite interval mapping. QTL Cartographer was used to perform the analysis. Important parameters used in the analysis were:

Mapping function: Kosambi

QTL mapping method: Composite interval mapping

Significance threshold: LOD=2.5

Significance test for linear regression and backward stepwise linear regression: á=0.05

There appeared to be a QTL for the germ weight trait of high oil seed on chromosome.7. The putative QTL is in the region where EST p0121.cfrn62r (zmGE1) was mapped.

Example 17

Expression Analysis of Maize GE Homologs

In order to investigate a possible correlation between GE homologs and high oil traits, the expression pattern of zmGE2 was analyzed.

The expression study was conducted by comparing MPSS (Massively Parallel Signature Sequencing) data (Brenner et al. 2000. *Nature Biotechnology* 18:630-634; Brenner et al. (2000) *Proc Natl Acad Sci USA* 97:1665-1670), obtained from various corn tissues of different lines. MPSS data enabled a survey of expression levels in terms of looking at the abundance of particular cDNA clones among 1,000,000 clones for each library. The relative abundance of a particular tagged sequence, which is unique to a single cDNA, correlates with the relative level of accumulation of the corresponding RNA in that tissue. The expression of the GE homolog zmGE2 was detected, in all cultivars tested, by the presence of a specific tag sequence, GATCGATGGAACTGAGT (SEQ ID NO:111), in cDNAs from embryo tissues isolated 15 days after pollination. In corn cultivars with normal oil accumulation in seeds, zmGE2 was expressed with a frequency of $^{238}/_{1,000,000}$ (238 parts-per-million or ppm) for the wild-type cultivar B73, and 263 ppm for the wild-type ASK cycle 0. In contrast, the expression of zmGE2 in high oil corn lines was reduced by more than 50%. In the high oil line, QX47, zmGE2 was expressed with a significantly lower frequency of 89 ppm. In another high oil line, ASK 28 cycles, the expression level was 113 ppm. A third high oil cultivar, IHO, gave an accumulation rate of 78 ppm. The reduction of expression is especially significant between ASK 0 (normal) and 28 cycles (high oil) because the two lines are derived from the same genetic background.

These data showed that one of the corn GE homologs, zmGE2, was substantially down-regulated in its expression in developing embryos of high oil lines. The result of the expression study confirmed that this GE homolog has a negative correlation with the high oil trait in corn seed. This is consistent with the rice result where mutations in GE genes result in enlarged embryos and high-oil phenotypes.

Example 18

Reduced Embryo Size and Enhanced Endosperm Size through GE Ectopic Expression in Maize For GE over expression, the GE ORF (nucleotides 8301-9969 of SEQ ID NO:3) was amplified from the 5.1 kb EcoRI fragment described in Example 10, which complemented ge mutations. The 5.1 kb EcoRI fragment served as the template from which the GE ORF was amplified using primers GE-ORF1 and GE-ORF2

GE-ORF1 5'-ACACCAGGTGCTCGAGAATTCGGTCTCCCATGGCGCTCTCCTCCATGGC-3' (SEQ ID NO: 112)

GE-ORF2 5'-GCCGACGGAGAGCGACATCA-3' (SEQ ID NO:113)

The amplified PCR fragment was digested with DraIII and ligated with DraIII-digested EcoRI 5 kb. The entire GE coding region was PCR amplified out of this construct with a 5' primer called "Construct 5'" and "Construct 3'"

Construct 5' 5'-CACCAGGTGCTCGAGMTTCGGTCTCCCATG-3' (SEQ ID NO:114)

Construct 3' 5'-TTCATGGGAGACCTCGAGCTGCAGTCAGGCCCTAGCCACGGCCTTGC-3' (SEQ ID NO:115).

"Construct 5'" primer contained DraIII, XhoI, EcoRI and BsaI restrictions sites. "Construct 3" primer contains a BsaI, XhoI and PstI restriction sites. The PCR fragment was digested with BsaI and was then ligated to a maize ubiquitin promoter along with 2-1A terminator to form UBI::GE:2-1A. (SEQ ID NO:116 and SEQ ID NO:117, respectively) UBI::GE:2-1A was then cloned into the binary vector PHP18422 (SEQ ID NO:118), which was subsequently transformed into *Agrobacterium* ABA4404.

The maize plant having genotype Hi-II was used for transformation in this study [Armstrong, C. L., et al. (1991) *Maize Genet. Coop. Newslett.* 65:92-93]. Hi-II transformation and plant regeneration were carried out according to the procedure described in Zhao et al. [Zhao, Z., et al. (2002) *Mol. Breed.* 8: 323-333]. The pollen from the resultant T0 plants was used to pollinate ears of wild-type plants. T1 seed from the cross was analyzed for embryo and endosperm size.

Figure 3:
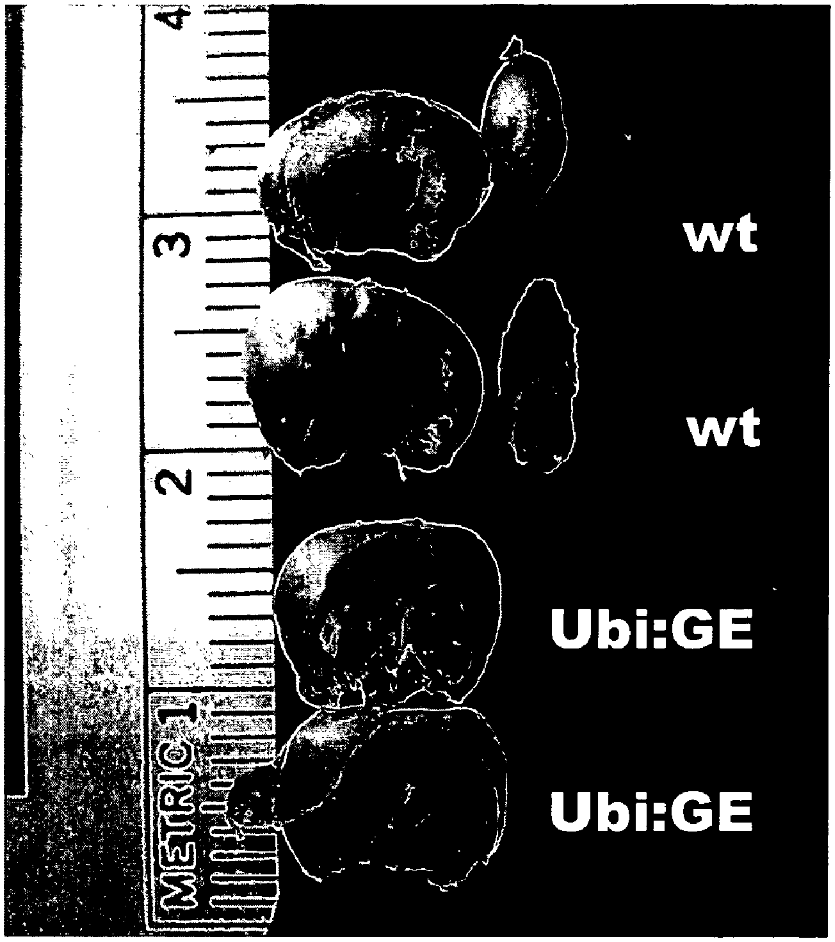
Figure 4A:
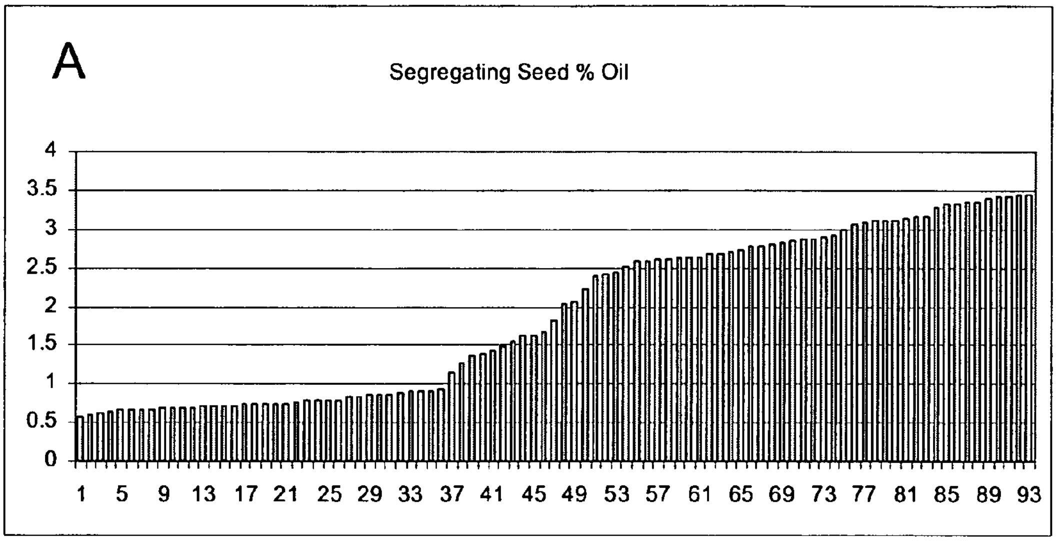
Figure 4B:
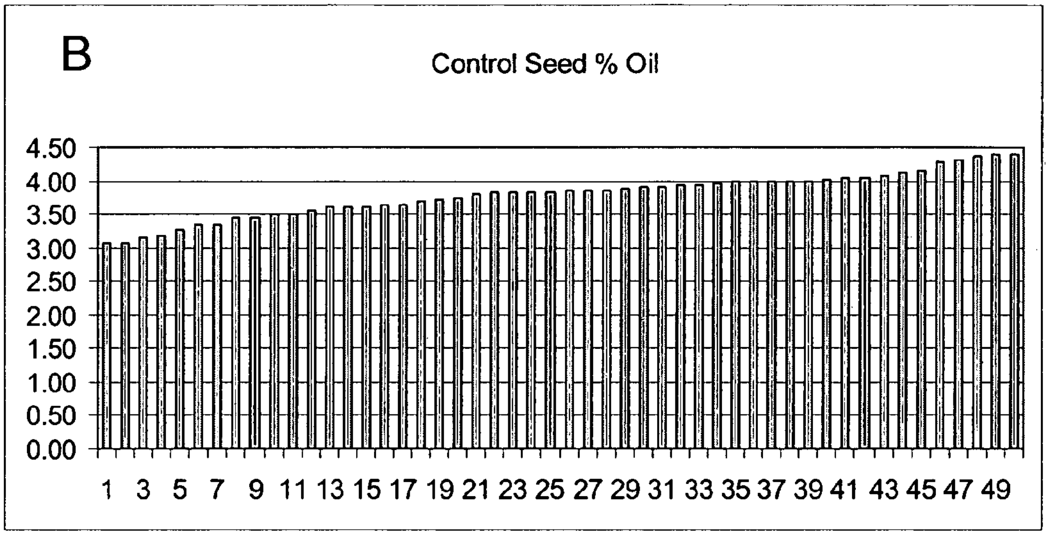

T1 seed without the transgene produced wild-type seed with normal embryos (see FIG. 3, top two kernels) and T1 seed over-expressing the transgene produced seed with significantly smaller embryos and enlarged endosperm filling the embryo cavity (see FIG. 3, lower two kernels). The oil content of the embryos was determined according to the method described in Applicants' Assignee's U.S. patent application Ser. No. 10/183,687 filed Jun. 27, 2002, the contents of which are hereby incorporated by reference. The analysis of oil content in the embryo revealed that the reduced embryo phenotype of transgenic seeds correlated with reduced oil content (see FIG. 4).

Thus, ectopic expression of a rice GE in maize results in altered embryo and endosperm size. The altered embryo size also leads to a reduced oil phenotype in the transgenic maize.

Example 19

Seed Size Enhancement through GE Ectopic Expression in Rice

Further analysis of GE function was accomplished through the creation of two constructs, GE3XMyc Hyg and ATG* GE 5 Kbp Hyg.

The first construct, GE3XMyc Hyg, incorporates three c-Myc epitope sequences into the GE coding sequence. This construct is useful for determining the expression pattern of GE in plant tissues.

An approximately 420 bp DNA fragment was amplified from the 3'-end of the GE ORF contained in the 5.1 Kb EcoRI plasmid (in Example 10) to make the construct GE 1XMyc.

A set of primers was used to amplify the 3'-end of the GE ORF from the AscI site up to the termination codon and a c-Myc epitope was put in-frame to the 3'-end of GE. The primer sequences are:

GE AscI F: 5'-GCCCGCTCCTGTCGTGGGCGCGC-CTCGCCGTG-3' (SEQ ID NO:119, corresponding to nucleotides 9575-9606 of SEQ ID NO:3)

GEMycR: 5'-GGCGCGCCCTACTCGAGGTCCTCCTC-CGAGATGAGCTTCTGCTCGGCCCTAG CCACGGC-CTTGCACACGA-3' (SEQ ID NO:120, first 44 nucleotides are the complement of the c-Myc epitope, the remaining 26 nucleotides are complementary to the region 9941-9966 of SEQ ID NO:3)

The amplified DNA fragment incorporated a single c-Myc epitope fused to the 3' end of GE ORF and was cloned into pGEM-T-easy vector to create GE1XMyc pGEM-T (Promega Corporation). The sequence of the new AscI fragment with 1xMyc is shown in SEQ ID NO:121, where the 1xMyc sequence is found between nucleotides 377 and 406.

The following two oligonucleotides were used to make two additional repeats of c-Myc epitope tags to create GE3XMyc pGEM-T.

```
cmyc2XGD:                              (SEQ ID NO:122)
5'-CTCGAGCAGAAGCTCATCTCGGAGGAGGACCTCGGCGAGCAGAAGCT
CATCTCGGAGGAGGACCTCGAG-3'

cmyc2XDC:                              (SEQ ID NO:123)
5'-CTCGAGGTCCTCCTCCGAGATGAGCTTCTGCTCGCCGAGGTCCTCCT
CCGAGATGAGCTTCTGCTCGAG-3'
```

Oligonucleotides cmyc2XGD and cmyc2XDC were annealed and digested with XhoI and cloned into the XhoI site of GE1XMyc pGEM-T to create the GE3XMyc pGEM-T plasmid. GE 3XMyc pGEM-T and GE EcoRI 5.1 Kb plasmid from Example 10 were digested with AscI and the 416 bp fragment from GE3X Myc pGEM-T was extracted from gel and cloned into GE EcoRI 5 Kb vector to create GE EcoRI 3X myc.

A HygR selection marker was added as follows: GE EcoRI 3X myc vector was digested with endonuclease PstI and BamHI. In order to make compartible ends, the adaptor sequence Pst BsphI: 5'-CATGTGCA-3' (SEQ ID NO:124) was ligated to the PstI site to produce an end compatible to the BsphI site. Vector pML18 (described in Example 10) was digested with restriction endonuclease BspHI and BamHI to obtain a 4.3 Kbp DNA fragment containing CaMV35S PRO: HYG which was then subsequently ligated into the BamHI and BspHI sites of GE EcoRI 3X Myc to form the GE3X cMyc Hyg construct.

The second construct, ATG* GE 5 kbp HYG, was made, as described below, in order to investigate the translation initiation site of GE.

The GE ORF possessed an in-frame ATG sequence that was present about 62 nucleotides upstream of the 5' end of the longest GE cDNA identified. This in-frame ATG sequence was removed by in vitro mutagenesis from the construct to determine whether this ATG had any effect on GE expression/function.

Parenthetically, it was observed that GE ORF shared sequence identity with other CYP78 proteins. Based on this, it was unlikely that the GE ORF might encode a polypeptide that would be about 30 amino acids longer due to the presence of this in-frame ATG sequence.

The determination as to whether this ATG had any effect on GE expression involved mutagenesis to change the ATG codon to a TTG codon. It was found, as is discussed below, that the mutagenized ATG was not required for GE function. The determination was made as follows:

Specifically, in vitro mutagenesis was performed on the 5.1 kb EcoRI genomic fragment (described in Example 10) containing all cis elements and the GE gene.

The following primer was designed to change ATG to TTG:

```
GE_ATG-TTG-1:
5'-GAGTGGCAAATTGGTCTATTTAAA-3'    (SEQ ID NO:125)
```

The resulting ATG* GE 5 Kbp plasmid was digested with endonuclease PstI and BamHI. Similar to GE3X cMyc Hyg as mentioned above, the ATG-mutagenized 5 kb EcoRI clone was digested with PstI and BamHI and the same linker Pst-BsphI was ligated to the PstI end.

Vector pML18 (described in Example 10) was digested with restriction endnuclease BspHI and BamHI to obtain a 4.3-kb DNA fragment containing CaMV35S PRO:HYG which was then ligated into BamHI and BspHI sites of the 5 kb EcoRI clone to form the construct, ATG* GE 5-kb HYG.

These two constructs, GE3X cMyc Hyg and ATG* GE 5 Kbp HYG, were transformed into rice homozygous for the ge-2 mutation. The rice transformation procedure was described in Example 10 except that 2 μg of each construct was used for the biolistic based transformation.

Figure 5:

Seeds were obtained from 7 independent transformants of GE3X cMyc Hyg. 4 of 7 transformants segregated wild-type size embryo, suggesting the transgenic GE protein fused with c-Myc epitope was functional to complement the ge mutation (see FIG. 5 for an example of the complemented ge3-1 seed phenotype, this is representative of the complementation results obtained in this example).

Figure 6:
FIG. 6 shows seed expressing GE 5 Kbp HYG in a ge background (2-15), seed expressing GE 5 Kbp HYG in a wild-type T65 background (3-23), and wild type seed (T65).

Furthermore, 2 out of 7 transformants produced intermediate sized embryos with the seeds with that were significantly larger than normal wild-type seed due to an alteration in embryo and endosperm size (see FIG. 6). The phenotype of these two transformants was different than the ge-2 mutants. The embryo/endosperm ratio was closer to wild-type although the larger embryo size resulted in an overall increase in seed size when compared to either wild-type or ge2-1 mutant rice seed.

Figure 7:
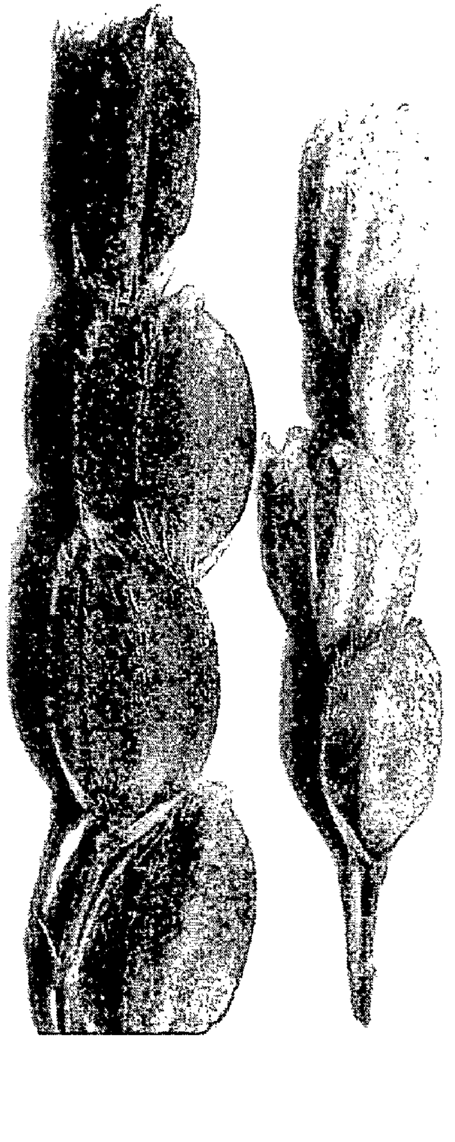
FIG. 7 shows GE ectopic expression leads to enlarged seed in rice
Figure 8:
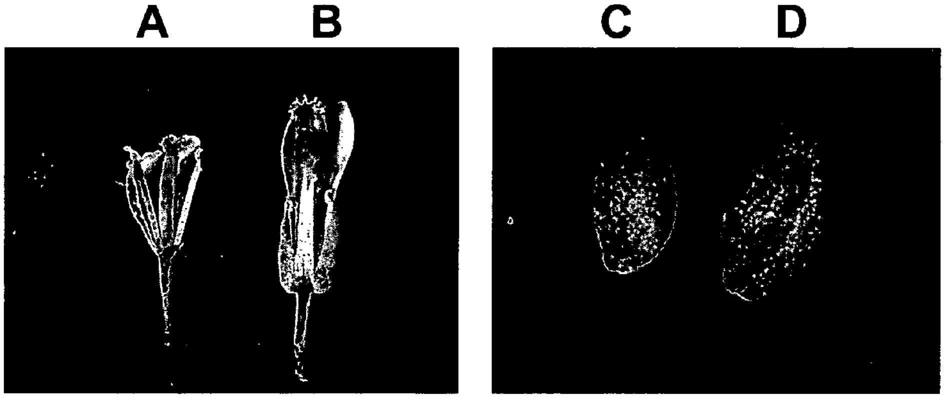

Transformations with ATG*GE5 Kbp HYG yielded 4 transgenic plants, where 3 out of 4 plants produced seed showing segregation of seeds with wild-type embryo, indicating that the mutagenized ATG was not required for GE function. An additional 11 transformants of ATG* GE 5 Kbp Hyg in a wild-type background were recovered. 8 of the 11 transformants produced the large seed phenotype similar to that found with the GE3X cMyc Hyg construct (see FIG. 7).

In order to correlate this large seed phenotype with GE ectopic expression, expression of GE in young panicle was examined using RT-PCR. Specifically, GE expression was examined in young panicles of 5 wild-type and 10 large seed siblings derived from two independent lines, 1001-3-2 and 1001-3-4 with ATG* GE 5 Kbp Hyg. Clear ectopic GE expression was detected in young panicle of large seed plants (5.5±0.2 mm in length and 3.1±0.1 mm in width), where no GE expression was observed in transgenic plants with wild-type seeds (5.0±0.2 mm in length and 2.8±0.1 mm in width).

These results showed that GE ectopic expression enhances seed size, enlarging both embryo and endosperm size.

Example 20

Seed Size Enhancement through GE Ectopic Expression in Arabidoipsis

GE was expressed in *Arabidopsis* under the 35 S CaMV promoter in order to examine efficacy of GE for seed size enhancement in other species. The GE gene was amplified from the complementing 5 kb EcoRI genomic fragment using primers that carried XhoI restriction sites directly upstream of the initiation codon and downstream of the stop codon.

```
                                    (SEQ ID NO:126)
XhoIORF5' 5'-AACTCGAGATGGCGCTCTCCTCCATGGC-3'
and

                                    (SEQ ID NO:127)
XhoIORF3' 5'-AACTCGAGTCAGGCCCTAGCCACGGCC-3'
```

The correct PCR fragment was digested with XhoI and fused to a 35S promoter in the binary vector pBE851 (Aukerman, M., and Sakai, H. (2003) Plant Cell 15:2730-2741). The resulting clone was transformed into *Agrobacterium* and subsequently into wild-type *Arabidopsis* Columbia ecotype, following standard procedures (Clough, S. J., and Bent, A. F. (1998) Plant Journal 16:735-743).

T1 transgenic plants were selected with Basta herbicide. All transgenic plants (>30 individual events) produced enlarged flowers. On average, petals and sepals were 1.5-2 times larger than wild type (see FIG. 8). Upon fertilization with the wild-type pollen or pollen from their own, they produced enlarged seed (see FIG. 8). The transgenic seeds were twice as large as the wild type in volume. A cross section of the transgenic seed revealed that the enlargement was associated with an enlarged embryo.

In order to examine whether or not any *Arabidopsis* GE homologs have a similar function, two *Arabidopsis* CYP78 genes closest to rice GE from the genomic DNA (CYP78A10 and CYP78A5) were amplified. CYP78A10 (=At1g74110, accession number NM_106071) has 54% sequence identity with GE at the amino acid residue level, and CYP78A5 (=At1g13710, accession# NM_101240) has 52% identity with GE. These two genes were fused to 35S promoter of pBE851 (Aukerman, M. and Sakai, H. (2003) Plant Cell 15: 2730-2741) to make the 35S::CYP constructs.

The resulting constructs were transformed into wild-type *Arabidopsis* plants following standard procedures. More than 30 independent T1 lines were produced for each construct. However, none of them showed a phenotype with large flowers and seeds.

Example 21

GE Ectopic Expression in Soybean

In order to test the efficacy of GE in soybean, the 35S::GE construct described above was transformed into Jack cultures using the biolistic method essentially as described in Example 5. The construct was previously introduced into *Arabidopsis* and led to the large flower and seed phenotype.

35S::GE was co-transformed with pKS59 (SEQ ID NO:128), which carried the HPT selection marker. 11 events with 35S::GE and two events with a control that did not contain 35S::GE were recovered. A total of 30 lines from 11 events were grown to maturation and set T1 seeds. Three lines produced seeds with reduced size and one line with enlarged seeds (see FIG. 9).

Based on experience with soybean transformation, transgenic lines with small seed size had been occasionally observed with several different constructs. However, lines with enlarged seeds had not been reported in the past, indicating the significance of this particular transgenic event. This large seed phenotype in soybean was in accordance with the result obtained in *Arabidopsis*, where 35S::GE gave an enlarged seed phenotype (see EXAMPLE 20.) In the both cases, the enlargement of the embryo apparently resulted from over-expression of the GE gene.

What is claimed is:

1. An isolated nucleotide fragment comprising a nucleic acid sequence encoding a cytochrome P450 polypeptide having an amino acid identity of at least 95% based on the Clustal method of alignment when compared to SEQ ID NO:2, or the complement thereof, wherein a dicot transformed with said isolated nucleotide fragment exhibits increased embryo size and a monocot transformed with said isolated nucleotide fragment exhibits decreased embryo size.

2. The isolated nucleotide fragment of claim 1, wherein the polypeptide it encodes comprises a motif corresponding to the amino acid sequence set forth in SEQ ID NO:88 wherein said motif is a conserved subsequence.

3. A chimeric construct comprising the isolated nucleotide fragment of claim 1 or 2 operably linked to at least one regulatory sequence.

4. A plant comprising in its genome the chimeric construct of claim 3.

5. Transgenic seeds obtained from the plant of claim 4 wherein the seed comprise said construct.

6. The plant of claim 4 wherein said plant is selected from the group consisting of rice, corn, sorghum, millet, rye, soybean, canola, wheat, barley, oat and beans.

7. Transformed plant tissue or plant cells comprising the chimeric construct of claim 3.

8. The plant tissue or plant cells of claim 7 wherein the plant is selected from the group consisting of rice, corn, sorghum, millet, rye, soybean, canola, wheat, barley, oat and beans.

9. A method of controlling embryo size during seed development comprising:

(a) transforming a plant with the chimeric construct of claim 3;

(b) growing the transformed plant under conditions suitable for the expression of the chimeric construct; and (c) selecting those transformed plants which produce seeds having an altered embryo size, wherein if said plants are dicots, embryo size is increased, and if said plants are monocots, embryo size is decreased.

* * * * *

UNITED STATES PATENT AND TRADEMARK OFFICE

CERTIFICATE OF CORRECTION

PATENT NO. : 7,655,840 B2
APPLICATION NO. : 11/394442
DATED : February 2, 2010
INVENTOR(S) : Cahoon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 304 days.

Signed and Sealed this

Thirtieth Day of November, 2010

David J. Kappos

*Director of the United States Patent and Trademark Office*